US010577290B2

(12) United States Patent
Schmid et al.

(10) Patent No.: US 10,577,290 B2
(45) Date of Patent: *Mar. 3, 2020

(54) COMPOSITIONS WITH IMPROVED UREASE-INHIBITING EFFECT COMPRISING (THIO)PHOSPHORIC ACID TRIAMIDE AND FURTHER COMPOUNDS SUCH AS AMINES AND COLORANTS

(71) Applicant: BASF SE, Ludwigshafen (DE)

(72) Inventors: Markus Schmid, Deidesheim (DE); Wolfram Zerulla, St. Martin (DE); Gregor Pasda, Neustadt (DE); Alexander Wissemeier, Speyer (DE); Tobias Lang, Dossenheim (DE); Karl-Heinrich Schneider, Kleinkarlbach (DE); Zoltan Baan, Maxdorf (DE); Maarten Staal, Limburgerhof (DE); Ansgar Gereon Altenhoff, Heidelberg (DE); Kian Molawi, Ludwigshafen am Rhein (DE); Sophia Ebert, Mannheim (DE); Olivier Fleischel, Eckbolsheim (FR)

(73) Assignee: BASF SE, Ludwigshafen (DE)

( * ) Notice: Subject to any disclaimer, the term of this patent is extended or adjusted under 35 U.S.C. 154(b) by 105 days.

This patent is subject to a terminal disclaimer.

(21) Appl. No.: 15/538,963

(22) PCT Filed: Dec. 22, 2015

(86) PCT No.: PCT/IB2015/059864
§ 371 (c)(1),
(2) Date: Jun. 22, 2017

(87) PCT Pub. No.: WO2016/103168
PCT Pub. Date: Jun. 30, 2016

(65) Prior Publication Data
US 2017/0369385 A1    Dec. 28, 2017

(30) Foreign Application Priority Data
Dec. 23, 2014 (EP) .................................. 14200088

(51) Int. Cl.
*C05G 3/00* (2006.01)
*C05G 3/08* (2006.01)
*C07F 9/22* (2006.01)

(52) U.S. Cl.
CPC ............. *C05G 3/0041* (2013.01); *C05G 3/08* (2013.01); *C07F 9/224* (2013.01)

(58) Field of Classification Search
CPC .................... C05G 3/0041; C05G 3/08
See application file for complete search history.

(56) References Cited

U.S. PATENT DOCUMENTS

| 3,565,599 | A | 2/1971 | Sor et al. |
| 4,435,548 | A | 3/1984 | Tomalia et al. |
| 4,517,007 | A | 5/1985 | Swerdloff et al. |
| 4,530,714 | A | 7/1985 | Kolc et al. |
| 4,539,037 | A | 9/1985 | Swerdloff et al. |
| 5,352,265 | A | 10/1994 | Weston et al. |
| 6,830,603 | B2 | 12/2004 | Whitehurst et al. |
| 7,182,537 | B2 | 2/2007 | Policicchio et al. |
| 8,888,886 | B1 | 11/2014 | Whitehurst et al. |
| 10,150,712 | B2 * | 12/2018 | Schneider ............... C05G 3/08 |
| 2010/0218575 | A1 | 9/2010 | Wissemeier et al. |
| 2011/0154874 | A1 | 6/2011 | Rahn et al. |
| 2016/0376452 | A1 * | 12/2016 | Sugita ................. C09D 11/322 347/100 |
| 2017/0158575 | A1 | 6/2017 | Schneider et al. |
| 2017/0305807 | A1 * | 10/2017 | Iannotta .................... C07F 9/11 |

FOREIGN PATENT DOCUMENTS

| CN | 1204310 | A | | 1/1999 |
| CN | 1989144 | A | | 6/2007 |
| CN | 101157588 | A | | 4/2008 |
| CN | 101384523 | A | | 3/2009 |
| CN | 101479282 | A | | 7/2009 |
| CN | 102264748 | A | | 11/2011 |
| CN | 102408283 | A | * | 4/2012 |
| CN | 102557814 | A | | 7/2012 |
| CN | 103896672 | A | | 7/2014 |
| DE | 102005053540 | A1 | | 5/2007 |
| DE | 102007062614 | A1 | | 6/2009 |

(Continued)

OTHER PUBLICATIONS

Machine translation of CN 102408283 A, published Apr. 11, 2012. (Year: 2012).*

(Continued)

*Primary Examiner* — Vickey Nerangis
(74) *Attorney, Agent, or Firm* — Armstrong Teasdale LLP

(57) ABSTRACT

A composition comprising: (A) a mixture comprising at least one (thio)phosphoric acid triamide according to the general formula (I) $R^1R^2N-P(X)(NH_2)_2$, wherein X is oxygen or sulfur; $R^1$ is a $C_1$ to $C_{20}$ alkyl, $C_3$ to $C_{20}$ cycloalkyl, $C_6$ to $C_{20}$ aryl, or dialkylaminocarbonyl group; $R^2$ is H, or $R^1$ and $R^2$ together with the nitrogen atom linking them define a 5- or 6-membered saturated or unsaturated heterocyclic radical, which optionally comprises 1 or 2 further heteroatoms selected from the group consisting of nitrogen, oxygen, and sulfur, and (L1) at least one amine selected from the group consisting of (L10), (L11), (L12), (L13), (L14), (L15), (L16), (L17), (L18), (L19), (L20), (L21), (L22), (L23), (L24), and (L29).

8 Claims, 1 Drawing Sheet

(56) References Cited

FOREIGN PATENT DOCUMENTS

| | | |
|---|---|---|
| DE | 102009056566 A1 | 6/2011 |
| EP | 0115771 A2 | 8/1984 |
| EP | 0119487 A1 | 9/1984 |
| EP | 0234408 A2 | 9/1987 |
| EP | 0802215 A1 | 10/1997 |
| EP | 2460404 A1 | 6/2012 |
| WO | 9314147 A1 | 7/1993 |
| WO | 9615097 A1 | 5/1996 |
| WO | 0061522 A1 | 10/2000 |
| WO | 2009060059 A2 | 5/2009 |
| WO | 2013055483 A1 | 4/2013 |
| WO | 2015001391 A1 | 1/2015 |
| WO | 2016103168 A1 | 6/2016 |

OTHER PUBLICATIONS

International Search Report and Written Opinion for International Patent Application No. PCT/IB2015/059864, dated Apr. 15, 2016, 12 pages.
Supplementary European Search Report and Written Opinion for EP Patent Application No. 15872070.6, dated Jul. 11, 2018, 12 pages.

* cited by examiner

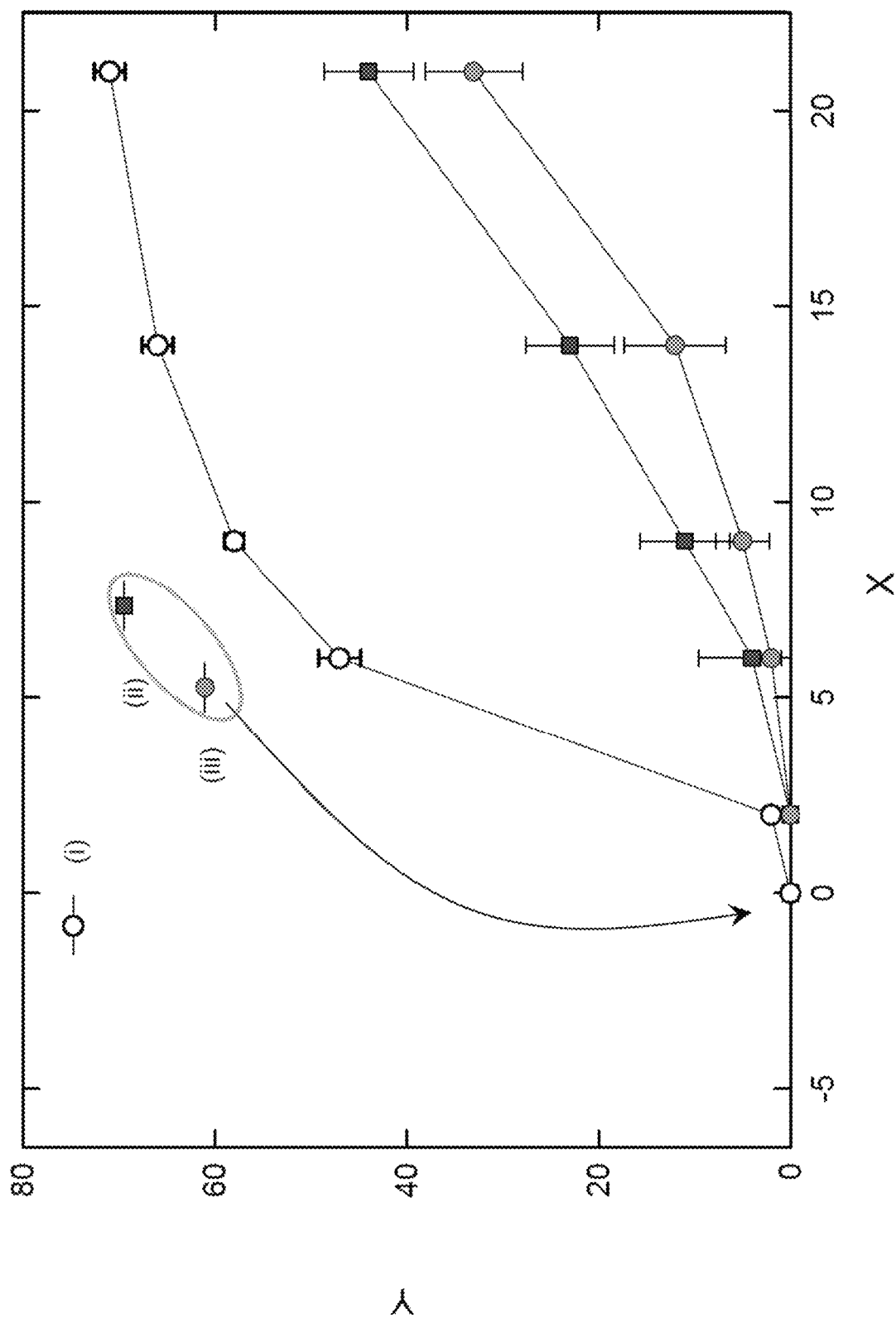

COMPOSITIONS WITH IMPROVED UREASE-INHIBITING EFFECT COMPRISING (THIO)PHOSPHORIC ACID TRIAMIDE AND FURTHER COMPOUNDS SUCH AS AMINES AND COLORANTS

CROSS-REFERENCE TO RELATED APPLICATIONS

This application is a U.S. National Phase Application of PCT/IB2015/059864, filed Dec. 22, 2015, which claims the benefit of priority to European Patent Application No. 14200088.4, filed Dec. 23, 2014, the entire contents of which are hereby incorporated by reference herein.

BACKGROUND

This invention essentially relates to compositions with improved urease-inhibiting effect comprising (thio)phosphoric acid triamide and further compounds and the use of such compositions as additive or coating material for nitrogen-containing fertilizers.

Worldwide, the predominant and further-increasing amount of the nitrogen used for fertilizing is employed in the form of urea or urea-containing fertilizers. Urea itself, however, is a form of nitrogen which is absorbed very little if at all, being hydrolyzed relatively rapidly by the enzyme urease, which is present ubiquitously in the soil, to form ammonia and carbon dioxide. In this process, in certain circumstances, gaseous ammonia is emitted to the atmosphere, and is then no longer available in the soil for the plants, thereby lowering the efficiency of fertilization.

It is known that the degree of utilization of the nitrogen when using urea-containing fertilizers can be improved by spreading urea-containing fertilizers together with substances which are able to inhibit or decrease the enzymatic cleavage of urea (for a general review, see Kiss, S. Simihäian, M. (2002) Improving Efficiency of Urea Fertilizers by Inhibition of Soil Urease Activity, ISBN 1-4020-0493-1, Kluwer Academic Publishers, Dordrecht, The Netherlands). Among the most potent known urease inhibitors are N-alkylthiophosphoric acid triamides and N-alkylphosphoric acid triamides, which are described in EP 0 119 487, for example.

Additionally, mixtures of N-alkylthiophosphoric acid triamides such as N-(n-butyl)thiophosphoric acid triamide (NBPT) and N-(n-propyl)thiophosphoric acid triamide (NPPT) can be used. The mixtures and their preparation are described in US 2010/218575 A1, for example.

These urease inhibitors are described in U.S. Pat. No. 4,530,714, for example. In order for this class of compound to be able to act as a urease inhibitor, there must first be a conversion to the corresponding oxo form. That form reacts subsequently with the urease, causing its inhibition.

It is advisable to apply the urease inhibitors together with the urea onto or into the soil, since this ensures that the inhibitor comes into contact, together with the fertilizer, with the soil. The urease inhibitor may be incorporated in the urea by, for example, dissolving it into the melt prior to urea granulation or prilling. A process of this kind is described in U.S. Pat. No. 5,352,265, for example. A further option is to apply the urease inhibitor to the urea granules or prills, in the form of a solution, for example.

Corresponding processes for application, and suitable solvents, are described in US 2010/218575 A1, for example. Other suitable additives, for example amines selected from methyldiethanolamine, tetrahydroxypropylethylenediamine, trimethylaminoethylethanolamine, N,N,N',N'-tetramethyl-1,6-hexanediamine, N,N',N"-tris(dimethylaminopropyl)hexahydrotriazine, and 2,2'-dimorpholinyldiethyl ether, are described in US 2011/0154874 A1.

The storage life of the urease inhibitor is limited. The higher the temperature, the shorter the storage life. If, for example, urea is stored under tropical conditions, a major part of the urease inhibitor has undergone decomposition, generally, after about four weeks of storage. If the urease inhibitor is introduced into the urea melt, the decomposition is less. For the commercialization of the urea stabilized with the urease inhibitor, however, it is often vital to apply the urease inhibitor to urea and to store the treated fertilizer until the time of its spreading to the soil.

One of the objects of the present invention was to provide a composition containing (thio)phosphoric acid triamide which
(i) enhances the stability of the (thio)phosphoric acid triamide(s), and/or
(ii) enhances the urease inhibiting effect of the (thio) phosphoric acid triamide(s), and/or
(iii) enhances the yield increase effect of the (thio)phosphoric acid triamide(s), and/or
(iv) has a relatively long storage life, particularly before being applied to or coated on nitrogen-containing fertilizers, and/or
(v) enhances the stability of the (thio)phosphoric acid triamide particularly when applied to or coated on nitrogen-containing fertilizers such as urea, and/or
(vi) protects the (thio)phosphoric acid triamide applied to or coated on nitrogen-containing fertilizers such as urea from decomposition or loss, and/or
(vii) is toxicologically unobjectionable, and/or
(viii) does not adversely affect the urease-inhibiting effect and/or activity of the (thio)phosphoric acid triamide, and/or
(ix) can be easily and safely packaged, transported and shipped, even in large quantities, and/or
(x) can be easily and safely handled and applied for soil treatment, even in large quantities, and/or
(xi) can be easily recognized and distinguished in case several different compositions are used for different purposes.

DETAILED DESCRIPTION

Accordingly, a composition (Q4) was found which comprises:
(A) a mixture comprising at least one (thio)phosphoric acid triamide according to the general formula (I)

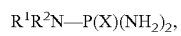

wherein
X is oxygen or sulfur;
$R^1$ is a $C_1$ to $C_{20}$ alkyl, $C_3$ to $C_{20}$ cycloalkyl, $C_6$ to $C_{20}$ aryl, or dialkylaminocarbonyl group;
$R^2$ is H, or
$R^1$ and $R^2$ together with the nitrogen atom linking them define a 5- or 6-membered saturated or unsaturated heterocyclic radical, which optionally comprises 1 or 2 further heteroatoms selected from the group consisting of nitrogen, oxygen, and sulfur,
and
(L1) at least one amine selected from the group consisting of (L10), (L11), (L12), (L13), (L14), (L15), (L16), (L17), (L18), (L19), (L20), (L21), (L22), (L23), (L24) and (L29) as described further below.

Accordingly, a composition (Q5) was found which comprises:

(A) a mixture comprising at least one (thio)phosphoric acid triamide according to the general formula (I)

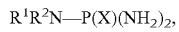

wherein

X is oxygen or sulfur;

$R^1$ is a $C_1$ to $C_{20}$ alkyl, $C_3$ to $C_{20}$ cycloalkyl, $C_6$ to $C_{20}$ aryl, or dialkylaminocarbonyl group;

$R^2$ is H, or $R^1$ and $R^2$ together with the nitrogen atom linking them define a 5- or 6-membered saturated or unsaturated heterocyclic radical, which optionally comprises 1 or 2 further heteroatoms selected from the group consisting of nitrogen, oxygen, and sulfur, and (L2) at least one colorant selected from the group consisting of (L700) to (L848) as described further below.

Accordingly, a further composition (Q2) was found which comprises:

(A) a mixture comprising at least one (thio)phosphoric acid triamide according to the general formula (I)

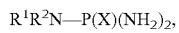

wherein

X is oxygen or sulfur;

$R^1$ is a $C_1$ to $C_{20}$ alkyl, $C_3$ to $C_{20}$ cycloalkyl, $C_6$ to $C_{20}$ aryl, or dialkylaminocarbonyl group;

$R^2$ is H, or $R^1$ and $R^2$ together with the nitrogen atom linking them define a 5- or 6-membered saturated or unsaturated heterocyclic radical, which optionally comprises 1 or 2 further heteroatoms selected from the group consisting of nitrogen, oxygen, and sulfur, and (C) at least one amine selected from the group consisting of (C1) a polymeric polyamine, and (C2) an amine containing not more than one amino group and at least three alkoxy- or hydroxy-substituted $C_2$ to $C_{12}$ alkyl groups $R^{21}$, wherein at least one of the groups $R^{21}$ is different to the other groups $R^{21}$, and (C3) an amine containing not more than one amino group and at least two alkoxy- or hydroxy-substituted $C_2$ to $C_{12}$ alkyl groups $R^{22}$, wherein at least one of the groups $R^{22}$ bears the alkoxy or hydroxy substituent at a secondary or tertiary carbon atom and wherein at least one of the groups $R^{22}$ is different to the other group(s) $R^{22}$, and (C4) an amine containing at least one saturated or unsaturated $C_8$ to $C40$ alkyl group $R^{23}$, and (C5) a saturated or unsaturated heterocyclic amine which contains at least one oxygen atom as ring atom and which does not contain a further alkoxy group.

Accordingly, yet a further composition (Q3) was found which comprises:

(A) a mixture comprising at least one (thio)phosphoric acid triamide according to the general formula (I)

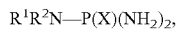

wherein

X is oxygen or sulfur;

$R^1$ is a $C_1$ to $C_{20}$ alkyl, $C_3$ to $C_{20}$ cycloalkyl, $C_6$ to $C_{20}$ aryl, or dialkylaminocarbonyl group;

$R^2$ is H, or $R^1$ and $R^2$ together with the nitrogen atom linking them define a 5- or 6-membered saturated or unsaturated heterocyclic radical, which optionally comprises 1 or 2 further heteroatoms selected from the group consisting of nitrogen, oxygen, and sulfur, and (D) at least one amide according to the general formula (VI)

wherein $R^{31}CO$ is an acyl radical having 1 to 22 carbon atoms, $R^{32}$ is hydrogen or alkyl, and $R^{33}$ is hydrogen or alkyl, or $R^{32}$ and $R^{33}$ together with the nitrogen atom linking them define a 5- or 6-membered saturated or unsaturated heterocyclic radical, which optionally comprises 1 or 2 further heteroatoms selected from the group consisting of nitrogen, oxygen, and sulfur.

In addition, a process for treating the soil comprising applying the compositions of the invention into the soil in-furrow and/or as side dress and/or as broadcast was found.

Moreover, the use of the compositions of the invention as additive or coating material for nitrogen-containing fertilizers has been found.

Preferred embodiments are explained in the claims and the specification. It is understood that combinations of preferred embodiments are within the scope of the present invention.

The term "at least one" is to be understood as 1, 2, 3 or more. A mixture comprising at least one amine refers for example to a mixture comprising 1, 2, 3 or more amines.

The term "soil" is to be understood as a natural body comprised of living (e.g. microorganisms (such as bacteria and fungi), animals and plants) and non-living matter (e.g. minerals and organic matter (e.g. organic compounds in varying degrees of decomposition), liquid, and gases) that occurs on the land surface, and is characterized by soil horizons that are distinguishable from the initial material as a result of various physical, chemical, biological, and anthropogenic processes. From an agricultural point of view, soils are predominantly regarded as the anchor and primary nutrient base for plants (plant habitat).

The term "fertilizer" is to be understood as chemical compounds applied to promote plant and fruit growth. Fertilizers are typically applied either through the soil (for uptake by plant roots) or by foliar feeding (for uptake through leaves). The term "fertilizer" can be subdivided into two major categories: a) organic fertilizers (composed of decayed plant/animal matter) and b) inorganic fertilizers (composed of chemicals and minerals). Organic fertilizers include manure, slurry, worm castings, peat, seaweed, sewage, and guano. Green manure crops are also regularly grown to add nutrients (especially nitrogen) to the soil. Manufactured organic fertilizers include compost, blood meal, bone meal and seaweed extracts. Further examples are enzymatically digested proteins, fish meal, and feather meal. The decomposing crop residue from prior years is another source of fertility. In addition, naturally occurring minerals such as mine rock phosphate, sulfate of potash and limestone are also considered inorganic fertilizers. Inorganic fertilizers are usually manufactured through chemical processes (such as the Haber-Bosch process), also using naturally occurring deposits, while chemically altering them (e.g. concentrated triple superphosphate). Naturally occurring inorganic fertilizers include Chilean sodium nitrate, mine rock phosphate, and limestone.

"Manure" is organic matter used as organic fertilizer in agriculture. Depending on its structure, manure can be divided into liquid manure, semi-liquid manure, stable or solid manure and straw manure. Depending on its origin, manure can be divided into manure derived from animals or plants. Common forms of animal manure include feces, urine, farm slurry (liquid manure) or farmyard manure (FYM) whereas FYM also contains a certain amount of plant material (typically straw), which may have been used as bedding for animals. Animals from which manure can be used comprise horses, cattle, pigs, sheep, chickens, turkeys, rabbits, and guano from seabirds and bats. The application rates of animal manure when used as fertilizer highly depends on the origin (type of animals). Plant manures may derive from any kind of plant whereas the plant may also be grown explicitly for the purpose of plowing them in (e.g. leguminous plants), thus improving the structure and fertility of the soil. Furthermore, plant matter used as manure may include the contents of the rumens of slaughtered ruminants, spent hops (left over from brewing beer) or seaweed.

The compositions of the invention are referred to as the compositions (Q2), (Q3), (Q4) and (Q5) in the following. The composition (Q2) comprises (A) and (C) and optionally further components as described below. The composition (Q3) comprises (A) and (D) and optionally further components as described below. The composition (Q4) comprises (A) and (L1) and optionally further components as described below. The composition (Q5) comprises (A) and (L2) and optionally further components as described below.

According to the invention, the compositions (Q2), (Q3), (Q4) and (Q5) comprises—as one of their essential components—

(A) a mixture comprising at least one (thio)phosphoric acid triamide according to the general formula (I)

$$R^1R^2N-P(X)(NH_2)_2,$$

wherein

X is oxygen or sulfur;

$R^1$ is a $C_1$ to $C_{20}$ alkyl, $C_3$ to $C_{20}$ cycloalkyl, $C_6$ to $C_{20}$ aryl, or dialkylaminocarbonyl group;

$R^2$ is H, or $R^1$ and $R^2$ together with the nitrogen atom linking them define a 5- or 6-membered saturated or unsaturated heterocyclic radical, which optionally comprises 1 or 2 further heteroatoms selected from the group consisting of nitrogen, oxygen, and sulfur.

X in the general formula (I) of (A) is preferably sulfur.

$R^1$ in the general formula (I) of (A) is preferably $C_1$-$C_{20}$-alkyl, more preferably $C_1$-$C_{10}$-alkyl, most preferably $C_2$-$C_7$ alkyl, for example $C_3$-$C_4$ alkyl.

Examples of alkyl groups are methyl, ethyl, propyl, isopropyl, butyl, isobutyl, sec-butyl, tertbutyl, pentyl, isopentyl, neopentyl, tert-pentyl, hexyl, 2-methylpentyl, heptyl, octyl, 2-ethylhexyl, isooctyl, nonyl, isononyl, decyl and isodecyl. Examples of cycloalkyl groups are cyclopropyl, cyclobutyl, cyclopentyl, cyclohexyl and cyclooctyl, examples of aryl groups are phenyl or naphthyl. Examples of heterocyclic radicals $R_1R_2N$— are piperazinyl, morpholinyl, pyrrolyl, pyrazolyl, triazolyl, oxazolyl, thiazolyl or imidazolyl groups.

According to one embodiment, (A) is N-n-butylthiophosphoric acid triamide (NBPT).

According to another embodiment, (A) is N-n-propylthiophosphoric acid triamide (NPPT).

According to another embodiment, (A) is a mixture of NBPT and NPPT.

According to another embodiment, (A) comprises at least two different (thio)phosphoric acid triamides having structures of the general formula (I) and wherein said at least two different (thio)phosphoric acid triamides differ in at least one of radicals $R^1$ or $R^2$, and preferably, one of said at least two different (thio)phosphoric acid triamides is N-n-butylthiophosphoric acid triamide (NBPT), and more preferably, the other of said at least two different (thio)phosphoric acid triamides is selected from the group consisting of N-cyclohexyl-, N-pentyl-, N-isobutyl- and N-npropylphosphoric acid triamide and -thiophosphoric acid triamide. Especially preferred are mixtures (A) which comprise NBPT in amounts of from 40 to 95 wt. %, most preferably from 60 to 85% wt. %, particularly preferably from 72 to 80 wt. %, in each case based on the total weight of (A).

Generally, the mixture (A) can be contained in varying amounts in the composition (Q2), (Q3), (Q4), or (Q5). Preferably, the amount of (A) is not more than 85 wt. % (wt. % stands for "percent by weight"), more preferably not more than 60 wt. %, most preferably not more than 45 wt. %, most particularly preferably not more than 35 wt. %, particularly not more than 30 wt. %, for example not more than 27 wt. %, based on the total weight of the composition (Q2), (Q3), (Q4), or (Q5). Preferably, the amount of (A) is at least 1 wt. %, more preferably at least 4 wt. %, most preferably at least 10 wt. %, most particularly preferably at least 15 wt. %, particularly at least 20 wt. %, for example at least 23 wt. %, based on the total weight of the composition (Q2), (Q3), (Q4), or (Q5).

According to the invention, a composition (Q4) was found which comprises:

(A) a mixture comprising at least one (thio)phosphoric acid triamide according to the general formula (I)

$$R^1R^2N-P(X)(NH_2)_2,$$

wherein

X is oxygen or sulfur;

$R^1$ is a $C_1$ to $C_{20}$ alkyl, $C_3$ to $C_{20}$ cycloalkyl, $C_6$ to $C_{20}$ aryl, or dialkylaminocarbonyl group;

$R^2$ is H, or $R^1$ and $R^2$ together with the nitrogen atom linking them define a 5- or 6-membered saturated or unsaturated heterocyclic radical, which optionally comprises 1 or 2 further heteroatoms selected from the group consisting of nitrogen, oxygen, and sulfur, and (L1) at least one amine selected from the group consisting of (L10), (L11), (L12), (L13), (L14), (L15), (L16), (L17), (L18), (L19), (L20), (L21), (L22), (L23), (L24) and (L29):

(L10) an aliphatic alkylenediamine according to the general formula (IA)

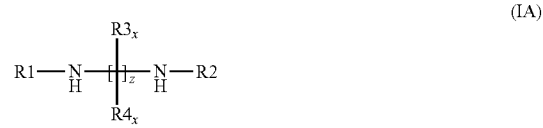

wherein the radicals are defined as follows:

$R^1$ and $R^2$ are simultaneously or each independently hydrogen, linear or branched $C_1$- to $C_{12}$-alkyl, $C_7$- to $C_{12}$-aralkyl, $C_6$- to $C_{10}$-aryl, $C_3$- to $C_8$-cycloalkyl or $C_3$- to $C_8$-cycloalkyl in which optionally—preferably mandatorily—one or more $CH_2$ groups have been replaced by O, NH or NR10; or alternatively $R^1$ and $R^2$ jointly represents a linear or branched $C_1$- to $C_{12}$-alkyl, $C_7$- to $C_{12}$-aralkyl, $C_6$- to $C_{10}$-aryl, $C_3$- to $C_8$-cycloalkyl or $C_3$- to $C_8$-cycloalkyl in which optionally—preferably mandatorily—one or more $CH_2$ groups have been replaced by O, NH or NR10; and $R3_x$ and $R4_x$ are simultaneously or each independently hydrogen, linear or branched $C_1$- to $C_{12}$-alkyl, $C_7$- to $C_{12}$-aralkyl, $C_6$- to $C_{10}$-aryl, $C_3$- to $C_8$-cycloalkyl or $C_3$- to $C_8$-cycloalkyl in which optionally—preferably mandatorily—one or more $CH_2$ groups have been replaced by O, NH or NR10; and R10 is linear or branched $C_1$- to $C_{12}$-alkyl, $C_7$- to $C_{12}$-aralkyl, $C_6$- to $C_{10}$-aryl or $C_3$- to $C_8$-cycloalkyl; and z is a value from 2 to 20, preferably from 2 to 12; and x is an index which can assume all values from 1 to z;

(L11) oligomeric polyalkyleneamines according to the general formula (II)

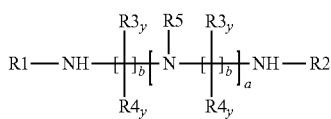

(II)

wherein the radicals are each defined as follows:

$R^1$, $R^2$ and $R^5$ are simultaneously or each independently hydrogen, linear or branched $C_1$- to $C_{12}$-alkyl, $C_7$- to $C_{12}$-aralkyl, $C_6$- to $C_{10}$-aryl, $C_3$- to $C_8$-cycloalkyl or $C_3$- to $C_8$-cycloalkyl in which optionally—preferably mandatorily—one or more $CH_2$ groups have been replaced by O, NH or NR10; or two of the three radicals $R^1$, $R^2$ and $R^5$ are covalently bonded to each other to form a linear or branched $C_1$- to $C_{12}$-alkyl, $C_7$- to $C_{12}$-aralkyl, $C_6$- to $C_{10}$-aryl, $C_3$- to $C_8$-cycloalkyl or $C_3$- to $C_8$-cycloalkyl in which optionally—preferably mandatorily—one or more $CH_2$ groups have been replaced by O, NH or NR10, and the remaining one of the three radicals $R^1$, $R^2$ and $R^5$ is hydrogen, linear or branched $C_1$- to $C_{12}$-alkyl, $C_7$- to $C_{12}$-aralkyl, $C_6$- to $C_{10}$-aryl, $C_3$- to $C_8$-cycloalkyl or $C_3$- to $C_8$-cycloalkyl in which optionally—preferably mandatorily—one or more $CH_2$ groups have been replaced by O, NH or NR10; and $R3_y$ and $R4_y$ are simultaneously or each independently hydrogen, linear or branched $C_1$- to $C_{12}$-alkyl, $C_7$- to $C_{12}$-aralkyl, $C_6$- to $C_{10}$-aryl, $C_3$- to $C_8$-cycloalkyl or $C_3$- to $C_8$-cycloalkyl in which optionally—preferably mandatorily—one or more $CH_2$ groups have been replaced by O, NH or NR10;

R10 is linear or branched $C_1$- to $C_{12}$-alkyl, $C_7$- to $C_{12}$-aralkyl, $C_6$- to $C_{10}$-aryl or $C_3$- to $C_8$-cycloalkyl;

a is a value of 2 to 5;

b is a value of 2 to 12;

and y is an index which can assume all values between 1 and b;

(L12) polyetheramines according to general formula (III):

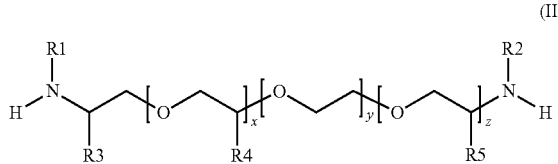

(III)

wherein the radicals are each defined as follows:

$R^1$ and $R^2$ are simultaneously or each independently hydrogen, linear or branched $C_1$- to $C_{12}$-alkyl, $C_7$- to $C_{12}$-aralkyl, $C_6$- to $C_{10}$-aryl, $C_3$- to $C_8$-cycloalkyl or $C_3$- to $C_8$-cycloalkyl in which optionally—preferably mandatorily—one or more $CH_2$ groups have been replaced by O, NH or NR10;

alternatively $R^1$ and $R^2$ jointly represents a linear or branched C1- to $C_{12}$-alkyl, $C_7$- to $C_{12}$-aralkyl, $C_6$- to $C_{10}$-aryl, $C_3$- to $C_8$-cycloalkyl or $C_3$- to $C_8$-cycloalkyl in which optionally—preferably mandatorily—one or more $CH_2$ groups have been replaced by O, NH or NR10; and R3, R4 and R5 are simultaneously or each independently hydrogen, linear or branched $C_1$- to $C_{12}$-alkyl, $C_7$- to $C_{12}$-aralkyl, $C_6$- to $C_{10}$-aryl, $C_3$- to $C_8$-cycloalkyl or $C_3$- to $C_8$-cycloalkyl in which optionally—preferably mandatorily—one or more $CH_2$ groups have been replaced by O, NH or NR10;

R10 is linear or branched $C_1$- to $C_{12}$-alkyl, $C_7$- to $C_{12}$-aralkyl, $C_6$- to $C_{10}$-aryl or $C_3$- to $C_8$-cycloalkyl;

x, y and z are each independently a value from 0 to 100 and the sum of x, y and z are at least 2;

(L13) polyvinylamine-related polymers selected from the group consisting of (L501) polyvinylamine, (L502) a polyvinylamine according to the general formula (IV)

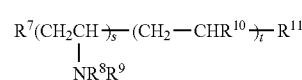

(IV)

which has an average molar mass (Mw) of from 200 to 2,000,000 g/mol and wherein $R^7$ to $R^{11}$ are independently from each other hydrogen, linear or branched $C_1$- to $C_{20}$-alkyl, -alkoxy, -polyoxyethylene, -hydroxyalkyl, -(alkyl)carboxy, -phosphonoalkyl, -alkylamino radicals, formamidyl, pyrrolidonyl-, imidazolyl radicats, $C_2$- to $C_{20}$-alkenyl radicals or $C_6$- to $C_{20}$-aryl, -aryloxy, o-Hydroxybenzoyl, Phthalimidoyl, o-Carboxamidobenzoyl, o-($C_1$- to $C_8$-Alkoxycarbonyl)benzoyl, o-Aminobenzoyl, o-(Mono-$C_1$- to $C_8$-alkylamino)benzoyl, o-(Di-C1- to $C_8$-alkylamino)benzoyl, 2-Cyano-3,3-diphenylacryloyl, or m-Benzimidazolyl-p-hydroxybenzoyl radicals which may be optionally further substituted, wherein s is an integer, t is 0 or an integer, wherein the sum of s and t must be chosen in such a way that the average molar mass is within the specified range, (L503) polyallylamine, (L504) poly(diallyldimethylammonium chloride), (L505) cationic polyvinylformamide, (L506) cationic polyvinylpyrrolidone, (L507) cationic polyvinylacetamide, (L508) cationic polyvinylmethylformamide, (L509) cationic polyvinylmethylacetamide, (L510) poly(dimethylaminopropylmethacrylamide), (L511) poly(dimethylaminoethyl acrylate), (L512) poly(diethylaminoethyl acrylate), (L513) poly(acryloylethyltrimethylammonium chloride), (L514) poly(acrylamido propyltrimethylammonium chloride), (L515) poly(methacrylamidotripropyltrimethyla-mmonium chloride), (L516) cationic polyacrylamide, (L517) poly(vinylpyridine), (L518) hexadimethrine bromide, (L519) poly(dimethylamine-co-epichlorohydrin), (L520) poly(dimethylamine-co-epichlorohydrin-co-ethylenediamine), (L521) poly(amidoamine-epichlorohydrin), (L522) linear, branched or hyperbranched polyamidoamines, or (L523) polyamidoamines having an average molar mass (MW) of from 1,000 to 200,000 g/mol, (L524) cationic starch, or copolymers which contain N-vinylformamide, allylamine, diallyldimethylammonium chloride, N-vinylacetamide, N-vinylpyrrolidone, N-methyl-N-vinylformamide, N-methyl-N-vinylacetamide, dimethylaminopropylmethacrylamide, dimethylaminoethyl acrylate, diethylaminoethyl acrylate, acryloylethyltrimethylammonium chloride or methacrylamidopropyltrimethylammonium chloride in the form of polymerized units and, if desired, in cleaved form, and the salts thereof when the polymers are basic polymers;

(L14) polyethyleneimine according to the general formula (V)

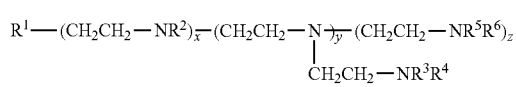

(V)

which has an average molar mass (MW) of from 200 to 1,000,000 g/mol and in which $R^1$ to $R^6$ are—independently from each other—hydrogen, linear or branched $C_1$- to $C_{20}$-alkyl, -alkoxy, -polyoxyalkylene, -polyoxyethylene, -hydroxyalkyl, -(alkyl)carboxy, -phosphonoalkyl, -alkylamino radicals, $C_2$- to $C_{20}$-alkenyl radicals or $C_6$- to $C_{20}$-aryl, -aryloxy, -hydroxyaryl, -arylcarboxy or -arylamino radicals which are optionally further substituted, and $R^2$, $R^3$ and $R^5$ may—independently from each other—optionally be each additionally further polyethyleneimine polymer chains, and $R^1$ may optionally be an $NR^3R^4$ or an $NH_2$ radical, and x, y and z are—independently from each other—0 or an integer, wherein the sum of x, y and z must be chosen in such a way that the average molar mass is within the specified range;

(L15) polyethyleneimine according to the general formula (V) wherein at least one of the radicals $R^2$ to $R^6$ is a polyoxyalkylene radical;

(L16) a polymer obtainable by the process (L16P) comprising the step L16a)

L16a) condensation of at least one compound selected from N-(hydroxyalkyl)amines of formulae (I.a) and/or (I.b),

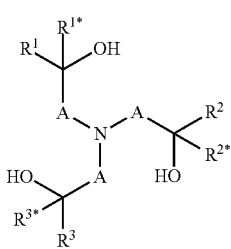

(I.a)

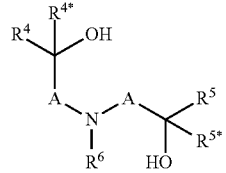

(I.b)

wherein

A are independently selected from $C_1$-$C_6$-alkylene;

$R^1$, $R^{1*}$, $R^2$, $R^{2*}$, $R^3$, $R^{3*}$, $R^4$, $R^{4*}$, $R^5$ and $R^{5*}$ are independently of one another selected from hydrogen, alkyl, cycloalkyl or aryl, wherein the last three mentioned radicals may be optionally substituted; and $R^6$ is selected from hydrogen, alkyl, cycloalkyl or aryl, which may be optionally substituted;

(L17) a polymer obtainable by the process (L17P) comprising the two steps L17a) and L17b)

L17a) condensation of at least one compound selected from N-(hydroxyalkyl)amines of formulae (I.a) and/or (I.b),

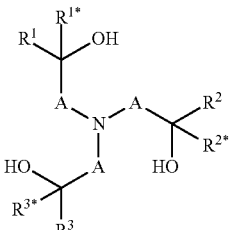

(I.a)

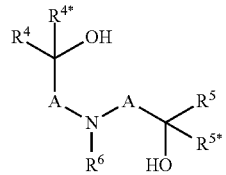

(I.b)

wherein

A are independently selected from $C_1$-$C_6$-alkylene;

$R^1$, $R^{1*}$, $R^2$, $R^{2*}$, $R^3$, $R^{3*}$, $R^4$, $R^{4*}$, $R^5$ and $R^{5*}$ are independently of one another selected from hydrogen, alkyl, cycloalkyl or aryl, wherein the last three mentioned radicals may be optionally substituted; and $R^6$ is selected from hydrogen, alkyl, cycloalkyl or aryl, which may be optionally substituted; and L17b) reacting at least a part of the remaining hydroxy groups and/or, if present, at least a part of the secondary amino groups of the polyether provided in step L17a) with at least one alkylene oxide;

(L18) a derivative obtainable by quaternization, protonation, sulphation and/or phosphation of the polymer (L16) or (L17);

(L19) dendritic polyamines or their precursors selected from (L554) N,N,N',N'-tetraaminopropylalkylenediamine, (L555) dendritic amines obtainable from N,N,N',N'-tetraaminopropylalkylenediamine by amino-n-propylation (for example known as N14-, N30-, N62- and N128-amine according to the number of their nitrogen atoms), (L556) N,N,N',N'-tetraaminopropylethylenediamine, (L557) dendritic amines obtainable from N,N,N',N'-tetraaminopropylethylenediamine by amino-n-propylation (for example known as N14-, N30-, N62- and N128-amine according to the number of their nitrogen atoms), (L558) N,N,N',N'-tetraaminopropylpropylenediamine, (L559) dendritic amines obtainable from N,N,N',N'-tetraaminopropylpropylenediamine by amino-n-propylation (for example known as N14-, N30-, N62- and N128-amine according to the number of their nitrogen atoms), (L560) N,N,N',N'-tetraaminopropylbutylenediamine, (L561) dendritic amines obtainable from N,N,N',N'-tetraaminopropylbutylenediamine by amino-n-propylation (for example known as N14-, N30-, N62- and N128-amine according to the number of their nitrogen atoms);

(L20) a bicyclic, tricyclic or higher polycyclic polyamine;

(L21) an amine containing not more than one amino group and two alkoxy- or hydroxy-substituted $C_2$ to $C_{12}$ alkyl groups $R^{21a}$ and one $C_1$ to $C_{10}$ alkyl group $R^{21b}$, wherein the $R^{21a}$ group bears the alkoxy or hydroxy substituent at a secondary or tertiary carbon atom and wherein the two groups $R^{21a}$ are identical;

(L22) an amine containing not more than one amino group and one alkoxy- or hydroxy-substituted $C_2$ to $C_{12}$ alkyl group $R^{22a}$ and two $C_1$ to $C_{10}$ alkyl groups $R^{22b}$, wherein the two groups $R^{22b}$ are identical;

(L23) imidazolidinones N-substituted on one or two of its nitrogen atoms with alkyl groups $R^{23}$ wherein $R^{23}$ may optionally be substituted with OH groups;

(L24) morpholines N-substituted with alkyl groups $R^{24}$ wherein $R^{24}$ may optionally be substituted with OH groups;

(L29) homo- or copolymers of amino acids.

Generally, the amine(s) (L1) can be contained in varying amounts in the composition (Q4).

Preferably, the amount of (L1) is not more than 90 wt. % (wt. % stands for "percent by weight"), more preferably not more than 65 wt. %, most preferably not more than 45 wt. %, most particularly preferably not more than 30 wt. %, particularly not more than 22 wt. %, for example not more than 16 wt. %, based on the total weight of the composition (Q4). Preferably, the amount of (L1) is at least 1 wt. %, more preferably at least 3 wt. %, most preferably at least 6 wt. %, most particularly preferably at least 9 wt. %, particularly at least 12 wt. %, for example at least 15 wt. %, based on the total weight of the composition (Q4).

If present, the amine(s) (L1) can generally be contained in varying amounts in the composition (Q2), (Q3), or (Q5). If present, the amount of (L1) is preferably not more than 90 wt. % (wt. % stands for "percent by weight"), more preferably not more than 65 wt. %, most preferably not more than 45 wt. %, most particularly preferably not more than 30 wt. %, particularly not more than 22 wt. %, for example not more than 16 wt. %, based on the total weight of the composition (Q2), (Q3), or (Q5). If present, the amount of (L1) is preferably at least 1 wt. %, more preferably at least 3 wt. %, most preferably at least 6 wt. %, most particularly preferably at least 9 wt. %, particularly at least 12 wt. %, for example at least 15 wt. %, based on the total weight of the composition (Q2), (Q3), or (Q5).

BRIEF DESCRIPTION OF THE DRAWINGS

FIG. 1 shows the gaseous NH3 losses from urea treated or not treated with different (A1) formulations at urea fertilization.

DETAILED DESCRIPTION

Preferably, the composition (Q2) or (Q4) comprises the mixture (A) and a) at least one low molecular weight or non-polymeric amine selected from the group consisting of (L101) to (L222) and b) at least one polymeric amine selected from the group consisting of (L501) to (L571).

The compositions (Q2), (Q3) or (Q5) can optionally further comprise (L1) at least one amine selected from the group consisting of (L10), (L11), (L12), (L13), (L14), (L15), (L16), (L17), (L18), (L19), (L20), (L21), (L22), (L23), (L24) and (L29) as described above.

Particularly preferred aliphatic alkylenediamines (L10) are those alkylenediamines selected from the list consisting of:

(L101) ethylenediamine,
(L102) 1,3-propylenediamine,
(L103) 1,2-propylenediamine,
(L104) 1,4-butylenediamine (alternative names: 1,4-diaminobutane, or putrescine),
(L105) 1,2-butylenediamine,
(L106) 1,5-diaminopentane,
(L107) 1,2-diaminopentane,
(L108) 1,5-diamino-2-methylpentane,
(L109) 1,6-diaminohexane,
(L110) 1,2-diaminohexane,
(L111) 1,7-diaminoheptane,
(L112) 1,2-diaminoheptane,
(L113) 1,8-diaminooctane,
(L114) 1,2-diaminooctane,
(L115) 1,9-nonamethylenediamine,
(L116) 1,10-decamethylenediamine,
(L117) 1,2-diaminodecane,
(L118) 1,11-undecamethylenediamine,
(L119) 1,2-diaminoundecane,
(L120) 1,12-dodecamethylenediamine,
(L121) 1,2-diaminododecane,
(L122) 2,2-dimethylpropane-1,3-diamine,
(L123) 4,7,10-trioxatridecane-1,13-diamine,
(L124) 4,9-dioxadodecane-1,12-diamine,
(L125) d3-(methylamino)propylamine,
(L126) 3,3'-dimethyl-4,4'-diaminodicyclohexylmethane,
(L127) 4,4'-diaminodicyclohexylmethane,
(L128) isophoronediamine,
(L129) [bis(4-aminocyclohexyl)methane],
(L130) [bis(4-amino-3,5-dimethylcyclohexyl)methane],
(L131) [bis(4-amino-3-methylcyclohexyl)methane],
(L132) 3-(cyclohexylamino)propylamine,
(L133) bis(aminoethyl)piperazine,
(L134) bis(aminomethyl)piperazine,
(L135) piperazine,
(L136) isomeric bis(aminomethyl)benzenes,
(L137) meta-xylenediamine (MXDA),
(L138) isomeric bis(aminomethyl)benzenes,
(L139) isomers of aminobenzylamine (2-aminobenzylamine, 4-aminobenzylamine),
(L140) 4-(2-aminoethyl)aniline,
(L141) m-xylylenediamine,
(L142) o-xylylenediamine,
(L143) 2,2'-biphenyldiamines,
(L144) oxydianilines,
(L145) 4,4'-oxydianiline,
(L146) isomers of diaminofluorene,
(L147) isomers of diaminophenanthrene
(L148) 4,4'-ethylenedianiline,
or mixtures thereof.

Further preferred aliphatic alkylenediamines (L10) are
(L149) alkylenediamines according to general formula (IA) wherein $R^1$, $R^2$, $R3_x$ and $R4_x$ in formula (IA) are each hydrogen and z in formula (IA) is a value from 2 to 8.

Further preferred aliphatic alkylenediamines (L10) are
(L150) alkylenediamines according to general formula (IA) which are at least partially N-ethoxylated,
(L151) alkylenediamines according to general formula (IA) which are at least partially N-propoxylated,
(L152) alkylenediamines according to general formula (IA) which are at least partially N-butoxylated, or
(L153) alkylenediamines according to general formula (IA) which are at least partially N-alkoxylated.

Further preferred diamines (L10) are cyclic diamines in which the amino groups are joined either directly or indirectly to one or more mutually connected unsubstituted or substituted cycloaliphatic or heteroaliphatic, aromatic or heteroaromatic rings. Particularly preferred cyclic diamines are alicyclic diamines, particularly 3,3'-dimethyl-4,4'-diaminodicyclohexylmethane, 4,4'-diaminodicyclohexylmethane, isophoronediamine, [bis(4-aminocyclohexyl)methane], [bis(4-amino-3,5-dimethylcyclohexyl)methane] or [bis(4-amino-3-methylcyclohexyl)methane], 3-(cyclohexylamino)propylamine, bis(aminoethyl)piperazine, bis(aminomethyl)piperazine, or piperazine. Particularly preferred aromatic cyclic diamines are aromatic diamines in which the amino group is not substituted directly on the aromatic ring. Preferred aromatic diamines are the isomeric bis(aminomethyl)benzenes, especially meta-xylenediamine (MXDA), or the isomeric bis(aminomethyl)benzenes, isomers of aminobenzylamine (2-aminobenzylamine, 4-aminobenzylamine), 4-(2-aminoethyl)aniline, m-xylylenediamine, o-xylylenediamine, or 2,2'-biphenyldiamines, or oxydianilines, for example 4,4'-oxydianiline, isomers of diaminofluorene, isomers of diaminophenanthrene and 4,4'-ethylenedianiline.

Particularly preferred oligomeric polyalkyeneamines (L11) are
(L154) N,N-bis(3-aminopropyl)methylamine,
(L155) diethylenetriamine (DETA),
(L156) triethylenetetramine (TETA),
(L157) tetraethylenepentamine (TEPA),
(L158) di-1,3-propylenetriamine,
(L159) tri-1,3-propylenetetramine,
(L160) tetra-1,3-propylenepentamine,
(L161) di-1,2-propylenetriamine,
(L162) tri-1,2-propylenetetramine,
(L163) tetra-1,2-propylenepentamine,
(L164) dihexamethylenetriamine,
(L165) trihexamethylenetetramine,
(L166) tetrahexamethylenepentamine,
(L167) spermidine (CAS no. 124-20-9), or
(L168) spermine (CAS no. 71-44-3)

Further preferred oligomeric polyalkyeneamines (L11) are
(L169) polyalkyeneamines according to general formula (II) which are at least partially N-ethoxylated,
(L170) polyalkyeneamines according to general formula (II) which are at least partially N-propoxylated,
(L171) polyalkyeneamines according to general formula (II) which are at least partially N-alkoxylated.

Preferred polyetheramines (L12) are
(L562) polyetheramines according to the general formula (III) in which in formula (III) x and z each assume a value of 0 and y assumes a value >0, and the substituents $R^1$ to $R^5$ in formula (III) are preferably hydrogen (polyetheramines based on ethylene glycol).

Further preferred polyetheramines (L12) are
(L563) polyetheramines according to the general formula (III) in which in formula (III) y assumes a value of 0 and (x+z) a value of >0, and the substituents $R^1$ and $R^2$ are preferably hydrogen and the substituents $R^3$ to $R^5$ are preferably methyl (polyetheramines based on propylene glycol).

Further preferred polyetheramines (L12) are
(L564) polyetheramines according to the general formula (III) in which in formula (III) y assumes a value of >0 and (x+z) a value of >0, and the substituents $R^1$ to $R^2$ are preferably hydrogen and the substituents $R^3$ to $R^5$ are preferably methyl (block polyetheramines having a central block based on polyethylene glycol and outer blocks based on propylene glycol).

Very particularly preferred polyetheramines (L12) are
(L565) 4,7,10-trioxatridecane-1,13-diamine,
(L566) 4,9-dioxadodecane-1,12-diamine,
(L567) Jeffamines® from Huntsman, especially Jeffamine D230, Jeffamine D400, Jeffamine D2000, Jeffamine D4000, Jeffamine ED600, Jeffamine ED900, Jeffamine ED2003, Jeffamine EDR148, or Jeffamine EDR176 (names from the product brochure from Alfa Chemicals Ltd with reference number "Hunt32").

Among the polyvinylamine-related polymers (L13), the linear, branched or hyperbranched polyamidoamines (L221) are for example described in U.S. Pat. No. 4,435,548, EP 115 771, EP 234 408, EP 802 215, in L. J. Hobson und W. J. Feast, Polymer 1999, 40, 1279-1297 or in H.-B. Mekelburger, W. Jaworek and F. Vögtle, Angewandte Chemie 1992, 104, No. 12, 1609-1614.

Preferred polyamidoamines have an average molar mass ($M_W$) of 500 to 1,000,000 g/mol, more preferably 1000 to 200,000 g/mol.

Preferred polyethyleneimines (L14) are
(L525) polyethyleneimine according to the general formula (V) having an average molar mass (MW) of from 250 to 100,000 g/mol;
(L526) polyethyleneimine according to the general formula (V) having an average molar mass (MW) of from 300 to 25,000 g/mol;
(L527) polyethyleneimine according to the general formula (V) in which $R^1$ to $R^6$ are each hydrogen, methyl, ethyl, carboxymethyl, carboxyethyl, phosphonomethyl, 2-hydroxyethyl, 2-(2'-hydroxyethoxy)ethyl or 2-[2'-(2"-hydroxyethoxy)-ethoxy]ethyl;
(L528) branched polyethyleneimine having a molecular weight of approx. 800 (GPC) and a charge density of approx. 16 meq/g of dry substance, determined at pH 4.5, and having a ratio primary/secondary/tertiary amino (as determined by 13C-NMR) of 1/0.9/0.5;
(L529) Branched polyethyleneimine having a molecular weight of approx. 25000 (GPC), a charge density of approx. 17 meq/g of dry substance, determined at pH 4.5, and having a ratio primary/secondary/tertiary amino (as determined by 13C-NMR) of 1/1.1/0.7.

Other preferred polyethyleneimines (L14) are
(L610) a linear polyethyleneimine;
(L611) a linear polyethyleneimine showing a single peak at 2.72 ppm in 1H-NMR, wherein other peaks have not more than 15%, preferably not more than 10%, more preferably not more than 6%, most preferably not more than 3%, particularly not more than 1% of the intensity of the single peak at 2.72 ppm;
(L612) a linear polyethyleneimine prepared as follows:
1500 g of 2-methyl-2-oxazoline, 212 g of N-methyl-2-ethyl-2-oxazoline methylsulfate and 3000 g of acetonitrile were heated to 80° C. during 24 h. Afterwards the acetonitrile was removed via steam distillation and the product was obtained as an aqueous solution containing 38% of poly(2-methyl-2-oxazoline). GPC analysis: Mn=2550 g/mol; Mw=3180; 1579 g of a solution of 38% poly(2-methyl-2-oxazoline) in water was mixed with 1899 g of a solution of 25% potassium hydroxide in water. The mixture was heated under reflux during 72 h. Upon cooling to 23° C. the linear polyethyleneimine precipitated, was filtered off, washed with water and dried in a vacuum oven. 223 g of the product were obtained as white powder. The 1H-NMR-spectrum of the product showed a single peak at 2.72 ppm indicating the strict linearity of the polyethyleneimine. GPC analysis: Mn=900 g/mol.

Polyethyleneimines (L15) are preferably obtainable by reacting at least a part of the primary or secondary amino groups of the polyethyleneimine (L14) with at least one alkylene oxide.

Preferred polyethyleneimines (L15) are polyethyleneimines according to the general formula (V) wherein at least one of the radicals $R^2$ to $R^6$ is a polyoxyethylene or polyoxypropylene radical.

Preferred polyethyleneimines (L15) are (L530) Polymer obtainable by reacting at least a part of the primary or secondary amino groups of the polyethyleneimine (L14) with epoxyethane (=ethylene oxide);

(L531) Polymer obtainable by reacting at least a part of the primary or secondary amino groups of the polyethyleneimine (L14) with epoxypropane (=propylene oxide);

(L532) Polymer obtainable by reacting at least a part of the primary or secondary amino groups of the polyethyleneimine (L14) with 1,2-epoxybutane (=alpha butylene oxide);

(L533) Polymer obtainable by reacting at least a part of the primary or secondary amino groups of the polyethyleneimine (L14) with 2,3-epoxybutane (=beta butylene oxide), 1,2 epoxy-2 methyl-propane (=isobutylene oxide), 1,2-epoxypentane, 2,3-epoxypentane, 1,2-epoxy-2 methylbutane, or 2,3-epoxy-2 methylbutane, 1,2-epoxyhexane, 2,3-epoxyhexane, 3,4-epoxyhexane, or optionally substituted (1,2-epoxyethylene)benzene (=styrene oxide) compound;

(L534) Polyethyleneimine according to the general formula (V) wherein at least one of the radicals $R^2$ to $R^6$ is a polyoxyethylene radical;

(L535) N-ethoxylated polyethyleneimine;

(L536) Polyethyleneimine with 5 to 40, preferably 10 to 30, most preferably 15 to 25 ethoxylate groups per-NH;

(L537) Polyethyleneimine (MW=600) with 20 ethoxylate groups per-NH;

(L538) Ethoxylated polyethylenimine comprising 5 parts by weight of a branched polyethyleneimine core of molecular weight of approx. 600-800 (GPC) and approx. 95 parts by weight of moieties of formula —CH2-CH2-O—;

Particularly preferred polyethyleneimines (L15) are (L613) polyethyleneimine with 0.75 to 0.99 EO (ethylene oxide) per NH unit, and (L614) polyethyleneimine with 0.75 to 0.99 PO (propylene oxide) per NH unit, and (L615) polyethyleneimine with 0.85 to 0.95 EO (ethylene oxide) per NH unit, and (L616) polyethyleneimine with 0.85 to 0.95 PO (propylene oxide) per NH unit, and (L617) PEI600 (=polyethyleneimine with a weight average molecular weight of 600 g/mol as measured by GPC) plus 0.9 EO (ethylene oxide) per NH unit, free of water, (L618) PEI600 plus 0.9 PO (propylene oxide) per NH unit, free of water.

The polyethyleneimine (L613) to (L618) are preferably prepared by the synthesis procedure disclosed in WO2009/060059.

In yet another embodiment, particularly preferred polyethyleneimines (L15) are (L619) Polytriethanolamine, and (L620) a polytriethanolamine with a weight average molecular weight in the range of from 1,000 to 10,000 g/mol, and (L621) a polytriethanolamine with a weight average molecular weight in the range of from 7,000 to 9,000 g/mol.

Preferred polytriethanolamines are those polytriethanolamines in which more than 90%, preferably more than 95%, more preferably more than 98% of the amine groups are tertiary amine groups, and in which more than 90%, preferably more than 95%, more preferably more than 98% of the hydroxyl groups are primary hydroxyl groups.

Regarding (L16) or (L17), the term "alkyl" as used herein and in the term alkoxy refers to saturated straight-chain or branched hydrocarbon radicals. $C_1$-$C_4$-alkyl refers to saturated straight-chain or branched hydrocarbon radicals having 1 to 4 carbon atoms such as methyl, ethyl, propyl, 1-methylethyl, butyl, 1-methylpropyl, 2-methylpropyl and 1,1-dimethylethyl. Optionally substituted alkyl refers to an alkyl radical which is unsubstituted or wherein a part or all of the hydrogen atoms are replaced by hydroxy, halogen, cyano or $C_1$-$C_4$-alkoxy. Preferably alkyl is unsubstituted.

Regarding (L16) or (L17), the term "cycloalkyl" as used herein refers to saturated or partially unsaturated mono- or bicyclic hydrocarbon radicals. Preferably the term cycloalkyl relates to monocyclic hydrocarbon radicals having 3 to 8, in particular 3 to 6 carbon atoms ($C_3$-$C_8$-cycloalkyl, $C_3$-$C_6$-cycloalkyl). Examples of such preferred cycloalkyl radicals are cyclopropyl, cyclobutyl, cyclopentyl, cyclohexyl, cycloheptyl and cyclooctyl. Optionally substituted cycloalkyl refers to a cycloalkyl radical which is unsubstituted or wherein a part or all of the hydrogen atoms are replaced by hydroxy, halogen, cyano, $C_1$-$C_4$-alkyl or $C_1$-$C_4$-alkoxy. Preferably cycloalkyl is unsubstituted or carries 1, 2 or 3 $C_1$-$C_4$-alkyl radicals.

Regarding (L16) or (L17), the term "aryl" as used herein refers to phenyl or naphthyl, preferably phenyl. Optionally substituted aryl refers to an aryl radical which is unsubstituted or wherein a part or all of the hydrogen atoms are replaced by hydroxy, halogen, cyano, $C_1$-$C_4$-alkyl or $C_1$-$C_4$-alkoxy. Preferably cycloalkyl is unsubstituted or carries 1, 2 or 3 $C_1$-$C_4$-alkyl radicals.

Regarding (L16) or (L17), the term "$C_1$-$C_6$-alkylene" as used herein refers to a saturated, divalent straight chain or branched hydrocarbon chains of 2, 3, 4, 5 or 6 carbon groups, examples including methylene, ethane-1,2-diyl, propane-1,3-diyl, propane-1,2-diyl, 2-methylpropane-1,2-diyl, 2,2-dimethylpropane-1,3-diyl, butane-1,4-diyl, butane-1,3-diyl (=1-methylpropane-1,3-diyl), butane-1,2-diyl, butane-2,3-diyl, 2-methyl-butan-1,3-diyl, 3-methyl-butan-1,3-diyl (=1,1-dimethylpropane-1,3-diyl), pentane-1,4-diyl, pentane-1,5-diyl, pentane-2,5-diyl, 2-methylpentane-2,5-diyl (=1,1-dimethylbutane-1,3-diyl) and hexane-1,6-diyl.

Regarding (L15) or (L17), the term "alkylene oxide" as used herein relates to alkyl or alkylaryl compounds carrying at least one, preferably 1 or 2, in particular 1 epoxy group at the alkyl moieties of the compound. Regarding (L17), examples of alkyl compounds carrying one epoxy group are epoxyethane (=ethylene oxide), epoxypropane (=propylene oxide), 1,2-epoxybutane (=alpha butylene oxide), 2,3-epoxybutane (=beta butylene oxide), 1,2 epoxy-2 methyl-propane (=isobutylene oxide), 1,2-epoxypentane, 2,3-epoxypentane, 1,2-epoxy-2 methylbutane, 2,3-epoxy-2 methylbutane, 1,2-epoxyhexane, 2,3-epoxyhexane and 3,4-epoxyhexane. Examples of alkylaryl compounds carrying one epoxy group are optionally substituted (1,2-epoxyethylene)benzene (=styrene oxide) compounds.

Regarding (L16) or (L17), the term "condensation" as used herein refers to a chemical reaction wherein a covalent bond between two corresponding functional groups is formed together with the formal loss of a small molecule such as water. Preferably the term condensation refers to an etherification together with a dehydration reaction.

Regarding (L16) or (L17), examples of N-(Hydroxyalkyl) amines (I.a) are e.g. N-tri-(2-hydroxyalkyl)-amines. N-tri-(2-hydroxyalkyl)-amines are e.g. obtainable by reacting ammonia with three equivalents of an alkylene oxides (ammonolysis). Preferred examples of such compounds (I.a) are triethanolamine, triisopropanolamine and tributan-2-olamine.

Regarding (L16) or (L17), examples of N-(Hydroxyalkyl) amines (I.b) are e.g. N-di-(2-hydroxyalkyl)-amines which are obtainable by reacting a primary amine of formula $H_2N-R^6$, wherein $R^6$ has one of the meanings given above, with two equivalents of an alkylene oxide (aminolysis). Preferred examples of such compounds (I.b) are e.g. N-methyldiethanolamine, N,N-bis-(2-hydroxypropyl)-N-methylamine, N,N-bis-(2-hydroxybutyl)-N-methylamine, N-isopropyldiethanolamine, N-n-butyldiethanolamine, N-sec-butyldiethanolamine, N-cyclohexyldiethanolamine, N-benzyldiethanolamine, N-4-tolyldiethanolamine, N,N-Bis-(2-hydroxyethyl)-anilin and the like.

Regarding (L16) or (L17), preferred are polymers obtainable from compounds selected from N-(hydroxyalkyl) amines of formulae (I.a) and/or (I.b), wherein A is a methylene group, which is unsubstituted or carries one substituent selected from $C_1$-$C_4$-alkyl. More preferred are polymers obtainable from compounds (I.a) and/or (I.b), wherein A is methylene or methylene carrying one methyl group. Particularly preferred are polymers obtainable from compounds (I.a) and/or (I.b), wherein A is unsubstituted methylene.

Regarding (L16) or (L17), preferred are polymers obtainable from compounds selected from N-(hydroxyalkyl) amines of formulae (I.a) and/or (I.b), wherein $R^1$, $R^{1*}$, $R^2$, $R^{2*}$, $R^3$, $R^{3*}$, $R^4$, $R^{4*}$, $R^5$ and $R^{5*}$ are independently of one another selected from hydrogen and $C_1$-$C_4$-alkyl, i.e. hydrogen, methyl, ethyl, n-propyl, isopropyl, n-butyl, sec.-butyl and tert.-butyl. More preferably $R^1$, $R^{1*}$, $R^2$, $R^{2*}$, $R^3$, $R^{3*}$, $R^4$, $R^{4*}$, $R^5$ and $R^{5*}$ are independently of one another selected from hydrogen and methyl.

Regarding (L16) or (L17), preferred are polymers obtainable from N-(hydroxyalkyl)amines of formulae (I.a) and/or (I.b), wherein $R^{1*}$, $R^{2*}$, $R^{3*}$, $R^{4*}$ and $R^{5*}$ are hydrogen and $R^1$, $R^2$, $R^3$, $R^4$, and $R^5$ are independently of one another selected from hydrogen and $C_1$-$C_4$-alkyl. More preferably $R^{1*}$, $R^{2*}$, $R^{3*}$, $R^{4*}$ and $R^{5*}$ are hydrogen and $R^1$, $R^2$, $R^3$, $R^4$, and $R^5$ are independently of one another selected from hydrogen and methyl.

Regarding (L16) or (L17), preferred are polymers obtainable from N-(hydroxyalkyl)amines of formula (I.b) wherein $R^6$, if present, is preferably selected from hydrogen and $C_1$-$C_4$-alkyl.

Regarding (L17), the polymer is preferably obtainable by reacting 1 to 100 moles, preferably 2 to 80 moles of the at least one alkylene oxide with 1 mol of the remaining hydroxy groups and, if present, of the secondary amino groups of the polyether obtainable by condensation of the at least one compound of formulae (I.a) and/or (I.b).

Regarding (L16) or (L17), the polymer preferably has a number average molecular weight in the range of 500 to 100 000 g/mol, more preferably in the range of 1000 to 80 000 g/mol, and in particular in the range of from 2 000 to 50 000 g/mol.

Regarding (L16) or (L17), the polymer preferably has a polydispersity (Mw/Mn) in the range of 1 to 10, and in particular in the range of 1 to 5.

Regarding (L16) or (L17), in one particular embodiment the polymer s obtainable by a process wherein in step a) less than 5% by weight, preferably less than 1% by weight and more preferably substantially no, i.e. less than 0.1% by weight, of co-condensable compounds different from compounds of formulae (I.a) and/or (I.b), are employed (i.e. co-condensed) based on the amount of the compounds of formulae (I.a) and/or (I.b).

Preferred polymers (L16) are:

(L539) Polymer obtainable by the process (L16P) wherein the N-(Hydroxyalkyl)amine (I.a) is triethanolamine;

(L540) Polymer obtainable by the process (L16P) wherein the N-(Hydroxyalkyl)amine (I.a) is triisopropanolamine;

(L541) Polymer obtainable by the process (L16P) wherein the N-(Hydroxyalkyl)amine (I.a) is tributan-2-olamine;

(L542) Polymer obtainable by the process (L16P) wherein the N-(Hydroxyalkyl)amine (I.b) is N-methyldiethanolamine;

(L543) Polymer obtainable by the process (L16P) wherein the N-(Hydroxyalkyl)amine (I.b) is N,N-bis-(2-hydroxypropyl)-N-methylamine, N,N-bis-(2-hydroxybutyl)-N-methylamine, N-isopropyldiethanolamine, N-n-butyldiethanolamine, N-sec-butyldiethanolamine, N-cyclohexyldiethanolamine, N-benzyldiethanolamine, N-4-tolyldiethanolamine, or N,N-Bis-(2-hydroxyethyl)-anilin;

Preferred polymers (L17) are (L544) Polymer obtainable by the process (L17P) wherein the N-(Hydroxyalkyl)amine (I.a) is triethanolamine;

(L545) Polymer obtainable by the process (L17P) wherein the N-(Hydroxyalkyl)amine (I.a) is triisopropanolamine;

(L546) Polymer obtainable by the process (L17P) wherein the N-(Hydroxyalkyl)amine (I.a) is tributan-2-olamine;

(L547) Polymer obtainable by the process (L17P) wherein the N-(Hydroxyalkyl)amine (I.b) is N-methyldiethanolamine;

(L548) Polymer obtainable by the process (L17P) wherein the N-(Hydroxyalkyl)amine (I.b) is N,N-bis-(2-hydroxypropyl)-N-methylamine, N,N-bis-(2-hydroxybutyl)-N-methylamine, N-isopropyldiethanolamine, N-n-butyldiethanolamine, N-sec-butyldiethanolamine, N-cyclohexyldiethanolamine, N-benzyldiethanolamine, N-4-tolyldiethanolamine, or N,N-Bis-(2-hydroxyethyl)-anilin;

(L549) Polymer obtainable by the process (L17P) wherein the alkylene oxide is epoxyethane (=ethylene oxide);

(L550) Polymer obtainable by the process (L17P) wherein the alkylene oxide is epoxypropane (=propylene oxide);

(L551) Polymer obtainable by the process (L17P) wherein the alkylene oxide is 1,2-epoxybutane (=alpha butylene oxide);

(L552) Polymer obtainable by the process (L17P) wherein the alkylene oxide is 2,3-epoxybutane (=beta butylene oxide), 1,2 epoxy-2 methyl-propane (=isobutylene oxide), 1,2-epoxypentane, 2,3-epoxypentane, 1,2-epoxy-2 methylbutane, or 2,3-epoxy-2 methylbutane, 1,2-epoxyhexane, 2,3-epoxyhexane or 3,4-epoxyhexane;

(L553) Polymer obtainable by the process (L17P) wherein the alkylene oxide is an optionally substituted (1,2-epoxyethylene)benzene (=styrene oxide) compound;

Dendritic polyamines or their precursors (L19) include N,N,N',N'-tetraaminopropylalkylenediamine, also known as N6-amine, and the dendritic amines obtainable therefrom by aminopropylation and known as N14-, N30-, N62- and N128-amine according to the number of their nitrogen atoms. These amines have for example a basic ethylenediamine, propylenediamine or butylenediamine skeleton whose hydrogen atoms are substituted by amino(n-propyl) radicals on the nitrogen. The terminal amino groups may in turn be substituted by corresponding aminopropyl groups (NI 4-amine) etc. Methods for preparing these amines are described in WO 96/15097 starting from ethylenediamine. Likewise preferred examples of these amines are corresponding N-amines as described in WO 93/14147, which are prepared from butylenediamine.

The bicyclic, tricyclic or higher polycyclic polyamine (L20) is preferably selected from the group consisting of:
(L172) bicylic polyamine;
(L173) tricyclic polyamine;
(L174) n-cyclic polyamine with n (number of cyclic structures) being larger than 3;
(L175) bicyclic aliphatic diamine;
(L176) bicyclic aliphatic diamine wherein both of the two amino groups of the diamine are tertiary amino groups, more preferably wherein additionally both of the two nitrogen atoms of the two amino groups of the diamine are bridgehead atoms;
(L177) 1,4-Diazabicyclo[2.2.2]octan (DABCO);
(L178) Substituted 1,4-Diazabicyclo[2.2.2]octan (DABCO);

The amine (L21) is preferably selected from the group consisting of
(L179) Methyldiisopropanolamine
(L180) Butyldiethanolamine The amine (L22) is preferably selected from the group consisting of
(L181) N,N-Dibutylethanolamine
(L182) N,N,-Dimethylisopropanolamine The imidazolidinone (L23) is preferably
(L183) 1-(2-Hydroxyethyl)-2-imidazolidinone [alternative name: (2-Hydroxyethyl)ethyleneurea].

The morpholine (L24) is preferably
(L184) N-(2-Hydroxyethyl)morpholine.

The homo- or copolymer of amino acids (L29) is preferably selected from the group consisting of
(L573) a homo- or copolymer of an alpha-amino acid (α-amino acid),
(L574) a homo- or copolymer of a naturally occurring alpha-amino acid,
(L575) a homo- or copolymer of a proteinogenic alpha-amino acid,
(L576) a homo- or copolymer of alanine,
(L577) a homo- or copolymer of arginine,
(L578) a homo- or copolymer of asparagine,
(L579) a homo- or copolymer of aspartic acid,
(L580) a homo- or copolymer of cysteine,
(L581) a homo- or copolymer of glutamic acid,
(L582) a homo- or copolymer of glutamine,
(L583) a homo- or copolymer of glycine,
(L584) a homo- or copolymer of histidine,
(L585) a homo- or copolymer of isoleucine,
(L586) a homo- or copolymer of leucine,
(L587) a homo- or copolymer of lysine,
(L588) a homo- or copolymer of methionine,
(L589) a homo- or copolymer of phenylalanine,
(L590) a homo- or copolymer of proline,
(L591) a homo- or copolymer of serine,
(L592) a homo- or copolymer of threonine,
(L593) a homo- or copolymer of tryptophan,
(L594) a homo- or copolymer of tyrosine,
(L595) a homo- or copolymer of valine,
(L596) a homo- or copolymer of selenocysteine,
(L597) a homo- or copolymer of pyrrolysine,
(L598) a homo- or copolymer of N-formylmethionine, and
(L599) a homo- or copolymer of ornithine.

The homo- or copolymer of amino acids (L29) is preferably a homopolymer of amino acids.

In another embodiment, the homo- or copolymer of amino acids (L29) is preferably a copolymer of amino acids.

The homo- or copolymer of lysine (L587) is preferably selected from the group consisting of
(L600a) a homopolymer of L-lysine,
(L601a) a homopolymer of D-lysine,
(L600b) a copolymer of D-lysine,
(L601 b) a copolymer of D-lysine,
(L602) alpha-polylysine,
(L603) epsilon-polylysine.

The homo- or copolymer of lysine (L587) has preferably a weight average molecular weight of from 250 to 10,000 g/mol, more preferably from 500 to 5,000 g/mol, most preferably from 800 to 3,500 g/mol, particularly preferably from 1,200 to 2,800 g/mol, particularly from 1,700 to 2,300 g/mol. In another embodiment, the homo- or copolymer of lysine (L587) has preferably a weight average molecular weight of from 800 to 1,100 g/mol. In yet another embodiment, the homo- or copolymer of lysine (L587) has preferably a weight average molecular weight of from 3,000 to 3,500 g/mol.

The homo- or copolymer of lysine (L587) has preferably a number average molecular weight of from 250 to 10,000 g/mol, more preferably from 500 to 5,000 g/mol, most preferably from 700 to 3,000 g/mol, particularly preferably from 750 to 2,000 g/mol, particularly from 1,200 to 1,500 g/mol. In another embodiment, the homo- or copolymer of lysine (L587) has preferably a number average molecular weight of from 750 to 900 g/mol. In yet another embodiment, the homo- or copolymer of lysine (L587) has preferably a number average molecular weight of from 1500 to 1750 g/mol.

The homo- or copolymer of lysine (L587) has preferably a amine number of from 100 to 2,000 mgKOH/g, more preferably from 200 to 1,000 mgKOH/g, most preferably from 300 to 700 mgKOH/g, particularly preferably from 370 to 630 mgKOH/g, particularly from 420 to 500 mgKOH/g. In another embodiment, the homo- or copolymer of lysine (L587) has preferably a amine number of from 360 to 440 mgKOH/g. In yet another embodiment, the homo- or copolymer of lysine (L587) has preferably a amine number of from 560 to 640 mgKOH/g.

The homo- or copolymer of lysine (L587) is preferably prepared through one of the processes of the below process embodiments (L587P1) to (L587P16):

(L587P1) A process for preparing a polylysine, comprising the steps of
(a) heating a boiling aqueous reaction mixture comprising lysine and water in a weight ratio of 1:10 to 3:1 within 2 to 8 hours to a temperature in the range from 135 to 165° C., and
(b) keeping the reaction mixture of step (a) at a temperature in a range from 135 to 165° C. at a pressure below atmospheric pressure, wherein water is removed from the mixture, and any temperature increase is <30° C. in 60 minutes;

(L587P2) The process of embodiment (L587P1), wherein water is removed from the mixture in both steps;

(L587P3) The process of embodiment (L587P1) or (L587P2), wherein the first step is carried out at atmospheric pressure;

(L587P4) The process of any of the embodiments (L587P1) to (L587P3), wherein the pressure is reduced in the second step to a pressure in the range from 0.1 to 500 mbar, preferably to a pressure in the range from 50 to 350 mbar;

(L587P5) The process of any of the embodiments (L587P1) to (L587P4), wherein water is removed from the mixture in the second step until a product consisting essentially of molten polylysine is obtained.

(L587P6) The process of any of the embodiments (L587P1) to (L587P5), wherein the polylysine obtained in the second step is cooled to solidify it.

(L587P7) The process of any of the embodiments (L587P1) to (L587P6), wherein in the second step the reaction mixture is kept for 1 to 5 hours at a temperature in a range from 135 to 165° C.

(L587P8) The process of any of the embodiments (L587P1) to (L587P7), wherein the heating time for the first and second step together is 4.5 to 11 hours.

(L587P9) The process of any of the embodiments (L587P1) to (L587P8), wherein the mixture is kept at a temperature of 160° C. or more for at most 6 hours.

(L587P10) The process of any of the embodiments (L587P1) to (L587P9), wherein the boiling aqueous reaction mixture of the first step is provided by heating a starting mixture comprising lysine and water in a weight ratio of 1:10 to 3:1.

(L587P11) The process of any of the embodiments (L587P1) to (L587P10) further comprising a chemical modification of the polylysine to obtain a chemically modified polylysine.

(L587P12) The process of any of the embodiments (L587P1) to (L587P11), wherein the polylysine is a non-crosslinked branched polylysine.

(L587P13) The process of any of the embodiments (L587P1) to (L587P12), wherein the polylysine has a weight-average molecular weight in the range from 1 000 Da to 10 000 Da.

The polylysin prepared by the process (L587P1) is referred to as polylysine (L607).

In another embodiment, the homo- or copolymer of lysine (L587) is preferably a branched polylysine obtainable by the process of any of process embodiments (L587P1) to (L587P13).

In another embodiment, the homo- or copolymer of lysine (L587) has preferably a weight-average molecular weight in the range from 1500 Da to 4000 Da and a polydispersity of <2.

In another embodiment, the homo- or copolymer of lysine (L587) has preferably a degree of branching of from 0.21 to 0.28.

In another embodiment, the homo- or copolymer of lysine (L587) is preferably (L604) a polylysine prepared as follows:

800 g of 50% water solution of L-Lysine were placed in a 2 L four-necked flask equipped with a stirrer a condensation column, a thermometer and a Nitrogen inlet. The L-Lysine solution was heated to the boiling point. Then the temperature of the external heat source was increased according to the following profile 1 h at 150 C, 1 h at 160 and 1 h at 170 and 1 h at 180 C while water was distilled off. The pressure was then decreased to 200 mbar while the external heat source was maintained at 180° C. The reaction for circa 2 hours continued under vacuo (200 mbar). The warm reaction melt was collected in an aluminum vessel. At room temperature a solid material was obtained. The polymer was characterized via Gel permeation Chromatography in water and regarding amino numbers: Mn: 1690 g/mol; Mw: 3298 g/mol; polydispersity ($M_w/M_n$): 1.9; amine number**: 396 mgKOH/g (given for 100% pure polylysine).

In yet another embodiment, the homo- or copolymer of lysine (L587) is preferably (L605) a polylysine prepared as follows:

1700 g of 50% water solution of L-Lysine were placed in a 2 L four-necked flask equipped with a stirrer a condensation column, a thermometer and a nitrogen inlet. The L-Lysine solution was heated to the boiling point. Then the temperature of the external heat source was increased according to the following profile 1 h at 150 C, 1 h at 160 and 1 h at 170 and 1 h at 180 C while water was distilled off. The pressure was then decreased to 200 mbar while the external heat source was maintained at 180° C. and the reaction for circa 1+% hour continued under vacuo (200 mbar). The warm reaction melt was collected in an aluminum vessel. At room temperature a solid material was obtained. The polymer was characterized via Gel permeation Chromatography in water and regarding amino numbers: Mn: 1380 g/mol; Mw: 1980 g/mol; polydispersity ($M_w/M_n$): 1.4; amine number**: 458 mgKOH/g* (given for 100% pure polylysine).

In yet another embodiment, the homo- or copolymer of lysine (L587) is preferably (L606) a polylysine prepared as follows:

1700 g of 50% water solution of L-Lysine were placed in a 2 L four-necked flask equipped with a stirrer a condensation column, a thermometer and a nitrogen inlet. The L-Lysine solution was heated to the boiling point. Then the temperature of the external heat source was increased according to the following profile 1 h at 150 C, 1 h at 160 and 1 h at 170 and 1 h at 180 C while water was distilled off. The pressure was then decreased to 200 mbar while the external heat source was maintained at 180° C. and the reaction for circa 15 minutes continued under vacuo (200 mbar). The warm reaction melt was collected in an aluminum vessel. At room temperature a solid material was obtained. The polymer was characterized via Gel permeation Chromatography in water and regarding amine numbers: Mn: 840 g/mol; Mw: 940 g/mol; polydispersity ($M_w/M_n$): 1.1; Amine number: 598 mgKOH/g (given for 100% pure polylysine).

According to the invention, a further composition (Q5) was found which comprises:

(A) a mixture comprising at least one (thio)phosphoric acid triamide according to the general formula (I)

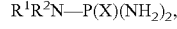

$R^1R^2N\!-\!P(X)(NH_2)_2$, wherein

X is oxygen or sulfur;

$R^1$ is a $C_1$ to $C_{20}$ alkyl, $C_3$ to $C_{20}$ cycloalkyl, $C_6$ to $C_{20}$ aryl, or dialkylaminocarbonyl group;

$R^2$ is H, or $R^1$ and $R^2$ together with the nitrogen atom linking them define a 5- or 6-membered saturated or unsaturated heterocyclic radical, which optionally comprises 1 or 2 further heteroatoms selected from the group consisting of nitrogen, oxygen, and sulfur, and (L2) at least one colorant selected from the group consisting of (L700) CI 20470 (Acid Black 1; C22H14N6Na2O9S2; EINECS 213-903-1; CAS 1064-48-8);

(L701) CI 50420 (Acid Black 2; -; EINECS -; CAS 8005-03-6);

(L702) CI 42045 (Acid Blue 1; C27H31N2NaO6S2; EINECS 204-934-1; CAS 129-17-9);

(L703) CI 42735 (Acid Blue 104; C43H49N3NaO6S2; EINECS 229-390-2; CAS 6505-30-2);

(L704) CI 42051 (Acid Blue 3; C54H62CaN4O14S4; EINECS 222-573-8; CAS 3536-49-0);

(L705) CI 62045 (Acid Blue 62; C20H19N2NaO5S; EINECS 224-460-9; CAS 4368-56-3);

(L706) CI 42080 (Acid Blue 7; C37H35N2NaO6S2; EINECS 222-476-0; CAS 3486-30-4);

(L707) CI 73015 (Acid Blue 74; C16H8N2Na2O8S2; EINECS 212-728-8; CAS 860-22-0);

(L708) CI 61585 (Acid Blue 80; C32H28N2Na2O8S2; EINECS 224-748-4; CAS 4474-24-2);

(L709) CI 42090 (Acid Blue 9; C37H34N2Na2O9S3; EINECS 223-339-8; CAS 3844-45-9);

(L710) CI 10020 (Acid Green 1; C30H15FeN3Na3O15S3; EINECS 243-010-2; CAS 19381-50-1);

(L711) CI 42170 (Acid Green 22; C39H38ClN2NaO6S2; EINECS 227-513-4; CAS 5863-51-4);

(L712) CI 61570 (Acid Green 25; C28H20N2Na2O8S2; EINECS 224-546-6; CAS 4403-90-1);

(L713) CI 44090 (Acid Green 50; C27H25N2NaO7S2; EINECS 221-409-2; CAS 3087-16-9);

(L714) CI 42100 (Acid Green 9; C37H34ClN2NaO6S2; EINECS 225-458-0; CAS 4857-81-2);

(L715) CI 16230 (Acid Orange 10; C16H10N2Na2O7S2; EINECS 217-705-6; CAS 1936-15-8);

(L716) CI 45370 (Acid Orange 11; C20H8Br2Na2O5; EINECS 224-468-2; CAS 4372-02-5);

(L717) CI 14270 (Acid Orange 6; C12H10N2O5SNa; EINECS 208-924-8; CAS 547-57-9);

(L718) CI 15510 (Acid Orange 7; C16H11N2O4SNa; EINECS 211-199-0; CAS 633-96-5);

(L719) CI 18050 (Acid Red 1; C18H13N3Na2O8S2; EINECS 223-098-9; CAS 3734-67-6);

(L720) CI 14720 (Acid Red 14; C20H12N2Na2O7S2; EINECS 222-657-4; CAS 3567-69-9);

(L721) CI 14720:1 (Acid Red 14 Aluminum Lake; C60H36Al2N6O21S6; EINECS 282-478-2; CAS 84238-07-3);

(L722) CI 18130 (Acid Red 155; -; EINECS -; CAS 10236-37-0);

(L723) CI 24790 (Acid Red 163; C44H34N4Na2O12S3; EINECS 236-531-1; CAS 13421-53-9);

(L724) CI 16255 (Acid Red 18; C20H11N2Na3O10S3; EINECS 220-036-2; CAS 2611-82-7);

(L725) CI 16255:1 (Acid Red 18 Aluminum Red; C20H14AlN2O10S3; EINECS 235-438-3; CAS 12227-64-4);

(L726) CI 18736 (Acid Red 180; C34H27Cl2CrN8Na2O4; EINECS 229-051-9; CAS 6408-26-0);

(L727) CI 16185 (Acid Red 27; C20H11N2Na3O10S3; EINECS 213-022-2; CAS 915-67-3);

(L728) CI 17200 (Acid Red 33; C16H11N3Na2O7S2; EINECS 222-656-9; CAS 3567-66-6);

(L729) CI 16290 (Acid Red 41; C20H10N2Na4O13S4; EINECS 227-454-4; CAS 5850-44-2);

(L730) CI 16250 (Acid Red 44; C20H12N2Na2O7S2; EINECS -; CAS 2766-77-0);

(L731) CI 45220 (Acid Red 50; C25H25N2NaO7S2; EINECS 227-528-6; CAS 5873-16-5);

(L732) CI 45430 (Acid Red 51; C20H6I4Na2O5; EINECS 240-474-8; CAS 16423-68-0);

(L733) CI 45100 (Acid Red 52; C27H29N2NaO7S2; EINECS 222-529-8; CAS 3520-42-1);

(L734) CI 45380 (Acid Red 87; C20H6Br4Na2O5; EINECS 241-409-6; CAS 17372-87-1);

(L735) CI 15620 (Acid Red 88; C20H13N2NaO4S; EINECS 216-760-3; CAS 1658-56-6);

(L736) CI 45410 (Acid Red 92; C20H2Br4Cl4Na2O5; EINECS 242-355-6; CAS 18472-87-2);

(L737) CI 45405 (Acid Red 98; C20H4Br4Cl2K2O5; EINECS 229-225-4; CAS 6441-77-6);

(L738) CI 60730 (Acid Violet 43; C21H14NNaO6S; EINECS 224-618-7; CAS 4430-18-6);

(L739) CI 50325 (Acid Violet 50; C29H22N4NaO7S2; EINECS 229-951-1; CAS 6837-46-3);

(L740) CI 45190 (Acid Violet 9; C34H26N2NaO6S; EINECS 228-377-9; CAS 6252-76-2);

(L741) CI 10316 (Acid Yellow 1; C10H4N2Na2O8S; EINECS 212-690-2; CAS 846-70-8);

(L742) CI 18820 (Acid Yellow 11; C16H13N4NaO4S; EINECS 228-808-0; CAS 6359-82-6);

(L743) CI 18965 (Acid Yellow 17; C16H10Na2N4O7S2; EINECS 228-819-0; CAS 6359-98-4);

(L744) CI 19140 (Acid Yellow 23; C16H9N4Na3O9S2; EINECS 217-699-5; CAS 1934-21-0);

(L745) CI 47005 (Acid Yellow 3; C18H9NNa2O8S2; EINECS 305-897-5; CAS 8004-92-0);

(L746) CI 13065 (Acid Yellow 36; C18H14N3NaO3S; EINECS 209-608-2; CAS 587-98-4);

(L747) CI 18690 (Acid Yellow 59; C34H25CrN8O6; EINECS 227-022-5; CAS 5601-29-6);

(L748) CI 45350 (Acid Yellow 73; C20H10Na2O5; EINECS 208-253-0; CAS 518-47-8);

(L749) CI 13015 (Acid Yellow 9; C12H11N3NaO6S2; EINECS 220-293-0; CAS 2706-28-7);

(L750) CI 16035 (Allurarot AC; C18H14N2Na2O8S2; EINECS 247-368-0; CAS 25956-17-6);

(L751) CI 44045 (Basic Blue 26; C33H32ClN3; EINECS 219-943-6; CAS 2580-56-5);

(L752) CI 12251 (Basic Brown 17; C19H20ClN5O3; EINECS 269-944-0; CAS 68391-32-2);

(L753) CI 12251:1 (Basic Red 118; -; EINECS 275-216-3; CAS 71134-97-9);

(L754) CI 42510 (Basic Violet 14; C20H19N3.HCl; EINECS 211-189-6; CAS 632-99-5);

(L755) CI 42520 (Basic Violet 2; C22H24N3Cl; EINECS 221-831-7; CAS 3248-91-7);

(L756) CI 40215 (Direct Orange 39; -; EINECS 215-397-8; CAS 1325-54-8);

(L757) CI 40215 (Direct Orange 46; -; EINECS 256-783-6; CAS 50814-31-8);

(L758) CI 60724 (Disperse Violet 27; C20H13NO3; EINECS 242-939-0; CAS 19286-75-0);

(L759) CI 28440 (Food Black 1; C28H17N5Na4O14S4; EINECS 219-746-5; CAS 2519-30-4);

(L760) CI 27755 (Food Black 2; C26H15N5Na4O13S4; EINECS 218-326-9; CAS 2118-39-0);

(L761) CI 42053 (Food Green 3; C37H34N2Na2O10S3; EINECS 219-091-5; CAS 2353-45-9);

(L762) CI 40800 (Food Orange 5; C40H56; EINECS 230-636-6; CAS 7235-40-7);

(L763) CI 40820 (Food Orange 6; C30H40O; EINECS 214-171-6; CAS 1962-15-8);
(L764) CI 40825 (Food Orange 7; C32H44O2; EINECS 214-173-7; CAS 1109-11-1);
(L765) CI 40850 (Food Orange 8; C40H52O2; EINECS 208-187-2; CAS 514-78-3);
(L766) CI 14700 (Food Red 1; C18H14N2Na2O7S2; EINECS 224-909-9; CAS 4548-53-2);
(L767) CI 14815 (Food Red 2; C18H14N2Na2O7S2; EINECS 221-856-3; CAS 3257-28-1);
(L768) CI 15985 (Food Yellow 3; C16H10N2Na2O7S2; EINECS 220-491-7; CAS 2783-94-0);
(L769) CI 74160 (Pigment Blue 15; C32H16CuN8; EINECS 205-685-1; CAS 147-14-8);
(L770) CI 74100 (Pigment Blue 16; C32H18N8; EINECS 209-378-3; CAS 574-93-6);
(L771) CI 69800 (Pigment Blue 60; C28H14N2O4; EINECS 201-375-5; CAS 81-77-6);
(L772) CI 69825 (Pigment Blue 64; C28H12Cl2N2O4; EINECS 204-980-2; CAS 130-20-1);
(L773) CI 73000 (Pigment Blue 66; C16H10N2O2; EINECS 207-586-9; CAS 482-89-3);
(L774) CI 12480 (Pigment Brown 1; C25H19Cl2N3O4; EINECS 229-106-7; CAS 6410-40-8);
(L775) CI 74260 (Pigment Green 7; -; EINECS 215-524-7; CAS 1328-53-6);
(L776) CI 10006 (Pigment Green 8; C30H18FeN3NaO6; EINECS 240-299-7; CAS 16143-80-9);
(L777) CI 11725 (Pigment Orange 1; C18H18N4O5; EINECS 228-901-6; CAS 6371-96-6);
(L778) CI 71105 (Pigment Orange 43; C26H12N4O2; EINECS 224-597-4; CAS 4424-06-0);
(L779) CI 12370 (Pigment Red 112; C24H16Cl3N3O2; EINECS 229-440-3; CAS 6535-46-2);
(L780) CI 73915 (Pigment Red 122; C22H16N2O2; EINECS 213-561-3; CAS 980-26-7);
(L781) CI 45430:1 (Pigment Red 172; C60H27AlI12O15; EINECS 235-440-4; CAS 12227-78-0);
(L782) CI 73360 (Pigment Red 181; C18H10Cl2O2S2; EINECS 219-163-6; CAS 2379-74-0);
(L783) CI 12120 (Pigment Red 3; C17H13N3O3; EINECS 219-372-2; CAS 2425-85-6);
(L784) CI 12085 (Pigment Red 4; C16H10ClN3O3; EINECS 220-562-2; CAS 2814-77-9);
(L785) CI 15865 (Pigment Red 48; C18H11ClN2Na2O6S; EINECS 222-642-2; CAS 3564-21-4);
(L786) CI 15865:1 (Pigment Red 48:1; C18H11BaClN2O6S; EINECS 231-494-8; CAS 7585-41-3);
(L787) CI 15865:2 (Pigment Red 48:2; C18H11CaClN2O6S; EINECS 230-303-5; CAS 7023-61-2);
(L788) CI 15865:3 (Pigment Red 48:3; C18H11ClN2O6SSr; EINECS 239-879-2; CAS 15782-05-5);
(L789) CI 15865:4 (Pigment Red 48:4; C18H11ClMnN2O6S; EINECS 226-102-7; CAS 5280-66-0);
(L790) CI 15630 (Pigment Red 49; C17H12Cl2NaO4S; EINECS 214-998-2; CAS 1248-18-6);
(L791) CI 15630:1 (Pigment Red 49:1; C40H26BaN4O8S2; EINECS 214-160-6; CAS 1103-38-4);
(L792) CI 15630:2 (Pigment Red 49:2; C40H26CaN4O8S2; EINECS 214-161-1; CAS 1103-39-5);
(L793) CI 12490 (Pigment Red 5; C30H31ClN4O7S; EINECS 229-107-2; CAS 6410-41-9);

(L794) CI 15580 (Pigment Red 51; C34H26BaN4O8S2; EINECS 227-459-1; CAS 5850-87-3);
(L795) CI 15585 (Pigment Red 53; C17H12ClN2NaO4S; EINECS 218-248-5; CAS 2092-56-0);
(L796) CI 15585:1 (Pigment Red 53:1; C34H24BaCl2N4O8S2; EINECS 218-248-5; CAS 5160-02-1);
(L797) CI 15585:2 (Pigment Red 53:2; C34H24CaCl2N4O8S2; EINECS 288-057-6; CAS 67990-35-6);
(L798) CI 15850 (Pigment Red 57; -; EINECS 227-497-9; CAS 5858-81-1);
(L799) CI 15850 (Pigment Red 57:1; C18H12CaN2O6S; EINECS 226-109-5; CAS 5281-04-9);
(L800) CI 15880 (Pigment Red 63; -; EINECS -; CAS 5858-84-4);
(L801) CI 15980 ? (Pigment Red 63:?; -; EINECS 219-073-7; CAS 2347-72-0);
(L802) CI 15880:1 (Pigment Red 63:1; C21H12CaN2O6S; EINECS 229-142-3; CAS 6417-83-0);
(L803) CI 15800 (Pigment Red 64:1; C34H22CaN4O6; EINECS 228-899-7; CAS 6371-76-2);
(L804) CI 15525 (Pigment Red 68; C34H18CaCl2N4Na2O12S2; EINECS 227-456-5; CAS 5850-80-6);
(L805) CI 12420 (Pigment Red 7; C25H19Cl12N3O2; EINECS 229-315-3; CAS 6471-51-8);
(L806) CI 58000 (Pigment Red 83; C14H8O4; EINECS 200-782-5; CAS 72-48-0);
(L807) CI 45380:3 (Pigment Red 90:1; -; EINECS 240-005-7; CAS 15876-39-8);
(L808) CI 73900 (Pigment Violet 19; C20H12N2O2; EINECS 213-879-2; CAS 1047-16-1);
(L809) CI 45170 (Pigment Violet 19; C28H31ClN2O3; EINECS; CAS 81-88-9);
(L810) CI 51319 (Pigment Violet 23; C34H22Cl2N4O2; EINECS 228-767-9; CAS 6358-30-1);
(L811) CI 73385 (Pigment Violet 36; C18H10Cl2O2S2; EINECS 226-750-0; CAS 5462-29-3);
(L812) CI 58055 (Pigment Violet 5; C14H8O7S; EINECS -; CAS 145-48-2);
(L813) CI 11680 (Pigment Yellow 1; C17H16O4N4; EINECS 219-730-8; CAS 2512-29-0);
(L814) CI 19140:1 (Pigment Yellow 100; C48H33AlN12O27S6; EINECS 235-428-9; CAS 12225-21-7);
(L815) CI 15985:1 (Pigment Yellow 104; C16H12AlN2O7S2; EINECS 239-888-1; CAS 15790-07-5);
(L816) CI 21100 (Pigment Yellow 13; C36H34Cl2N6O4; EINECS 225-822-9; CAS 5102-83-0);
(L817) CI 13980 (Pigment Yellow 151; C18H15N5O5; EINECS -; CAS 31837-42-0);
(L818) CI 20040 (Pigment Yellow 16; C34H28Cl4N6O4; EINECS 227-783-3; CAS 5979-28-2);
(L819) CI 11710 (Pigment Yellow 3; C16H12Cl2N4O4; EIN ECS 229-355-1; CAS 6486-23-3);
(L820) CI 21108 (Pigment Yellow 83; C36H32Cl4N6O8; EINECS 226-939-8; CAS 5567-15-7);
(L821) CI 74180 (Solvent Blue 38; -; EINECS 215-523-1; CAS 1328-51-4);
(L822) CI 61565 (Solvent Green 3; C28H22N2O2; EINECS 204-909-5; CAS 128-80-3);
(L823) CI 59040 (Solvent Green 7; C16H7Na3O10S3; EINECS 228-783-6; CAS 6358-69-6);
(L824) CI 11920 (Solvent Orange 1; C12H10N2O2; EINECS 218-131-9; CAS 2051-85-6);

(L825) CI 45396 (Solvent Orange 16; C20H10N2O9; EINECS 246-308-0; CAS 24545-86-6);

(L826) CI 12100 (Solvent Orange 2; C17H14N2O; EINECS 220-162-8; CAS 2646-17-5);

(L827) CI 12140 (Solvent Orange 7; C18H16N2O; EINECS 221-490-4; CAS 3118-97-6);

(L828) CI 12150 (Solvent Red 1; C17H14N2O2; EINECS 214-968-9; CAS 1229-55-6);

(L829) CI 26100 (Solvent Red 23; C22H16N4O; EINECS 201-638-4; CAS 85-86-9);

(L830) CI 26105 (Solvent Red 24; C24H20N4O; EINECS -; CAS 85-83-6);

(L831) CI 12010 (Solvent Red 3; C18H16N2O2; EINECS 229-439-8; CAS 6535-42-8);

(L832) CI 45380:2 (Solvent Red 43; C20H8Br4O5; EINECS 239-138-3; CAS 15086-94-9);

(L833) CI 45410 (Solvent Red 48; C20H4Br4Cl4O5; EINECS 236-747-6; CAS 13473-26-2);

(L834) CI 45370 (Solvent Red 72; C20H10Br2O5; EINECS 209-876-0; CAS 596-03-2);

(L835) CI 12156 (Solvent Red 80; C18H16N2O3; EINECS 228-778-9; CAS 6358-53-8);

(L836) CI 60725 (Solvent Violet 13; C21H15NO3; EINECS 201-353-5; CAS 81-48-1);

(L837) CI 12055 (Solvent Yellow 14; C16H12N2O; EINECS -; CAS 842-07-9);

(L838) CI 12700 (Solvent Yellow 16; C16H14N4O; EINECS 224-330-1; CAS 4314-14-1);

(L839) CI 21230 (Solvent Yellow 29; -; EINECS 229-754-0; CAS 6706-82-7);

(L840) CI 47000 (Solvent Yellow 33; C18H11NO2; EINECS 232-318-2; CAS 8003-22-3);

(L841) CI 73300 (Vat Red 41; C16H8O2S2; EINECS -; CAS 522-75-8);

(L842) CI 47005 (-; -; EINECS 305-632-3; CAS 94891-32-4);

(L843) Orasol Yellow 141

(L844) C.I. Pigment Blue 29 (CAS 57455-37-5) (Alternative names: Ultramarine blue; CI 77007; Ultrablue; Gunjo 8000; gunjo 4000; Gunjo 2000; FRENCH BLUE; ultramarine; LAUNDRY BLUE; gunjo ap 201);

(L845) C.I. Acid Red 33 (CAS 3567-66-6) (Alternative names: D&C Red No. 33, Azo grenadine, Azo fuchsine, Acid fuchsine D, Redusol Z, Azo magenta G, Certicol Red B, Fast acid magenta, Hexalan Red B, Acetyl Red B, Naphthalene Red B, C.I. 17200);

(L846) Benzenemethanaminium, N-ethyl-N-(4-((4-(ethyl((3-sulfophenyl)methyl)amino)phenyl)(2-sulfophenyl)methylene)-2,5-cyclohexadien-1-ylidene)-3-sulfo-, hydroxide, inner salt, disodium salt (CAS 3844-45-9) (Alternative names: FD&C Blue No. 1, Acid Blue 9, D&C Blue No. 4, Alzen Food Blue No. 1, Atracid Blue FG, Erioglaucine, Eriosky blue, Patent Blue AR, Xylene Blue VSG, C.I. 42090);

(L847) 1H-Pyrazole-3-carboxylic acid, 4,5-dihydro-5-oxo-1-(4-sulfophenyl)-4-((4-sulfophenyl)azo)-, trisodium salt (CAS 1934-21-0) (Alternative names: FD&C Yellow No. 5, Acid Yellow 23, Tartrazin)

(L848) Orasol Orange 251 (CAS 85029-59-0) [Alternative name: Amines, $C_{10-14}$-branched and linear alkyl, [2,4-dihydro-4-[(2-hydroxy-5-nitrophenyl)azo]-5-methyl-2-phenyl-3H-pyrazol-3-onato(2-)][2-[(4,5-dihydro-3-methyl-5-oxo-1-phenyl-1H-pyrazol-4-yl)azo]benzoato(2-)]chromate(1-)]

Generally, the colorant(s) (L2) can be contained in varying amounts in the composition (Q5). Preferably, the amount of (L2) is not more than 30 wt. % (wt. % stands for "percent by weight"), more preferably not more than 15 wt. %, most preferably not more than 10 wt. %, most particularly preferably not more than 5 wt. %, particularly not more than 2 wt. %, for example not more than 1.1 wt. %, based on the total weight of the composition (Q5). Preferably, the amount of (L2) is at least 0.01 wt. %, more preferably at least 0.1 wt. %, most preferably at least 0.2 wt. %, most particularly preferably at least 0.4 wt. %, particularly at least 0.5 wt. %, for example at least 0.9 wt. %, based on the total weight of the composition (Q5).

If present, the colorant(s) (L2) can generally be contained in varying amounts in the composition (Q2), (Q3), or (Q4). If present, the amount of (L2) is preferably not more than 30 wt. % (wt. % stands for "percent by weight"), more preferably not more than 15 wt. %, most preferably not more than 10 wt. %, most particularly preferably not more than 5 wt. %, particularly not more than 2 wt. %, for example not more than 1.1 wt. %, based on the total weight of the composition (Q2), (Q3), or (Q4). If present, the amount of (L2) is preferably at least 0.01 wt. %, more preferably at least 0.1 wt. %, most preferably at least 0.2 wt. %, most particularly preferably at least 0.4 wt. %, particularly at least 0.5 wt. %, for example at least 0.9 wt. %, based on the total weight of the composition (Q2), (Q3), or (Q4).

The compositions (Q2), (Q3), or (Q4) can optionally further comprise (L2) at least one colorant selected from the group consisting of (L700) to (L848) as described above.

Preferably, the addition of the colorant(s) (L2) improves the stability and/or the urease inhibiting effect and/or yield increasing effect of the (thio)phosphoric acid triamide(s), most preferably in a synergistic way.

According to the invention, the composition (Q2) comprises—as one of its essential components—and the compositions (Q3), (Q4), and (Q5) can further comprise—as one of its optional components—

(C) at least one amine selected from the group consisting of (C1) a polymeric polyamine, and (C2) an amine containing not more than one amino group and at least three alkoxy- or hydroxy-substituted $C_2$ to $C_{12}$ alkyl groups $R^{21}$, wherein at least one of the groups $R^{21}$ is different to the other groups $R^{21}$, and (C3) an amine containing not more than one amino group and at least two alkoxy- or hydroxy-substituted $C_2$ to $C_{12}$ alkyl groups $R^{22}$, wherein at least one of the groups $R^{22}$ bears the alkoxy or hydroxy substituent at a secondary or tertiary carbon atom and wherein at least one of the groups $R^{22}$ is different to the other group(s) $R^{22}$, and (C4) an amine containing at least one saturated or unsaturated $C_8$ to C40 alkyl group $R^{23}$, and (C5) a saturated or unsaturated heterocyclic amine which contains at least one oxygen atom as ring atom and which does not contain a further alkoxy group.

Generally, the amine(s) (C) can be contained in varying amounts in the composition (Q2). Preferably, the amount of (C) is not more than 90 wt. % (wt. % stands for "percent by weight"), more preferably not more than 65 wt. %, most preferably not more than 48 wt. %, most particularly preferably not more than 37 wt. %, particularly not more than 30 wt. %, for example not more than 24 wt. %, based on the total weight of the composition (Q2). Preferably, the amount of (C) is at least 1 wt. %, more preferably at least 3 wt. %, most preferably at least 6 wt. %, most particularly preferably at least 9 wt. %, particularly at least 14 wt. %, for example at least 18 wt. %, based on the total weight of the composition (Q2).

If present, the amine(s) (C) can generally be contained in varying amounts in the composition (Q3), (Q4), or (Q5). If present, the amount of (C) is preferably not more than 90 wt. % (wt. % stands for "percent by weight"), more preferably not more than 65 wt. %, most preferably not more than 48 wt. %, most particularly preferably not more than 37 wt. %, particularly not more than 30 wt. %, for example not more than 24 wt. %, based on the total weight of the composition (Q3), (Q4), or (Q5). If present, the amount of (C) is preferably at least 1 wt. %, more preferably at least 3 wt. %, most preferably at least 6 wt. %, most particularly preferably at least 9 wt. %, particularly at least 14 wt. %, for example at least 18 wt. %, based on the total weight of the composition (Q3), (Q4), or (Q5).

In another embodiment, if present, the amount of polymeric polyamine (L572), polyalkyleneimine (L568), or polyethyleneimine (L569) is preferably not more than 35 wt. %, more preferably not more than 24 wt. %, most preferably not more than 17 wt. %, most particularly preferably not more than 12 wt. %, particularly not more than 9 wt. %, for example not more than 7 wt. %, based on the total weight of the composition (Q3), (Q4), or (Q5). If present, the amount of polymeric polyamine (L572), polyalkyleneimine (L568), or polyethyleneimine (L569) is preferably at least 0.2 wt. %, more preferably at least 1 wt. %, most preferably at least 2.5 wt. %, most particularly preferably at least 4 wt. %, particularly at least 5 wt. %, for example at least 5.5 wt. %, based on the total weight of the composition (Q3), (Q4), or (Q5).

According to one embodiment, (C) is (C1) a polymeric polyamine.

Generally, (C1) can be any polymeric polyamine, and is preferably a polyalkyleneimine or polyvinylamine, more preferably a (L568) polyalkyleneimine, and (C1) is most preferably (L569) polyethyleneimine, (L570) polypropyleneimine, or (L571) polybutyleneimine, and is particularly a polyethyleneimine.

According to one embodiment, (C1) is preferably any polymeric polyamine comprising ethyleneimine (—CH2CH2NH—) as monomeric units, including homo- or copolymers and any copolymers of ethyleneimine, and is preferably a homo- or copolymer of ethyleneimine. Copolymers can be alternating, periodic, statistical or block copolymers.

Generally, (C1) can be of any polymer structure, for example a linear polymer, a ring polymer, a cross-linked polymer, a branched polymer, a star polymer, a comb polymer, a brush polymer, a dendronized polymer, or a dendrimer etc. According to one embodiment, (C1) is an essentially linear polymer, and is preferably a linear polymer.

Polyethyleneimines which may be used are polyethyleneimine homo- or copolymers which may be present in uncrosslinked or crosslinked form. The polyethyleneimine homo- or copolymers can be prepared by known processes, as described, for example, in Rdmpps (Chemie Lexikon, 8th edition, 1992, pages 3532-3533), or in Ullmanns Enzyklopadie der Technischen Chemie, 4th edition, 1974, vol. 8, pages 212-213. and the literature stated there. They have a molecular weight in the range from about 200 to 1 000 000 g/mol. Corresponding commercial products are for example available under the name Lupasol® from BASF SE.

According to one embodiment of the invention, the polyethyleneimine (C1) is preferably a polyethylenimine having a degree of branching in the range of from 0.1 to 0.95 (also referred to as "highly branched polyethyleneimine"), and more preferably a polyethylenimine having a degree of branching in the range of from 0.25 to 0.90, more preferably a polyethylenimine having a degree of branching in the range of from 0.30 to 0.80, und most preferably a polyethylenimine having a degree of branching in the range of 0.50 to 0.80.

Highly branched polyethyleneimines are characterized by its high degree of branching, which can be determined for example via $^{13}$C-NMR spectroscopy, preferably in $D_2O$, and is defined as follows:

$$\text{Degree of branching}=D+T/D+T+L$$

D (dendritic) equals the percentage of tertiary amino groups, L (linear) equals the percentage of secondary amino groups, and T (terminal) equals the percentage of primary amino groups.

Generally, the polymeric polyamine (C1) can have different weight average molecular weights. The weight average molecular weight of (C1) is preferably at least 200, more preferably at least 400, most preferably at least 550, particularly at least 650, for example at least 750. The weight average molecular weight of (C1) is preferably not more than 10,000, more preferably not more than 4,000, most preferably not more than 1,900, particularly not more than 1,500, for example not more than 1,350. The weight average molecular weight can be determined by standard gel permeation chromatography (GPC) known to the person skilled in the art.

According to another embodiment, (C) is (C2) an amine containing not more than one amino group and at least three alkoxy- or hydroxy-substituted $C_2$ to $C_{12}$ alkyl groups $R^{21}$, wherein at least one of the groups $R^{21}$ is different to the other groups $R^{21}$.

A number of groups $R^{21}$ within (C2) is at least 3, preferably 3 to 5, more preferably 3 to 4, and most preferably 3.

The number of carbon atoms in each group $R^{21}$ within (C2) is 2 to 12, preferably 2 to 9, more preferably 2 to 7, most preferably 2 to 5, particularly preferably 2 to 4, particularly 2 to 3, for example 3, wherein said number of carbon atoms does not include carbon atoms in any alkoxy groups or any other substituents of $R^{21}$.

The groups $R^{21}$ within (C2) are alkoxy- or hydroxy-substituted, preferably hydroxy-substituted.

For one amine (C2), among the at least three groups $R^{21}$, at least one of the groups $R^{21}$ is different to the other groups $R^{21}$, preferably one of the groups $R^{21}$ is different to the other groups $R^{21}$.

Preferably at least one of the groups $R^{21}$, more preferably at least two of the groups $R^{21}$, most preferably at least three of the groups $R^{21}$, particularly all groups $R^{21}$ is or are covalently bound to the amino group of the amine (C2).

According to another preferred embodiment, (C2) is (L185) an amine containing not more than one amino group and at least three hydroxy-substituted $C_2$ to $C_8$- or preferably $C_2$ to $C_5$-alkyl groups $R^{21}$, wherein at least one of the groups $R^{21}$ is different to the other groups $R^{21}$, and (C2) is preferably (L186) an amine containing not more than one amino group and at least three hydroxy-substituted $C_2$ to $C_3$ alkyl groups $R^{21}$, wherein at least one of the groups $R^{21}$ is different to the other groups $R^{21}$, and (C2) is more preferably (L187) an amine containing not more than one amino group and three hydroxy-substituted $C_2$ to $C_3$ alkyl groups $R^{21}$ which are covalently bound to the amino group, wherein one of the groups $R^{21}$ is different to the other groups $R^{21}$, and (C2) is for example an amine selected from the group consisting of (L188) N,N-Bis(2-hydroxyethyl)-isopropanolamine (DEIPA), and (L189) 1,1'-((2-Hydroxyethyl)imino)dipropan-2-ol.

According to another preferred embodiment, (C2) is (L190) an amine $N(R^{21})_3$ wherein $R^{21}$ is a an alkoxy- or hydroxy-substituted—preferably a hydroxyl-substituted —$C_2$ to $C_{12}$—preferably a $C_2$ to $C_7$, more preferably a $C_2$ to $C_3$-alkyl group and wherein one of the groups $R^{21}$ is different to the other group $R^{21}$.

According to another preferred embodiment, (C2) is (L191) an amine $N(R^{21})_3$ wherein $R^{21}$ is a an alkoxy- or hydroxy-substituted—preferably a hydroxyl-substituted —$C_2$ to $C_{12}$—preferably a $C_2$ to $C_7$, more preferably a $C_2$ to $C_3$-alkyl group and wherein one of the groups $R^{21}$ is different to the other group $R^{21}$ and wherein at least one of the groups $R^{21}$ bears the alkoxy or hydroxy substituent at a secondary or tertiary carbon atom.

According to another embodiment, (C) is (C3) an amine containing not more than one amino group and at least two alkoxy- or hydroxy-substituted $C_2$ to $C_{12}$ alkyl groups $R^{22}$, wherein at least one of the groups $R^{22}$ bears the alkoxy or hydroxy substituent at a secondary or tertiary carbon atom and wherein at least one of the groups $R^{22}$ is different to the other group(s) $R^{22}$.

A number of groups $R^{22}$ within (C3) is at least 2, preferably 2 to 5, more preferably 2 to 4, and most preferably 2 to 3, for example 2.

The number of carbon atoms in each group $R^{22}$ within (C3) is 2 to 12, preferably 2 to 9, more preferably 2 to 7, most preferably 2 to 5, particularly preferably 2 to 4, particularly 2 to 3, for example 3, wherein said number of carbon atoms does not include carbon atoms in any alkoxy groups or any other substituents of $R^{22}$.

The groups $R^{22}$ within (C3) are alkoxy- or hydroxy-substituted, preferably hydroxy-substituted. For one amine (C3), among the at least two groups $R^{22}$, at least one of the groups $R^{22}$ is different to the other group(s) $R^{22}$, preferably one of the groups $R^{22}$ is different to the other group(s) $R^{22}$.

Preferably at least one of the groups $R^{22}$, more preferably at least two of the groups $R^{22}$, most preferably all groups $R^{22}$ is or are covalently bound to the amino group of the amine (C3).

Preferably at least one of the groups $R^{22}$, more preferably one of the groups $R^{22}$ bears the alkoxy or hydroxy substituent at a secondary or tertiary carbon atom, particularly at a secondary carbon atom.

According to another preferred embodiment, (C3) is (L192) an amine containing not more than one amino group and at least two hydroxy-substituted $C_2$ to C7 alkyl groups $R^{22}$, wherein at least one of the groups $R^{22}$ bears the hydroxy substituent at a secondary or tertiary carbon atom and wherein at least one of the groups $R^{22}$ is different to the other group(s) $R^{22}$, and (C3) is more preferably (L193) an amine containing not more than one amino group and at least two hydroxy-substituted $C_2$ to $C_4$ alkyl groups $R^{22}$, wherein at least one of the groups $R^{22}$ bears the hydroxy substituent at a secondary carbon atom and wherein at least one of the groups $R^{22}$ is different to the other group(s) $R^{22}$, and (C3) is most preferably (L194) an amine containing not more than one amino group and two hydroxy-substituted $C_2$ to $C_3$ alkyl groups $R^{22}$ which are covalently bound to the amino group of the amine (C3), wherein at least one of the groups $R^{22}$ bears the hydroxy substituent at a secondary carbon atom and wherein one of the groups $R^{22}$ is different to the other group $R^{22}$, and (C2) is for example an amine selected from the group consisting of (L195) 1-((2-hydroxyethyl)amino)propan-2-ol, and (L196) N-Methyl-N-hydroxyethyl-isopropanolamine.

According to another preferred embodiment, (C3) is (L197) an amine $R^{24}N(R^{22})_2$ wherein $R^{24}$ is H or a $C_1$ to $C_{12}$—preferably a $C_1$ to $C_7$, more preferably a $C_1$ to $C_3$-alkyl group and $R^{22}$ is an alkoxy- or hydroxy-substituted—preferably a hydroxyl-substituted —$C_2$ to $C_{12}$—preferably a $C_2$ to $C_7$, more preferably a $C_2$ to $C_3$-alkyl group and wherein at least one of the groups $R^{22}$ bears the hydroxy substituent at a secondary carbon atom and wherein one of the groups $R^{22}$ is different to the other group $R^{22}$.

According to another embodiment, (C) is (C4) an amine containing at least one saturated or unsaturated $C_8$ to C40 alkyl group $R^{23}$.

The number of carbon atoms in each group $R^{23}$ within (C4) is 8 to 40, preferably 8 to 32, more preferably 8 to 24, most preferably 8 to 19, particularly preferably 8 to 16.

The group $R^{23}$ within (C4) is saturated or unsaturated, preferably unsaturated.

According to another preferred embodiment, (C4) contains at least one alkoxy or hydroxy group, more preferably at least one alkoxy and at least one hydroxy groups, most preferably at least two alkoxy and at least one hydroxyl group, particularly (C4) is (L198) an amine containing at least one saturated or unsaturated $C_8$ to C40 alkyl group $R^{23}$ and containing at least four alkoxy and at least one hydroxyl group.

For example, (C4) is an amine selected from the group consisting of:

(L199) ethoxylated (2) cocoalkylamine, (L200) ethoxylated (5) cocoalkylamine, (L201) ethoxylated (15) cocoalkylamine, (L202) ethoxylated (2) oleylamine, (L203) lauryl-dimethylamine, (L204) oleyl-dimethylamine, (L205) 2-propylheptylamine ethoxylate (5 EO), (L206) 2-propylheptylamine ethoxylate (10 EO), and (L207) 2-propylheptylamine ethoxylate (20 EO).

According to another embodiment, (C) is (C5) a saturated or unsaturated heterocyclic amine which contains at least one oxygen atom as ring atom and which does not contain a further alkoxy group.

The term "heterocyclic amine" stands for a heterocyclic compound in which at least one ring atom of the heterocyclic ring is a nitrogen atom.

The heterocyclic amine (C5) is saturated or unsaturated, preferably saturated.

The heterocyclic amine (C5) contains preferably a 5-, 6- or 7-membered heterocyclic ring, more preferably a 5- or 6-membered ring, most preferably a 6-membered ring.

The heterocyclic amine (C5) contains at least one, more preferably 1 to 3, most preferably 1 to 2, particularly one oxygen atom(s) as ring atom(s) of the heterocyclic ring.

The heterocyclic amine (C5) is preferably (L208) a morpholine or morpholine derivative, and (C5) is more preferably (L209) N-alkyl morpholine, and (C5) is most preferably N-methyl, N-ethyl, N-propyl, or N-butyl morpholine, for example is (L210) N-methyl morpholine.

According to the invention, the composition (Q3) comprises—as one of its essential components—and the composition (Q2), (Q4) or (Q5) can further comprise—as one of its optional components—

(D) at least one amide according to the general formula (VI)

wherein $R^{31}CO$ is an acyl radical having 1 to 22 carbon atoms;
$R^{32}$ is H or alkyl, and
$R^{33}$ is H or alkyl, or
$R^{32}$ and $R^{33}$ together with the nitrogen atom linking them define a 5- or 6-membered saturated or unsaturated heterocyclic radical, which optionally comprises 1 or 2 further heteroatoms selected from the group consisting of nitrogen, oxygen, and sulfur.

Generally, the amide(s) (D) can be contained in varying amounts in the composition (Q3). Preferably, the amount of (D) is not more than 90 wt. % (wt. % stands for "percent by weight"), more preferably not more than 65 wt. %, most preferably not more than 45 wt. %, most particularly preferably not more than 30 wt. %, particularly not more than 22 wt. %, for example not more than 16 wt. %, based on the total weight of the composition (Q3). Preferably, the amount of (D) is at least 1 wt. %, more preferably at least 3 wt. %, most preferably at least 6 wt. %, most particularly preferably at least 9 wt. %, particularly at least 12 wt. %, for example at least 15 wt. %, based on the total weight of the composition (Q3).

If present, the amide (D) can generally be contained in varying amounts in the composition (Q2), (Q4), or (Q5). If present, the amount of (D) is preferably not more than 90 wt. % (wt. % stands for "percent by weight"), more preferably not more than 65 wt. %, most preferably not more than 45 wt. %, most particularly preferably not more than 30 wt. %, particularly not more than 22 wt. %, for example not more than 16 wt. %, based on the total weight of the composition (Q2), (Q4), or (Q5). If present, the amount of (D) is preferably at least 1 wt. %, more preferably at least 3 wt. %, most preferably at least 6 wt. %, most particularly preferably at least 9 wt. %, particularly at least 12 wt. %, for example at least 15 wt. %, based on the total weight of the composition (Q2), (Q4), or (Q5).

In the general formula (VI) of (D) $R^{32}$ is H or alkyl, preferably H or $C_1$ to C40 alkyl, more preferably H or $C_1$ to $C_{20}$ alkyl, most preferably H or $C_1$ to $C_{10}$ alkyl, particularly preferably H or $C_1$ to $C_4$ alkyl, most particularly preferably $C_1$ to $C_4$ alkyl, particularly $C_1$ to $C_2$ alkyl, for example methyl.

In the general formula (VI) of (D) $R^{33}$ is H or alkyl, preferably H or $C_1$ to C40 alkyl, more preferably H or $C_1$ to $C_{20}$ alkyl, most preferably H or $C_1$ to $C_{10}$ alkyl, particularly preferably H or $C_1$ to $C_4$ alkyl, most particularly preferably $C_1$ to $C_4$ alkyl, particularly $C_1$ to $C_2$ alkyl, for example methyl.

According to one preferred embodiment, in the general formula (VI) of (D) $R^{32}$ is H or $C_1$ to $C_4$ alkyl, and $R^{33}$ is H or $C_1$ to $C_4$ alkyl, more preferably, $R^{32}$ is $C_1$ to $C_4$ alkyl, and $R^{33}$ is $C_1$ to $C_4$ alkyl, most preferably, $R^{32}$ is $C_1$ to $C_2$ alkyl, and $R^{33}$ is $C_1$ to $C_2$ alkyl.

According to another preferred embodiment (D1PE), in the general formula (VI) of (D) $R^{31}CO$ is a hydroxy-substituted acyl radical having 1 to 22 carbon atoms, and more preferably, $R^{31}CO$ is a hydroxy-substituted acyl radical having 1 to 22 carbon atoms, and $R^{32}$ is alkyl, and $R^{33}$ is alkyl, and most preferably, $R^{31}CO$ is a hydroxy-substituted acyl radical having 1 to 7 carbon atoms, and $R^{32}$ is $C_1$ to $C_4$ alkyl, and $R^{33}$ is $C_1$ to $C_4$ alkyl.

According to another preferred embodiment, the amide (D) is
(L401) a N,N-dialkyl amide based on lactic acid, citric acid, tartaric acid, ricinoleic acid, 12-hydroxy stearic acid, or their mixtures, and the amide (D) is preferably
(L402) a N,N-dialkyl amide based on lactic acid, citric acid, tartaric acid, or their mixtures, and the amide (D) is most preferably
(L403) a N,N-dimethyl amide based on lactic acid, citric acid, tartaric acid, and the amide (D) is particularly
(L404) a lactic acid N,N-dimethylamide (=N,N-dimethyllactamide).

According to another preferred embodiment (D2PE), in the general formula (VI) of (D) $R^{31}CO$ is an acyl radical having 6 to 12 carbon atoms, more preferably, $R^{31}CO$ is an acyl radical having 8 to 10 carbon atoms.

According to another preferred embodiment, in the general formula (VI) of (D) $R^{31}CO$ does not contain a hydroxy group, and more preferably, $R^{31}CO$ does not contain a hydroxy group and is an acyl radical having 6 to 12 carbon atoms, and most preferably, $R^{31}CO$ does not contain a hydroxy group and is an acyl radical having 8 to 10 carbon atoms. For example, the amide (D) is selected from the group consisting of
(L405) N,N-dimethyloctanamide,
(L406) N,N-dimethylnonanamide, and
(L407) N,N-dimethyldecanamide.

According to another preferred embodiment (D3PE), in the general formula (VI) of (D) $R^{31}CO$ is an acyl radical having 1 to 3 carbon atoms, more preferably, $R^{31}CO$ is an acyl radical having 1 to 2 carbon atoms.

According to another preferred embodiment, in the general formula (VI) of (D) $R^{32}$ and $R^{33}$ together with the nitrogen atom linking them define a 5- or 6-membered saturated or unsaturated heterocyclic radical which optionally comprises 1 or 2 further heteroatoms selected from the group consisting of nitrogen, oxygen, and sulfur, and more preferably, $R^{32}$ and $R^{33}$ together with the nitrogen atom linking them define a 6-membered saturated or unsaturated heterocyclic radical which optionally comprises one further heteroatom selected from the group consisting of nitrogen, oxygen, and sulfur, most preferably $R^{32}$ and $R^{33}$ together with the nitrogen atom linking them define a 6-membered saturated heterocyclic radical which comprises one further oxygen heteroatom, particularly $R^{32}$ and $R^{33}$ together with the nitrogen atom linking them define a morpholinyl radical. For example, the amide (D) is
(L408) N-acylmorpholine (alternative term: N-alkylcarbonyl-morpholine),
(L409) N-acetylmorpholine, or
(L410) N-formylmorpholine.

According to another preferred embodiment (D4PE), in the general formula (VI) of (D) $R^{32}$ and $R^{33}$ together with the nitrogen atom linking them define a 5-membered saturated or unsaturated heterocyclic radical which optionally comprises 1 or 2 further heteroatoms selected from the group consisting of nitrogen, oxygen, and sulfur, and more preferably, $R^{32}$ and $R^{33}$ together with the nitrogen atom linking them define a 5-membered saturated heterocyclic radical which optionally comprises one further nitrogen heteroatoms, most preferably $R^{32}$ and $R^{33}$ together with the nitrogen atom linking them define a 5-membered saturated heterocyclic radical which comprises one further nitrogen heteroatom which is covalently bound to the carbon atom of the carbonyl group of $R^{31}CO$, particularly $R^{32}$ and $R^{33}$ together with the nitrogen atom linking them define a imidazolidinonyl radical. For example, the amide (D) is (L411) 1,3-Dimethyl-2-imidazolidinone (also referred to as dimethylethylenurea).

According to another preferred embodiment (D5PE), in the general formula (VI) of (D) $R^{32}$ is an acyloxy substituted alkyl group, more preferably, $R^{31}CO$ is an acyl radical having 1 to 4 carbon atoms, and $R^{32}$ is an acyloxy substituted alkyl group, most preferably, $R^{31}CO$ is an acyl radical having 1 to 4 carbon atoms, $R^{32}$ is an acyloxy substituted alkyl group and $R^{33}$ is $C_1$ to $C_4$ alkyl.

For example, the amide (D) is (L412) N-[2-(acetyloxy)ethyl]-N-methyl acetamide.

The composition (Q2), (Q3), (Q4), or (Q5) can further optionally comprise (E) an alcohol comprising at least two hydroxy groups which are not dissociable in the aqueous medium. The alcohol (E) is different from the components (A), (L1), (L2), (C) and (D).

"Not dissociable" means that the $pK_a$ value (logarithmic measure of the acid dissociation constant) for the reaction alcohol (D)→deprotonated alcohol (D)+$H^+$ of the hydroxy group in the neutral aqueous phase is more than 9.9, more preferably more than 11, most preferably more than 12, particularly preferably more than 13, for example more than 14 as measured in de-ionized water at 25° C. and atmospheric pressure. For example, propane-1,2-diol (alpha-propylene glycol) has a $pK_a$ value of 14.9 as measured in de-ionized water at 25° C. and atmospheric pressure.

If present, the alcohol (E) is preferably used as solvent in the compositions (Q2), (Q3), (Q4), or (Q5).

Preferably, the alcohol (E) is a diol, triol, tetraol, pentaol, hexaol, heptaol, octaol, nonaol, decaol, or a polyol. More preferably, (E) is a diol, triol, tetraol, pentaol, or hexaol. Most preferably, (E) is a diol. Particularly most preferably, the alcohol (E) is (L421) ethanediol (ethylene glycol), propanediol (propylene glycol), or butanediol (butylene glycol).

Particularly, (E) is propanediol (propylene glycol). For example, (E) is (L422) propane-1,2-diol (alpha-propylene glycol; CAS 57-55-6).

According to another preferred embodiment, the alcohol (E) is (L423) diethylene glycol.

According to another preferred embodiment, the alcohol (E) is (L424) 3-Methoxy-3-methyl-1-butanol (CAS 56539-66-3).

The alcohol (E) is preferably an alcohol having 2 to 50 carbon atoms, more preferably an alcohol having 2 to 20 carbon atoms, most preferably an alcohol having 2 to 11 carbon atoms, particularly preferably an alcohol having 2 to 7 carbon atoms, in particular an alcohol having 2 to 4 carbon atoms, for example an alcohol having 3 carbon atoms.

If present, the alcohol (E) can be contained in varying amounts in the composition (Q2), (Q3), (Q4), or (Q5). If present, the amount of (E) is preferably not more than 99 wt. % (wt. % stands for "percent by weight"), more preferably not more than 93 wt. %, most preferably not more than 87 wt. %, most particularly preferably not more than 80 wt. %, particularly not more than 75 wt. %, for example not more than 70 wt. %, based on the total weight of the composition (Q2), (Q3), (Q4), or (Q5). If present, the amount of (E) is at least 13 wt. %, more preferably at least 20 wt. %, most preferably at least 35 wt. %, most particularly preferably at least 45 wt. %, particularly at least 55 wt. %, for example at least 60 wt. %, based on the total weight of the composition (Q2), (Q3), (Q4), or (Q5).

According to another embodiment, the amount of (E) is preferably not more than 78 wt. %, more preferably not more than 67 wt. %, most preferably not more than 61 wt. %, most particularly preferably not more than 56 wt. %, particularly not more than 53 wt. %, for example not more than 50 wt. %, based on the total weight of the composition (Q2), (Q3), (Q4), or (Q5). Preferably, the amount of (E) is at least 16 wt. %, more preferably at least 21 wt. %, most preferably at least 26 wt. %, most particularly preferably at least 30 wt. %, particularly at least 37 wt. %, for example at least 40 wt. %, based on the total weight of the composition (Q2), (Q3), (Q4), or (Q5).

The composition (Q2), (Q3), (Q4), or (Q5) can further optionally comprise (F) a nitrogen-containing fertilizer. The nitrogen-containing fertilizer (F) is different from the components (A), (L1), (L2), (C) and (D).

The nitrogen-containing fertilizer (F) preferably comprises manure, ammonium sulfate, ammonium nitrate, ammonium chloride, cyanamide, dicyandiamide (DCD), calcium nitrate, or urea-containing fertilizer (F1), more preferably comprises urea-containing fertilizer (F1), most preferably comprises urea, for example is urea.

The urea-containing fertilizer (F1) is defined as a fertilizer comprising at least one component selected from the group consisting of urea, urea ammonium nitrate (UAN), isobutylidene diurea (IBDU), crotonylidene diurea (CDU) and urea formaldehyde (UF), urea-acetaldehyde, urea-glyoxal condensates, complex NPK fertilizer with urea as nitrogen source, physical blend of NPK fertilizer with urea as one mixing component.

In customary commercial fertilizer quality, the urea has a purity of at least 90%, and may for example be in crystalline, granulated, compacted, prilled, ground or liquid form.

In another preferred embodiment, the urea is coated urea, sulfur-coated urea, polymer-coated urea, fully coated urea, or partly coated urea.

The combination of the composition (Q2), (Q3), (Q4), or (Q5) and the fertilizer (F) can be done in different ways:

Incorporation during the fertilizer production process (composition is within the solid fertilizer granules, prills etc.)

application of the composition after fertilizer production process (composition is on the surface of the solid fertilizer granules, prills etc.)

Composition mixed with liquid fertilizer (tank mix).

If present, the fertilizer (F) can be contained in varying amounts in the composition (Q2), (Q3), (Q4), or (Q5). If present, the amount of (F) is preferably not more than 99.99 wt. % (wt. % stands for "percent by weight"), more preferably not more than 99.9 wt. %, most preferably not more than 99.5 wt. %, most particularly preferably not more than 99 wt. %, particularly not more than 98 wt. %, for example not more than 97 wt. %, based on the total weight of the composition (Q2), (Q3), (Q4), or (Q5). If present, the amount of (F) is preferably at least 96 wt. %, more preferably at least 93 wt. %, most preferably at least 90 wt. %, most particularly preferably at least 82 wt. %, particularly at least 70 wt. %, for example at least 50 wt. %, based on the total weight of the composition (Q2), (Q3), (Q4), or (Q5).

The properties of the composition (Q2), (Q3), (Q4), or (Q5)—such as stability, storage life, or stability when applied to or coated on nitrogen-containing fertilizers (F) such as urea—may depend on the pH of the corresponding composition. In general, the composition (Q2), (Q3), (Q4), or (Q5) can have any pH value. The pH value of the composition (Q2), (Q3), (Q4), or (Q5) is preferably not more than 14, more preferably not more than 13, most preferably not more than 12, particularly preferably not more than 11.6, particularly most preferably not more than 11.3, particularly not more than 11, for example not more than 10.7. The pH value of the composition (Q2), (Q3), (Q4), or (Q5) is preferably at least 6, more preferably at least 7, most preferably at least 7.5, particularly preferably at least 8.0, particularly most preferably at least 8.2, particularly at least 8.5, for example at least 8.7. The pH value of the composition (Q2), (Q3), (Q4), or (Q5) is preferably in the range of from 6 to 14, more preferably from 7 to 13, most preferably from 7.5 to 12, particularly preferably from 8 to 11.6, particularly most preferably from 8.2 to 11.3, particularly from 8.5 to 11, for example from 8.7 to 10.7.

The composition (Q2), (Q3), (Q4), or (Q5) can further optionally contain at least one pH adjusting agent (G). The pH adjusting agent (G) is different from the components (A), (L1), (L2), (C) and (D). In general, the pH adjusting agent (G) is a compound which is added to the composition (Q2), (Q3), (Q4), or (Q5) to have its pH value adjusted to the required value. Preferably, the composition (Q2), (Q3), (Q4), or (Q5) contains at least one pH adjusting agent (G). Preferred pH adjusting agents are inorganic acids, carboxylic acids, amine bases, alkali hydroxides, ammonium hydroxides, including tetraalkylammonium hydroxides. Particularly, the pH adjusting agent (G) is nitric acid, sulfuric acid, ammonia, sodium hydroxide, or potassium hydroxide. For example, the pH adjusting agent (G) is potassium hydroxide.

If present, the pH adjusting agent (G) can be contained in varying amounts in the composition (Q2), (Q3), (Q4), or (Q5). If present, the amount of (G) is preferably not more than 10 wt. %, more preferably not more than 2 wt. %, most preferably not more than 0.5 wt. %, particularly not more than 0.1 wt. %, for example not more than 0.05 wt. %, based on the total weight of the corresponding composition (Q2), (Q3), (Q4), or (Q5). If present, the amount of (G) is preferably at least 0.0005 wt. %, more preferably at least 0.005 wt. %, most preferably at least 0.025 wt. %, particularly at least 0.1 wt. %, for example at least 0.4 wt. %, based on the total weight of the corresponding composition (Q2), (Q3), (Q4), or (Q5).

The composition (Q2), (Q3), (Q4), or (Q5) can further optionally contain the compound (K) selected from the group consisting of (K1) an amine selected from the group consisting of
(L211) methyldiethanolamine,
(L212) tetrahydroxypropylethylenediamine,
(L213) trimethylaminoethylethanolamine,
(L214) N,N,N',N'-tetramethyl-1,6-hexanediamine,
(L215) N,N',N''-tris(dimethylaminopropyl)hexahydrotriazine, and
(L216) 2,2'-dimorpholinyldiethyl ether,
(K2) an amine containing not more than one amino group and at least three alkoxy- or hydroxy-substituted $C_2$ to $C_{12}$ alkyl groups $R^{41}$, wherein all groups $R^{41}$ within said amine are identical, and
(K3) an amine containing not more than one amino group and at least two alkoxy- or hydroxy-substituted $C_2$ to $C_{12}$ alkyl groups $R^{42}$, wherein at least one of the groups $R^{42}$ bears the alkoxy or hydroxy substituent at a secondary or tertiary carbon atom and wherein all groups $R^{42}$ with said amine are identical.

(K2) or (K3) are preferably
(L217) triethanolamine,
(L218) tripropanolamine,
(L219) diisopropanolamine,
(L220) triisopropanolamine,
(L221) diethanolamine, or
(L222) methyldipropanolamine.

If present, the compound (K) can generally be contained in varying amounts in the composition (Q2), (Q3), (Q4), or (Q5). If present, the amount of (K) is preferably not more than 40 wt. % (wt. % stands for "percent by weight"), more preferably not more than 30 wt. %, most preferably not more than 25 wt. %, most particularly preferably not more than 20 wt. %, particularly not more than 18 wt. %, for example not more than 15 wt. %, based on the total weight of the composition (Q2), (Q3), (Q4), or (Q5).). If present, the amount of (K) is preferably at least 1 wt. %, more preferably at least 3 wt. %, most preferably at least 5 wt. %, most particularly preferably at least 8 wt. %, particularly at least 11 wt. %, for example at least 14 wt. %, based on the total weight of the composition (Q2), (Q3), (Q4), or (Q5).

The composition (Q2), (Q3), (Q4), or (Q5) can further optionally contain a solvent or liquid carrier (M). (M) is preferably different from the components (A), (L1), (L2), (C) and (D).

Suitable solvents and liquid carriers are water and organic solvents, such as mineral oil fractions of medium to high boiling point, e.g. kerosene, diesel oil; oils of vegetable or animal origin; aliphatic, cyclic and aromatic hydrocarbons, e. g. toluene, paraffin, tetrahydronaphthalene, alkylated naphthalenes; alcohols, e.g. ethanol, propanol, butanol, cyclohexanol; glycols; DMSO; ketones, e.g. cyclohexanone; esters, e.g. lactates, carbonates, fatty acid esters, gamma-butyrolactone; fatty acids; phosphonates; amines; amides, e.g. N-methylpyrrolidone, fatty acid dimethylamides; and mixtures thereof.

If present, the solvent or liquid carrier (M) can be contained in varying amounts in the composition (Q2), (Q3), (Q4), or (Q5). If present, the amount of (M) is preferably not more than 99 wt. %, more preferably not more than 93 wt. %, most preferably not more than 87 wt. %, particularly preferably not more than 80 wt. %, most particularly preferably not more than 72 wt. %, particularly not more than 62 wt. %, for example not more than 50 wt. %, based on the total weight of the composition (Q2), (Q3), (Q4), or (Q5). If present, the amount of (M) is at least 15 wt. %, more preferably at least 25 wt. %, most preferably at least 35 wt. %, particularly preferably at least 45 wt. %, most particularly preferably at least 55 wt. %, particularly at least 65 wt. %, for example at least 74 wt. %, based on the total weight of the composition (Q2), (Q3), (Q4), or (Q5).

Preferred solvents or liquid carriers (M) are
(L425) benzyl alcohol;
(L418) DMSO;
(L419) sulfolane (alternative name: tetramethylene sulfone);
(L420) N-Methylpyrrolidone;
(L426) a mixture of propane-1,2-diol (alpha-propylene glycol; CAS 57-55-6) and DMSO;
(L427) a mixture of propane-1,2-diol (alpha-propylene glycol; CAS 57-55-6) and N,N-dimethyllactamide;
(L428) a mixture of propane-1,2-diol (alpha-propylene glycol; CAS 57-55-6) and N-formylmorpholine;
(L429) a mixture of benzyl alcohol and DMSO;
(L430) a mixture of benzyl alcohol and N,N-dimethyllactamide; or
(L431) a mixture of benzyl alcohol and N-formylmorpholine.

If present, the amount of DMSO is preferably not more than 70 wt. %, more preferably not more than 60 wt. %, most preferably not more than 50 wt. %, particularly preferably not more than 40 wt. %, most particularly preferably not more than 30 wt. %, particularly not more than 26 wt. %, for example not more than 22 wt. %, based on the total weight of the composition (Q2), (Q3), (Q4), or (Q5). If present, the amount of DMSO is at least 3 wt. %, more preferably at least 6 wt. %, most preferably at least 9 wt. %, particularly preferably at least 11 wt. %, most particularly preferably at least 13 wt. %, particularly at least 15 wt. %, for example at least 18 wt. %, based on the total weight of the composition (Q2), (Q3), (Q4), or (Q5).

The composition (Q2), (Q3), (Q4), or (Q5) can further optionally contain components (H) which are selected from the group consisting of auxiliaries, solid carriers, surfactants, adjuvants, thickeners, bactericides, anti-freezing agents, anti-foaming agents, colorants, tackifiers, binders, preservatives, antioxidants, and odorants. The component (H) is different from the components (A), (L1), (L2), (C) and (D).

Suitable auxiliaries are solid carriers or fillers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers and binders. One of the preferred auxiliaries is Neem oil or an extract of the Neem plant or Neem seed.

Suitable solid carriers or fillers are mineral earths, e.g. silicates, silica gels, talc, kaolins, limestone, lime, chalk, clays, dolomite, diatomaceous earth, bentonite, calcium sulfate, magnesium sulfate, magnesium oxide; polysaccharides, e.g. cellulose, starch; fertilizers, e.g. ammonium sulfate, ammonium phosphate, ammonium nitrate, ureas; products of vegetable origin, e.g. cereal meal, tree bark meal, wood meal, nutshell meal, and mixtures thereof.

Suitable surfactants are surface-active compounds, such as anionic, cationic, nonionic and amphoteric surfactants, block polymers, polyelectrolytes, and mixtures thereof. Such surfactants can be used as emulsifier, dispersant, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International Ed. or North American Ed.).

Suitable anionic surfactants are alkali, alkaline earth or ammonium salts of sulfonates, sulfates, phosphates, carboxylates, and mixtures thereof. Examples of sulfonates are alkylarylsulfonates, diphenylsulfonates, alpha-olefin sulfonates, lignine sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkylnaphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates.

Suitable nonionic surfactants are alkoxylates, N-substituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Examples of N-substituted fatty acid amides are fatty acid glucamides or fatty acid alkanolamides.

Examples of esters are fatty acid esters, glycerol esters or monoglycerides. Examples of sugar-based surfactants are sorbitans, ethoxylated sorbitans, sucrose and glucose esters or alkylpolyglucosides. Examples of polymeric surfactants are home- or copolymers of vinylpyrrolidone, vinylalcohols, or vinylacetate.

Suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B-C type comprising alkanol, polyethylene oxide and polypropylene oxide. Suitable polyelectrolytes are polyacids or polybases. Examples of polyacids are alkali salts of polyacrylic acid or polyacid comb polymers. Examples of polybases are polyvinylamines or polyethyleneamines.

Suitable adjuvants are compounds, which have a neglectable or even no pesticidal activity themselves, and which improve the biological performance of the compound I on the target. Examples are surfactants, mineral or vegetable oils, and other auxiliaries. Further examples are listed by Knowles, Adjuvants and additives, Agrow Reports DS256, T&F Informa UK, 2006, chapter 5.

Suitable thickeners are polysaccharides (e.g. xanthan gum, carboxymethylcellulose), anorganic clays (organically modified or unmodified), polycarboxylates, and silicates.

Suitable bactericides are bronopol and isothiazolinone derivatives such as alkylisothiazolinones and benzisothiazolinones.

Suitable anti-freezing agents are ethylene glycol, propylene glycol, urea and glycerin.

Suitable anti-foaming agents are silicones, long chain alcohols, and salts of fatty acids.

Suitable colorants (e.g. in red, blue, or green) are pigments of low water solubility and water-soluble dyes. Examples are
  inorganic colorants, such as iron oxide, titan oxide, iron hexacyanoferrate,
  metal-complex dyes such as chromium-complex dyes, for example Orasol Yellow 141,
  organic colorants such as alizarin-, azo- and phthalocyanine colorants.

Preferred colorants are metal-complex dyes, more preferably chromium-complex dyes, for example Orasol Yellow 141.

Suitable tackifiers or binders are polyvinylpyrrolidones, polyvinylacetates, polyvinyl alcohols, polyacrylates, biological or synthetic waxes, and cellulose ethers.

Suitable preservatives include e.g. sodium benzoate, benzoic acid, sorbic acid, and derivatives thereof.

Suitable antioxidants include sulfites, ascorbic acid, tocopherol, tocopherol acetate, tocotrienol, melatonin, carotene, beta-carotene, ubiquinol, and derivatives thereof. Tocophercol acetate is preferred as antioxidant.

Suitable odorants include perfume materials which are for example mentioned in U.S. Pat. No. 7,182,537, including allo-ocimene, Allyl cyclohexanepropionate, Allyl heptanoate, trans-Anethole, Benzyl butyrate, Camphene, Cadinene, Carvacrol, cis-3-Hexenyl tiglate, Citronellol, Citronellyl acetate, Citronellyl nitrile, Citronellyl propionate, Cyclohexylethyl acetate, Decyl Aldehyde (Capraldehyde), Dihydromyrcenol, Dihydromyrcenyl acetate, 3,7-Dimethyl-1-octanol, Diphenyloxide, Fenchyl Acetate (1,3,3-Trimethyl-2-norbornanyl acetate), Geranyl acetate, Geranyl formate, Geranyl nitrile, cis-3-Hexenyl isobutyrate, Hexyl Neopentanoate, Hexyl tiglate, alpha-Ionone, Ethyl Vanillin L80, Isoeugenol, Methyl cinnamate, Methyl dihydrojasmonate, Methyl beta-naphthyl ketone, Phenoxy ethyl isobutyrate, Vanillin L28, Isobornyl acetate, Isobutyl benzoate, Isononyl acetate, Isononyl alcohol (3,5,5-Trimethyl-1-hexanol), Isopulegyl acetate, Lauraldehyde, d-Limonene, Linalyl acetate, (−)-L-Menthyl acetate, Methyl Chavicol (Estragole), Methyl n-nonyl acetaldehyde, methyl octyl acetaldehyde, beta-Myrcene, Neryl acetate, Nonyl acetate, Nonaldehyde, p-Cymene, alpha-Pinene, beta-Pinene, alpha-Terpinene, gamma-Terpinene, alpha-Terpinyl acetate, Tetrahydrolinalool, Tetrahydromyrcenol, 2-Undecenal, Verdox (o-t-Butylcyclohexyl acetate), Vertenex (4-tert,Butylcyclohexyl acetate). Citronellyl nitrile is preferred as odorant.

According to one embodiment, individual components of the compositions (Q2), (Q3), (Q4), or (Q5) such as parts of a kit or parts of a binary or ternary mixture may be mixed by the user himself in a spray tank and further auxiliaries may be added, if appropriate.

If present, the component (H) can be contained in varying amounts in the composition (Q2), (Q3), (Q4), or (Q5). If present, the amount of (H) is preferably not more than 10 wt. %, more preferably not more than 4 wt. %, most preferably not more than 2 wt. %, particularly not more than 1 wt. %, for example not more than 0.5 wt. %, based on the total weight of the corresponding composition (Q2), (Q3), (Q4), or (Q5). If present, the amount of (H) is preferably at least 0.0005 wt. %, more preferably at least 0.005 wt. %, most preferably at least 0.025 wt. %, particularly at least 0.1 wt. %, for example at least 0.4 wt. %, based on the total weight of the corresponding composition (Q2), (Q3), (Q4), or (Q5).

With respect to the composition (Q2), (Q3), (Q4), or (Q5), the weight ratio of the mixture (A) to the amine (L1)—in case of (Q2), (Q3) or (Q5) only as far as (L1) is present—is preferably between 50:1 and 1:50, more preferably between 10:1 and 1:10, most preferably between 5:1 and 1:5, particularly preferably between 3:1 and 1:3, particularly most preferably between 2.5:1 and 1:2, particularly between 2:1 and 1:1, for example between 1.8:1 to 1.2:1

With respect to the composition (Q2), (Q3), (Q4), or (Q5), the weight ratio of the mixture (A) to the amine (C)—in case of (Q3), (Q4), or (Q5) only as far as (C) is present—is preferably between 100:1 and 1:20, more preferably between 40:1 and 1:8, most preferably between 30:1 and 1:6, particularly preferably between 20:1 and 1:5, particularly most preferably between 10:1 and 1:2, particularly between 5:1 and 1:1.2, for example between 2:1 to 1:1.

With respect to the composition (Q2), (Q3), (Q4), or (Q5), the weight ratio of the mixture (A) to the amide (D)—in case of (Q2), (Q4), or (Q5) only as far as (D) is present—is preferably between 50:1 and 1:50, more preferably between 10:1 and 1:10, most preferably between 5:1 and 1:5, particularly preferably between 3:1 and 1:3, particularly most preferably between 2.5:1 and 1:2, particularly between 2:1 and 1:1, for example between 1.8:1 to 1.2:1.

According to the invention, a process for treating the soil comprising applying the compositions (Q2), (Q3), (Q4), or (Q5) into the soil in-furrow and/or as side-dress and/or as broadcast was found.

Preferably, said process comprises: applying the compositions (Q2), (Q3), (Q4), or (Q5) by spraying it onto the soil. More preferably, said process are conducted in a way wherein the compositions (Q2), (Q3), (Q4), or (Q5) are—either at the same time (i.e. simultaneously) or with a time difference (i.e. separately)—applied together with at least one nitrogen-containing fertilizer (F) into the soil in-furrow and/or as side-dress and/or as broadcast.

According to the invention, the compositions (Q2), (Q3), (Q4), or (Q5) can be used as additive or as coating material for nitrogen-containing fertilizers (F), particularly for urea-containing fertilizer (F1), for example for urea. According to one preferred embodiment, the compositions (Q2), (Q3), (Q4), or (Q5) are used as coating material for nitrogen-containing fertilizers (F), particularly for urea-containing fertilizer (F1), for example for urea. The nitrogen-containing fertilizer (F) cam be in crystalline, granulated, compacted, prilled or ground form, and is preferably in granulated from.

The compositions (Q2), (Q3), (Q4), or (Q5) can be applied to or on nitrogen-containing fertilizers (F) by either mixing the (Q2), (Q3), (Q4), or (Q5), in either liquid or solid form, with the nitrogen-containing fertilizer (F), or incorporating them into (F) by granulation, compacting or prilling, by addition to a corresponding fertilizer mixture or to a mash or melt. Preferably, the compositions (Q2), (Q3), (Q4), or (Q5) are applied to the surface of existing granules, compacts or prills of the nitrogen-containing fertilizer (F)— particularly of the urea-containing fertilizer (F1)—by means of spraying, powder application or impregnating, for example. This can also be done using further auxiliaries such as adhesive promoters or encasing materials. Examples of apparatuses suitable for performing such application include plates, drums, mixers or fluidized-bed apparatus, although application may also take place on conveyor belts or their discharge points or by means of pneumatic conveyors for solids. A concluding treatment with anticaking agents and/or antidust agents is likewise possible. The compositions (Q2), (Q3), (Q4), or (Q5) are used in the context of fertilization with nitrogen-containing fertilizer (F), particularly with urea-containing fertilizer (F1). Application takes place preferably to an agriculturally or horticulturally exploited plot.

In parallel with the improvement of the utilization of nitrogen in the urea-containing, mineral and organic fertilizers, the use of the compositions (Q2), (Q3), (Q4), or (Q5) has the effect that there is an increase—in some cases considerably—in the yields or production of biomass of crop plants.

The compositions (Q2), (Q3), (Q4), or (Q5) may be added to organic fertilizers, such as liquid manure, for example, during the actual storage of such fertilizers, in order thus to prevent nitrogen nutrient losses, by virtue of decelerated conversion of the individual forms of nitrogen into gaseous nitrogen compounds, which are therefore volatile, and in order as a result, at the same time, to contribute to a lowering of the ammonia load in animal stables.

In this context it is immaterial whether the compositions (Q2), (Q3), (Q4), or (Q5) are incorporated, by melting, for example, into the nitrogen-containing fertilizer (F), or else are applied to the fertilizer surface or applied separately from the spreading of the fertilizer, in the form, for example, of a (suspension) concentrate, a solution or a formulation.

For the below examples, the below Table 1 and FIG. 1, the following abbreviations have been used:

"A" in the table header stands for mixture (A).

"(A1)"=technical mixture (with a 84.27% concentration of NxPT based on the total amount of the technical mixture) containing 23.7% NPPT and 76.3% NBPT, based on the total amount of NxPT within the technical mixture "AD25 formulation" stands for a composition comprising approx. 12-18 wt. % N,N-dimethyllactamide, approx. 30-35 wt. % benzyl alcohol, approx. 17-23 wt. % polyethyleneimine and approx. 27-33 wt. % (A1).

"i #" stands for the serial number of the composition.

"L #" stands for (L #) as listed above [for example, L101 stands for (L101)=ethylenediamine as listed above]

"(L)i"=first component [except mixture (A)] of the composition

"(L)ii"=second component [except mixture (A)] of the composition

"(L)iii"=third component [except mixture (A)] of the composition

"NBPT"=N-(n-butyl)thiophosphoric acid triamide

"NPPT"=N-(n-propyl)thiophosphoric acid triamide

"NxPT"=Mixture (A) comprising NBPT and NPPT (the content of NxPT is the sum of the content of NBPT and NPPT)

"Y"=Mixture (A) comprising NBPT and/or NPPT

For the preferred embodiments as listed in Table 1, the following abbreviations are used in addition to the abbreviations listed above:

(C1)=(L572) is a polymeric polyamine;

(C2)=(L25) is an amine containing not more than one amino group and at least three alkoxy- or hydroxy-substituted $C_2$ to $C_{12}$ alkyl groups $R^{21}$, wherein at least one of the groups $R^{21}$ is different to the other groups $R^{21}$;

(C3)=(L26) is an amine containing not more than one amino group and at least two alkoxy- or hydroxy-substituted $C_2$ to $C_{12}$ alkyl groups $R^{22}$, wherein at least one of the groups $R^{22}$ bears the alkoxy or hydroxy substituent at a secondary or tertiary carbon atom and wherein at least one of the groups $R^{22}$ is different to the other group(s) $R^{22}$;

(C4)=(L27) is an amine containing at least one saturated or unsaturated $C_8$ to $C40$ alkyl group $R^{23}$, and (C5)=(L28) is a saturated or unsaturated heterocyclic amine which contains at least one oxygen atom as ring atom and which does not contain a further alkoxy group.

(D1)=(L413) is an amide according to the general formula (VI)

wherein $R^{31}CO$ is a hydroxy-substituted acyl radical having 1 to 22 carbon atoms;

$R^{32}$ is H or $C_1$ to $C_4$ alkyl, and $R^{33}$ is H or $C_1$ to $C_4$ alkyl.

(D2)=(L414) is an amide according to the general formula (VI)

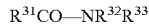

wherein $R^{31}CO$ is a is an acyl radical having 1 to 22 carbon atoms which do not contain a hydroxyl group;

$R^{32}$ is H or $C_1$ to $C_4$ alkyl, and $R^{33}$ is H or $C_1$ to $C_4$ alkyl.

(D3)=(L415) is an amide according to the general formula (VI)

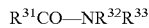

wherein $R^{31}CO$ is an acyl radical having 1 to 22 carbon atoms;

$R^{32}$ and $R^{33}$ together with the nitrogen atom linking them define a 6-membered saturated heterocyclic radical which comprises one further oxygen heteroatom.

(D4)=(L416) is an amide according to the general formula (VI)

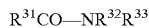

wherein $R^{31}CO$ is an acyl radical having 1 to 22 carbon atoms;

$R^{32}$ and $R^{33}$ together with the nitrogen atom linking them define a 5-membered saturated heterocyclic radical which comprises one further nitrogen heteroatom.

(D5)=(L417) is an amide according to the general formula (VI)

wherein $R^{31}CO$ is an acyl radical having 1 to 22 carbon atoms;

$R^{32}$ is an acyloxy substituted alkyl group, and $R^{33}$ is H or alkyl.

The most preferred composition (Q2), (Q3), or (Q4) is the AD25 formulation comprising approx. 13-17 wt. % N,N-dimethyllactamide, approx. 30-35 wt. % benzyl alcohol, approx. 18-22 wt. % polyethyleneimine and approx. 28-32 wt. % (A1). The most preferred polyethyleneimine is branched polyethyleneimine having a molecular weight of approx. 800 (GPC) and a charge density of approx. 16 meq/g of dry substance, determined at pH 4.5, and having a ratio primary/secondary/tertiary amino (as determined by 13C-NMR) of 1/0.9/0.5.

A particularly preferred composition (Q2) or (Q4) is a composition comprising (a) NBPT and/or NPPT, (b) propylene glycol (L422), and (c) polytriethanolamine (L619).

A further preferred composition (Q2) or (Q4) is a composition comprising (a) NBPT and/or NPPT, (b) propylene glycol (L422), and (c) a polytriethanolamine with a weight average molecular weight in the range of from 1,000 to 10,000 g/mol (L620).

A further preferred composition (Q2) or (Q4) is a composition comprising (a) NBPT and/or NPPT, (b) propylene glycol (L422), and (c) linear polyethyleneimine (L610).

A further preferred composition (Q2) or (Q4) is a composition comprising (a) NBPT and/or NPPT, (b) propylene glycol (L422), and (c) linear polyethyleneimine (L611).

A further preferred composition (Q2) or (Q4) is a composition comprising (a) NBPT and/or NPPT, (b) propylene glycol (L422), and (c) polyethyleneimine with 0.75 to 0.99 EO (ethylene oxide) per NH unit (L613).

A further preferred composition (Q2) or (Q4) is a composition comprising (a) NBPT and/or NPPT, (b) propylene glycol (L422), and (c) polyethyleneimine with 0.75 to 0.99 PO (propylene oxide) per NH unit (L614).

A further preferred composition (Q2) or (Q4) is a composition comprising (a) NBPT and/or NPPT, (b) propylene glycol (L422), and (c) a polymeric polyamine (L572).

A further preferred composition (Q2) or (Q4) is a composition comprising (a) NBPT and/or NPPT, (b) propylene glycol (L422), and (c) polyalkyleneimine (L568).

A further preferred composition (Q2) or (Q4) is a composition comprising (a) NBPT and/or NPPT, (b) propylene glycol (L422), and (c) polyethyleneimine (L569).

A further preferred composition (Q2) or (Q4) is a composition comprising (a) NBPT and/or NPPT, (b) propylene glycol (L422), and (c) homo- or copolymer of lysine (L587).

A further preferred composition (Q2) or (Q4) is a composition comprising (a) NBPT and/or NPPT, (b) propylene glycol (L422), and (c) a polylysin prepared by the above-specified process (L587P1) (L607).

A particularly preferred composition (Q2) or (Q4) is a composition comprising (a) NBPT and/or NPPT, (b) DMSO (L418), and (c) polytriethanolamine (L619).

A further preferred composition (Q2) or (Q4) is a composition comprising (a) NBPT and/or NPPT, (b) DMSO (L418), and (c) a polytriethanolamine with a weight average molecular weight in the range of from 1,000 to 10,000 g/mol (L620).

A further preferred composition (Q2) or (Q4) is a composition comprising (a) NBPT and/or NPPT, (b) DMSO (L418), and (c) linear polyethyleneimine (L610).

A further preferred composition (Q2) or (Q4) is a composition comprising (a) NBPT and/or NPPT, (b) DMSO (L418), and (c) linear polyethyleneimine (L611).

A further preferred composition (Q2) or (Q4) is a composition comprising (a) NBPT and/or NPPT, (b) DMSO (L418), and (c) polyethyleneimine with 0.75 to 0.99 EO (ethylene oxide) per NH unit (L613).

A further preferred composition (Q2) or (Q4) is a composition comprising (a) NBPT and/or NPPT, (b) DMSO (L418), and (c) polyethyleneimine with 0.75 to 0.99 PO (propylene oxide) per NH unit (L614).

A further preferred composition (Q2) or (Q4) is a composition comprising (a) NBPT and/or NPPT, (b) DMSO (L418), and (c) polymeric polyamine (L572).

A further preferred composition (Q2) or (Q4) is a composition comprising (a) NBPT and/or NPPT, (b) DMSO (L418), and (c) polyalkyleneimine (L568).

A further preferred composition (Q2) or (Q4) is a composition comprising (a) NBPT and/or NPPT, (b) DMSO (L418), and (c) polyethyleneimine (L569).

A further preferred composition (Q2) or (Q4) is a composition comprising (a) NBPT and/or NPPT, (b) DMSO (L418), and (c) homo- or copolymer of lysine (L587).

A further preferred composition (Q2) or (Q4) is a composition comprising (a) NBPT and/or NPPT, (b) DMSO (L418), and (c) a polylysin prepared by the above-specified process (L587P1) (L607).

A particularly preferred composition (Q2), (Q3) or (Q4) is a composition comprising (a) NBPT and/or NPPT, (b) N,N-dimethyllactamide (L427), and (c) polytriethanolamine (L619).

A further preferred composition (Q2), (Q3) or (Q4) is a composition comprising (a) NBPT and/or NPPT, (b) N,N-dimethyllactamide (L427), and (c) a polytriethanolamine with a weight average molecular weight in the range of from 1,000 to 10,000 g/mol (L620).

A further preferred composition (Q2), (Q3) or (Q4) is a composition comprising (a) NBPT and/or NPPT, (b) N,N-dimethyllactamide (L427), and (c) linear polyethyleneimine (L610).

A further preferred composition (Q2), (Q3) or (Q4) is a composition comprising (a) NBPT and/or NPPT, (b) N,N-dimethyllactamide (L427), and (c) linear polyethyleneimine (L611).

A further preferred composition (Q2), (Q3) or (Q4) is a composition comprising (a) NBPT and/or NPPT, (b) N,N-dimethyllactamide (L427), and (c) polyethyleneimine with 0.75 to 0.99 EO (ethylene oxide) per NH unit (L613).

A further preferred composition (Q2), (Q3) or (Q4) is a composition comprising (a) NBPT and/or NPPT, (b) N,N-dimethyllactamide (L427), and (c) polyethyleneimine with 0.75 to 0.99 PO (propylene oxide) per NH unit (L614).

A further preferred composition (Q2), (Q3) or (Q4) is a composition comprising (a) NBPT and/or NPPT, (b) N,N-dimethyllactamide (L427), and (c) polymeric polyamine (L572).

A further preferred composition (Q2), (Q3) or (Q4) is a composition comprising (a) NBPT and/or NPPT, (b) N,N-dimethyllactamide (L427), and (c) polyalkyleneimine (L568).

A further preferred composition (Q2), (Q3) or (Q4) is a composition comprising (a) NBPT and/or NPPT, (b) N,N-dimethyllactamide (L427), and (c) polyethyleneimine (L569).

A further preferred composition (Q2), (Q3) or (Q4) is a composition comprising (a) NBPT and/or NPPT, (b) N,N-dimethyllactamide (L427), and (c) homo- or copolymer of lysine (L587).

A further preferred composition (Q2), (Q3) or (Q4) is a composition comprising (a) NBPT and/or NPPT, (b) N,N-dimethyllactamide (L427), and (c) a polylysin prepared by the above-specified process (L587P1) (L607).

A particularly preferred composition (Q2), (Q3) or (Q4) is a composition comprising (a) NBPT and/or NPPT, (b) a mixture of propylene glycol and N,N-dimethyllactamide (L427), and (c) polytriethanolamine (L619).

A further preferred composition (Q2), (Q3) or (Q4) is a composition comprising (a) NBPT and/or NPPT, (b) a mixture of propylene glycol and N,N-dimethyllactamide (L427), and (c) a polytriethanolamine with a weight average molecular weight in the range of from 1,000 to 10,000 g/mol (L620).

A further preferred composition (Q2), (Q3) or (Q4) is a composition comprising (a) NBPT and/or NPPT, (b) a mixture of propylene glycol and N,N-dimethyllactamide (L427), and (c) linear polyethyleneimine (L610).

A further preferred composition (Q2), (Q3) or (Q4) is a composition comprising (a) NBPT and/or NPPT, (b) a mixture of propylene glycol and N,N-dimethyllactamide (L427), and (c) linear polyethyleneimine (L611).

A further preferred composition (Q2), (Q3) or (Q4) is a composition comprising (a) NBPT and/or NPPT, (b) a mixture of propylene glycol and N,N-dimethyllactamide (L427), and (c) polyethyleneimine with 0.75 to 0.99 EO (ethylene oxide) per NH unit (L613).

A further preferred composition (Q2), (Q3) or (Q4) is a composition comprising (a) NBPT and/or NPPT, (b) a mixture of propylene glycol and N,N-dimethyllactamide (L427), and (c) polyethyleneimine with 0.75 to 0.99 PO (propylene oxide) per NH unit (L614).

A further preferred composition (Q2), (Q3) or (Q4) is a composition comprising (a) NBPT and/or NPPT, (b) a mixture of propylene glycol and N,N-dimethyllactamide (L427), and (c) polymeric polyamine (L572).

A further preferred composition (Q2), (Q3) or (Q4) is a composition comprising (a) NBPT and/or NPPT, (b) a mixture of propylene glycol and N,N-dimethyllactamide (L427), and (c) polyalkyleneimine (L568).

A further preferred composition (Q2), (Q3) or (Q4) is a composition comprising (a) NBPT and/or NPPT, (b) a mixture of propylene glycol and N,N-dimethyllactamide (L427), and (c) polyethyleneimine (L569).

A further preferred composition (Q2), (Q3) or (Q4) is a composition comprising (a) NBPT and/or NPPT, (b) a mixture of propylene glycol and N,N-dimethyllactamide (L427), and (c) homo- or copolymer of lysine (L587).

A further preferred composition (Q2), (Q3) or (Q4) is a composition comprising (a) NBPT and/or NPPT, (b) a mixture of propylene glycol and N,N-dimethyllactamide (L427), and (c) a polylysin prepared by the above-specified process (L587P1) (L607).

A particularly preferred composition (Q2) or (Q4) is a composition comprising (a) NBPT and/or NPPT, (b) a mixture of propylene glycol and DMSO (L426), and (c) polytriethanolamine (L619).

A further preferred composition (Q2) or (Q4) is a composition comprising (a) NBPT and/or NPPT, (b) a mixture of propylene glycol and DMSO (L426), and (c) a polytriethanolamine with a weight average molecular weight in the range of from 1,000 to 10,000 g/mol (L620).

A further preferred composition (Q2) or (Q4) is a composition comprising (a) NBPT and/or NPPT, (b) a mixture of propylene glycol and DMSO (L426), and (c) linear polyethyleneimine (L610).

A further preferred composition (Q2) or (Q4) is a composition comprising (a) NBPT and/or NPPT, (b) a mixture of propylene glycol and DMSO (L426), and (c) linear polyethyleneimine (L611).

A further preferred composition (Q2) or (Q4) is a composition comprising (a) NBPT and/or NPPT, (b) a mixture of propylene glycol and DMSO (L426), and (c) polyethyleneimine with 0.75 to 0.99 EO (ethylene oxide) per NH unit (L613).

A further preferred composition (Q2) or (Q4) is a composition comprising (a) NBPT and/or NPPT, (b) a mixture of propylene glycol and DMSO (L426), and (c) polyethyleneimine with 0.75 to 0.99 PO (propylene oxide) per NH unit (L614).

A further preferred composition (Q2) or (Q4) is a composition comprising (a) NBPT and/or NPPT, (b) a mixture of propylene glycol and DMSO (L426), and (c) polymeric polyamine (L572).

A further preferred composition (Q2) or (Q4) is a composition comprising (a) NBPT and/or NPPT, (b) a mixture of propylene glycol and DMSO (L426), and (c) polyalkyleneimine (L568).

A further preferred composition (Q2) or (Q4) is a composition comprising (a) NBPT and/or NPPT, (b) a mixture of propylene glycol and DMSO (L426), and (c) polyethyleneimine (L569).

A further preferred composition (Q2) or (Q4) is a composition comprising (a) NBPT and/or NPPT, (b) a mixture of propylene glycol and DMSO (L426), and (c) homo- or copolymer of lysine (L587).

A further preferred composition (Q2) or (Q4) is a composition comprising (a) NBPT and/or NPPT, (b) a mixture of propylene glycol and DMSO (L426), and (c) a polylysin prepared by the above-specified process (L587P1) (L607).

A particularly preferred composition (Q2) or (Q4) is a composition comprising (a) 10-40 wt. %, preferably 20-30 wt. % NBPT and/or NPPT, (b) a mixture of 30-65 wt. %, preferably 40-55 wt. % propylene glycol and of 10-30 wt. %, preferably 15-25 wt. % DMSO (L426), and (c) 1-15 wt. %, preferably 4-11 wt. % polytriethanolamine (L619).

A further preferred composition (Q2) or (Q4) is a composition comprising (a) 10-40 wt. %, preferably 20-30 wt. % NBPT and/or NPPT, (b) a mixture of 30-65 wt. %, preferably 40-55 wt. % propylene glycol and of 10-30 wt. %, preferably 15-25 wt. % DMSO (L426), and (c) 1-15 wt. %, preferably 4-11 wt. % of a polytriethanolamine with a weight average molecular weight in the range of from 1,000 to 10,000 g/mol (L620).

A further preferred composition (Q2) or (Q4) is a composition comprising (a) 10-40 wt. %, preferably 20-30 wt. % NBPT and/or NPPT, (b) a mixture of 30-65 wt. %, preferably 40-55 wt. % propylene glycol and of 10-30 wt. %, preferably 15-25 wt. % DMSO (L426), and (c) 1-15 wt. %, preferably 4-11 wt. % linear polyethyleneimine (L610).

A further preferred composition (Q2) or (Q4) is a composition comprising (a) 10-40 wt. %, preferably 20-30 wt. % NBPT and/or NPPT, (b) a mixture of 30-65 wt. %, preferably 40-55 wt. % propylene glycol and of 10-30 wt. %, preferably 15-25 wt. % DMSO (L426), and (c) 1-15 wt. %, preferably 4-11 wt. % linear polyethyleneimine (L611).

A further preferred composition (Q2) or (Q4) is a composition comprising (a) 10-40 wt. %, preferably 20-30 wt. % NBPT and/or NPPT, (b) a mixture of 30-65 wt. %, preferably 40-55 wt. % propylene glycol and of 10-30 wt. %, preferably 15-25 wt. % DMSO (L426), and (c) 1-15 wt. %, preferably 4-11 wt. % polyethyleneimine with 0.75 to 0.99 EO (ethylene oxide) per NH unit (L613).

A further preferred composition (Q2) or (Q4) is a composition comprising (a) 10-40 wt. %, preferably 20-30 wt. % NBPT and/or NPPT, (b) a mixture of 30-65 wt. %, preferably 40-55 wt. % propylene glycol and of 10-30 wt. %, preferably 15-25 wt. % DMSO (L426), and (c) 1-15 wt. %, preferably 4-11 wt. % polyethyleneimine with 0.75 to 0.99 PO (propylene oxide) per NH unit (L614).

A further preferred composition (Q2) or (Q4) is a composition comprising (a) 10-40 wt. %, preferably 20-30 wt. % NBPT and/or NPPT, (b) a mixture of 30-65 wt. %, preferably 40-55 wt. % propylene glycol and of 10-30 wt. %, preferably 15-25 wt. % DMSO (L426), and (c) 1-15 wt. %, preferably 4-11 wt. % polymeric polyamine (L572).

A further preferred composition (Q2) or (Q4) is a composition comprising (a) 10-40 wt. %, preferably 20-30 wt. % NBPT and/or NPPT, (b) a mixture of 30-65 wt. %, preferably 40-55 wt. % propylene glycol and of 10-30 wt. %, preferably 15-25 wt. % DMSO (L426), and (c) 1-15 wt. %, preferably 4-11 wt. % polyalkyleneimine (L568).

A further preferred composition (Q2) or (Q4) is a composition comprising (a) 10-40 wt. %, preferably 20-30 wt. % NBPT and/or NPPT, (b) a mixture of 30-65 wt. %, preferably 40-55 wt. % propylene glycol and of 10-30 wt. %, preferably 15-25 wt. % DMSO (L426), and (c) 1-15 wt. %, preferably 4-11 wt. % polyethyleneimine (L569).

A further preferred composition (Q2) or (Q4) is a composition comprising (a) 10-40 wt. %, preferably 20-30 wt. % NBPT and/or NPPT, (b) a mixture of 30-65 wt. %, preferably 40-55 wt. % propylene glycol and of 10-30 wt. %, preferably 15-25 wt. % DMSO (L426), and (c) 1-15 wt. %, preferably 4-11 wt. % homo- or copolymer of lysine (L587).

A further preferred composition (Q2) or (Q4) is a composition comprising (a) 10-40 wt. %, preferably 20-30 wt. % NBPT and/or NPPT, (b) a mixture of 30-65 wt. %, preferably 40-55 wt. % propylene glycol and of 10-30 wt. %, preferably 15-25 wt. % DMSO (L426), and (c) 1-15 wt. %, preferably 4-11 wt. % of a polylysin prepared by the above-specified process (L587P1) (L607).

The above compositions comprising (a) NBPT and/or NPPT, (b) a mixture of propylene glycol and N,N-dimethyllactamide (L427), and (c) an amine are preferably prepared by (i) first dissolving NBPT and/or NPPT completely in propylene glycol, preferably under heating, and (ii) then adding N,N-dimethyllactamide and the amine and optionally further components such as the colorant to the mixture obtained in step (i).

The above compositions comprising (a) NBPT and/or NPPT, (b) a mixture of propylene glycol and DMSO (L426) and (c) an amine are preferably prepared by (i) first dissolving NBPT and/or NPPT completely in propylene glycol, preferably under heating, and (ii) then adding DMSO and the amine and optionally further components such as the colorant to the mixture obtained in step (i).

FIG. 1 shows the gaseous NH3 losses from urea treated or not treated with different (A1) formulations at urea fertilization.

The following compositions as listed in Table 1 are preferred embodiments of the present invention. The compositions "i1" to "i7840" as listed in Table 1 comprise the components (A), (L)i and (L)ii. The compositions "i7841" to "i9919" comprise the components (A), (L)i, (L)ii, and (L)iii.

TABLE 1

Compositions "i1" to "i9919"

| i# | A | (L)i | (L)ii | i# | A | (L)i | (L)ii | i# | A | (L)i | (L)ii | i# | A | (L)i | (L)ii |
|---|---|---|---|---|---|---|---|---|---|---|---|---|---|---|---|
| i1 | Y | L10 | — | i2 | Y | L10 | L422 | i3 | Y | L10 | L425 | i4 | Y | L10 | L418 |
| i5 | Y | L11 | — | i6 | Y | L11 | L422 | i7 | Y | L11 | L425 | i8 | Y | L11 | L418 |
| i9 | Y | L20 | — | i10 | Y | L20 | L422 | i11 | Y | L20 | L425 | i12 | Y | L20 | L418 |
| i13 | Y | L21 | — | i14 | Y | L21 | L422 | i15 | Y | L21 | L425 | i16 | Y | L21 | L418 |
| i17 | Y | L22 | — | i18 | Y | L22 | L422 | i19 | Y | L22 | L425 | i20 | Y | L22 | L418 |
| i21 | Y | L23 | — | i22 | Y | L23 | L422 | i23 | Y | L23 | L425 | i24 | Y | L23 | L418 |
| i25 | Y | L24 | — | i26 | Y | L24 | L422 | i27 | Y | L24 | L425 | i28 | Y | L24 | L418 |
| i29 | Y | L25 | — | i30 | Y | L25 | L422 | i31 | Y | L25 | L425 | i32 | Y | L25 | L418 |
| i33 | Y | L26 | — | i34 | Y | L26 | L422 | i35 | Y | L26 | L425 | i36 | Y | L26 | L418 |
| i37 | Y | L27 | — | i38 | Y | L27 | L422 | i39 | Y | L27 | L425 | i40 | Y | L27 | L418 |
| i41 | Y | L28 | — | i42 | Y | L28 | L422 | i43 | Y | L28 | L425 | i44 | Y | L28 | L418 |
| i45 | Y | L12 | — | i46 | Y | L12 | L422 | i47 | Y | L12 | L425 | i48 | Y | L12 | L418 |
| i49 | Y | L13 | — | i50 | Y | L13 | L422 | i51 | Y | L13 | L425 | i52 | Y | L13 | L418 |
| i53 | Y | L14 | — | i54 | Y | L14 | L422 | i55 | Y | L14 | L425 | i56 | Y | L14 | L418 |
| i57 | Y | L15 | — | i58 | Y | L15 | L422 | i59 | Y | L15 | L425 | i60 | Y | L15 | L418 |
| i61 | Y | L16 | — | i62 | Y | L16 | L422 | i63 | Y | L16 | L425 | i64 | Y | L16 | L418 |
| i65 | Y | L17 | — | i66 | Y | L17 | L422 | i67 | Y | L17 | L425 | i68 | Y | L17 | L418 |
| i69 | Y | L18 | — | i70 | Y | L18 | L422 | i71 | Y | L18 | L425 | i72 | Y | L18 | L418 |
| i73 | Y | L19 | — | i74 | Y | L19 | L422 | i75 | Y | L19 | L425 | i76 | Y | L19 | L418 |
| i77 | Y | L2 | — | i78 | Y | L2 | L422 | i79 | Y | L2 | L425 | i80 | Y | L2 | L418 |
| i81 | Y | L101 | — | i82 | Y | L101 | L422 | i83 | Y | L101 | L425 | i84 | Y | L101 | L418 |
| i85 | Y | L102 | — | i86 | Y | L102 | L422 | i87 | Y | L102 | L425 | i88 | Y | L102 | L418 |
| i89 | Y | L103 | — | i90 | Y | L103 | L422 | i91 | Y | L103 | L425 | i92 | Y | L103 | L418 |
| i93 | Y | L104 | — | i94 | Y | L104 | L422 | i95 | Y | L104 | L425 | i96 | Y | L104 | L418 |
| i97 | Y | L105 | — | i98 | Y | L105 | L422 | i99 | Y | L105 | L425 | i100 | Y | L105 | L418 |
| i101 | Y | L106 | — | i102 | Y | L106 | L422 | i103 | Y | L106 | L425 | i104 | Y | L106 | L418 |
| i105 | Y | L107 | — | i106 | Y | L107 | L422 | i107 | Y | L107 | L425 | i108 | Y | L107 | L418 |
| i109 | Y | L108 | — | i110 | Y | L108 | L422 | i111 | Y | L108 | L425 | i112 | Y | L108 | L418 |
| i113 | Y | L109 | — | i114 | Y | L109 | L422 | i115 | Y | L109 | L425 | i116 | Y | L109 | L418 |
| i117 | Y | L110 | — | i118 | Y | L110 | L422 | i119 | Y | L110 | L425 | i120 | Y | L110 | L418 |
| i121 | Y | L111 | — | i122 | Y | L111 | L422 | i123 | Y | L111 | L425 | i124 | Y | L111 | L418 |
| i125 | Y | L112 | — | i126 | Y | L112 | L422 | i127 | Y | L112 | L425 | i128 | Y | L112 | L418 |
| i129 | Y | L113 | — | i130 | Y | L113 | L422 | i131 | Y | L113 | L425 | i132 | Y | L113 | L418 |
| i133 | Y | L114 | — | i134 | Y | L114 | L422 | i135 | Y | L114 | L425 | i136 | Y | L114 | L418 |
| i137 | Y | L115 | — | i138 | Y | L115 | L422 | i139 | Y | L115 | L425 | i140 | Y | L115 | L418 |
| i141 | Y | L116 | — | i142 | Y | L116 | L422 | i143 | Y | L116 | L425 | i144 | Y | L116 | L418 |
| i145 | Y | L117 | — | i146 | Y | L117 | L422 | i147 | Y | L117 | L425 | i148 | Y | L117 | L418 |
| i149 | Y | L118 | — | i150 | Y | L118 | L422 | i151 | Y | L118 | L425 | i152 | Y | L118 | L418 |
| i153 | Y | L119 | — | i154 | Y | L119 | L422 | i155 | Y | L119 | L425 | i156 | Y | L119 | L418 |
| i157 | Y | L120 | — | i158 | Y | L120 | L422 | i159 | Y | L120 | L425 | i160 | Y | L120 | L418 |
| i161 | Y | L121 | — | i162 | Y | L121 | L422 | i163 | Y | L121 | L425 | i164 | Y | L121 | L418 |
| i165 | Y | L122 | — | i166 | Y | L122 | L422 | i167 | Y | L122 | L425 | i168 | Y | L122 | L418 |
| i169 | Y | L123 | — | i170 | Y | L123 | L422 | i171 | Y | L123 | L425 | i172 | Y | L123 | L418 |
| i173 | Y | L124 | — | i174 | Y | L124 | L422 | i175 | Y | L124 | L425 | i176 | Y | L124 | L418 |
| i177 | Y | L125 | — | i178 | Y | L125 | L422 | i179 | Y | L125 | L425 | i180 | Y | L125 | L418 |
| i181 | Y | L126 | — | i182 | Y | L126 | L422 | i183 | Y | L126 | L425 | i184 | Y | L126 | L418 |
| i185 | Y | L127 | — | i186 | Y | L127 | L422 | i187 | Y | L127 | L425 | i188 | Y | L127 | L418 |
| i189 | Y | L128 | — | i190 | Y | L128 | L422 | i191 | Y | L128 | L425 | i192 | Y | L128 | L418 |
| i193 | Y | L129 | — | i194 | Y | L129 | L422 | i195 | Y | L129 | L425 | i196 | Y | L129 | L418 |
| i197 | Y | L130 | — | i198 | Y | L130 | L422 | i199 | Y | L130 | L425 | i200 | Y | L130 | L418 |
| i201 | Y | L131 | — | i202 | Y | L131 | L422 | i203 | Y | L131 | L425 | i204 | Y | L131 | L418 |
| i205 | Y | L132 | — | i206 | Y | L132 | L422 | i207 | Y | L132 | L425 | i208 | Y | L132 | L418 |
| i209 | Y | L133 | — | i210 | Y | L133 | L422 | i211 | Y | L133 | L425 | i212 | Y | L133 | L418 |
| i213 | Y | L134 | — | i214 | Y | L134 | L422 | i215 | Y | L134 | L425 | i216 | Y | L134 | L418 |
| i217 | Y | L135 | — | i218 | Y | L135 | L422 | i219 | Y | L135 | L425 | i220 | Y | L135 | L418 |
| i221 | Y | L136 | — | i222 | Y | L136 | L422 | i223 | Y | L136 | L425 | i224 | Y | L136 | L418 |
| i225 | Y | L137 | — | i226 | Y | L137 | L422 | i227 | Y | L137 | L425 | i228 | Y | L137 | L418 |
| i229 | Y | L138 | — | i230 | Y | L138 | L422 | i231 | Y | L138 | L425 | i232 | Y | L138 | L418 |
| i233 | Y | L139 | — | i234 | Y | L139 | L422 | i235 | Y | L139 | L425 | i236 | Y | L139 | L418 |
| i237 | Y | L140 | — | i238 | Y | L140 | L422 | i239 | Y | L140 | L425 | i240 | Y | L140 | L418 |
| i241 | Y | L141 | — | i242 | Y | L141 | L422 | i243 | Y | L141 | L425 | i244 | Y | L141 | L418 |
| i245 | Y | L142 | — | i246 | Y | L142 | L422 | i247 | Y | L142 | L425 | i248 | Y | L142 | L418 |
| i249 | Y | L143 | — | i250 | Y | L143 | L422 | i251 | Y | L143 | L425 | i252 | Y | L143 | L418 |
| i253 | Y | L144 | — | i254 | Y | L144 | L422 | i255 | Y | L144 | L425 | i256 | Y | L144 | L418 |
| i257 | Y | L145 | — | i258 | Y | L145 | L422 | i259 | Y | L145 | L425 | i260 | Y | L145 | L418 |
| i261 | Y | L146 | — | i262 | Y | L146 | L422 | i263 | Y | L146 | L425 | i264 | Y | L146 | L418 |
| i265 | Y | L147 | — | i266 | Y | L147 | L422 | i267 | Y | L147 | L425 | i268 | Y | L147 | L418 |
| i269 | Y | L148 | — | i270 | Y | L148 | L422 | i271 | Y | L148 | L425 | i272 | Y | L148 | L418 |
| i273 | Y | L149 | — | i274 | Y | L149 | L422 | i275 | Y | L149 | L425 | i276 | Y | L149 | L418 |
| i277 | Y | L150 | — | i278 | Y | L150 | L422 | i279 | Y | L150 | L425 | i280 | Y | L150 | L418 |
| i281 | Y | L151 | — | i282 | Y | L151 | L422 | i283 | Y | L151 | L425 | i284 | Y | L151 | L418 |

TABLE 1-continued

Compositions "i1" to "i9919"

| | | | | | | | | | | | | | | | |
|---|---|---|---|---|---|---|---|---|---|---|---|---|---|---|---|
| i285 | Y | L152 | — | i286 | Y | L152 | L422 | i287 | Y | L152 | L425 | i288 | Y | L152 | L418 |
| i289 | Y | L153 | — | i290 | Y | L153 | L422 | i291 | Y | L153 | L425 | i292 | Y | L153 | L418 |
| i293 | Y | L154 | — | i294 | Y | L154 | L422 | i295 | Y | L154 | L425 | i296 | Y | L154 | L418 |
| i297 | Y | L155 | — | i298 | Y | L155 | L422 | i299 | Y | L155 | L425 | i300 | Y | L155 | L418 |
| i301 | Y | L156 | — | i302 | Y | L156 | L422 | i303 | Y | L156 | L425 | i304 | Y | L156 | L418 |
| i305 | Y | L157 | — | i306 | Y | L157 | L422 | i307 | Y | L157 | L425 | i308 | Y | L157 | L418 |
| i309 | Y | L158 | — | i310 | Y | L158 | L422 | i311 | Y | L158 | L425 | i312 | Y | L158 | L418 |
| i313 | Y | L159 | — | i314 | Y | L159 | L422 | i315 | Y | L159 | L425 | i316 | Y | L159 | L418 |
| i317 | Y | L160 | — | i318 | Y | L160 | L422 | i319 | Y | L160 | L425 | i320 | Y | L160 | L418 |
| i321 | Y | L161 | — | i322 | Y | L161 | L422 | i323 | Y | L161 | L425 | i324 | Y | L161 | L418 |
| i325 | Y | L162 | — | i326 | Y | L162 | L422 | i327 | Y | L162 | L425 | i328 | Y | L162 | L418 |
| i329 | Y | L163 | — | i330 | Y | L163 | L422 | i331 | Y | L163 | L425 | i332 | Y | L163 | L418 |
| i333 | Y | L164 | — | i334 | Y | L164 | L422 | i335 | Y | L164 | L425 | i336 | Y | L164 | L418 |
| i337 | Y | L165 | — | i338 | Y | L165 | L422 | i339 | Y | L165 | L425 | i340 | Y | L165 | L418 |
| i341 | Y | L166 | — | i342 | Y | L166 | L422 | i343 | Y | L166 | L425 | i344 | Y | L166 | L418 |
| i345 | Y | L167 | — | i346 | Y | L167 | L422 | i347 | Y | L167 | L425 | i348 | Y | L167 | L418 |
| i349 | Y | L168 | — | i350 | Y | L168 | L422 | i351 | Y | L168 | L425 | i352 | Y | L168 | L418 |
| i353 | Y | L169 | — | i354 | Y | L169 | L422 | i355 | Y | L169 | L425 | i356 | Y | L169 | L418 |
| i357 | Y | L170 | — | i358 | Y | L170 | L422 | i359 | Y | L170 | L425 | i360 | Y | L170 | L418 |
| i361 | Y | L171 | — | i362 | Y | L171 | L422 | i363 | Y | L171 | L425 | i364 | Y | L171 | L418 |
| i365 | Y | L172 | — | i366 | Y | L172 | L422 | i367 | Y | L172 | L425 | i368 | Y | L172 | L418 |
| i369 | Y | L173 | — | i370 | Y | L173 | L422 | i371 | Y | L173 | L425 | i372 | Y | L173 | L418 |
| i373 | Y | L174 | — | i374 | Y | L174 | L422 | i375 | Y | L174 | L425 | i376 | Y | L174 | L418 |
| i377 | Y | L175 | — | i378 | Y | L175 | L422 | i379 | Y | L175 | L425 | i380 | Y | L175 | L418 |
| i381 | Y | L176 | — | i382 | Y | L176 | L422 | i383 | Y | L176 | L425 | i384 | Y | L176 | L418 |
| i385 | Y | L177 | — | i386 | Y | L177 | L422 | i387 | Y | L177 | L425 | i388 | Y | L177 | L418 |
| i389 | Y | L178 | — | i390 | Y | L178 | L422 | i391 | Y | L178 | L425 | i392 | Y | L178 | L418 |
| i393 | Y | L179 | — | i394 | Y | L179 | L422 | i395 | Y | L179 | L425 | i396 | Y | L179 | L418 |
| i397 | Y | L180 | — | i398 | Y | L180 | L422 | i399 | Y | L180 | L425 | i400 | Y | L180 | L418 |
| i401 | Y | L181 | — | i402 | Y | L181 | L422 | i403 | Y | L181 | L425 | i404 | Y | L181 | L418 |
| i405 | Y | L182 | — | i406 | Y | L182 | L422 | i407 | Y | L182 | L425 | i408 | Y | L182 | L418 |
| i409 | Y | L183 | — | i410 | Y | L183 | L422 | i411 | Y | L183 | L425 | i412 | Y | L183 | L418 |
| i413 | Y | L184 | — | i414 | Y | L184 | L422 | i415 | Y | L184 | L425 | i416 | Y | L184 | L418 |
| i417 | Y | L185 | — | i418 | Y | L185 | L422 | i419 | Y | L185 | L425 | i420 | Y | L185 | L418 |
| i421 | Y | L186 | — | i422 | Y | L186 | L422 | i423 | Y | L186 | L425 | i424 | Y | L186 | L418 |
| i425 | Y | L187 | — | i426 | Y | L187 | L422 | i427 | Y | L187 | L425 | i428 | Y | L187 | L418 |
| i429 | Y | L188 | — | i430 | Y | L188 | L422 | i431 | Y | L188 | L425 | i432 | Y | L188 | L418 |
| i433 | Y | L189 | — | i434 | Y | L189 | L422 | i435 | Y | L189 | L425 | i436 | Y | L189 | L418 |
| i437 | Y | L190 | — | i438 | Y | L190 | L422 | i439 | Y | L190 | L425 | i440 | Y | L190 | L418 |
| i441 | Y | L191 | — | i442 | Y | L191 | L422 | i443 | Y | L191 | L425 | i444 | Y | L191 | L418 |
| i445 | Y | L192 | — | i446 | Y | L192 | L422 | i447 | Y | L192 | L425 | i448 | Y | L192 | L418 |
| i449 | Y | L193 | — | i450 | Y | L193 | L422 | i451 | Y | L193 | L425 | i452 | Y | L193 | L418 |
| i453 | Y | L194 | — | i454 | Y | L194 | L422 | i455 | Y | L194 | L425 | i456 | Y | L194 | L418 |
| i457 | Y | L195 | — | i458 | Y | L195 | L422 | i459 | Y | L195 | L425 | i460 | Y | L195 | L418 |
| i461 | Y | L196 | — | i462 | Y | L196 | L422 | i463 | Y | L196 | L425 | i464 | Y | L196 | L418 |
| i465 | Y | L197 | — | i466 | Y | L197 | L422 | i467 | Y | L197 | L425 | i468 | Y | L197 | L418 |
| i469 | Y | L198 | — | i470 | Y | L198 | L422 | i471 | Y | L198 | L425 | i472 | Y | L198 | L418 |
| i473 | Y | L199 | — | i474 | Y | L199 | L422 | i475 | Y | L199 | L425 | i476 | Y | L199 | L418 |
| i477 | Y | L200 | — | i478 | Y | L200 | L422 | i479 | Y | L200 | L425 | i480 | Y | L200 | L418 |
| i481 | Y | L201 | — | i482 | Y | L201 | L422 | i483 | Y | L201 | L425 | i484 | Y | L201 | L418 |
| i485 | Y | L202 | — | i486 | Y | L202 | L422 | i487 | Y | L202 | L425 | i488 | Y | L202 | L418 |
| i489 | Y | L203 | — | i490 | Y | L203 | L422 | i491 | Y | L203 | L425 | i492 | Y | L203 | L418 |
| i493 | Y | L204 | — | i494 | Y | L204 | L422 | i495 | Y | L204 | L425 | i496 | Y | L204 | L418 |
| i497 | Y | L205 | — | i498 | Y | L205 | L422 | i499 | Y | L205 | L425 | i500 | Y | L205 | L418 |
| i501 | Y | L206 | — | i502 | Y | L206 | L422 | i503 | Y | L206 | L425 | i504 | Y | L206 | L418 |
| i505 | Y | L207 | — | i506 | Y | L207 | L422 | i507 | Y | L207 | L425 | i508 | Y | L207 | L418 |
| i509 | Y | L208 | — | i510 | Y | L208 | L422 | i511 | Y | L208 | L425 | i512 | Y | L208 | L418 |
| i513 | Y | L209 | — | i514 | Y | L209 | L422 | i515 | Y | L209 | L425 | i516 | Y | L209 | L418 |
| i517 | Y | L210 | — | i518 | Y | L210 | L422 | i519 | Y | L210 | L425 | i520 | Y | L210 | L418 |
| i521 | Y | L211 | — | i522 | Y | L211 | L422 | i523 | Y | L211 | L425 | i524 | Y | L211 | L418 |
| i525 | Y | L212 | — | i526 | Y | L212 | L422 | i527 | Y | L212 | L425 | i528 | Y | L212 | L418 |
| i529 | Y | L213 | — | i530 | Y | L213 | L422 | i531 | Y | L213 | L425 | i532 | Y | L213 | L418 |
| i533 | Y | L214 | — | i534 | Y | L214 | L422 | i535 | Y | L214 | L425 | i536 | Y | L214 | L418 |
| i537 | Y | L215 | — | i538 | Y | L215 | L422 | i539 | Y | L215 | L425 | i540 | Y | L215 | L418 |
| i541 | Y | L216 | — | i542 | Y | L216 | L422 | i543 | Y | L216 | L425 | i544 | Y | L216 | L418 |
| i545 | Y | L217 | — | i546 | Y | L217 | L422 | i547 | Y | L217 | L425 | i548 | Y | L217 | L418 |
| i549 | Y | L218 | — | i550 | Y | L218 | L422 | i551 | Y | L218 | L425 | i552 | Y | L218 | L418 |
| i553 | Y | L219 | — | i554 | Y | L219 | L422 | i555 | Y | L219 | L425 | i556 | Y | L219 | L418 |
| i557 | Y | L220 | — | i558 | Y | L220 | L422 | i559 | Y | L220 | L425 | i560 | Y | L220 | L418 |
| i561 | Y | L221 | — | i562 | Y | L221 | L422 | i563 | Y | L221 | L425 | i564 | Y | L221 | L418 |
| i565 | Y | L222 | — | i566 | Y | L222 | L422 | i567 | Y | L222 | L425 | i568 | Y | L222 | L418 |
| i569 | Y | L401 | — | i570 | Y | L401 | L422 | i571 | Y | L401 | L425 | i572 | Y | L401 | L418 |
| i573 | Y | L402 | — | i574 | Y | L402 | L422 | i575 | Y | L402 | L425 | i576 | Y | L402 | L418 |
| i577 | Y | L403 | — | i578 | Y | L403 | L422 | i579 | Y | L403 | L425 | i580 | Y | L403 | L418 |
| i581 | Y | L404 | — | i582 | Y | L404 | L422 | i583 | Y | L404 | L425 | i584 | Y | L404 | L418 |
| i585 | Y | L405 | — | i586 | Y | L405 | L422 | i587 | Y | L405 | L425 | i588 | Y | L405 | L418 |
| i589 | Y | L406 | — | i590 | Y | L406 | L422 | i591 | Y | L406 | L425 | i592 | Y | L406 | L418 |
| i593 | Y | L407 | — | i594 | Y | L407 | L422 | i595 | Y | L407 | L425 | i596 | Y | L407 | L418 |

TABLE 1-continued

Compositions "i1" to "i9919"

| | | | | | | | | | | | | | | | |
|---|---|---|---|---|---|---|---|---|---|---|---|---|---|---|---|
| i597 | Y | L408 | — | i598 | Y | L408 | L422 | i599 | Y | L408 | L425 | i600 | Y | L408 | L418 |
| i601 | Y | L409 | — | i602 | Y | L409 | L422 | i603 | Y | L409 | L425 | i604 | Y | L409 | L418 |
| i605 | Y | L410 | — | i606 | Y | L410 | L422 | i607 | Y | L410 | L425 | i608 | Y | L410 | L418 |
| i609 | Y | L411 | — | i610 | Y | L411 | L422 | i611 | Y | L411 | L425 | i612 | Y | L411 | L418 |
| i613 | Y | L412 | — | i614 | Y | L412 | L422 | i615 | Y | L412 | L425 | i616 | Y | L412 | L418 |
| i617 | Y | L413 | — | i618 | Y | L413 | L422 | i619 | Y | L413 | L425 | i620 | Y | L413 | L418 |
| i621 | Y | L414 | — | i622 | Y | L414 | L422 | i623 | Y | L414 | L425 | i624 | Y | L414 | L418 |
| i625 | Y | L415 | — | i626 | Y | L415 | L422 | i627 | Y | L415 | L425 | i628 | Y | L415 | L418 |
| i629 | Y | L416 | — | i630 | Y | L416 | L422 | i631 | Y | L416 | L425 | i632 | Y | L416 | L418 |
| i633 | Y | L417 | — | i634 | Y | L417 | L422 | i635 | Y | L417 | L425 | i636 | Y | L417 | L418 |
| i637 | Y | L418 | — | i638 | Y | L418 | L422 | i639 | Y | L418 | L425 | i640 | Y | L418 | L418 |
| i641 | Y | L419 | — | i642 | Y | L419 | L422 | i643 | Y | L419 | L425 | i644 | Y | L419 | L418 |
| i645 | Y | L420 | — | i646 | Y | L420 | L422 | i647 | Y | L420 | L425 | i648 | Y | L420 | L418 |
| i649 | Y | L421 | — | i650 | Y | L421 | L422 | i651 | Y | L421 | L425 | i652 | Y | L421 | L418 |
| i653 | Y | L422 | — | i654 | Y | L422 | L422 | i655 | Y | L422 | L425 | i656 | Y | L422 | L418 |
| i657 | Y | L423 | — | i658 | Y | L423 | L422 | i659 | Y | L423 | L425 | i660 | Y | L423 | L418 |
| i661 | Y | L424 | — | i662 | Y | L424 | L422 | i663 | Y | L424 | L425 | i664 | Y | L424 | L418 |
| i665 | Y | L425 | — | i666 | Y | L425 | L422 | i667 | Y | L425 | L425 | i668 | Y | L425 | L418 |
| i669 | Y | L501 | — | i670 | Y | L501 | L422 | i671 | Y | L501 | L425 | i672 | Y | L501 | L418 |
| i673 | Y | L502 | — | i674 | Y | L502 | L422 | i675 | Y | L502 | L425 | i676 | Y | L502 | L418 |
| i677 | Y | L503 | — | i678 | Y | L503 | L422 | i679 | Y | L503 | L425 | i680 | Y | L503 | L418 |
| i681 | Y | L504 | — | i682 | Y | L504 | L422 | i683 | Y | L504 | L425 | i684 | Y | L504 | L418 |
| i685 | Y | L505 | — | i686 | Y | L505 | L422 | i687 | Y | L505 | L425 | i688 | Y | L505 | L418 |
| i689 | Y | L506 | — | i690 | Y | L506 | L422 | i691 | Y | L506 | L425 | i692 | Y | L506 | L418 |
| i693 | Y | L507 | — | i694 | Y | L507 | L422 | i695 | Y | L507 | L425 | i696 | Y | L507 | L418 |
| i697 | Y | L508 | — | i698 | Y | L508 | L422 | i699 | Y | L508 | L425 | i700 | Y | L508 | L418 |
| i701 | Y | L509 | — | i702 | Y | L509 | L422 | i703 | Y | L509 | L425 | i704 | Y | L509 | L418 |
| i705 | Y | L510 | — | i706 | Y | L510 | L422 | i707 | Y | L510 | L425 | i708 | Y | L510 | L418 |
| i709 | Y | L511 | — | i710 | Y | L511 | L422 | i711 | Y | L511 | L425 | i712 | Y | L511 | L418 |
| i713 | Y | L512 | — | i714 | Y | L512 | L422 | i715 | Y | L512 | L425 | i716 | Y | L512 | L418 |
| i717 | Y | L513 | — | i718 | Y | L513 | L422 | i719 | Y | L513 | L425 | i720 | Y | L513 | L418 |
| i721 | Y | L514 | — | i722 | Y | L514 | L422 | i723 | Y | L514 | L425 | i724 | Y | L514 | L418 |
| i725 | Y | L515 | — | i726 | Y | L515 | L422 | i727 | Y | L515 | L425 | i728 | Y | L515 | L418 |
| i729 | Y | L516 | — | i730 | Y | L516 | L422 | i731 | Y | L516 | L425 | i732 | Y | L516 | L418 |
| i733 | Y | L517 | — | i734 | Y | L517 | L422 | i735 | Y | L517 | L425 | i736 | Y | L517 | L418 |
| i737 | Y | L518 | — | i738 | Y | L518 | L422 | i739 | Y | L518 | L425 | i740 | Y | L518 | L418 |
| i741 | Y | L519 | — | i742 | Y | L519 | L422 | i743 | Y | L519 | L425 | i744 | Y | L519 | L418 |
| i745 | Y | L520 | — | i746 | Y | L520 | L422 | i747 | Y | L520 | L425 | i748 | Y | L520 | L418 |
| i749 | Y | L521 | — | i750 | Y | L521 | L422 | i751 | Y | L521 | L425 | i752 | Y | L521 | L418 |
| i753 | Y | L522 | — | i754 | Y | L522 | L422 | i755 | Y | L522 | L425 | i756 | Y | L522 | L418 |
| i757 | Y | L523 | — | i758 | Y | L523 | L422 | i759 | Y | L523 | L425 | i760 | Y | L523 | L418 |
| i761 | Y | L524 | — | i762 | Y | L524 | L422 | i763 | Y | L524 | L425 | i764 | Y | L524 | L418 |
| i765 | Y | L525 | — | i766 | Y | L525 | L422 | i767 | Y | L525 | L425 | i768 | Y | L525 | L418 |
| i769 | Y | L526 | — | i770 | Y | L526 | L422 | i771 | Y | L526 | L425 | i772 | Y | L526 | L418 |
| i773 | Y | L527 | — | i774 | Y | L527 | L422 | i775 | Y | L527 | L425 | i776 | Y | L527 | L418 |
| i777 | Y | L528 | — | i778 | Y | L528 | L422 | i779 | Y | L528 | L425 | i780 | Y | L528 | L418 |
| i781 | Y | L529 | — | i782 | Y | L529 | L422 | i783 | Y | L529 | L425 | i784 | Y | L529 | L418 |
| i785 | Y | L530 | — | i786 | Y | L530 | L422 | i787 | Y | L530 | L425 | i788 | Y | L530 | L418 |
| i789 | Y | L531 | — | i790 | Y | L531 | L422 | i791 | Y | L531 | L425 | i792 | Y | L531 | L418 |
| i793 | Y | L532 | — | i794 | Y | L532 | L422 | i795 | Y | L532 | L425 | i796 | Y | L532 | L418 |
| i797 | Y | L533 | — | i798 | Y | L533 | L422 | i799 | Y | L533 | L425 | i800 | Y | L533 | L418 |
| i801 | Y | L534 | — | i802 | Y | L534 | L422 | i803 | Y | L534 | L425 | i804 | Y | L534 | L418 |
| i805 | Y | L535 | — | i806 | Y | L535 | L422 | i807 | Y | L535 | L425 | i808 | Y | L535 | L418 |
| i809 | Y | L536 | — | i810 | Y | L536 | L422 | i811 | Y | L536 | L425 | i812 | Y | L536 | L418 |
| i813 | Y | L537 | — | i814 | Y | L537 | L422 | i815 | Y | L537 | L425 | i816 | Y | L537 | L418 |
| i817 | Y | L538 | — | i818 | Y | L538 | L422 | i819 | Y | L538 | L425 | i820 | Y | L538 | L418 |
| i821 | Y | L539 | — | i822 | Y | L539 | L422 | i823 | Y | L539 | L425 | i824 | Y | L539 | L418 |
| i825 | Y | L540 | — | i826 | Y | L540 | L422 | i827 | Y | L540 | L425 | i828 | Y | L540 | L418 |
| i829 | Y | L541 | — | i830 | Y | L541 | L422 | i831 | Y | L541 | L425 | i832 | Y | L541 | L418 |
| i833 | Y | L542 | — | i834 | Y | L542 | L422 | i835 | Y | L542 | L425 | i836 | Y | L542 | L418 |
| i837 | Y | L543 | — | i838 | Y | L543 | L422 | i839 | Y | L543 | L425 | i840 | Y | L543 | L418 |
| i841 | Y | L544 | — | i842 | Y | L544 | L422 | i843 | Y | L544 | L425 | i844 | Y | L544 | L418 |
| i845 | Y | L545 | — | i846 | Y | L545 | L422 | i847 | Y | L545 | L425 | i848 | Y | L545 | L418 |
| i849 | Y | L546 | — | i850 | Y | L546 | L422 | i851 | Y | L546 | L425 | i852 | Y | L546 | L418 |
| i853 | Y | L547 | — | i854 | Y | L547 | L422 | i855 | Y | L547 | L425 | i856 | Y | L547 | L418 |
| i857 | Y | L548 | — | i858 | Y | L548 | L422 | i859 | Y | L548 | L425 | i860 | Y | L548 | L418 |
| i861 | Y | L549 | — | i862 | Y | L549 | L422 | i863 | Y | L549 | L425 | i864 | Y | L549 | L418 |
| i865 | Y | L550 | — | i866 | Y | L550 | L422 | i867 | Y | L550 | L425 | i868 | Y | L550 | L418 |
| i869 | Y | L551 | — | i870 | Y | L551 | L422 | i871 | Y | L551 | L425 | i872 | Y | L551 | L418 |
| i873 | Y | L552 | — | i874 | Y | L552 | L422 | i875 | Y | L552 | L425 | i876 | Y | L552 | L418 |
| i877 | Y | L553 | — | i878 | Y | L553 | L422 | i879 | Y | L553 | L425 | i880 | Y | L553 | L418 |
| i881 | Y | L554 | — | i882 | Y | L554 | L422 | i883 | Y | L554 | L425 | i884 | Y | L554 | L418 |
| i885 | Y | L555 | — | i886 | Y | L555 | L422 | i887 | Y | L555 | L425 | i888 | Y | L555 | L418 |
| i889 | Y | L556 | — | i890 | Y | L556 | L422 | i891 | Y | L556 | L425 | i892 | Y | L556 | L418 |
| i893 | Y | L557 | — | i894 | Y | L557 | L422 | i895 | Y | L557 | L425 | i896 | Y | L557 | L418 |
| i897 | Y | L558 | — | i898 | Y | L558 | L422 | i899 | Y | L558 | L425 | i900 | Y | L558 | L418 |
| i901 | Y | L559 | — | i902 | Y | L559 | L422 | i903 | Y | L559 | L425 | i904 | Y | L559 | L418 |
| i905 | Y | L560 | — | i906 | Y | L560 | L422 | i907 | Y | L560 | L425 | i908 | Y | L560 | L418 |

TABLE 1-continued

Compositions "i1" to "i9919"

| | | | | | | | | | | | | | | |
|---|---|---|---|---|---|---|---|---|---|---|---|---|---|---|
| i909 | Y | L561 | — | i910 | Y | L561 | L422 | i911 | Y | L561 | L425 | i912 | Y | L561 | L418 |
| i913 | Y | L562 | — | i914 | Y | L562 | L422 | i915 | Y | L562 | L425 | i916 | Y | L562 | L418 |
| i917 | Y | L563 | — | i918 | Y | L563 | L422 | i919 | Y | L563 | L425 | i920 | Y | L563 | L418 |
| i921 | Y | L564 | — | i922 | Y | L564 | L422 | i923 | Y | L564 | L425 | i924 | Y | L564 | L418 |
| i925 | Y | L565 | — | i926 | Y | L565 | L422 | i927 | Y | L565 | L425 | i928 | Y | L565 | L418 |
| i929 | Y | L566 | — | i930 | Y | L566 | L422 | i931 | Y | L566 | L425 | i932 | Y | L566 | L418 |
| i933 | Y | L567 | — | i934 | Y | L567 | L422 | i935 | Y | L567 | L425 | i936 | Y | L567 | L418 |
| i937 | Y | L568 | — | i938 | Y | L568 | L422 | i939 | Y | L568 | L425 | i940 | Y | L568 | L418 |
| i941 | Y | L569 | — | i942 | Y | L569 | L422 | i943 | Y | L569 | L425 | i944 | Y | L569 | L418 |
| i945 | Y | L570 | — | i946 | Y | L570 | L422 | i947 | Y | L570 | L425 | i948 | Y | L570 | L418 |
| i949 | Y | L571 | — | i950 | Y | L571 | L422 | i951 | Y | L571 | L425 | i952 | Y | L571 | L418 |
| i953 | Y | L572 | — | i954 | Y | L572 | L422 | i955 | Y | L572 | L425 | i956 | Y | L572 | L418 |
| i957 | Y | L843 | — | i958 | Y | L843 | L422 | i959 | Y | L843 | L425 | i960 | Y | L843 | L418 |
| i961 | Y | L844 | — | i962 | Y | L844 | L422 | i963 | Y | L844 | L425 | i964 | Y | L844 | L418 |
| i965 | Y | L845 | — | i966 | Y | L845 | L422 | i967 | Y | L845 | L425 | i968 | Y | L845 | L418 |
| i969 | Y | L846 | — | i970 | Y | L846 | L422 | i971 | Y | L846 | L425 | i972 | Y | L846 | L418 |
| i973 | Y | L847 | — | i974 | Y | L847 | L422 | i975 | Y | L847 | L425 | i976 | Y | L847 | L418 |
| i977 | Y | L848 | — | i978 | Y | L848 | L422 | i979 | Y | L848 | L425 | i980 | Y | L848 | L418 |
| i981 | Y | L10 | L423 | i982 | Y | L10 | L424 | i983 | Y | L10 | L419 | i984 | Y | L10 | L410 |
| i985 | Y | L11 | L423 | i986 | Y | L11 | L424 | i987 | Y | L11 | L419 | i988 | Y | L11 | L410 |
| i989 | Y | L20 | L423 | i990 | Y | L20 | L424 | i991 | Y | L20 | L419 | i992 | Y | L20 | L410 |
| i993 | Y | L21 | L423 | i994 | Y | L21 | L424 | i995 | Y | L21 | L419 | i996 | Y | L21 | L410 |
| i997 | Y | L22 | L423 | i998 | Y | L22 | L424 | i999 | Y | L22 | L419 | i1000 | Y | L22 | L410 |
| i1001 | Y | L23 | L423 | i1002 | Y | L23 | L424 | i1003 | Y | L23 | L419 | i1004 | Y | L23 | L410 |
| i1005 | Y | L24 | L423 | i1006 | Y | L24 | L424 | i1007 | Y | L24 | L419 | i1008 | Y | L24 | L410 |
| i1009 | Y | L25 | L423 | i1010 | Y | L25 | L424 | i1011 | Y | L25 | L419 | i1012 | Y | L25 | L410 |
| i1013 | Y | L26 | L423 | i1014 | Y | L26 | L424 | i1015 | Y | L26 | L419 | i1016 | Y | L26 | L410 |
| i1017 | Y | L27 | L423 | i1018 | Y | L27 | L424 | i1019 | Y | L27 | L419 | i1020 | Y | L27 | L410 |
| i1021 | Y | L28 | L423 | i1022 | Y | L28 | L424 | i1023 | Y | L28 | L419 | i1024 | Y | L28 | L410 |
| i1025 | Y | L12 | L423 | i1026 | Y | L12 | L424 | i1027 | Y | L12 | L419 | i1028 | Y | L12 | L410 |
| i1029 | Y | L13 | L423 | i1030 | Y | L13 | L424 | i1031 | Y | L13 | L419 | i1032 | Y | L13 | L410 |
| i1033 | Y | L14 | L423 | i1034 | Y | L14 | L424 | i1035 | Y | L14 | L419 | i1036 | Y | L14 | L410 |
| i1037 | Y | L15 | L423 | i1038 | Y | L15 | L424 | i1039 | Y | L15 | L419 | i1040 | Y | L15 | L410 |
| i1041 | Y | L16 | L423 | i1042 | Y | L16 | L424 | i1043 | Y | L16 | L419 | i1044 | Y | L16 | L410 |
| i1045 | Y | L17 | L423 | i1046 | Y | L17 | L424 | i1047 | Y | L17 | L419 | i1048 | Y | L17 | L410 |
| i1049 | Y | L18 | L423 | i1050 | Y | L18 | L424 | i1051 | Y | L18 | L419 | i1052 | Y | L18 | L410 |
| i1053 | Y | L19 | L423 | i1054 | Y | L19 | L424 | i1055 | Y | L19 | L419 | i1056 | Y | L19 | L410 |
| i1057 | Y | L2 | L423 | i1058 | Y | L2 | L424 | i1059 | Y | L2 | L419 | i1060 | Y | L2 | L410 |
| i1061 | Y | L101 | L423 | i1062 | Y | L101 | L424 | i1063 | Y | L101 | L419 | i1064 | Y | L101 | L410 |
| i1065 | Y | L102 | L423 | i1066 | Y | L102 | L424 | i1067 | Y | L102 | L419 | i1068 | Y | L102 | L410 |
| i1069 | Y | L103 | L423 | i1070 | Y | L103 | L424 | i1071 | Y | L103 | L419 | i1072 | Y | L103 | L410 |
| i1073 | Y | L104 | L423 | i1074 | Y | L104 | L424 | i1075 | Y | L104 | L419 | i1076 | Y | L104 | L410 |
| i1077 | Y | L105 | L423 | i1078 | Y | L105 | L424 | i1079 | Y | L105 | L419 | i1080 | Y | L105 | L410 |
| i1081 | Y | L106 | L423 | i1082 | Y | L106 | L424 | i1083 | Y | L106 | L419 | i1084 | Y | L106 | L410 |
| i1085 | Y | L107 | L423 | i1086 | Y | L107 | L424 | i1087 | Y | L107 | L419 | i1088 | Y | L107 | L410 |
| i1089 | Y | L108 | L423 | i1090 | Y | L108 | L424 | i1091 | Y | L108 | L419 | i1092 | Y | L108 | L410 |
| i1093 | Y | L109 | L423 | i1094 | Y | L109 | L424 | i1095 | Y | L109 | L419 | i1096 | Y | L109 | L410 |
| i1097 | Y | L110 | L423 | i1098 | Y | L110 | L424 | i1099 | Y | L110 | L419 | i1100 | Y | L110 | L410 |
| i1101 | Y | L111 | L423 | i1102 | Y | L111 | L424 | i1103 | Y | L111 | L419 | i1104 | Y | L111 | L410 |
| i1105 | Y | L112 | L423 | i1106 | Y | L112 | L424 | i1107 | Y | L112 | L419 | i1108 | Y | L112 | L410 |
| i1109 | Y | L113 | L423 | i1110 | Y | L113 | L424 | i1111 | Y | L113 | L419 | i1112 | Y | L113 | L410 |
| i1113 | Y | L114 | L423 | i1114 | Y | L114 | L424 | i1115 | Y | L114 | L419 | i1116 | Y | L114 | L410 |
| i1117 | Y | L115 | L423 | i1118 | Y | L115 | L424 | i1119 | Y | L115 | L419 | i1120 | Y | L115 | L410 |
| i1121 | Y | L116 | L423 | i1122 | Y | L116 | L424 | i1123 | Y | L116 | L419 | i1124 | Y | L116 | L410 |
| i1125 | Y | L117 | L423 | i1126 | Y | L117 | L424 | i1127 | Y | L117 | L419 | i1128 | Y | L117 | L410 |
| i1129 | Y | L118 | L423 | i1130 | Y | L118 | L424 | i1131 | Y | L118 | L419 | i1132 | Y | L118 | L410 |
| i1133 | Y | L119 | L423 | i1134 | Y | L119 | L424 | i1135 | Y | L119 | L419 | i1136 | Y | L119 | L410 |
| i1137 | Y | L120 | L423 | i1138 | Y | L120 | L424 | i1139 | Y | L120 | L419 | i1140 | Y | L120 | L410 |
| i1141 | Y | L121 | L423 | i1142 | Y | L121 | L424 | i1143 | Y | L121 | L419 | i1144 | Y | L121 | L410 |
| i1145 | Y | L122 | L423 | i1146 | Y | L122 | L424 | i1147 | Y | L122 | L419 | i1148 | Y | L122 | L410 |
| i1149 | Y | L123 | L423 | i1150 | Y | L123 | L424 | i1151 | Y | L123 | L419 | i1152 | Y | L123 | L410 |
| i1153 | Y | L124 | L423 | i1154 | Y | L124 | L424 | i1155 | Y | L124 | L419 | i1156 | Y | L124 | L410 |
| i1157 | Y | L125 | L423 | i1158 | Y | L125 | L424 | i1159 | Y | L125 | L419 | i1160 | Y | L125 | L410 |
| i1161 | Y | L126 | L423 | i1162 | Y | L126 | L424 | i1163 | Y | L126 | L419 | i1164 | Y | L126 | L410 |
| i1165 | Y | L127 | L423 | i1166 | Y | L127 | L424 | i1167 | Y | L127 | L419 | i1168 | Y | L127 | L410 |
| i1169 | Y | L128 | L423 | i1170 | Y | L128 | L424 | i1171 | Y | L128 | L419 | i1172 | Y | L128 | L410 |
| i1173 | Y | L129 | L423 | i1174 | Y | L129 | L424 | i1175 | Y | L129 | L419 | i1176 | Y | L129 | L410 |
| i1177 | Y | L130 | L423 | i1178 | Y | L130 | L424 | i1179 | Y | L130 | L419 | i1180 | Y | L130 | L410 |
| i1181 | Y | L131 | L423 | i1182 | Y | L131 | L424 | i1183 | Y | L131 | L419 | i1184 | Y | L131 | L410 |
| i1185 | Y | L132 | L423 | i1186 | Y | L132 | L424 | i1187 | Y | L132 | L419 | i1188 | Y | L132 | L410 |
| i1189 | Y | L133 | L423 | i1190 | Y | L133 | L424 | i1191 | Y | L133 | L419 | i1192 | Y | L133 | L410 |
| i1193 | Y | L134 | L423 | i1194 | Y | L134 | L424 | i1195 | Y | L134 | L419 | i1196 | Y | L134 | L410 |
| i1197 | Y | L135 | L423 | i1198 | Y | L135 | L424 | i1199 | Y | L135 | L419 | i1200 | Y | L135 | L410 |
| i1201 | Y | L136 | L423 | i1202 | Y | L136 | L424 | i1203 | Y | L136 | L419 | i1204 | Y | L136 | L410 |
| i1205 | Y | L137 | L423 | i1206 | Y | L137 | L424 | i1207 | Y | L137 | L419 | i1208 | Y | L137 | L410 |
| i1209 | Y | L138 | L423 | i1210 | Y | L138 | L424 | i1211 | Y | L138 | L419 | i1212 | Y | L138 | L410 |
| i1213 | Y | L139 | L423 | i1214 | Y | L139 | L424 | i1215 | Y | L139 | L419 | i1216 | Y | L139 | L410 |
| i1217 | Y | L140 | L423 | i1218 | Y | L140 | L424 | i1219 | Y | L140 | L419 | i1220 | Y | L140 | L410 |

TABLE 1-continued

Compositions "i1" to "i9919"

| | | | | | | | | | | | | |
|---|---|---|---|---|---|---|---|---|---|---|---|---|
| i1221 | Y | L141 | L423 | i1222 | Y | L141 | L424 | i1223 | Y | L141 | L419 | i1224 | Y | L141 | L410 |
| i1225 | Y | L142 | L423 | i1226 | Y | L142 | L424 | i1227 | Y | L142 | L419 | i1228 | Y | L142 | L410 |
| i1229 | Y | L143 | L423 | i1230 | Y | L143 | L424 | i1231 | Y | L143 | L419 | i1232 | Y | L143 | L410 |
| i1233 | Y | L144 | L423 | i1234 | Y | L144 | L424 | i1235 | Y | L144 | L419 | i1236 | Y | L144 | L410 |
| i1237 | Y | L145 | L423 | i1238 | Y | L145 | L424 | i1239 | Y | L145 | L419 | i1240 | Y | L145 | L410 |
| i1241 | Y | L146 | L423 | i1242 | Y | L146 | L424 | i1243 | Y | L146 | L419 | i1244 | Y | L146 | L410 |
| i1245 | Y | L147 | L423 | i1246 | Y | L147 | L424 | i1247 | Y | L147 | L419 | i1248 | Y | L147 | L410 |
| i1249 | Y | L148 | L423 | i1250 | Y | L148 | L424 | i1251 | Y | L148 | L419 | i1252 | Y | L148 | L410 |
| i1253 | Y | L149 | L423 | i1254 | Y | L149 | L424 | i1255 | Y | L149 | L419 | i1256 | Y | L149 | L410 |
| i1257 | Y | L150 | L423 | i1258 | Y | L150 | L424 | i1259 | Y | L150 | L419 | i1260 | Y | L150 | L410 |
| i1261 | Y | L151 | L423 | i1262 | Y | L151 | L424 | i1263 | Y | L151 | L419 | i1264 | Y | L151 | L410 |
| i1265 | Y | L152 | L423 | i1266 | Y | L152 | L424 | i1267 | Y | L152 | L419 | i1268 | Y | L152 | L410 |
| i1269 | Y | L153 | L423 | i1270 | Y | L153 | L424 | i1271 | Y | L153 | L419 | i1272 | Y | L153 | L410 |
| i1273 | Y | L154 | L423 | i1274 | Y | L154 | L424 | i1275 | Y | L154 | L419 | i1276 | Y | L154 | L410 |
| i1277 | Y | L155 | L423 | i1278 | Y | L155 | L424 | i1279 | Y | L155 | L419 | i1280 | Y | L155 | L410 |
| i1281 | Y | L156 | L423 | i1282 | Y | L156 | L424 | i1283 | Y | L156 | L419 | i1284 | Y | L156 | L410 |
| i1285 | Y | L157 | L423 | i1286 | Y | L157 | L424 | i1287 | Y | L157 | L419 | i1288 | Y | L157 | L410 |
| i1289 | Y | L158 | L423 | i1290 | Y | L158 | L424 | i1291 | Y | L158 | L419 | i1292 | Y | L158 | L410 |
| i1293 | Y | L159 | L423 | i1294 | Y | L159 | L424 | i1295 | Y | L159 | L419 | i1296 | Y | L159 | L410 |
| i1297 | Y | L160 | L423 | i1298 | Y | L160 | L424 | i1299 | Y | L160 | L419 | i1300 | Y | L160 | L410 |
| i1301 | Y | L161 | L423 | i1302 | Y | L161 | L424 | i1303 | Y | L161 | L419 | i1304 | Y | L161 | L410 |
| i1305 | Y | L162 | L423 | i1306 | Y | L162 | L424 | i1307 | Y | L162 | L419 | i1308 | Y | L162 | L410 |
| i1309 | Y | L163 | L423 | i1310 | Y | L163 | L424 | i1311 | Y | L163 | L419 | i1312 | Y | L163 | L410 |
| i1313 | Y | L164 | L423 | i1314 | Y | L164 | L424 | i1315 | Y | L164 | L419 | i1316 | Y | L164 | L410 |
| i1317 | Y | L165 | L423 | i1318 | Y | L165 | L424 | i1319 | Y | L165 | L419 | i1320 | Y | L165 | L410 |
| i1321 | Y | L166 | L423 | i1322 | Y | L166 | L424 | i1323 | Y | L166 | L419 | i1324 | Y | L166 | L410 |
| i1325 | Y | L167 | L423 | i1326 | Y | L167 | L424 | i1327 | Y | L167 | L419 | i1328 | Y | L167 | L410 |
| i1329 | Y | L168 | L423 | i1330 | Y | L168 | L424 | i1331 | Y | L168 | L419 | i1332 | Y | L168 | L410 |
| i1333 | Y | L169 | L423 | i1334 | Y | L169 | L424 | i1335 | Y | L169 | L419 | i1336 | Y | L169 | L410 |
| i1337 | Y | L170 | L423 | i1338 | Y | L170 | L424 | i1339 | Y | L170 | L419 | i1340 | Y | L170 | L410 |
| i1341 | Y | L171 | L423 | i1342 | Y | L171 | L424 | i1343 | Y | L171 | L419 | i1344 | Y | L171 | L410 |
| i1345 | Y | L172 | L423 | i1346 | Y | L172 | L424 | i1347 | Y | L172 | L419 | i1348 | Y | L172 | L410 |
| i1349 | Y | L173 | L423 | i1350 | Y | L173 | L424 | i1351 | Y | L173 | L419 | i1352 | Y | L173 | L410 |
| i1353 | Y | L174 | L423 | i1354 | Y | L174 | L424 | i1355 | Y | L174 | L419 | i1356 | Y | L174 | L410 |
| i1357 | Y | L175 | L423 | i1358 | Y | L175 | L424 | i1359 | Y | L175 | L419 | i1360 | Y | L175 | L410 |
| i1361 | Y | L176 | L423 | i1362 | Y | L176 | L424 | i1363 | Y | L176 | L419 | i1364 | Y | L176 | L410 |
| i1365 | Y | L177 | L423 | i1366 | Y | L177 | L424 | i1367 | Y | L177 | L419 | i1368 | Y | L177 | L410 |
| i1369 | Y | L178 | L423 | i1370 | Y | L178 | L424 | i1371 | Y | L178 | L419 | i1372 | Y | L178 | L410 |
| i1373 | Y | L179 | L423 | i1374 | Y | L179 | L424 | i1375 | Y | L179 | L419 | i1376 | Y | L179 | L410 |
| i1377 | Y | L180 | L423 | i1378 | Y | L180 | L424 | i1379 | Y | L180 | L419 | i1380 | Y | L180 | L410 |
| i1381 | Y | L181 | L423 | i1382 | Y | L181 | L424 | i1383 | Y | L181 | L419 | i1384 | Y | L181 | L410 |
| i1385 | Y | L182 | L423 | i1386 | Y | L182 | L424 | i1387 | Y | L182 | L419 | i1388 | Y | L182 | L410 |
| i1389 | Y | L183 | L423 | i1390 | Y | L183 | L424 | i1391 | Y | L183 | L419 | i1392 | Y | L183 | L410 |
| i1393 | Y | L184 | L423 | i1394 | Y | L184 | L424 | i1395 | Y | L184 | L419 | i1396 | Y | L184 | L410 |
| i1397 | Y | L185 | L423 | i1398 | Y | L185 | L424 | i1399 | Y | L185 | L419 | i1400 | Y | L185 | L410 |
| i1401 | Y | L186 | L423 | i1402 | Y | L186 | L424 | i1403 | Y | L186 | L419 | i1404 | Y | L186 | L410 |
| i1405 | Y | L187 | L423 | i1406 | Y | L187 | L424 | i1407 | Y | L187 | L419 | i1408 | Y | L187 | L410 |
| i1409 | Y | L188 | L423 | i1410 | Y | L188 | L424 | i1411 | Y | L188 | L419 | i1412 | Y | L188 | L410 |
| i1413 | Y | L189 | L423 | i1414 | Y | L189 | L424 | i1415 | Y | L189 | L419 | i1416 | Y | L189 | L410 |
| i1417 | Y | L190 | L423 | i1418 | Y | L190 | L424 | i1419 | Y | L190 | L419 | i1420 | Y | L190 | L410 |
| i1421 | Y | L191 | L423 | i1422 | Y | L191 | L424 | i1423 | Y | L191 | L419 | i1424 | Y | L191 | L410 |
| i1425 | Y | L192 | L423 | i1426 | Y | L192 | L424 | i1427 | Y | L192 | L419 | i1428 | Y | L192 | L410 |
| i1429 | Y | L193 | L423 | i1430 | Y | L193 | L424 | i1431 | Y | L193 | L419 | i1432 | Y | L193 | L410 |
| i1433 | Y | L194 | L423 | i1434 | Y | L194 | L424 | i1435 | Y | L194 | L419 | i1436 | Y | L194 | L410 |
| i1437 | Y | L195 | L423 | i1438 | Y | L195 | L424 | i1439 | Y | L195 | L419 | i1440 | Y | L195 | L410 |
| i1441 | Y | L196 | L423 | i1442 | Y | L196 | L424 | i1443 | Y | L196 | L419 | i1444 | Y | L196 | L410 |
| i1445 | Y | L197 | L423 | i1446 | Y | L197 | L424 | i1447 | Y | L197 | L419 | i1448 | Y | L197 | L410 |
| i1449 | Y | L198 | L423 | i1450 | Y | L198 | L424 | i1451 | Y | L198 | L419 | i1452 | Y | L198 | L410 |
| i1453 | Y | L199 | L423 | i1454 | Y | L199 | L424 | i1455 | Y | L199 | L419 | i1456 | Y | L199 | L410 |
| i1457 | Y | L200 | L423 | i1458 | Y | L200 | L424 | i1459 | Y | L200 | L419 | i1460 | Y | L200 | L410 |
| i1461 | Y | L201 | L423 | i1462 | Y | L201 | L424 | i1463 | Y | L201 | L419 | i1464 | Y | L201 | L410 |
| i1465 | Y | L202 | L423 | i1466 | Y | L202 | L424 | i1467 | Y | L202 | L419 | i1468 | Y | L202 | L410 |
| i1469 | Y | L203 | L423 | i1470 | Y | L203 | L424 | i1471 | Y | L203 | L419 | i1472 | Y | L203 | L410 |
| i1473 | Y | L204 | L423 | i1474 | Y | L204 | L424 | i1475 | Y | L204 | L419 | i1476 | Y | L204 | L410 |
| i1477 | Y | L205 | L423 | i1478 | Y | L205 | L424 | i1479 | Y | L205 | L419 | i1480 | Y | L205 | L410 |
| i1481 | Y | L206 | L423 | i1482 | Y | L206 | L424 | i1483 | Y | L206 | L419 | i1484 | Y | L206 | L410 |
| i1485 | Y | L207 | L423 | i1486 | Y | L207 | L424 | i1487 | Y | L207 | L419 | i1488 | Y | L207 | L410 |
| i1489 | Y | L208 | L423 | i1490 | Y | L208 | L424 | i1491 | Y | L208 | L419 | i1492 | Y | L208 | L410 |
| i1493 | Y | L209 | L423 | i1494 | Y | L209 | L424 | i1495 | Y | L209 | L419 | i1496 | Y | L209 | L410 |
| i1497 | Y | L210 | L423 | i1498 | Y | L210 | L424 | i1499 | Y | L210 | L419 | i1500 | Y | L210 | L410 |
| i1501 | Y | L211 | L423 | i1502 | Y | L211 | L424 | i1503 | Y | L211 | L419 | i1504 | Y | L211 | L410 |
| i1505 | Y | L212 | L423 | i1506 | Y | L212 | L424 | i1507 | Y | L212 | L419 | i1508 | Y | L212 | L410 |
| i1509 | Y | L213 | L423 | i1510 | Y | L213 | L424 | i1511 | Y | L213 | L419 | i1512 | Y | L213 | L410 |
| i1513 | Y | L214 | L423 | i1514 | Y | L214 | L424 | i1515 | Y | L214 | L419 | i1516 | Y | L214 | L410 |
| i1517 | Y | L215 | L423 | i1518 | Y | L215 | L424 | i1519 | Y | L215 | L419 | i1520 | Y | L215 | L410 |
| i1521 | Y | L216 | L423 | i1522 | Y | L216 | L424 | i1523 | Y | L216 | L419 | i1524 | Y | L216 | L410 |
| i1525 | Y | L217 | L423 | i1526 | Y | L217 | L424 | i1527 | Y | L217 | L419 | i1528 | Y | L217 | L410 |
| i1529 | Y | L218 | L423 | i1530 | Y | L218 | L424 | i1531 | Y | L218 | L419 | i1532 | Y | L218 | L410 |

TABLE 1-continued

Compositions "i1" to "i9919"

| | | | | | | | | | | | | | | |
|---|---|---|---|---|---|---|---|---|---|---|---|---|---|---|
| i1533 | Y | L219 | L423 | i1534 | Y | L219 | L424 | i1535 | Y | L219 | L419 | i1536 | Y | L219 | L410 |
| i1537 | Y | L220 | L423 | i1538 | Y | L220 | L424 | i1539 | Y | L220 | L419 | i1540 | Y | L220 | L410 |
| i1541 | Y | L221 | L423 | i1542 | Y | L221 | L424 | i1543 | Y | L221 | L419 | i1544 | Y | L221 | L410 |
| i1545 | Y | L222 | L423 | i1546 | Y | L222 | L424 | i1547 | Y | L222 | L419 | i1548 | Y | L222 | L410 |
| i1549 | Y | L401 | L423 | i1550 | Y | L401 | L424 | i1551 | Y | L401 | L419 | i1552 | Y | L401 | L410 |
| i1553 | Y | L402 | L423 | i1554 | Y | L402 | L424 | i1555 | Y | L402 | L419 | i1556 | Y | L402 | L410 |
| i1557 | Y | L403 | L423 | i1558 | Y | L403 | L424 | i1559 | Y | L403 | L419 | i1560 | Y | L403 | L410 |
| i1561 | Y | L404 | L423 | i1562 | Y | L404 | L424 | i1563 | Y | L404 | L419 | i1564 | Y | L404 | L410 |
| i1565 | Y | L405 | L423 | i1566 | Y | L405 | L424 | i1567 | Y | L405 | L419 | i1568 | Y | L405 | L410 |
| i1569 | Y | L406 | L423 | i1570 | Y | L406 | L424 | i1571 | Y | L406 | L419 | i1572 | Y | L406 | L410 |
| i1573 | Y | L407 | L423 | i1574 | Y | L407 | L424 | i1575 | Y | L407 | L419 | i1576 | Y | L407 | L410 |
| i1577 | Y | L408 | L423 | i1578 | Y | L408 | L424 | i1579 | Y | L408 | L419 | i1580 | Y | L408 | L410 |
| i1581 | Y | L409 | L423 | i1582 | Y | L409 | L424 | i1583 | Y | L409 | L419 | i1584 | Y | L409 | L410 |
| i1585 | Y | L410 | L423 | i1586 | Y | L410 | L424 | i1587 | Y | L410 | L419 | i1588 | Y | L410 | L410 |
| i1589 | Y | L411 | L423 | i1590 | Y | L411 | L424 | i1591 | Y | L411 | L419 | i1592 | Y | L411 | L410 |
| i1593 | Y | L412 | L423 | i1594 | Y | L412 | L424 | i1595 | Y | L412 | L419 | i1596 | Y | L412 | L410 |
| i1597 | Y | L413 | L423 | i1598 | Y | L413 | L424 | i1599 | Y | L413 | L419 | i1600 | Y | L413 | L410 |
| i1601 | Y | L414 | L423 | i1602 | Y | L414 | L424 | i1603 | Y | L414 | L419 | i1604 | Y | L414 | L410 |
| i1605 | Y | L415 | L423 | i1606 | Y | L415 | L424 | i1607 | Y | L415 | L419 | i1608 | Y | L415 | L410 |
| i1609 | Y | L416 | L423 | i1610 | Y | L416 | L424 | i1611 | Y | L416 | L419 | i1612 | Y | L416 | L410 |
| i1613 | Y | L417 | L423 | i1614 | Y | L417 | L424 | i1615 | Y | L417 | L419 | i1616 | Y | L417 | L410 |
| i1617 | Y | L418 | L423 | i1618 | Y | L418 | L424 | i1619 | Y | L418 | L419 | i1620 | Y | L418 | L410 |
| i1621 | Y | L419 | L423 | i1622 | Y | L419 | L424 | i1623 | Y | L419 | L419 | i1624 | Y | L419 | L410 |
| i1625 | Y | L420 | L423 | i1626 | Y | L420 | L424 | i1627 | Y | L420 | L419 | i1628 | Y | L420 | L410 |
| i1629 | Y | L421 | L423 | i1630 | Y | L421 | L424 | i1631 | Y | L421 | L419 | i1632 | Y | L421 | L410 |
| i1633 | Y | L422 | L423 | i1634 | Y | L422 | L424 | i1635 | Y | L422 | L419 | i1636 | Y | L422 | L410 |
| i1637 | Y | L423 | L423 | i1638 | Y | L423 | L424 | i1639 | Y | L423 | L419 | i1640 | Y | L423 | L410 |
| i1641 | Y | L424 | L423 | i1642 | Y | L424 | L424 | i1643 | Y | L424 | L419 | i1644 | Y | L424 | L410 |
| i1645 | Y | L425 | L423 | i1646 | Y | L425 | L424 | i1647 | Y | L425 | L419 | i1648 | Y | L425 | L410 |
| i1649 | Y | L501 | L423 | i1650 | Y | L501 | L424 | i1651 | Y | L501 | L419 | i1652 | Y | L501 | L410 |
| i1653 | Y | L502 | L423 | i1654 | Y | L502 | L424 | i1655 | Y | L502 | L419 | i1656 | Y | L502 | L410 |
| i1657 | Y | L503 | L423 | i1658 | Y | L503 | L424 | i1659 | Y | L503 | L419 | i1660 | Y | L503 | L410 |
| i1661 | Y | L504 | L423 | i1662 | Y | L504 | L424 | i1663 | Y | L504 | L419 | i1664 | Y | L504 | L410 |
| i1665 | Y | L505 | L423 | i1666 | Y | L505 | L424 | i1667 | Y | L505 | L419 | i1668 | Y | L505 | L410 |
| i1669 | Y | L506 | L423 | i1670 | Y | L506 | L424 | i1671 | Y | L506 | L419 | i1672 | Y | L506 | L410 |
| i1673 | Y | L507 | L423 | i1674 | Y | L507 | L424 | i1675 | Y | L507 | L419 | i1676 | Y | L507 | L410 |
| i1677 | Y | L508 | L423 | i1678 | Y | L508 | L424 | i1679 | Y | L508 | L419 | i1680 | Y | L508 | L410 |
| i1681 | Y | L509 | L423 | i1682 | Y | L509 | L424 | i1683 | Y | L509 | L419 | i1684 | Y | L509 | L410 |
| i1685 | Y | L510 | L423 | i1686 | Y | L510 | L424 | i1687 | Y | L510 | L419 | i1688 | Y | L510 | L410 |
| i1689 | Y | L511 | L423 | i1690 | Y | L511 | L424 | i1691 | Y | L511 | L419 | i1692 | Y | L511 | L410 |
| i1693 | Y | L512 | L423 | i1694 | Y | L512 | L424 | i1695 | Y | L512 | L419 | i1696 | Y | L512 | L410 |
| i1697 | Y | L513 | L423 | i1698 | Y | L513 | L424 | i1699 | Y | L513 | L419 | i1700 | Y | L513 | L410 |
| i1701 | Y | L514 | L423 | i1702 | Y | L514 | L424 | i1703 | Y | L514 | L419 | i1704 | Y | L514 | L410 |
| i1705 | Y | L515 | L423 | i1706 | Y | L515 | L424 | i1707 | Y | L515 | L419 | i1708 | Y | L515 | L410 |
| i1709 | Y | L516 | L423 | i1710 | Y | L516 | L424 | i1711 | Y | L516 | L419 | i1712 | Y | L516 | L410 |
| i1713 | Y | L517 | L423 | i1714 | Y | L517 | L424 | i1715 | Y | L517 | L419 | i1716 | Y | L517 | L410 |
| i1717 | Y | L518 | L423 | i1718 | Y | L518 | L424 | i1719 | Y | L518 | L419 | i1720 | Y | L518 | L410 |
| i1721 | Y | L519 | L423 | i1722 | Y | L519 | L424 | i1723 | Y | L519 | L419 | i1724 | Y | L519 | L410 |
| i1725 | Y | L520 | L423 | i1726 | Y | L520 | L424 | i1727 | Y | L520 | L419 | i1728 | Y | L520 | L410 |
| i1729 | Y | L521 | L423 | i1730 | Y | L521 | L424 | i1731 | Y | L521 | L419 | i1732 | Y | L521 | L410 |
| i1733 | Y | L522 | L423 | i1734 | Y | L522 | L424 | i1735 | Y | L522 | L419 | i1736 | Y | L522 | L410 |
| i1737 | Y | L523 | L423 | i1738 | Y | L523 | L424 | i1739 | Y | L523 | L419 | i1740 | Y | L523 | L410 |
| i1741 | Y | L524 | L423 | i1742 | Y | L524 | L424 | i1743 | Y | L524 | L419 | i1744 | Y | L524 | L410 |
| i1745 | Y | L525 | L423 | i1746 | Y | L525 | L424 | i1747 | Y | L525 | L419 | i1748 | Y | L525 | L410 |
| i1749 | Y | L526 | L423 | i1750 | Y | L526 | L424 | i1751 | Y | L526 | L419 | i1752 | Y | L526 | L410 |
| i1753 | Y | L527 | L423 | i1754 | Y | L527 | L424 | i1755 | Y | L527 | L419 | i1756 | Y | L527 | L410 |
| i1757 | Y | L528 | L423 | i1758 | Y | L528 | L424 | i1759 | Y | L528 | L419 | i1760 | Y | L528 | L410 |
| i1761 | Y | L529 | L423 | i1762 | Y | L529 | L424 | i1763 | Y | L529 | L419 | i1764 | Y | L529 | L410 |
| i1765 | Y | L530 | L423 | i1766 | Y | L530 | L424 | i1767 | Y | L530 | L419 | i1768 | Y | L530 | L410 |
| i1769 | Y | L531 | L423 | i1770 | Y | L531 | L424 | i1771 | Y | L531 | L419 | i1772 | Y | L531 | L410 |
| i1773 | Y | L532 | L423 | i1774 | Y | L532 | L424 | i1775 | Y | L532 | L419 | i1776 | Y | L532 | L410 |
| i1777 | Y | L533 | L423 | i1778 | Y | L533 | L424 | i1779 | Y | L533 | L419 | i1780 | Y | L533 | L410 |
| i1781 | Y | L534 | L423 | i1782 | Y | L534 | L424 | i1783 | Y | L534 | L419 | i1784 | Y | L534 | L410 |
| i1785 | Y | L535 | L423 | i1786 | Y | L535 | L424 | i1787 | Y | L535 | L419 | i1788 | Y | L535 | L410 |
| i1789 | Y | L536 | L423 | i1790 | Y | L536 | L424 | i1791 | Y | L536 | L419 | i1792 | Y | L536 | L410 |
| i1793 | Y | L537 | L423 | i1794 | Y | L537 | L424 | i1795 | Y | L537 | L419 | i1796 | Y | L537 | L410 |
| i1797 | Y | L538 | L423 | i1798 | Y | L538 | L424 | i1799 | Y | L538 | L419 | i1800 | Y | L538 | L410 |
| i1801 | Y | L539 | L423 | i1802 | Y | L539 | L424 | i1803 | Y | L539 | L419 | i1804 | Y | L539 | L410 |
| i1805 | Y | L540 | L423 | i1806 | Y | L540 | L424 | i1807 | Y | L540 | L419 | i1808 | Y | L540 | L410 |
| i1809 | Y | L541 | L423 | i1810 | Y | L541 | L424 | i1811 | Y | L541 | L419 | i1812 | Y | L541 | L410 |
| i1813 | Y | L542 | L423 | i1814 | Y | L542 | L424 | i1815 | Y | L542 | L419 | i1816 | Y | L542 | L410 |
| i1817 | Y | L543 | L423 | i1818 | Y | L543 | L424 | i1819 | Y | L543 | L419 | i1820 | Y | L543 | L410 |
| i1821 | Y | L544 | L423 | i1822 | Y | L544 | L424 | i1823 | Y | L544 | L419 | i1824 | Y | L544 | L410 |
| i1825 | Y | L545 | L423 | i1826 | Y | L545 | L424 | i1827 | Y | L545 | L419 | i1828 | Y | L545 | L410 |
| i1829 | Y | L546 | L423 | i1830 | Y | L546 | L424 | i1831 | Y | L546 | L419 | i1832 | Y | L546 | L410 |
| i1833 | Y | L547 | L423 | i1834 | Y | L547 | L424 | i1835 | Y | L547 | L419 | i1836 | Y | L547 | L410 |
| i1837 | Y | L548 | L423 | i1838 | Y | L548 | L424 | i1839 | Y | L548 | L419 | i1840 | Y | L548 | L410 |
| i1841 | Y | L549 | L423 | i1842 | Y | L549 | L424 | i1843 | Y | L549 | L419 | i1844 | Y | L549 | L410 |

TABLE 1-continued

Compositions "i1" to "i9919"

| | | | | | | | | | | | |
|---|---|---|---|---|---|---|---|---|---|---|---|
| i1845 | Y | L550 | L423 | i1846 | Y | L550 | L424 | i1847 | Y | L550 | L419 | i1848 | Y | L550 | L410 |
| i1849 | Y | L551 | L423 | i1850 | Y | L551 | L424 | i1851 | Y | L551 | L419 | i1852 | Y | L551 | L410 |
| i1853 | Y | L552 | L423 | i1854 | Y | L552 | L424 | i1855 | Y | L552 | L419 | i1856 | Y | L552 | L410 |
| i1857 | Y | L553 | L423 | i1858 | Y | L553 | L424 | i1859 | Y | L553 | L419 | i1860 | Y | L553 | L410 |
| i1861 | Y | L554 | L423 | i1862 | Y | L554 | L424 | i1863 | Y | L554 | L419 | i1864 | Y | L554 | L410 |
| i1865 | Y | L555 | L423 | i1866 | Y | L555 | L424 | i1867 | Y | L555 | L419 | i1868 | Y | L555 | L410 |
| i1869 | Y | L556 | L423 | i1870 | Y | L556 | L424 | i1871 | Y | L556 | L419 | i1872 | Y | L556 | L410 |
| i1873 | Y | L557 | L423 | i1874 | Y | L557 | L424 | i1875 | Y | L557 | L419 | i1876 | Y | L557 | L410 |
| i1877 | Y | L558 | L423 | i1878 | Y | L558 | L424 | i1879 | Y | L558 | L419 | i1880 | Y | L558 | L410 |
| i1881 | Y | L559 | L423 | i1882 | Y | L559 | L424 | i1883 | Y | L559 | L419 | i1884 | Y | L559 | L410 |
| i1885 | Y | L560 | L423 | i1886 | Y | L560 | L424 | i1887 | Y | L560 | L419 | i1888 | Y | L560 | L410 |
| i1889 | Y | L561 | L423 | i1890 | Y | L561 | L424 | i1891 | Y | L561 | L419 | i1892 | Y | L561 | L410 |
| i1893 | Y | L562 | L423 | i1894 | Y | L562 | L424 | i1895 | Y | L562 | L419 | i1896 | Y | L562 | L410 |
| i1897 | Y | L563 | L423 | i1898 | Y | L563 | L424 | i1899 | Y | L563 | L419 | i1900 | Y | L563 | L410 |
| i1901 | Y | L564 | L423 | i1902 | Y | L564 | L424 | i1903 | Y | L564 | L419 | i1904 | Y | L564 | L410 |
| i1905 | Y | L565 | L423 | i1906 | Y | L565 | L424 | i1907 | Y | L565 | L419 | i1908 | Y | L565 | L410 |
| i1909 | Y | L566 | L423 | i1910 | Y | L566 | L424 | i1911 | Y | L566 | L419 | i1912 | Y | L566 | L410 |
| i1913 | Y | L567 | L423 | i1914 | Y | L567 | L424 | i1915 | Y | L567 | L419 | i1916 | Y | L567 | L410 |
| i1917 | Y | L568 | L423 | i1918 | Y | L568 | L424 | i1919 | Y | L568 | L419 | i1920 | Y | L568 | L410 |
| i1921 | Y | L569 | L423 | i1922 | Y | L569 | L424 | i1923 | Y | L569 | L419 | i1924 | Y | L569 | L410 |
| i1925 | Y | L570 | L423 | i1926 | Y | L570 | L424 | i1927 | Y | L570 | L419 | i1928 | Y | L570 | L410 |
| i1929 | Y | L571 | L423 | i1930 | Y | L571 | L424 | i1931 | Y | L571 | L419 | i1932 | Y | L571 | L410 |
| i1933 | Y | L572 | L423 | i1934 | Y | L572 | L424 | i1935 | Y | L572 | L419 | i1936 | Y | L572 | L410 |
| i1937 | Y | L843 | L423 | i1938 | Y | L843 | L424 | i1939 | Y | L843 | L419 | i1940 | Y | L843 | L410 |
| i1941 | Y | L844 | L423 | i1942 | Y | L844 | L424 | i1943 | Y | L844 | L419 | i1944 | Y | L844 | L410 |
| i1945 | Y | L845 | L423 | i1946 | Y | L845 | L424 | i1947 | Y | L845 | L419 | i1948 | Y | L845 | L410 |
| i1949 | Y | L846 | L423 | i1950 | Y | L846 | L424 | i1951 | Y | L846 | L419 | i1952 | Y | L846 | L410 |
| i1953 | Y | L847 | L423 | i1954 | Y | L847 | L424 | i1955 | Y | L847 | L419 | i1956 | Y | L847 | L410 |
| i1957 | Y | L848 | L423 | i1958 | Y | L848 | L424 | i1959 | Y | L848 | L419 | i1960 | Y | L848 | L410 |
| i1961 | Y | L10 | L14 | i1962 | Y | L10 | L572 | i1963 | Y | L10 | L569 | i1964 | Y | L10 | L528 |
| i1965 | Y | L11 | L14 | i1966 | Y | L11 | L572 | i1967 | Y | L11 | L569 | i1968 | Y | L11 | L528 |
| i1969 | Y | L20 | L14 | i1970 | Y | L20 | L572 | i1971 | Y | L20 | L569 | i1972 | Y | L20 | L528 |
| i1973 | Y | L21 | L14 | i1974 | Y | L21 | L572 | i1975 | Y | L21 | L569 | i1976 | Y | L21 | L528 |
| i1977 | Y | L22 | L14 | i1978 | Y | L22 | L572 | i1979 | Y | L22 | L569 | i1980 | Y | L22 | L528 |
| i1981 | Y | L23 | L14 | i1982 | Y | L23 | L572 | i1983 | Y | L23 | L569 | i1984 | Y | L23 | L528 |
| i1985 | Y | L24 | L14 | i1986 | Y | L24 | L572 | i1987 | Y | L24 | L569 | i1988 | Y | L24 | L528 |
| i1989 | Y | L25 | L14 | i1990 | Y | L25 | L572 | i1991 | Y | L25 | L569 | i1992 | Y | L25 | L528 |
| i1993 | Y | L26 | L14 | i1994 | Y | L26 | L572 | i1995 | Y | L26 | L569 | i1996 | Y | L26 | L528 |
| i1997 | Y | L27 | L14 | i1998 | Y | L27 | L572 | i1999 | Y | L27 | L569 | i2000 | Y | L27 | L528 |
| i2001 | Y | L28 | L14 | i2002 | Y | L28 | L572 | i2003 | Y | L28 | L569 | i2004 | Y | L28 | L528 |
| i2005 | Y | L12 | L14 | i2006 | Y | L12 | L572 | i2007 | Y | L12 | L569 | i2008 | Y | L12 | L528 |
| i2009 | Y | L13 | L14 | i2010 | Y | L13 | L572 | i2011 | Y | L13 | L569 | i2012 | Y | L13 | L528 |
| i2013 | Y | L14 | L14 | i2014 | Y | L14 | L572 | i2015 | Y | L14 | L569 | i2016 | Y | L14 | L528 |
| i2017 | Y | L15 | L14 | i2018 | Y | L15 | L572 | i2019 | Y | L15 | L569 | i2020 | Y | L15 | L528 |
| i2021 | Y | L16 | L14 | i2022 | Y | L16 | L572 | i2023 | Y | L16 | L569 | i2024 | Y | L16 | L528 |
| i2025 | Y | L17 | L14 | i2026 | Y | L17 | L572 | i2027 | Y | L17 | L569 | i2028 | Y | L17 | L528 |
| i2029 | Y | L18 | L14 | i2030 | Y | L18 | L572 | i2031 | Y | L18 | L569 | i2032 | Y | L18 | L528 |
| i2033 | Y | L19 | L14 | i2034 | Y | L19 | L572 | i2035 | Y | L19 | L569 | i2036 | Y | L19 | L528 |
| i2037 | Y | L2 | L14 | i2038 | Y | L2 | L572 | i2039 | Y | L2 | L569 | i2040 | Y | L2 | L528 |
| i2041 | Y | L101 | L14 | i2042 | Y | L101 | L572 | i2043 | Y | L101 | L569 | i2044 | Y | L101 | L528 |
| i2045 | Y | L102 | L14 | i2046 | Y | L102 | L572 | i2047 | Y | L102 | L569 | i2048 | Y | L102 | L528 |
| i2049 | Y | L103 | L14 | i2050 | Y | L103 | L572 | i2051 | Y | L103 | L569 | i2052 | Y | L103 | L528 |
| i2053 | Y | L104 | L14 | i2054 | Y | L104 | L572 | i2055 | Y | L104 | L569 | i2056 | Y | L104 | L528 |
| i2057 | Y | L105 | L14 | i2058 | Y | L105 | L572 | i2059 | Y | L105 | L569 | i2060 | Y | L105 | L528 |
| i2061 | Y | L106 | L14 | i2062 | Y | L106 | L572 | i2063 | Y | L106 | L569 | i2064 | Y | L106 | L528 |
| i2065 | Y | L107 | L14 | i2066 | Y | L107 | L572 | i2067 | Y | L107 | L569 | i2068 | Y | L107 | L528 |
| i2069 | Y | L108 | L14 | i2070 | Y | L108 | L572 | i2071 | Y | L108 | L569 | i2072 | Y | L108 | L528 |
| i2073 | Y | L109 | L14 | i2074 | Y | L109 | L572 | i2075 | Y | L109 | L569 | i2076 | Y | L109 | L528 |
| i2077 | Y | L110 | L14 | i2078 | Y | L110 | L572 | i2079 | Y | L110 | L569 | i2080 | Y | L110 | L528 |
| i2081 | Y | L111 | L14 | i2082 | Y | L111 | L572 | i2083 | Y | L111 | L569 | i2084 | Y | L111 | L528 |
| i2085 | Y | L112 | L14 | i2086 | Y | L112 | L572 | i2087 | Y | L112 | L569 | i2088 | Y | L112 | L528 |
| i2089 | Y | L113 | L14 | i2090 | Y | L113 | L572 | i2091 | Y | L113 | L569 | i2092 | Y | L113 | L528 |
| i2093 | Y | L114 | L14 | i2094 | Y | L114 | L572 | i2095 | Y | L114 | L569 | i2096 | Y | L114 | L528 |
| i2097 | Y | L115 | L14 | i2098 | Y | L115 | L572 | i2099 | Y | L115 | L569 | i2100 | Y | L115 | L528 |
| i2101 | Y | L116 | L14 | i2102 | Y | L116 | L572 | i2103 | Y | L116 | L569 | i2104 | Y | L116 | L528 |
| i2105 | Y | L117 | L14 | i2106 | Y | L117 | L572 | i2107 | Y | L117 | L569 | i2108 | Y | L117 | L528 |
| i2109 | Y | L118 | L14 | i2110 | Y | L118 | L572 | i2111 | Y | L118 | L569 | i2112 | Y | L118 | L528 |
| i2113 | Y | L119 | L14 | i2114 | Y | L119 | L572 | i2115 | Y | L119 | L569 | i2116 | Y | L119 | L528 |
| i2117 | Y | L120 | L14 | i2118 | Y | L120 | L572 | i2119 | Y | L120 | L569 | i2120 | Y | L120 | L528 |
| i2121 | Y | L121 | L14 | i2122 | Y | L121 | L572 | i2123 | Y | L121 | L569 | i2124 | Y | L121 | L528 |
| i2225 | Y | L122 | L14 | i2126 | Y | L122 | L572 | i2127 | Y | L122 | L569 | i2128 | Y | L122 | L528 |
| i2129 | Y | L123 | L14 | i2130 | Y | L123 | L572 | i2131 | Y | L123 | L569 | i2132 | Y | L123 | L528 |
| i2133 | Y | L124 | L14 | i2134 | Y | L124 | L572 | i2135 | Y | L124 | L569 | i2136 | Y | L124 | L528 |
| i2137 | Y | L125 | L14 | i2138 | Y | L125 | L572 | i2139 | Y | L125 | L569 | i2140 | Y | L125 | L528 |
| i2141 | Y | L126 | L14 | i2142 | Y | L126 | L572 | i2143 | Y | L126 | L569 | i2144 | Y | L126 | L528 |
| i2145 | Y | L127 | L14 | i2146 | Y | L127 | L572 | i2147 | Y | L127 | L569 | i2148 | Y | L127 | L528 |
| i2149 | Y | L128 | L14 | i2150 | Y | L128 | L572 | i2151 | Y | L128 | L569 | i2152 | Y | L128 | L528 |
| i2153 | Y | L129 | L14 | i2154 | Y | L129 | L572 | i2155 | Y | L129 | L569 | i2156 | Y | L129 | L528 |

TABLE 1-continued

Compositions "i1" to "i9919"

| | | | | | | | | | | | | | | |
|---|---|---|---|---|---|---|---|---|---|---|---|---|---|---|
| i2157 | Y | L130 | L14 | i2158 | Y | L130 | L572 | i2159 | Y | L130 | L569 | i2160 | Y | L130 | L528 |
| i2161 | Y | L131 | L14 | i2162 | Y | L131 | L572 | i2163 | Y | L131 | L569 | i2164 | Y | L131 | L528 |
| i2165 | Y | L132 | L14 | i2166 | Y | L132 | L572 | i2167 | Y | L132 | L569 | i2168 | Y | L132 | L528 |
| i2169 | Y | L133 | L14 | i2170 | Y | L133 | L572 | i2171 | Y | L133 | L569 | i2172 | Y | L133 | L528 |
| i2173 | Y | L134 | L14 | i2174 | Y | L134 | L572 | i2175 | Y | L134 | L569 | i2176 | Y | L134 | L528 |
| i2177 | Y | L135 | L14 | i2178 | Y | L135 | L572 | i2179 | Y | L135 | L569 | i2180 | Y | L135 | L528 |
| i2181 | Y | L136 | L14 | i2182 | Y | L136 | L572 | i2183 | Y | L136 | L569 | i2184 | Y | L136 | L528 |
| i2185 | Y | L137 | L14 | i2186 | Y | L137 | L572 | i2187 | Y | L137 | L569 | i2188 | Y | L137 | L528 |
| i2189 | Y | L138 | L14 | i2190 | Y | L138 | L572 | i2191 | Y | L138 | L569 | i2192 | Y | L138 | L528 |
| i2193 | Y | L139 | L14 | i2194 | Y | L139 | L572 | i2195 | Y | L139 | L569 | i2196 | Y | L139 | L528 |
| i2197 | Y | L140 | L14 | i2198 | Y | L140 | L572 | i2199 | Y | L140 | L569 | i2200 | Y | L140 | L528 |
| i2201 | Y | L141 | L14 | i2202 | Y | L141 | L572 | i2203 | Y | L141 | L569 | i2204 | Y | L141 | L528 |
| i2205 | Y | L142 | L14 | i2206 | Y | L142 | L572 | i2207 | Y | L142 | L569 | i2208 | Y | L142 | L528 |
| i2209 | Y | L143 | L14 | i2210 | Y | L143 | L572 | i2211 | Y | L143 | L569 | i2212 | Y | L143 | L528 |
| i2213 | Y | L144 | L14 | i2214 | Y | L144 | L572 | i2215 | Y | L144 | L569 | i2216 | Y | L144 | L528 |
| i2217 | Y | L145 | L14 | i2218 | Y | L145 | L572 | i2219 | Y | L145 | L569 | i2220 | Y | L145 | L528 |
| i2221 | Y | L146 | L14 | i2222 | Y | L146 | L572 | i2223 | Y | L146 | L569 | i2224 | Y | L146 | L528 |
| i2225 | Y | L147 | L14 | i2226 | Y | L147 | L572 | i2227 | Y | L147 | L569 | i2228 | Y | L147 | L528 |
| i2229 | Y | L148 | L14 | i2230 | Y | L148 | L572 | i2231 | Y | L148 | L569 | i2232 | Y | L148 | L528 |
| i2233 | Y | L149 | L14 | i2234 | Y | L149 | L572 | i2235 | Y | L149 | L569 | i2236 | Y | L149 | L528 |
| i2237 | Y | L150 | L14 | i2238 | Y | L150 | L572 | i2239 | Y | L150 | L569 | i2240 | Y | L150 | L528 |
| i2241 | Y | L151 | L14 | i2242 | Y | L151 | L572 | i2243 | Y | L151 | L569 | i2244 | Y | L151 | L528 |
| i2245 | Y | L152 | L14 | i2246 | Y | L152 | L572 | i2247 | Y | L152 | L569 | i2248 | Y | L152 | L528 |
| i2249 | Y | L153 | L14 | i2250 | Y | L153 | L572 | i2251 | Y | L153 | L569 | i2252 | Y | L153 | L528 |
| i2253 | Y | L154 | L14 | i2254 | Y | L154 | L572 | i2255 | Y | L154 | L569 | i2256 | Y | L154 | L528 |
| i2257 | Y | L155 | L14 | i2258 | Y | L155 | L572 | i2259 | Y | L155 | L569 | i2260 | Y | L155 | L528 |
| i2261 | Y | L156 | L14 | i2262 | Y | L156 | L572 | i2263 | Y | L156 | L569 | i2264 | Y | L156 | L528 |
| i2265 | Y | L157 | L14 | i2266 | Y | L157 | L572 | i2267 | Y | L157 | L569 | i2268 | Y | L157 | L528 |
| i2269 | Y | L158 | L14 | i2270 | Y | L158 | L572 | i2271 | Y | L158 | L569 | i2272 | Y | L158 | L528 |
| i2273 | Y | L159 | L14 | i2274 | Y | L159 | L572 | i2275 | Y | L159 | L569 | i2276 | Y | L159 | L528 |
| i2277 | Y | L160 | L14 | i2278 | Y | L160 | L572 | i2279 | Y | L160 | L569 | i2280 | Y | L160 | L528 |
| i2281 | Y | L161 | L14 | i2282 | Y | L161 | L572 | i2283 | Y | L161 | L569 | i2284 | Y | L161 | L528 |
| i2285 | Y | L162 | L14 | i2286 | Y | L162 | L572 | i2287 | Y | L162 | L569 | i2288 | Y | L162 | L528 |
| i2289 | Y | L163 | L14 | i2290 | Y | L163 | L572 | i2291 | Y | L163 | L569 | i2292 | Y | L163 | L528 |
| i2293 | Y | L164 | L14 | i2294 | Y | L164 | L572 | i2295 | Y | L164 | L569 | i2296 | Y | L164 | L528 |
| i2297 | Y | L165 | L14 | i2298 | Y | L165 | L572 | i2299 | Y | L165 | L569 | i2300 | Y | L165 | L528 |
| i2301 | Y | L166 | L14 | i2302 | Y | L166 | L572 | i2303 | Y | L166 | L569 | i2304 | Y | L166 | L528 |
| i2305 | Y | L167 | L14 | i2306 | Y | L167 | L572 | i2307 | Y | L167 | L569 | i2308 | Y | L167 | L528 |
| i2309 | Y | L168 | L14 | i2310 | Y | L168 | L572 | i2311 | Y | L168 | L569 | i2312 | Y | L168 | L528 |
| i2313 | Y | L169 | L14 | i2314 | Y | L169 | L572 | i2315 | Y | L169 | L569 | i2316 | Y | L169 | L528 |
| i2317 | Y | L170 | L14 | i2318 | Y | L170 | L572 | i2319 | Y | L170 | L569 | i2320 | Y | L170 | L528 |
| i2321 | Y | L171 | L14 | i2322 | Y | L171 | L572 | i2323 | Y | L171 | L569 | i2324 | Y | L171 | L528 |
| i2325 | Y | L172 | L14 | i2326 | Y | L172 | L572 | i2327 | Y | L172 | L569 | i2328 | Y | L172 | L528 |
| i2329 | Y | L173 | L14 | i2330 | Y | L173 | L572 | i2331 | Y | L173 | L569 | i2332 | Y | L173 | L528 |
| i2333 | Y | L174 | L14 | i2334 | Y | L174 | L572 | i2335 | Y | L174 | L569 | i2336 | Y | L174 | L528 |
| i2337 | Y | L175 | L14 | i2338 | Y | L175 | L572 | i2339 | Y | L175 | L569 | i2340 | Y | L175 | L528 |
| i2341 | Y | L176 | L14 | i2342 | Y | L176 | L572 | i2343 | Y | L176 | L569 | i2344 | Y | L176 | L528 |
| i2345 | Y | L177 | L14 | i2346 | Y | L177 | L572 | i2347 | Y | L177 | L569 | i2348 | Y | L177 | L528 |
| i2349 | Y | L178 | L14 | i2350 | Y | L178 | L572 | i2351 | Y | L178 | L569 | i2352 | Y | L178 | L528 |
| i2353 | Y | L179 | L14 | i2354 | Y | L179 | L572 | i2355 | Y | L179 | L569 | i2356 | Y | L179 | L528 |
| i2357 | Y | L180 | L14 | i2358 | Y | L180 | L572 | i2359 | Y | L180 | L569 | i2360 | Y | L180 | L528 |
| i2361 | Y | L181 | L14 | i2362 | Y | L181 | L572 | i2363 | Y | L181 | L569 | i2364 | Y | L181 | L528 |
| i2365 | Y | L182 | L14 | i2366 | Y | L182 | L572 | i2367 | Y | L182 | L569 | i2368 | Y | L182 | L528 |
| i2369 | Y | L183 | L14 | i2370 | Y | L183 | L572 | i2371 | Y | L183 | L569 | i2372 | Y | L183 | L528 |
| i2373 | Y | L184 | L14 | i2374 | Y | L184 | L572 | i2375 | Y | L184 | L569 | i2376 | Y | L184 | L528 |
| i2377 | Y | L185 | L14 | i2378 | Y | L185 | L572 | i2379 | Y | L185 | L569 | i2380 | Y | L185 | L528 |
| i2381 | Y | L186 | L14 | i2382 | Y | L186 | L572 | i2383 | Y | L186 | L569 | i2384 | Y | L186 | L528 |
| i2385 | Y | L187 | L14 | i2386 | Y | L187 | L572 | i2387 | Y | L187 | L569 | i2388 | Y | L187 | L528 |
| i2389 | Y | L188 | L14 | i2390 | Y | L188 | L572 | i2391 | Y | L188 | L569 | i2392 | Y | L188 | L528 |
| i2393 | Y | L189 | L14 | i2394 | Y | L189 | L572 | i2395 | Y | L189 | L569 | i2396 | Y | L189 | L528 |
| i2397 | Y | L190 | L14 | i2398 | Y | L190 | L572 | i2399 | Y | L190 | L569 | i2400 | Y | L190 | L528 |
| i2401 | Y | L191 | L14 | i2402 | Y | L191 | L572 | i2403 | Y | L191 | L569 | i2404 | Y | L191 | L528 |
| i2405 | Y | L192 | L14 | i2406 | Y | L192 | L572 | i2407 | Y | L192 | L569 | i2408 | Y | L192 | L528 |
| i2409 | Y | L193 | L14 | i2410 | Y | L193 | L572 | i2411 | Y | L193 | L569 | i2412 | Y | L193 | L528 |
| i2413 | Y | L194 | L14 | i2414 | Y | L194 | L572 | i2415 | Y | L194 | L569 | i2416 | Y | L194 | L528 |
| i2417 | Y | L195 | L14 | i2418 | Y | L195 | L572 | i2419 | Y | L195 | L569 | i2420 | Y | L195 | L528 |
| i2421 | Y | L196 | L14 | i2422 | Y | L196 | L572 | i2423 | Y | L196 | L569 | i2424 | Y | L196 | L528 |
| i2425 | Y | L197 | L14 | i2426 | Y | L197 | L572 | i2427 | Y | L197 | L569 | i2428 | Y | L197 | L528 |
| i2429 | Y | L198 | L14 | i2430 | Y | L198 | L572 | i2431 | Y | L198 | L569 | i2432 | Y | L198 | L528 |
| i2433 | Y | L199 | L14 | i2434 | Y | L199 | L572 | i2435 | Y | L199 | L569 | i2436 | Y | L199 | L528 |
| i2437 | Y | L200 | L14 | i2438 | Y | L200 | L572 | i2439 | Y | L200 | L569 | i2440 | Y | L200 | L528 |
| i2441 | Y | L201 | L14 | i2442 | Y | L201 | L572 | i2443 | Y | L201 | L569 | i2444 | Y | L201 | L528 |
| i2445 | Y | L202 | L14 | i2446 | Y | L202 | L572 | i2447 | Y | L202 | L569 | i2448 | Y | L202 | L528 |
| i2449 | Y | L203 | L14 | i2450 | Y | L203 | L572 | i2451 | Y | L203 | L569 | i2452 | Y | L203 | L528 |
| i2453 | Y | L204 | L14 | i2454 | Y | L204 | L572 | i2455 | Y | L204 | L569 | i2456 | Y | L204 | L528 |
| i2457 | Y | L205 | L14 | i2458 | Y | L205 | L572 | i2459 | Y | L205 | L569 | i2460 | Y | L205 | L528 |
| i2461 | Y | L206 | L14 | i2462 | Y | L206 | L572 | i2463 | Y | L206 | L569 | i2464 | Y | L206 | L528 |
| i2465 | Y | L207 | L14 | i2466 | Y | L207 | L572 | i2467 | Y | L207 | L569 | i2468 | Y | L207 | L528 |

TABLE 1-continued

Compositions "i1" to "i9919"

| | | | | | | | | | | | | | | | |
|---|---|---|---|---|---|---|---|---|---|---|---|---|---|---|---|
| i2469 | Y | L208 | L14 | i2470 | Y | L208 | L572 | i2471 | Y | L208 | L569 | i2472 | Y | L208 | L528 |
| i2473 | Y | L209 | L14 | i2474 | Y | L209 | L572 | i2475 | Y | L209 | L569 | i2476 | Y | L209 | L528 |
| i2477 | Y | L210 | L14 | i2478 | Y | L210 | L572 | i2479 | Y | L210 | L569 | i2480 | Y | L210 | L528 |
| i2481 | Y | L211 | L14 | i2482 | Y | L211 | L572 | i2483 | Y | L211 | L569 | i2484 | Y | L211 | L528 |
| i2485 | Y | L212 | L14 | i2486 | Y | L212 | L572 | i2487 | Y | L212 | L569 | i2488 | Y | L212 | L528 |
| i2489 | Y | L213 | L14 | i2490 | Y | L213 | L572 | i2491 | Y | L213 | L569 | i2492 | Y | L213 | L528 |
| i2493 | Y | L214 | L14 | i2494 | Y | L214 | L572 | i2495 | Y | L214 | L569 | i2496 | Y | L214 | L528 |
| i2497 | Y | L215 | L14 | i2498 | Y | L215 | L572 | i2499 | Y | L215 | L569 | i2500 | Y | L215 | L528 |
| i2501 | Y | L216 | L14 | i2502 | Y | L216 | L572 | i2503 | Y | L216 | L569 | i2504 | Y | L216 | L528 |
| i2505 | Y | L217 | L14 | i2506 | Y | L217 | L572 | i2507 | Y | L217 | L569 | i2508 | Y | L217 | L528 |
| i2509 | Y | L218 | L14 | i2510 | Y | L218 | L572 | i2511 | Y | L218 | L569 | i2512 | Y | L218 | L528 |
| i2513 | Y | L219 | L14 | i2514 | Y | L219 | L572 | i2515 | Y | L219 | L569 | i2516 | Y | L219 | L528 |
| i2517 | Y | L220 | L14 | i2518 | Y | L220 | L572 | i2519 | Y | L220 | L569 | i2520 | Y | L220 | L528 |
| i2521 | Y | L221 | L14 | i2522 | Y | L221 | L572 | i2523 | Y | L221 | L569 | i2524 | Y | L221 | L528 |
| i2525 | Y | L222 | L14 | i2526 | Y | L222 | L572 | i2527 | Y | L222 | L569 | i2528 | Y | L222 | L528 |
| i2529 | Y | L401 | L14 | i2530 | Y | L401 | L572 | i2531 | Y | L401 | L569 | i2532 | Y | L401 | L528 |
| i2533 | Y | L402 | L14 | i2534 | Y | L402 | L572 | i2535 | Y | L402 | L569 | i2536 | Y | L402 | L528 |
| i2537 | Y | L403 | L14 | i2538 | Y | L403 | L572 | i2539 | Y | L403 | L569 | i2540 | Y | L403 | L528 |
| i2541 | Y | L404 | L14 | i2542 | Y | L404 | L572 | i2543 | Y | L404 | L569 | i2544 | Y | L404 | L528 |
| i2545 | Y | L405 | L14 | i2546 | Y | L405 | L572 | i2547 | Y | L405 | L569 | i2548 | Y | L405 | L528 |
| i2549 | Y | L406 | L14 | i2550 | Y | L406 | L572 | i2551 | Y | L406 | L569 | i2552 | Y | L406 | L528 |
| i2553 | Y | L407 | L14 | i2554 | Y | L407 | L572 | i2555 | Y | L407 | L569 | i2556 | Y | L407 | L528 |
| i2557 | Y | L408 | L14 | i2558 | Y | L408 | L572 | i2559 | Y | L408 | L569 | i2560 | Y | L408 | L528 |
| i2561 | Y | L409 | L14 | i2562 | Y | L409 | L572 | i2563 | Y | L409 | L569 | i2564 | Y | L409 | L528 |
| i2565 | Y | L410 | L14 | i2566 | Y | L410 | L572 | i2567 | Y | L410 | L569 | i2568 | Y | L410 | L528 |
| i2569 | Y | L411 | L14 | i2570 | Y | L411 | L572 | i2571 | Y | L411 | L569 | i2572 | Y | L411 | L528 |
| i2573 | Y | L412 | L14 | i2574 | Y | L412 | L572 | i2575 | Y | L412 | L569 | i2576 | Y | L412 | L528 |
| i2577 | Y | L413 | L14 | i2578 | Y | L413 | L572 | i2579 | Y | L413 | L569 | i2580 | Y | L413 | L528 |
| i2581 | Y | L414 | L14 | i2582 | Y | L414 | L572 | i2583 | Y | L414 | L569 | i2584 | Y | L414 | L528 |
| i2585 | Y | L415 | L14 | i2586 | Y | L415 | L572 | i2587 | Y | L415 | L569 | i2588 | Y | L415 | L528 |
| i2589 | Y | L416 | L14 | i2590 | Y | L416 | L572 | i2591 | Y | L416 | L569 | i2592 | Y | L416 | L528 |
| i2593 | Y | L417 | L14 | i2594 | Y | L417 | L572 | i2595 | Y | L417 | L569 | i2596 | Y | L417 | L528 |
| i2597 | Y | L418 | L14 | i2598 | Y | L418 | L572 | i2599 | Y | L418 | L569 | i2600 | Y | L418 | L528 |
| i2601 | Y | L419 | L14 | i2602 | Y | L419 | L572 | i2603 | Y | L419 | L569 | i2604 | Y | L419 | L528 |
| i2605 | Y | L420 | L14 | i2606 | Y | L420 | L572 | i2607 | Y | L420 | L569 | i2608 | Y | L420 | L528 |
| i2609 | Y | L421 | L14 | i2610 | Y | L421 | L572 | i2611 | Y | L421 | L569 | i2612 | Y | L421 | L528 |
| i2613 | Y | L422 | L14 | i2614 | Y | L422 | L572 | i2615 | Y | L422 | L569 | i2616 | Y | L422 | L528 |
| i2617 | Y | L423 | L14 | i2618 | Y | L423 | L572 | i2619 | Y | L423 | L569 | i2620 | Y | L423 | L528 |
| i2621 | Y | L424 | L14 | i2622 | Y | L424 | L572 | i2623 | Y | L424 | L569 | i2624 | Y | L424 | L528 |
| i2625 | Y | L425 | L14 | i2626 | Y | L425 | L572 | i2627 | Y | L425 | L569 | i2628 | Y | L425 | L528 |
| i2629 | Y | L501 | L14 | i2630 | Y | L501 | L572 | i2631 | Y | L501 | L569 | i2632 | Y | L501 | L528 |
| i2633 | Y | L502 | L14 | i2634 | Y | L502 | L572 | i2635 | Y | L502 | L569 | i2636 | Y | L502 | L528 |
| i2637 | Y | L503 | L14 | i2638 | Y | L503 | L572 | i2639 | Y | L503 | L569 | i2640 | Y | L503 | L528 |
| i2641 | Y | L504 | L14 | i2642 | Y | L504 | L572 | i2643 | Y | L504 | L569 | i2644 | Y | L504 | L528 |
| i2645 | Y | L505 | L14 | i2646 | Y | L505 | L572 | i2647 | Y | L505 | L569 | i2648 | Y | L505 | L528 |
| i2649 | Y | L506 | L14 | i2650 | Y | L506 | L572 | i2651 | Y | L506 | L569 | i2652 | Y | L506 | L528 |
| i2653 | Y | L507 | L14 | i2654 | Y | L507 | L572 | i2655 | Y | L507 | L569 | i2656 | Y | L507 | L528 |
| i2657 | Y | L508 | L14 | i2658 | Y | L508 | L572 | i2659 | Y | L508 | L569 | i2660 | Y | L508 | L528 |
| i2661 | Y | L509 | L14 | i2662 | Y | L509 | L572 | i2663 | Y | L509 | L569 | i2664 | Y | L509 | L528 |
| i2665 | Y | L510 | L14 | i2666 | Y | L510 | L572 | i2667 | Y | L510 | L569 | i2668 | Y | L510 | L528 |
| i2669 | Y | L511 | L14 | i2670 | Y | L511 | L572 | i2671 | Y | L511 | L569 | i2672 | Y | L511 | L528 |
| i2673 | Y | L512 | L14 | i2674 | Y | L512 | L572 | i2675 | Y | L512 | L569 | i2676 | Y | L512 | L528 |
| i2677 | Y | L513 | L14 | i2678 | Y | L513 | L572 | i2679 | Y | L513 | L569 | i2680 | Y | L513 | L528 |
| i2681 | Y | L514 | L14 | i2682 | Y | L514 | L572 | i2683 | Y | L514 | L569 | i2684 | Y | L514 | L528 |
| i2685 | Y | L515 | L14 | i2686 | Y | L515 | L572 | i2687 | Y | L515 | L569 | i2688 | Y | L515 | L528 |
| i2689 | Y | L516 | L14 | i2690 | Y | L516 | L572 | i2691 | Y | L516 | L569 | i2692 | Y | L516 | L528 |
| i2693 | Y | L517 | L14 | i2694 | Y | L517 | L572 | i2695 | Y | L517 | L569 | i2696 | Y | L517 | L528 |
| i2697 | Y | L518 | L14 | i2698 | Y | L518 | L572 | i2699 | Y | L518 | L569 | i2700 | Y | L518 | L528 |
| i2701 | Y | L519 | L14 | i2702 | Y | L519 | L572 | i2703 | Y | L519 | L569 | i2704 | Y | L519 | L528 |
| i2705 | Y | L520 | L14 | i2706 | Y | L520 | L572 | i2707 | Y | L520 | L569 | i2708 | Y | L520 | L528 |
| i2709 | Y | L521 | L14 | i2710 | Y | L521 | L572 | i2711 | Y | L521 | L569 | i2712 | Y | L521 | L528 |
| i2713 | Y | L522 | L14 | i2714 | Y | L522 | L572 | i2715 | Y | L522 | L569 | i2716 | Y | L522 | L528 |
| i2717 | Y | L523 | L14 | i2718 | Y | L523 | L572 | i2719 | Y | L523 | L569 | i2720 | Y | L523 | L528 |
| i2721 | Y | L524 | L14 | i2722 | Y | L524 | L572 | i2723 | Y | L524 | L569 | i2724 | Y | L524 | L528 |
| i2725 | Y | L525 | L14 | i2726 | Y | L525 | L572 | i2727 | Y | L525 | L569 | i2728 | Y | L525 | L528 |
| i2729 | Y | L526 | L14 | i2730 | Y | L526 | L572 | i2731 | Y | L526 | L569 | i2732 | Y | L526 | L528 |
| i2733 | Y | L527 | L14 | i2734 | Y | L527 | L572 | i2735 | Y | L527 | L569 | i2736 | Y | L527 | L528 |
| i2737 | Y | L528 | L14 | i2738 | Y | L528 | L572 | i2739 | Y | L528 | L569 | i2740 | Y | L528 | L528 |
| i2741 | Y | L529 | L14 | i2742 | Y | L529 | L572 | i2743 | Y | L529 | L569 | i2744 | Y | L529 | L528 |
| i2745 | Y | L530 | L14 | i2746 | Y | L530 | L572 | i2747 | Y | L530 | L569 | i2748 | Y | L530 | L528 |
| i2749 | Y | L531 | L14 | i2750 | Y | L531 | L572 | i2751 | Y | L531 | L569 | i2752 | Y | L531 | L528 |
| i2753 | Y | L532 | L14 | i2754 | Y | L532 | L572 | i2755 | Y | L532 | L569 | i2756 | Y | L532 | L528 |
| i2757 | Y | L533 | L14 | i2758 | Y | L533 | L572 | i2759 | Y | L533 | L569 | i2760 | Y | L533 | L528 |
| i2761 | Y | L534 | L14 | i2762 | Y | L534 | L572 | i2763 | Y | L534 | L569 | i2764 | Y | L534 | L528 |
| i2765 | Y | L535 | L14 | i2766 | Y | L535 | L572 | i2767 | Y | L535 | L569 | i2768 | Y | L535 | L528 |
| i2769 | Y | L536 | L14 | i2770 | Y | L536 | L572 | i2771 | Y | L536 | L569 | i2772 | Y | L536 | L528 |
| i2773 | Y | L537 | L14 | i2774 | Y | L537 | L572 | i2775 | Y | L537 | L569 | i2776 | Y | L537 | L528 |
| i2777 | Y | L538 | L14 | i2778 | Y | L538 | L572 | i2779 | Y | L538 | L569 | i2780 | Y | L538 | L528 |

TABLE 1-continued

Compositions "i1" to "i9919"

| | | | | | | | | | | | | | | |
|---|---|---|---|---|---|---|---|---|---|---|---|---|---|---|
| i2781 | Y | L539 | L14 | i2782 | Y | L539 | L572 | i2783 | Y | L539 | L569 | i2784 | Y | L539 | L528 |
| i2785 | Y | L540 | L14 | i2786 | Y | L540 | L572 | i2787 | Y | L540 | L569 | i2788 | Y | L540 | L528 |
| i2789 | Y | L541 | L14 | i2790 | Y | L541 | L572 | i2791 | Y | L541 | L569 | i2792 | Y | L541 | L528 |
| i2793 | Y | L542 | L14 | i2794 | Y | L542 | L572 | i2795 | Y | L542 | L569 | i2796 | Y | L542 | L528 |
| i2797 | Y | L543 | L14 | i2798 | Y | L543 | L572 | i2799 | Y | L543 | L569 | i2800 | Y | L543 | L528 |
| i2801 | Y | L544 | L14 | i2802 | Y | L544 | L572 | i2803 | Y | L544 | L569 | i2804 | Y | L544 | L528 |
| i2805 | Y | L545 | L14 | i2806 | Y | L545 | L572 | i2807 | Y | L545 | L569 | i2808 | Y | L545 | L528 |
| i2809 | Y | L546 | L14 | i2810 | Y | L546 | L572 | i2811 | Y | L546 | L569 | i2812 | Y | L546 | L528 |
| i2813 | Y | L547 | L14 | i2814 | Y | L547 | L572 | i2815 | Y | L547 | L569 | i2816 | Y | L547 | L528 |
| i2817 | Y | L548 | L14 | i2818 | Y | L548 | L572 | i2819 | Y | L548 | L569 | i2820 | Y | L548 | L528 |
| i2821 | Y | L549 | L14 | i2822 | Y | L549 | L572 | i2823 | Y | L549 | L569 | i2824 | Y | L549 | L528 |
| i2825 | Y | L550 | L14 | i2826 | Y | L550 | L572 | i2827 | Y | L550 | L569 | i2828 | Y | L550 | L528 |
| i2829 | Y | L551 | L14 | i2830 | Y | L551 | L572 | i2831 | Y | L551 | L569 | i2832 | Y | L551 | L528 |
| i2833 | Y | L552 | L14 | i2834 | Y | L552 | L572 | i2835 | Y | L552 | L569 | i2836 | Y | L552 | L528 |
| i2837 | Y | L553 | L14 | i2838 | Y | L553 | L572 | i2839 | Y | L553 | L569 | i2840 | Y | L553 | L528 |
| i2841 | Y | L554 | L14 | i2842 | Y | L554 | L572 | i2843 | Y | L554 | L569 | i2844 | Y | L554 | L528 |
| i2845 | Y | L555 | L14 | i2846 | Y | L555 | L572 | i2847 | Y | L555 | L569 | i2848 | Y | L555 | L528 |
| i2849 | Y | L556 | L14 | i2850 | Y | L556 | L572 | i2851 | Y | L556 | L569 | i2852 | Y | L556 | L528 |
| i2853 | Y | L557 | L14 | i2854 | Y | L557 | L572 | i2855 | Y | L557 | L569 | i2856 | Y | L557 | L528 |
| i2857 | Y | L558 | L14 | i2858 | Y | L558 | L572 | i2859 | Y | L558 | L569 | i2860 | Y | L558 | L528 |
| i2861 | Y | L559 | L14 | i2862 | Y | L559 | L572 | i2863 | Y | L559 | L569 | i2864 | Y | L559 | L528 |
| i2865 | Y | L560 | L14 | i2866 | Y | L560 | L572 | i2867 | Y | L560 | L569 | i2868 | Y | L560 | L528 |
| i2869 | Y | L561 | L14 | i2870 | Y | L561 | L572 | i2871 | Y | L561 | L569 | i2872 | Y | L561 | L528 |
| i2873 | Y | L562 | L14 | i2874 | Y | L562 | L572 | i2875 | Y | L562 | L569 | i2876 | Y | L562 | L528 |
| i2877 | Y | L563 | L14 | i2878 | Y | L563 | L572 | i2879 | Y | L563 | L569 | i2880 | Y | L563 | L528 |
| i2881 | Y | L564 | L14 | i2882 | Y | L564 | L572 | i2883 | Y | L564 | L569 | i2884 | Y | L564 | L528 |
| i2885 | Y | L565 | L14 | i2886 | Y | L565 | L572 | i2887 | Y | L565 | L569 | i2888 | Y | L565 | L528 |
| i2889 | Y | L566 | L14 | i2890 | Y | L566 | L572 | i2891 | Y | L566 | L569 | i2892 | Y | L566 | L528 |
| i2893 | Y | L567 | L14 | i2894 | Y | L567 | L572 | i2895 | Y | L567 | L569 | i2896 | Y | L567 | L528 |
| i2897 | Y | L568 | L14 | i2898 | Y | L568 | L572 | i2899 | Y | L568 | L569 | i2900 | Y | L568 | L528 |
| i2901 | Y | L569 | L14 | i2902 | Y | L569 | L572 | i2903 | Y | L569 | L569 | i2904 | Y | L569 | L528 |
| i2905 | Y | L570 | L14 | i2906 | Y | L570 | L572 | i2907 | Y | L570 | L569 | i2908 | Y | L570 | L528 |
| i2909 | Y | L571 | L14 | i2910 | Y | L571 | L572 | i2911 | Y | L571 | L569 | i2912 | Y | L571 | L528 |
| i2913 | Y | L572 | L14 | i2914 | Y | L572 | L572 | i2915 | Y | L572 | L569 | i2916 | Y | L572 | L528 |
| i2917 | Y | L843 | L14 | i2918 | Y | L843 | L572 | i2919 | Y | L843 | L569 | i2920 | Y | L843 | L528 |
| i2921 | Y | L844 | L14 | i2922 | Y | L844 | L572 | i2923 | Y | L844 | L569 | i2924 | Y | L844 | L528 |
| i2925 | Y | L845 | L14 | i2926 | Y | L845 | L572 | i2927 | Y | L845 | L569 | i2928 | Y | L845 | L528 |
| i2929 | Y | L846 | L14 | i2930 | Y | L846 | L572 | i2931 | Y | L846 | L569 | i2932 | Y | L846 | L528 |
| i2933 | Y | L847 | L14 | i2934 | Y | L847 | L572 | i2935 | Y | L847 | L569 | i2936 | Y | L847 | L528 |
| i2937 | Y | L848 | L14 | i2938 | Y | L848 | L572 | i2939 | Y | L848 | L569 | i2940 | Y | L848 | L528 |
| i2941 | Y | L10 | L413 | i2942 | Y | L10 | L404 | i2943 | Y | L10 | L534 | i2944 | Y | L10 | L188 |
| i2945 | Y | L11 | L413 | i2946 | Y | L11 | L404 | i2947 | Y | L11 | L534 | i2948 | Y | L11 | L188 |
| i2949 | Y | L20 | L413 | i2950 | Y | L20 | L404 | i2951 | Y | L20 | L534 | i2952 | Y | L20 | L188 |
| i2953 | Y | L21 | L413 | i2954 | Y | L21 | L404 | i2955 | Y | L21 | L534 | i2956 | Y | L21 | L188 |
| i2957 | Y | L22 | L413 | i2958 | Y | L22 | L404 | i2959 | Y | L22 | L534 | i2960 | Y | L22 | L188 |
| i2961 | Y | L23 | L413 | i2962 | Y | L23 | L404 | i2963 | Y | L23 | L534 | i2964 | Y | L23 | L188 |
| i2965 | Y | L24 | L413 | i2966 | Y | L24 | L404 | i2967 | Y | L24 | L534 | i2968 | Y | L24 | L188 |
| i2969 | Y | L25 | L413 | i2970 | Y | L25 | L404 | i2971 | Y | L25 | L534 | i2972 | Y | L25 | L188 |
| i2973 | Y | L26 | L413 | i2974 | Y | L26 | L404 | i2975 | Y | L26 | L534 | i2976 | Y | L26 | L188 |
| i2977 | Y | L27 | L413 | i2978 | Y | L27 | L404 | i2979 | Y | L27 | L534 | i2980 | Y | L27 | L188 |
| i2981 | Y | L28 | L413 | i2982 | Y | L28 | L404 | i2983 | Y | L28 | L534 | i2984 | Y | L28 | L188 |
| i2985 | Y | L12 | L413 | i2986 | Y | L12 | L404 | i2987 | Y | L12 | L534 | i2988 | Y | L12 | L188 |
| i2989 | Y | L13 | L413 | i2990 | Y | L13 | L404 | i2991 | Y | L13 | L534 | i2992 | Y | L13 | L188 |
| i2993 | Y | L14 | L413 | i2994 | Y | L14 | L404 | i2995 | Y | L14 | L534 | i2996 | Y | L14 | L188 |
| i2997 | Y | L15 | L413 | i2998 | Y | L15 | L404 | i2999 | Y | L15 | L534 | i3000 | Y | L15 | L188 |
| i3001 | Y | L16 | L413 | i3002 | Y | L16 | L404 | i3003 | Y | L16 | L534 | i3004 | Y | L16 | L188 |
| i3005 | Y | L17 | L413 | i3006 | Y | L17 | L404 | i3007 | Y | L17 | L534 | i3008 | Y | L17 | L188 |
| i3009 | Y | L18 | L413 | i3010 | Y | L18 | L404 | i3011 | Y | L18 | L534 | i3012 | Y | L18 | L188 |
| i3013 | Y | L19 | L413 | i3014 | Y | L19 | L404 | i3015 | Y | L19 | L534 | i3016 | Y | L19 | L188 |
| i3017 | Y | L2 | L413 | i3018 | Y | L2 | L404 | i3019 | Y | L2 | L534 | i3020 | Y | L2 | L188 |
| i3021 | Y | L101 | L413 | i3022 | Y | L101 | L404 | i3023 | Y | L101 | L534 | i3024 | Y | L101 | L188 |
| i3025 | Y | L102 | L413 | i3026 | Y | L102 | L404 | i3027 | Y | L102 | L534 | i3028 | Y | L102 | L188 |
| i3029 | Y | L103 | L413 | i3030 | Y | L103 | L404 | i3031 | Y | L103 | L534 | i3032 | Y | L103 | L188 |
| i3033 | Y | L104 | L413 | i3034 | Y | L104 | L404 | i3035 | Y | L104 | L534 | i3036 | Y | L104 | L188 |
| i3037 | Y | L105 | L413 | i3038 | Y | L105 | L404 | i3039 | Y | L105 | L534 | i3040 | Y | L105 | L188 |
| i3041 | Y | L106 | L413 | i3042 | Y | L106 | L404 | i3043 | Y | L106 | L534 | i3044 | Y | L106 | L188 |
| i3045 | Y | L107 | L413 | i3046 | Y | L107 | L404 | i3047 | Y | L107 | L534 | i3048 | Y | L107 | L188 |
| i3049 | Y | L108 | L413 | i3050 | Y | L108 | L404 | i3051 | Y | L108 | L534 | i3052 | Y | L108 | L188 |
| i3053 | Y | L109 | L413 | i3054 | Y | L109 | L404 | i3055 | Y | L109 | L534 | i3056 | Y | L109 | L188 |
| i3057 | Y | L110 | L413 | i3058 | Y | L110 | L404 | i3059 | Y | L110 | L534 | i3060 | Y | L110 | L188 |
| i3061 | Y | L111 | L413 | i3062 | Y | L111 | L404 | i3063 | Y | L111 | L534 | i3064 | Y | L111 | L188 |
| i3065 | Y | L112 | L413 | i3066 | Y | L112 | L404 | i3067 | Y | L112 | L534 | i3068 | Y | L112 | L188 |
| i3069 | Y | L113 | L413 | i3070 | Y | L113 | L404 | i3071 | Y | L113 | L534 | i3072 | Y | L113 | L188 |
| i3073 | Y | L114 | L413 | i3074 | Y | L114 | L404 | i3075 | Y | L114 | L534 | i3076 | Y | L114 | L188 |
| i3077 | Y | L115 | L413 | i3078 | Y | L115 | L404 | i3079 | Y | L115 | L534 | i3080 | Y | L115 | L188 |
| i3081 | Y | L116 | L413 | i3082 | Y | L116 | L404 | i3083 | Y | L116 | L534 | i3084 | Y | L116 | L188 |
| i3085 | Y | L117 | L413 | i3086 | Y | L117 | L404 | i3087 | Y | L117 | L534 | i3088 | Y | L117 | L188 |
| i3089 | Y | L118 | L413 | i3090 | Y | L118 | L404 | i3091 | Y | L118 | L534 | i3092 | Y | L118 | L188 |

TABLE 1-continued

Compositions "i1" to "i9919"

| | | | | | | | | | | | | | | |
|---|---|---|---|---|---|---|---|---|---|---|---|---|---|---|
| i3093 | Y | L119 | L413 | i3094 | Y | L119 | L404 | i3095 | Y | L119 | L534 | i3096 | Y | L119 | L188 |
| i3097 | Y | L120 | L413 | i3098 | Y | L120 | L404 | i3099 | Y | L120 | L534 | i3100 | Y | L120 | L188 |
| i3101 | Y | L121 | L413 | i3102 | Y | L121 | L404 | i3103 | Y | L121 | L534 | i3104 | Y | L121 | L188 |
| i3105 | Y | L122 | L413 | i3106 | Y | L122 | L404 | i3107 | Y | L122 | L534 | i3108 | Y | L122 | L188 |
| i3109 | Y | L123 | L413 | i3110 | Y | L123 | L404 | i3111 | Y | L123 | L534 | i3112 | Y | L123 | L188 |
| i3113 | Y | L124 | L413 | i3114 | Y | L124 | L404 | i3115 | Y | L124 | L534 | i3116 | Y | L124 | L188 |
| i3117 | Y | L125 | L413 | i3118 | Y | L125 | L404 | i3119 | Y | L125 | L534 | i3120 | Y | L125 | L188 |
| i3121 | Y | L126 | L413 | i3122 | Y | L126 | L404 | i3123 | Y | L126 | L534 | i3124 | Y | L126 | L188 |
| i3125 | Y | L127 | L413 | i3126 | Y | L127 | L404 | i3127 | Y | L127 | L534 | i3128 | Y | L127 | L188 |
| i3129 | Y | L128 | L413 | i3130 | Y | L128 | L404 | i3131 | Y | L128 | L534 | i3132 | Y | L128 | L188 |
| i3133 | Y | L129 | L413 | i3134 | Y | L129 | L404 | i3135 | Y | L129 | L534 | i3136 | Y | L129 | L188 |
| i3137 | Y | L130 | L413 | i3138 | Y | L130 | L404 | i3139 | Y | L130 | L534 | i3140 | Y | L130 | L188 |
| i3141 | Y | L131 | L413 | i3142 | Y | L131 | L404 | i3143 | Y | L131 | L534 | i3144 | Y | L131 | L188 |
| i3145 | Y | L132 | L413 | i3146 | Y | L132 | L404 | i3147 | Y | L132 | L534 | i3148 | Y | L132 | L188 |
| i3149 | Y | L133 | L413 | i3150 | Y | L133 | L404 | i3151 | Y | L133 | L534 | i3152 | Y | L133 | L188 |
| i3153 | Y | L134 | L413 | i3154 | Y | L134 | L404 | i3155 | Y | L134 | L534 | i3156 | Y | L134 | L188 |
| i3157 | Y | L135 | L413 | i3158 | Y | L135 | L404 | i3159 | Y | L135 | L534 | i3160 | Y | L135 | L188 |
| i3161 | Y | L136 | L413 | i3162 | Y | L136 | L404 | i3163 | Y | L136 | L534 | i3164 | Y | L136 | L188 |
| i3165 | Y | L137 | L413 | i3166 | Y | L137 | L404 | i3167 | Y | L137 | L534 | i3168 | Y | L137 | L188 |
| i3169 | Y | L138 | L413 | i3170 | Y | L138 | L404 | i3171 | Y | L138 | L534 | i3172 | Y | L138 | L188 |
| i3173 | Y | L139 | L413 | i3174 | Y | L139 | L404 | i3175 | Y | L139 | L534 | i3176 | Y | L139 | L188 |
| i3177 | Y | L140 | L413 | i3178 | Y | L140 | L404 | i3179 | Y | L140 | L534 | i3180 | Y | L140 | L188 |
| i3181 | Y | L141 | L413 | i3182 | Y | L141 | L404 | i3183 | Y | L141 | L534 | i3184 | Y | L141 | L188 |
| i3185 | Y | L142 | L413 | i3186 | Y | L142 | L404 | i3187 | Y | L142 | L534 | i3188 | Y | L142 | L188 |
| i3189 | Y | L143 | L413 | i3190 | Y | L143 | L404 | i3191 | Y | L143 | L534 | i3192 | Y | L143 | L188 |
| i3193 | Y | L144 | L413 | i3194 | Y | L144 | L404 | i3195 | Y | L144 | L534 | i3196 | Y | L144 | L188 |
| i3197 | Y | L145 | L413 | i3198 | Y | L145 | L404 | i3199 | Y | L145 | L534 | i3200 | Y | L145 | L188 |
| i3201 | Y | L146 | L413 | i3202 | Y | L146 | L404 | i3203 | Y | L146 | L534 | i3204 | Y | L146 | L188 |
| i3205 | Y | L147 | L413 | i3206 | Y | L147 | L404 | i3207 | Y | L147 | L534 | i3208 | Y | L147 | L188 |
| i3209 | Y | L148 | L413 | i3210 | Y | L148 | L404 | i3211 | Y | L148 | L534 | i3212 | Y | L148 | L188 |
| i3213 | Y | L149 | L413 | i3214 | Y | L149 | L404 | i3215 | Y | L149 | L534 | i3216 | Y | L149 | L188 |
| i3217 | Y | L150 | L413 | i3218 | Y | L150 | L404 | i3219 | Y | L150 | L534 | i3220 | Y | L150 | L188 |
| i3221 | Y | L151 | L413 | i3222 | Y | L151 | L404 | i3223 | Y | L151 | L534 | i3224 | Y | L151 | L188 |
| i3225 | Y | L152 | L413 | i3226 | Y | L152 | L404 | i3227 | Y | L152 | L534 | i3228 | Y | L152 | L188 |
| i3229 | Y | L153 | L413 | i3230 | Y | L153 | L404 | i3231 | Y | L153 | L534 | i3232 | Y | L153 | L188 |
| i3233 | Y | L154 | L413 | i3234 | Y | L154 | L404 | i3235 | Y | L154 | L534 | i3236 | Y | L154 | L188 |
| i3237 | Y | L155 | L413 | i3238 | Y | L155 | L404 | i3239 | Y | L155 | L534 | i3240 | Y | L155 | L188 |
| i3241 | Y | L156 | L413 | i3242 | Y | L156 | L404 | i3243 | Y | L156 | L534 | i3244 | Y | L156 | L188 |
| i3245 | Y | L157 | L413 | i3246 | Y | L157 | L404 | i3247 | Y | L157 | L534 | i3248 | Y | L157 | L188 |
| i3249 | Y | L158 | L413 | i3250 | Y | L158 | L404 | i3251 | Y | L158 | L534 | i3252 | Y | L158 | L188 |
| i3253 | Y | L159 | L413 | i3254 | Y | L159 | L404 | i3255 | Y | L159 | L534 | i3256 | Y | L159 | L188 |
| i3257 | Y | L160 | L413 | i3258 | Y | L160 | L404 | i3259 | Y | L160 | L534 | i3260 | Y | L160 | L188 |
| i3261 | Y | L161 | L413 | i3262 | Y | L161 | L404 | i3263 | Y | L161 | L534 | i3264 | Y | L161 | L188 |
| i3265 | Y | L162 | L413 | i3266 | Y | L162 | L404 | i3267 | Y | L162 | L534 | i3268 | Y | L162 | L188 |
| i3269 | Y | L163 | L413 | i3270 | Y | L163 | L404 | i3271 | Y | L163 | L534 | i3272 | Y | L163 | L188 |
| i3273 | Y | L164 | L413 | i3274 | Y | L164 | L404 | i3275 | Y | L164 | L534 | i3276 | Y | L164 | L188 |
| i3277 | Y | L165 | L413 | i3278 | Y | L165 | L404 | i3279 | Y | L165 | L534 | i3280 | Y | L165 | L188 |
| i3281 | Y | L166 | L413 | i3282 | Y | L166 | L404 | i3283 | Y | L166 | L534 | i3284 | Y | L166 | L188 |
| i3285 | Y | L167 | L413 | i3286 | Y | L167 | L404 | i3287 | Y | L167 | L534 | i3288 | Y | L167 | L188 |
| i3289 | Y | L168 | L413 | i3290 | Y | L168 | L404 | i3291 | Y | L168 | L534 | i3292 | Y | L168 | L188 |
| i3293 | Y | L169 | L413 | i3294 | Y | L169 | L404 | i3295 | Y | L169 | L534 | i3296 | Y | L169 | L188 |
| i3297 | Y | L170 | L413 | i3298 | Y | L170 | L404 | i3299 | Y | L170 | L534 | i3300 | Y | L170 | L188 |
| i3301 | Y | L171 | L413 | i3302 | Y | L171 | L404 | i3303 | Y | L171 | L534 | i3304 | Y | L171 | L188 |
| i3305 | Y | L172 | L413 | i3306 | Y | L172 | L404 | i3307 | Y | L172 | L534 | i3308 | Y | L172 | L188 |
| i3309 | Y | L173 | L413 | i3310 | Y | L173 | L404 | i3311 | Y | L173 | L534 | i3312 | Y | L173 | L188 |
| i3313 | Y | L174 | L413 | i3314 | Y | L174 | L404 | i3315 | Y | L174 | L534 | i3316 | Y | L174 | L188 |
| i3317 | Y | L175 | L413 | i3318 | Y | L175 | L404 | i3319 | Y | L175 | L534 | i3320 | Y | L175 | L188 |
| i3321 | Y | L176 | L413 | i3322 | Y | L176 | L404 | i3323 | Y | L176 | L534 | i3324 | Y | L176 | L188 |
| i3325 | Y | L177 | L413 | i3326 | Y | L177 | L404 | i3327 | Y | L177 | L534 | i3328 | Y | L177 | L188 |
| i3329 | Y | L178 | L413 | i3330 | Y | L178 | L404 | i3331 | Y | L178 | L534 | i3332 | Y | L178 | L188 |
| i3333 | Y | L179 | L413 | i3334 | Y | L179 | L404 | i3335 | Y | L179 | L534 | i3336 | Y | L179 | L188 |
| i3337 | Y | L180 | L413 | i3338 | Y | L180 | L404 | i3339 | Y | L180 | L534 | i3340 | Y | L180 | L188 |
| i3341 | Y | L181 | L413 | i3342 | Y | L181 | L404 | i3343 | Y | L181 | L534 | i3344 | Y | L181 | L188 |
| i3345 | Y | L182 | L413 | i3346 | Y | L182 | L404 | i3347 | Y | L182 | L534 | i3348 | Y | L182 | L188 |
| i3349 | Y | L183 | L413 | i3350 | Y | L183 | L404 | i3351 | Y | L183 | L534 | i3352 | Y | L183 | L188 |
| i3353 | Y | L184 | L413 | i3354 | Y | L184 | L404 | i3355 | Y | L184 | L534 | i3356 | Y | L184 | L188 |
| i3357 | Y | L185 | L413 | i3358 | Y | L185 | L404 | i3359 | Y | L185 | L534 | i3360 | Y | L185 | L188 |
| i3361 | Y | L186 | L413 | i3362 | Y | L186 | L404 | i3363 | Y | L186 | L534 | i3364 | Y | L186 | L188 |
| i3365 | Y | L187 | L413 | i3366 | Y | L187 | L404 | i3367 | Y | L187 | L534 | i3368 | Y | L187 | L188 |
| i3369 | Y | L188 | L413 | i3370 | Y | L188 | L404 | i3371 | Y | L188 | L534 | i3372 | Y | L188 | L188 |
| i3373 | Y | L189 | L413 | i3374 | Y | L189 | L404 | i3375 | Y | L189 | L534 | i3376 | Y | L189 | L188 |
| i3377 | Y | L190 | L413 | i3378 | Y | L190 | L404 | i3379 | Y | L190 | L534 | i3380 | Y | L190 | L188 |
| i3381 | Y | L191 | L413 | i3382 | Y | L191 | L404 | i3383 | Y | L191 | L534 | i3384 | Y | L191 | L188 |
| i3385 | Y | L192 | L413 | i3386 | Y | L192 | L404 | i3387 | Y | L192 | L534 | i3388 | Y | L192 | L188 |
| i3389 | Y | L193 | L413 | i3390 | Y | L193 | L404 | i3391 | Y | L193 | L534 | i3392 | Y | L193 | L188 |
| i3393 | Y | L194 | L413 | i3394 | Y | L194 | L404 | i3395 | Y | L194 | L534 | i3396 | Y | L194 | L188 |
| i3397 | Y | L195 | L413 | i3398 | Y | L195 | L404 | i3399 | Y | L195 | L534 | i3400 | Y | L195 | L188 |
| i3401 | Y | L196 | L413 | i3402 | Y | L196 | L404 | i3403 | Y | L196 | L534 | i3404 | Y | L196 | L188 |

TABLE 1-continued

Compositions "i1" to "i9919"

| | | | | | | | | | | | | |
|---|---|---|---|---|---|---|---|---|---|---|---|---|
| i3405 | Y | L197 | L413 | i3406 | Y | L197 | L404 | i3407 | Y | L197 | L534 | i3408 | Y | L197 | L188 |
| i3409 | Y | L198 | L413 | i3410 | Y | L198 | L404 | i3411 | Y | L198 | L534 | i3412 | Y | L198 | L188 |
| i3413 | Y | L199 | L413 | i3414 | Y | L199 | L404 | i3415 | Y | L199 | L534 | i3416 | Y | L199 | L188 |
| i3417 | Y | L200 | L413 | i3418 | Y | L200 | L404 | i3419 | Y | L200 | L534 | i3420 | Y | L200 | L188 |
| i3421 | Y | L201 | L413 | i3422 | Y | L201 | L404 | i3423 | Y | L201 | L534 | i3424 | Y | L201 | L188 |
| i3425 | Y | L202 | L413 | i3426 | Y | L202 | L404 | i3427 | Y | L202 | L534 | i3428 | Y | L202 | L188 |
| i3429 | Y | L203 | L413 | i3430 | Y | L203 | L404 | i3431 | Y | L203 | L534 | i3432 | Y | L203 | L188 |
| i3433 | Y | L204 | L413 | i3434 | Y | L204 | L404 | i3435 | Y | L204 | L534 | i3436 | Y | L204 | L188 |
| i3437 | Y | L205 | L413 | i3438 | Y | L205 | L404 | i3439 | Y | L205 | L534 | i3440 | Y | L205 | L188 |
| i3441 | Y | L206 | L413 | i3442 | Y | L206 | L404 | i3443 | Y | L206 | L534 | i3444 | Y | L206 | L188 |
| i3445 | Y | L207 | L413 | i3446 | Y | L207 | L404 | i3447 | Y | L207 | L534 | i3448 | Y | L207 | L188 |
| i3449 | Y | L208 | L413 | i3450 | Y | L208 | L404 | i3451 | Y | L208 | L534 | i3452 | Y | L208 | L188 |
| i3453 | Y | L209 | L413 | i3454 | Y | L209 | L404 | i3455 | Y | L209 | L534 | i3456 | Y | L209 | L188 |
| i3457 | Y | L210 | L413 | i3458 | Y | L210 | L404 | i3459 | Y | L210 | L534 | i3460 | Y | L210 | L188 |
| i3461 | Y | L211 | L413 | i3462 | Y | L211 | L404 | i3463 | Y | L211 | L534 | i3464 | Y | L211 | L188 |
| i3465 | Y | L212 | L413 | i3466 | Y | L212 | L404 | i3467 | Y | L212 | L534 | i3468 | Y | L212 | L188 |
| i3469 | Y | L213 | L413 | i3470 | Y | L213 | L404 | i3471 | Y | L213 | L534 | i3472 | Y | L213 | L188 |
| i3473 | Y | L214 | L413 | i3474 | Y | L214 | L404 | i3475 | Y | L214 | L534 | i3476 | Y | L214 | L188 |
| i3477 | Y | L215 | L413 | i3478 | Y | L215 | L404 | i3479 | Y | L215 | L534 | i3480 | Y | L215 | L188 |
| i3481 | Y | L216 | L413 | i3482 | Y | L216 | L404 | i3483 | Y | L216 | L534 | i3484 | Y | L216 | L188 |
| i3485 | Y | L217 | L413 | i3486 | Y | L217 | L404 | i3487 | Y | L217 | L534 | i3488 | Y | L217 | L188 |
| i3489 | Y | L218 | L413 | i3490 | Y | L218 | L404 | i3491 | Y | L218 | L534 | i3492 | Y | L218 | L188 |
| i3493 | Y | L219 | L413 | i3494 | Y | L219 | L404 | i3495 | Y | L219 | L534 | i3496 | Y | L219 | L188 |
| i3497 | Y | L220 | L413 | i3498 | Y | L220 | L404 | i3499 | Y | L220 | L534 | i3500 | Y | L220 | L188 |
| i3501 | Y | L221 | L413 | i3502 | Y | L221 | L404 | i3503 | Y | L221 | L534 | i3504 | Y | L221 | L188 |
| i3505 | Y | L222 | L413 | i3506 | Y | L222 | L404 | i3507 | Y | L222 | L534 | i3508 | Y | L222 | L188 |
| i3509 | Y | L401 | L413 | i3510 | Y | L401 | L404 | i3511 | Y | L401 | L534 | i3512 | Y | L401 | L188 |
| i3513 | Y | L402 | L413 | i3514 | Y | L402 | L404 | i3515 | Y | L402 | L534 | i3516 | Y | L402 | L188 |
| i3517 | Y | L403 | L413 | i3518 | Y | L403 | L404 | i3519 | Y | L403 | L534 | i3520 | Y | L403 | L188 |
| i3521 | Y | L404 | L413 | i3522 | Y | L404 | L404 | i3523 | Y | L404 | L534 | i3524 | Y | L404 | L188 |
| i3525 | Y | L405 | L413 | i3526 | Y | L405 | L404 | i3527 | Y | L405 | L534 | i3528 | Y | L405 | L188 |
| i3529 | Y | L406 | L413 | i3530 | Y | L406 | L404 | i3531 | Y | L406 | L534 | i3532 | Y | L406 | L188 |
| i3533 | Y | L407 | L413 | i3534 | Y | L407 | L404 | i3535 | Y | L407 | L534 | i3536 | Y | L407 | L188 |
| i3537 | Y | L408 | L413 | i3538 | Y | L408 | L404 | i3539 | Y | L408 | L534 | i3540 | Y | L408 | L188 |
| i3541 | Y | L409 | L413 | i3542 | Y | L409 | L404 | i3543 | Y | L409 | L534 | i3544 | Y | L409 | L188 |
| i3545 | Y | L410 | L413 | i3546 | Y | L410 | L404 | i3547 | Y | L410 | L534 | i3548 | Y | L410 | L188 |
| i3549 | Y | L411 | L413 | i3550 | Y | L411 | L404 | i3551 | Y | L411 | L534 | i3552 | Y | L411 | L188 |
| i3553 | Y | L412 | L413 | i3554 | Y | L412 | L404 | i3555 | Y | L412 | L534 | i3556 | Y | L412 | L188 |
| i3557 | Y | L413 | L413 | i3558 | Y | L413 | L404 | i3559 | Y | L413 | L534 | i3560 | Y | L413 | L188 |
| i3561 | Y | L414 | L413 | i3562 | Y | L414 | L404 | i3563 | Y | L414 | L534 | i3564 | Y | L414 | L188 |
| i3565 | Y | L415 | L413 | i3566 | Y | L415 | L404 | i3567 | Y | L415 | L534 | i3568 | Y | L415 | L188 |
| i3569 | Y | L416 | L413 | i3570 | Y | L416 | L404 | i3571 | Y | L416 | L534 | i3572 | Y | L416 | L188 |
| i3573 | Y | L417 | L413 | i3574 | Y | L417 | L404 | i3575 | Y | L417 | L534 | i3576 | Y | L417 | L188 |
| i3577 | Y | L418 | L413 | i3578 | Y | L418 | L404 | i3579 | Y | L418 | L534 | i3580 | Y | L418 | L188 |
| i3581 | Y | L419 | L413 | i3582 | Y | L419 | L404 | i3583 | Y | L419 | L534 | i3584 | Y | L419 | L188 |
| i3585 | Y | L420 | L413 | i3586 | Y | L420 | L404 | i3587 | Y | L420 | L534 | i3588 | Y | L420 | L188 |
| i3589 | Y | L421 | L413 | i3590 | Y | L421 | L404 | i3591 | Y | L421 | L534 | i3592 | Y | L421 | L188 |
| i3593 | Y | L422 | L413 | i3594 | Y | L422 | L404 | i3595 | Y | L422 | L534 | i3596 | Y | L422 | L188 |
| i3597 | Y | L423 | L413 | i3598 | Y | L423 | L404 | i3599 | Y | L423 | L534 | i3600 | Y | L423 | L188 |
| i3601 | Y | L424 | L413 | i3602 | Y | L424 | L404 | i3603 | Y | L424 | L534 | i3604 | Y | L424 | L188 |
| i3605 | Y | L425 | L413 | i3606 | Y | L425 | L404 | i3607 | Y | L425 | L534 | i3608 | Y | L425 | L188 |
| i3609 | Y | L501 | L413 | i3610 | Y | L501 | L404 | i3611 | Y | L501 | L534 | i3612 | Y | L501 | L188 |
| i3613 | Y | L502 | L413 | i3614 | Y | L502 | L404 | i3615 | Y | L502 | L534 | i3616 | Y | L502 | L188 |
| i3617 | Y | L503 | L413 | i3618 | Y | L503 | L404 | i3619 | Y | L503 | L534 | i3620 | Y | L503 | L188 |
| i3621 | Y | L504 | L413 | i3622 | Y | L504 | L404 | i3623 | Y | L504 | L534 | i3624 | Y | L504 | L188 |
| i3625 | Y | L505 | L413 | i3626 | Y | L505 | L404 | i3627 | Y | L505 | L534 | i3628 | Y | L505 | L188 |
| i3629 | Y | L506 | L413 | i3630 | Y | L506 | L404 | i3631 | Y | L506 | L534 | i3632 | Y | L506 | L188 |
| i3633 | Y | L507 | L413 | i3634 | Y | L507 | L404 | i3635 | Y | L507 | L534 | i3636 | Y | L507 | L188 |
| i3637 | Y | L508 | L413 | i3638 | Y | L508 | L404 | i3639 | Y | L508 | L534 | i3640 | Y | L508 | L188 |
| i3641 | Y | L509 | L413 | i3642 | Y | L509 | L404 | i3643 | Y | L509 | L534 | i3644 | Y | L509 | L188 |
| i3645 | Y | L510 | L413 | i3646 | Y | L510 | L404 | i3647 | Y | L510 | L534 | i3648 | Y | L510 | L188 |
| i3649 | Y | L511 | L413 | i3650 | Y | L511 | L404 | i3651 | Y | L511 | L534 | i3652 | Y | L511 | L188 |
| i3653 | Y | L512 | L413 | i3654 | Y | L512 | L404 | i3655 | Y | L512 | L534 | i3656 | Y | L512 | L188 |
| i3657 | Y | L513 | L413 | i3658 | Y | L513 | L404 | i3659 | Y | L513 | L534 | i3660 | Y | L513 | L188 |
| i3661 | Y | L514 | L413 | i3662 | Y | L514 | L404 | i3663 | Y | L514 | L534 | i3664 | Y | L514 | L188 |
| i3665 | Y | L515 | L413 | i3666 | Y | L515 | L404 | i3667 | Y | L515 | L534 | i3668 | Y | L515 | L188 |
| i3669 | Y | L516 | L413 | i3670 | Y | L516 | L404 | i3671 | Y | L516 | L534 | i3672 | Y | L516 | L188 |
| i3673 | Y | L517 | L413 | i3674 | Y | L517 | L404 | i3675 | Y | L517 | L534 | i3676 | Y | L517 | L188 |
| i3677 | Y | L518 | L413 | i3678 | Y | L518 | L404 | i3679 | Y | L518 | L534 | i3680 | Y | L518 | L188 |
| i3681 | Y | L519 | L413 | i3682 | Y | L519 | L404 | i3683 | Y | L519 | L534 | i3684 | Y | L519 | L188 |
| i3685 | Y | L520 | L413 | i3686 | Y | L520 | L404 | i3687 | Y | L520 | L534 | i3688 | Y | L520 | L188 |
| i3689 | Y | L521 | L413 | i3690 | Y | L521 | L404 | i3691 | Y | L521 | L534 | i3692 | Y | L521 | L188 |
| i3693 | Y | L522 | L413 | i3694 | Y | L522 | L404 | i3695 | Y | L522 | L534 | i3696 | Y | L522 | L188 |
| i3697 | Y | L523 | L413 | i3698 | Y | L523 | L404 | i3699 | Y | L523 | L534 | i3700 | Y | L523 | L188 |
| i3701 | Y | L524 | L413 | i3702 | Y | L524 | L404 | i3703 | Y | L524 | L534 | i3704 | Y | L524 | L188 |
| i3705 | Y | L525 | L413 | i3706 | Y | L525 | L404 | i3707 | Y | L525 | L534 | i3708 | Y | L525 | L188 |
| i3709 | Y | L526 | L413 | i3710 | Y | L526 | L404 | i3711 | Y | L526 | L534 | i3712 | Y | L526 | L188 |
| i3713 | Y | L527 | L413 | i3714 | Y | L527 | L404 | i3715 | Y | L527 | L534 | i3716 | Y | L527 | L188 |

TABLE 1-continued

Compositions "i1" to "i9919"

| | | | | | | | | | | | | | | |
|---|---|---|---|---|---|---|---|---|---|---|---|---|---|---|
| i3717 | Y | L528 | L413 | i3718 | Y | L528 | L404 | i3719 | Y | L528 | L534 | i3720 | Y | L528 | L188 |
| i3721 | Y | L529 | L413 | i3722 | Y | L529 | L404 | i3723 | Y | L529 | L534 | i3724 | Y | L529 | L188 |
| i3725 | Y | L530 | L413 | i3726 | Y | L530 | L404 | i3727 | Y | L530 | L534 | i3728 | Y | L530 | L188 |
| i3729 | Y | L531 | L413 | i3730 | Y | L531 | L404 | i3731 | Y | L531 | L534 | i3732 | Y | L531 | L188 |
| i3733 | Y | L532 | L413 | i3734 | Y | L532 | L404 | i3735 | Y | L532 | L534 | i3736 | Y | L532 | L188 |
| i3737 | Y | L533 | L413 | i3738 | Y | L533 | L404 | i3739 | Y | L533 | L534 | i3740 | Y | L533 | L188 |
| i3741 | Y | L534 | L413 | i3742 | Y | L534 | L404 | i3743 | Y | L534 | L534 | i3744 | Y | L534 | L188 |
| i3745 | Y | L535 | L413 | i3746 | Y | L535 | L404 | i3747 | Y | L535 | L534 | i3748 | Y | L535 | L188 |
| i3749 | Y | L536 | L413 | i3750 | Y | L536 | L404 | i3751 | Y | L536 | L534 | i3752 | Y | L536 | L188 |
| i3753 | Y | L537 | L413 | i3754 | Y | L537 | L404 | i3755 | Y | L537 | L534 | i3756 | Y | L537 | L188 |
| i3757 | Y | L538 | L413 | i3758 | Y | L538 | L404 | i3759 | Y | L538 | L534 | i3760 | Y | L538 | L188 |
| i3761 | Y | L539 | L413 | i3762 | Y | L539 | L404 | i3763 | Y | L539 | L534 | i3764 | Y | L539 | L188 |
| i3765 | Y | L540 | L413 | i3766 | Y | L540 | L404 | i3767 | Y | L540 | L534 | i3768 | Y | L540 | L188 |
| i3769 | Y | L541 | L413 | i3770 | Y | L541 | L404 | i3771 | Y | L541 | L534 | i3772 | Y | L541 | L188 |
| i3773 | Y | L542 | L413 | i3774 | Y | L542 | L404 | i3775 | Y | L542 | L534 | i3776 | Y | L542 | L188 |
| i3777 | Y | L543 | L413 | i3778 | Y | L543 | L404 | i3779 | Y | L543 | L534 | i3780 | Y | L543 | L188 |
| i3781 | Y | L544 | L413 | i3782 | Y | L544 | L404 | i3783 | Y | L544 | L534 | i3784 | Y | L544 | L188 |
| i3785 | Y | L545 | L413 | i3786 | Y | L545 | L404 | i3787 | Y | L545 | L534 | i3788 | Y | L545 | L188 |
| i3789 | Y | L546 | L413 | i3790 | Y | L546 | L404 | i3791 | Y | L546 | L534 | i3792 | Y | L546 | L188 |
| i3793 | Y | L547 | L413 | i3794 | Y | L547 | L404 | i3795 | Y | L547 | L534 | i3796 | Y | L547 | L188 |
| i3797 | Y | L548 | L413 | i3798 | Y | L548 | L404 | i3799 | Y | L548 | L534 | i3800 | Y | L548 | L188 |
| i3801 | Y | L549 | L413 | i3802 | Y | L549 | L404 | i3803 | Y | L549 | L534 | i3804 | Y | L549 | L188 |
| i3805 | Y | L550 | L413 | i3806 | Y | L550 | L404 | i3807 | Y | L550 | L534 | i3808 | Y | L550 | L188 |
| i3809 | Y | L551 | L413 | i3810 | Y | L551 | L404 | i3811 | Y | L551 | L534 | i3812 | Y | L551 | L188 |
| i3813 | Y | L552 | L413 | i3814 | Y | L552 | L404 | i3815 | Y | L552 | L534 | i3816 | Y | L552 | L188 |
| i3817 | Y | L553 | L413 | i3818 | Y | L553 | L404 | i3819 | Y | L553 | L534 | i3820 | Y | L553 | L188 |
| i3821 | Y | L554 | L413 | i3822 | Y | L554 | L404 | i3823 | Y | L554 | L534 | i3824 | Y | L554 | L188 |
| i3825 | Y | L555 | L413 | i3826 | Y | L555 | L404 | i3827 | Y | L555 | L534 | i3828 | Y | L555 | L188 |
| i3829 | Y | L556 | L413 | i3830 | Y | L556 | L404 | i3831 | Y | L556 | L534 | i3832 | Y | L556 | L188 |
| i3833 | Y | L557 | L413 | i3834 | Y | L557 | L404 | i3835 | Y | L557 | L534 | i3836 | Y | L557 | L188 |
| i3837 | Y | L558 | L413 | i3838 | Y | L558 | L404 | i3839 | Y | L558 | L534 | i3840 | Y | L558 | L188 |
| i3841 | Y | L559 | L413 | i3842 | Y | L559 | L404 | i3843 | Y | L559 | L534 | i3844 | Y | L559 | L188 |
| i3845 | Y | L560 | L413 | i3846 | Y | L560 | L404 | i3847 | Y | L560 | L534 | i3848 | Y | L560 | L188 |
| i3849 | Y | L561 | L413 | i3850 | Y | L561 | L404 | i3851 | Y | L561 | L534 | i3852 | Y | L561 | L188 |
| i3853 | Y | L562 | L413 | i3854 | Y | L562 | L404 | i3855 | Y | L562 | L534 | i3856 | Y | L562 | L188 |
| i3857 | Y | L563 | L413 | i3858 | Y | L563 | L404 | i3859 | Y | L563 | L534 | i3860 | Y | L563 | L188 |
| i3861 | Y | L564 | L413 | i3862 | Y | L564 | L404 | i3863 | Y | L564 | L534 | i3864 | Y | L564 | L188 |
| i3865 | Y | L565 | L413 | i3866 | Y | L565 | L404 | i3867 | Y | L565 | L534 | i3868 | Y | L565 | L188 |
| i3869 | Y | L566 | L413 | i3870 | Y | L566 | L404 | i3871 | Y | L566 | L534 | i3872 | Y | L566 | L188 |
| i3873 | Y | L567 | L413 | i3874 | Y | L567 | L404 | i3875 | Y | L567 | L534 | i3876 | Y | L567 | L188 |
| i3877 | Y | L568 | L413 | i3878 | Y | L568 | L404 | i3879 | Y | L568 | L534 | i3880 | Y | L568 | L188 |
| i3881 | Y | L569 | L413 | i3882 | Y | L569 | L404 | i3883 | Y | L569 | L534 | i3884 | Y | L569 | L188 |
| i3885 | Y | L570 | L413 | i3886 | Y | L570 | L404 | i3887 | Y | L570 | L534 | i3888 | Y | L570 | L188 |
| i3889 | Y | L571 | L413 | i3890 | Y | L571 | L404 | i3891 | Y | L571 | L534 | i3892 | Y | L571 | L188 |
| i3893 | Y | L572 | L413 | i3894 | Y | L572 | L404 | i3895 | Y | L572 | L534 | i3896 | Y | L572 | L188 |
| i3897 | Y | L843 | L413 | i3898 | Y | L843 | L404 | i3899 | Y | L843 | L534 | i3900 | Y | L843 | L188 |
| i3901 | Y | L844 | L413 | i3902 | Y | L844 | L404 | i3903 | Y | L844 | L534 | i3904 | Y | L844 | L188 |
| i3905 | Y | L845 | L413 | i3906 | Y | L845 | L404 | i3907 | Y | L845 | L534 | i3908 | Y | L845 | L188 |
| i3909 | Y | L846 | L413 | i3910 | Y | L846 | L404 | i3911 | Y | L846 | L534 | i3912 | Y | L846 | L188 |
| i3913 | Y | L847 | L413 | i3914 | Y | L847 | L404 | i3915 | Y | L847 | L534 | i3916 | Y | L847 | L188 |
| i3917 | Y | L848 | L413 | i3918 | Y | L848 | L404 | i3919 | Y | L848 | L534 | i3920 | Y | L848 | L188 |
| i3921 | Y | L10 | L179 | i3922 | Y | L10 | L180 | i3923 | Y | L10 | L196 | i3924 | Y | L10 | L217 |
| i3925 | Y | L11 | L179 | i3926 | Y | L11 | L180 | i3927 | Y | L11 | L196 | i3928 | Y | L11 | L217 |
| i3929 | Y | L20 | L179 | i3930 | Y | L20 | L180 | i3931 | Y | L20 | L196 | i3932 | Y | L20 | L217 |
| i3933 | Y | L21 | L179 | i3934 | Y | L21 | L180 | i3935 | Y | L21 | L196 | i3936 | Y | L21 | L217 |
| i3937 | Y | L22 | L179 | i3938 | Y | L22 | L180 | i3939 | Y | L22 | L196 | i3940 | Y | L22 | L217 |
| i3941 | Y | L23 | L179 | i3942 | Y | L23 | L180 | i3943 | Y | L23 | L196 | i3944 | Y | L23 | L217 |
| i3945 | Y | L24 | L179 | i3946 | Y | L24 | L180 | i3947 | Y | L24 | L196 | i3948 | Y | L24 | L217 |
| i3949 | Y | L25 | L179 | i3950 | Y | L25 | L180 | i3951 | Y | L25 | L196 | i3952 | Y | L25 | L217 |
| i3953 | Y | L26 | L179 | i3954 | Y | L26 | L180 | i3955 | Y | L26 | L196 | i3956 | Y | L26 | L217 |
| i3957 | Y | L27 | L179 | i3958 | Y | L27 | L180 | i3959 | Y | L27 | L196 | i3960 | Y | L27 | L217 |
| i3961 | Y | L28 | L179 | i3962 | Y | L28 | L180 | i3963 | Y | L28 | L196 | i3964 | Y | L28 | L217 |
| i3965 | Y | L12 | L179 | i3966 | Y | L12 | L180 | i3967 | Y | L12 | L196 | i3968 | Y | L12 | L217 |
| i3969 | Y | L13 | L179 | i3970 | Y | L13 | L180 | i3971 | Y | L13 | L196 | i3972 | Y | L13 | L217 |
| i3973 | Y | L14 | L179 | i3974 | Y | L14 | L180 | i3975 | Y | L14 | L196 | i3976 | Y | L14 | L217 |
| i3977 | Y | L15 | L179 | i3978 | Y | L15 | L180 | i3979 | Y | L15 | L196 | i3980 | Y | L15 | L217 |
| i3981 | Y | L16 | L179 | i3982 | Y | L16 | L180 | i3983 | Y | L16 | L196 | i3984 | Y | L16 | L217 |
| i3985 | Y | L17 | L179 | i3986 | Y | L17 | L180 | i3987 | Y | L17 | L196 | i3988 | Y | L17 | L217 |
| i3989 | Y | L18 | L179 | i3990 | Y | L18 | L180 | i3991 | Y | L18 | L196 | i3992 | Y | L18 | L217 |
| i3993 | Y | L19 | L179 | i3994 | Y | L19 | L180 | i3995 | Y | L19 | L196 | i3996 | Y | L19 | L217 |
| i3997 | Y | L2 | L179 | i3998 | Y | L2 | L180 | i3999 | Y | L2 | L196 | i4000 | Y | L2 | L217 |
| i4001 | Y | L101 | L179 | i4002 | Y | L101 | L180 | i4003 | Y | L101 | L196 | i4004 | Y | L101 | L217 |
| i4005 | Y | L102 | L179 | i4006 | Y | L102 | L180 | i4007 | Y | L102 | L196 | i4008 | Y | L102 | L217 |
| i4009 | Y | L103 | L179 | i4010 | Y | L103 | L180 | i4011 | Y | L103 | L196 | i4012 | Y | L103 | L217 |
| i4013 | Y | L104 | L179 | i4014 | Y | L104 | L180 | i4015 | Y | L104 | L196 | i4016 | Y | L104 | L217 |
| i4017 | Y | L105 | L179 | i4018 | Y | L105 | L180 | i4019 | Y | L105 | L196 | i4020 | Y | L105 | L217 |
| i4021 | Y | L106 | L179 | i4022 | Y | L106 | L180 | i4023 | Y | L106 | L196 | i4024 | Y | L106 | L217 |
| i4025 | Y | L107 | L179 | i4026 | Y | L107 | L180 | i4027 | Y | L107 | L196 | i4028 | Y | L107 | L217 |

TABLE 1-continued

Compositions "i1" to "i9919"

| | | | | | | | | | | | | | | |
|---|---|---|---|---|---|---|---|---|---|---|---|---|---|---|
| i4029 | Y | L108 | L179 | i4030 | Y | L108 | L180 | i4031 | Y | L108 | L196 | i4032 | Y | L108 | L217 |
| i4033 | Y | L109 | L179 | i4034 | Y | L109 | L180 | i4035 | Y | L109 | L196 | i4036 | Y | L109 | L217 |
| i4037 | Y | L110 | L179 | i4038 | Y | L110 | L180 | i4039 | Y | L110 | L196 | i4040 | Y | L110 | L217 |
| i4041 | Y | L111 | L179 | i4042 | Y | L111 | L180 | i4043 | Y | L111 | L196 | i4044 | Y | L111 | L217 |
| i4045 | Y | L112 | L179 | i4046 | Y | L112 | L180 | i4047 | Y | L112 | L196 | i4048 | Y | L112 | L217 |
| i4049 | Y | L113 | L179 | i4050 | Y | L113 | L180 | i4051 | Y | L113 | L196 | i4052 | Y | L113 | L217 |
| i4053 | Y | L114 | L179 | i4054 | Y | L114 | L180 | i4055 | Y | L114 | L196 | i4056 | Y | L114 | L217 |
| i4057 | Y | L115 | L179 | i4058 | Y | L115 | L180 | i4059 | Y | L115 | L196 | i4060 | Y | L115 | L217 |
| i4061 | Y | L116 | L179 | i4062 | Y | L116 | L180 | i4063 | Y | L116 | L196 | i4064 | Y | L116 | L217 |
| i4065 | Y | L117 | L179 | i4066 | Y | L117 | L180 | i4067 | Y | L117 | L196 | i4068 | Y | L117 | L217 |
| i4069 | Y | L118 | L179 | i4070 | Y | L118 | L180 | i4071 | Y | L118 | L196 | i4072 | Y | L118 | L217 |
| i4073 | Y | L119 | L179 | i4074 | Y | L119 | L180 | i4075 | Y | L119 | L196 | i4076 | Y | L119 | L217 |
| i4077 | Y | L120 | L179 | i4078 | Y | L120 | L180 | i4079 | Y | L120 | L196 | i4080 | Y | L120 | L217 |
| i4081 | Y | L121 | L179 | i4082 | Y | L121 | L180 | i4083 | Y | L121 | L196 | i4084 | Y | L121 | L217 |
| i4085 | Y | L122 | L179 | i4086 | Y | L122 | L180 | i4087 | Y | L122 | L196 | i4088 | Y | L122 | L217 |
| i4089 | Y | L123 | L179 | i4090 | Y | L123 | L180 | i4091 | Y | L123 | L196 | i4092 | Y | L123 | L217 |
| i4093 | Y | L124 | L179 | i4094 | Y | L124 | L180 | i4095 | Y | L124 | L196 | i4096 | Y | L124 | L217 |
| i4097 | Y | L125 | L179 | i4098 | Y | L125 | L180 | i4099 | Y | L125 | L196 | i4100 | Y | L125 | L217 |
| i4101 | Y | L126 | L179 | i4102 | Y | L126 | L180 | i4103 | Y | L126 | L196 | i4104 | Y | L126 | L217 |
| i4105 | Y | L127 | L179 | i4106 | Y | L127 | L180 | i4107 | Y | L127 | L196 | i4108 | Y | L127 | L217 |
| i4109 | Y | L128 | L179 | i4110 | Y | L128 | L180 | i4111 | Y | L128 | L196 | i4112 | Y | L128 | L217 |
| i4113 | Y | L129 | L179 | i4114 | Y | L129 | L180 | i4115 | Y | L129 | L196 | i4116 | Y | L129 | L217 |
| i4117 | Y | L130 | L179 | i4118 | Y | L130 | L180 | i4119 | Y | L130 | L196 | i4120 | Y | L130 | L217 |
| i4121 | Y | L131 | L179 | i4122 | Y | L131 | L180 | i4123 | Y | L131 | L196 | i4124 | Y | L131 | L217 |
| i4125 | Y | L132 | L179 | i4126 | Y | L132 | L180 | i4127 | Y | L132 | L196 | i4128 | Y | L132 | L217 |
| i4129 | Y | L133 | L179 | i4130 | Y | L133 | L180 | i4131 | Y | L133 | L196 | i4132 | Y | L133 | L217 |
| i4133 | Y | L134 | L179 | i4134 | Y | L134 | L180 | i4135 | Y | L134 | L196 | i4136 | Y | L134 | L217 |
| i4137 | Y | L135 | L179 | i4138 | Y | L135 | L180 | i4139 | Y | L135 | L196 | i4140 | Y | L135 | L217 |
| i4141 | Y | L136 | L179 | i4142 | Y | L136 | L180 | i4143 | Y | L136 | L196 | i4144 | Y | L136 | L217 |
| i4145 | Y | L137 | L179 | i4146 | Y | L137 | L180 | i4147 | Y | L137 | L196 | i4148 | Y | L137 | L217 |
| i4149 | Y | L138 | L179 | i4150 | Y | L138 | L180 | i4151 | Y | L138 | L196 | i4152 | Y | L138 | L217 |
| i4153 | Y | L139 | L179 | i4154 | Y | L139 | L180 | i4155 | Y | L139 | L196 | i4156 | Y | L139 | L217 |
| i4157 | Y | L140 | L179 | i4158 | Y | L140 | L180 | i4159 | Y | L140 | L196 | i4160 | Y | L140 | L217 |
| i4161 | Y | L141 | L179 | i4162 | Y | L141 | L180 | i4163 | Y | L141 | L196 | i4164 | Y | L141 | L217 |
| i4165 | Y | L142 | L179 | i4166 | Y | L142 | L180 | i4167 | Y | L142 | L196 | i4168 | Y | L142 | L217 |
| i4169 | Y | L143 | L179 | i4170 | Y | L143 | L180 | i4171 | Y | L143 | L196 | i4172 | Y | L143 | L217 |
| i4173 | Y | L144 | L179 | i4174 | Y | L144 | L180 | i4175 | Y | L144 | L196 | i4176 | Y | L144 | L217 |
| i4177 | Y | L145 | L179 | i4178 | Y | L145 | L180 | i4179 | Y | L145 | L196 | i4180 | Y | L145 | L217 |
| i4181 | Y | L146 | L179 | i4182 | Y | L146 | L180 | i4183 | Y | L146 | L196 | i4184 | Y | L146 | L217 |
| i4185 | Y | L147 | L179 | i4186 | Y | L147 | L180 | i4187 | Y | L147 | L196 | i4188 | Y | L147 | L217 |
| i4189 | Y | L148 | L179 | i4190 | Y | L148 | L180 | i4191 | Y | L148 | L196 | i4192 | Y | L148 | L217 |
| i4193 | Y | L149 | L179 | i4194 | Y | L149 | L180 | i4195 | Y | L149 | L196 | i4196 | Y | L149 | L217 |
| i4197 | Y | L150 | L179 | i4198 | Y | L150 | L180 | i4199 | Y | L150 | L196 | i4200 | Y | L150 | L217 |
| i4201 | Y | L151 | L179 | i4202 | Y | L151 | L180 | i4203 | Y | L151 | L196 | i4204 | Y | L151 | L217 |
| i4205 | Y | L152 | L179 | i4206 | Y | L152 | L180 | i4207 | Y | L152 | L196 | i4208 | Y | L152 | L217 |
| i4209 | Y | L153 | L179 | i4210 | Y | L153 | L180 | i4211 | Y | L153 | L196 | i4212 | Y | L153 | L217 |
| i4213 | Y | L154 | L179 | i4214 | Y | L154 | L180 | i4215 | Y | L154 | L196 | i4216 | Y | L154 | L217 |
| i4217 | Y | L155 | L179 | i4218 | Y | L155 | L180 | i4219 | Y | L155 | L196 | i4220 | Y | L155 | L217 |
| i4221 | Y | L156 | L179 | i4222 | Y | L156 | L180 | i4223 | Y | L156 | L196 | i4224 | Y | L156 | L217 |
| i4225 | Y | L157 | L179 | i4226 | Y | L157 | L180 | i4227 | Y | L157 | L196 | i4228 | Y | L157 | L217 |
| i4229 | Y | L158 | L179 | i4230 | Y | L158 | L180 | i4231 | Y | L158 | L196 | i4232 | Y | L158 | L217 |
| i4233 | Y | L159 | L179 | i4234 | Y | L159 | L180 | i4235 | Y | L159 | L196 | i4236 | Y | L159 | L217 |
| i4237 | Y | L160 | L179 | i4238 | Y | L160 | L180 | i4239 | Y | L160 | L196 | i4240 | Y | L160 | L217 |
| i4241 | Y | L161 | L179 | i4242 | Y | L161 | L180 | i4243 | Y | L161 | L196 | i4244 | Y | L161 | L217 |
| i4245 | Y | L162 | L179 | i4246 | Y | L162 | L180 | i4247 | Y | L162 | L196 | i4248 | Y | L162 | L217 |
| i4249 | Y | L163 | L179 | i4250 | Y | L163 | L180 | i4251 | Y | L163 | L196 | i4252 | Y | L163 | L217 |
| i4253 | Y | L164 | L179 | i4254 | Y | L164 | L180 | i4255 | Y | L164 | L196 | i4256 | Y | L164 | L217 |
| i4257 | Y | L165 | L179 | i4258 | Y | L165 | L180 | i4259 | Y | L165 | L196 | i4260 | Y | L165 | L217 |
| i4261 | Y | L166 | L179 | i4262 | Y | L166 | L180 | i4263 | Y | L166 | L196 | i4264 | Y | L166 | L217 |
| i4265 | Y | L167 | L179 | i4266 | Y | L167 | L180 | i4267 | Y | L167 | L196 | i4268 | Y | L167 | L217 |
| i4269 | Y | L168 | L179 | i4270 | Y | L168 | L180 | i4271 | Y | L168 | L196 | i4272 | Y | L168 | L217 |
| i4273 | Y | L169 | L179 | i4274 | Y | L169 | L180 | i4275 | Y | L169 | L196 | i4276 | Y | L169 | L217 |
| i4277 | Y | L170 | L179 | i4278 | Y | L170 | L180 | i4279 | Y | L170 | L196 | i4280 | Y | L170 | L217 |
| i4281 | Y | L171 | L179 | i4282 | Y | L171 | L180 | i4283 | Y | L171 | L196 | i4284 | Y | L171 | L217 |
| i4285 | Y | L172 | L179 | i4286 | Y | L172 | L180 | i4287 | Y | L172 | L196 | i4288 | Y | L172 | L217 |
| i4289 | Y | L173 | L179 | i4290 | Y | L173 | L180 | i4291 | Y | L173 | L196 | i4292 | Y | L173 | L217 |
| i4293 | Y | L174 | L179 | i4294 | Y | L174 | L180 | i4295 | Y | L174 | L196 | i4296 | Y | L174 | L217 |
| i4297 | Y | L175 | L179 | i4298 | Y | L175 | L180 | i4299 | Y | L175 | L196 | i4300 | Y | L175 | L217 |
| i4301 | Y | L176 | L179 | i4302 | Y | L176 | L180 | i4303 | Y | L176 | L196 | i4304 | Y | L176 | L217 |
| i4305 | Y | L177 | L179 | i4306 | Y | L177 | L180 | i4307 | Y | L177 | L196 | i4308 | Y | L177 | L217 |
| i4309 | Y | L178 | L179 | i4310 | Y | L178 | L180 | i4311 | Y | L178 | L196 | i4312 | Y | L178 | L217 |
| i4313 | Y | L179 | L179 | i4314 | Y | L179 | L180 | i4315 | Y | L179 | L196 | i4316 | Y | L179 | L217 |
| i4317 | Y | L180 | L179 | i4318 | Y | L180 | L180 | i4319 | Y | L180 | L196 | i4320 | Y | L180 | L217 |
| i4321 | Y | L181 | L179 | i4322 | Y | L181 | L180 | i4323 | Y | L181 | L196 | i4324 | Y | L181 | L217 |
| i4325 | Y | L182 | L179 | i4326 | Y | L182 | L180 | i4327 | Y | L182 | L196 | i4328 | Y | L182 | L217 |
| i4329 | Y | L183 | L179 | i4330 | Y | L183 | L180 | i4331 | Y | L183 | L196 | i4332 | Y | L183 | L217 |
| i4333 | Y | L184 | L179 | i4334 | Y | L184 | L180 | i4335 | Y | L184 | L196 | i4336 | Y | L184 | L217 |
| i4337 | Y | L185 | L179 | i4338 | Y | L185 | L180 | i4339 | Y | L185 | L196 | i4340 | Y | L185 | L217 |

TABLE 1-continued

Compositions "i1" to "i9919"

| | | | | | | | | | | | | | | |
|---|---|---|---|---|---|---|---|---|---|---|---|---|---|---|
| i4341 | Y | L186 | L179 | i4342 | Y | L186 | L180 | i4343 | Y | L186 | L196 | i4344 | Y | L186 | L217 |
| i4345 | Y | L187 | L179 | i4346 | Y | L187 | L180 | i4347 | Y | L187 | L196 | i4348 | Y | L187 | L217 |
| i4349 | Y | L188 | L179 | i4350 | Y | L188 | L180 | i4351 | Y | L188 | L196 | i4352 | Y | L188 | L217 |
| i4353 | Y | L189 | L179 | i4354 | Y | L189 | L180 | i4355 | Y | L189 | L196 | i4356 | Y | L189 | L217 |
| i4357 | Y | L190 | L179 | i4358 | Y | L190 | L180 | i4359 | Y | L190 | L196 | i4360 | Y | L190 | L217 |
| i4361 | Y | L191 | L179 | i4362 | Y | L191 | L180 | i4363 | Y | L191 | L196 | i4364 | Y | L191 | L217 |
| i4365 | Y | L192 | L179 | i4366 | Y | L192 | L180 | i4367 | Y | L192 | L196 | i4368 | Y | L192 | L217 |
| i4369 | Y | L193 | L179 | i4370 | Y | L193 | L180 | i4371 | Y | L193 | L196 | i4372 | Y | L193 | L217 |
| i4373 | Y | L194 | L179 | i4374 | Y | L194 | L180 | i4375 | Y | L194 | L196 | i4376 | Y | L194 | L217 |
| i4377 | Y | L195 | L179 | i4378 | Y | L195 | L180 | i4379 | Y | L195 | L196 | i4380 | Y | L195 | L217 |
| i4381 | Y | L196 | L179 | i4382 | Y | L196 | L180 | i4383 | Y | L196 | L196 | i4384 | Y | L196 | L217 |
| i4385 | Y | L197 | L179 | i4386 | Y | L197 | L180 | i4387 | Y | L197 | L196 | i4388 | Y | L197 | L217 |
| i4389 | Y | L198 | L179 | i4390 | Y | L198 | L180 | i4391 | Y | L198 | L196 | i4392 | Y | L198 | L217 |
| i4393 | Y | L199 | L179 | i4394 | Y | L199 | L180 | i4395 | Y | L199 | L196 | i4396 | Y | L199 | L217 |
| i4397 | Y | L200 | L179 | i4398 | Y | L200 | L180 | i4399 | Y | L200 | L196 | i4400 | Y | L200 | L217 |
| i4401 | Y | L201 | L179 | i4402 | Y | L201 | L180 | i4403 | Y | L201 | L196 | i4404 | Y | L201 | L217 |
| i4405 | Y | L202 | L179 | i4406 | Y | L202 | L180 | i4407 | Y | L202 | L196 | i4408 | Y | L202 | L217 |
| i4409 | Y | L203 | L179 | i4410 | Y | L203 | L180 | i4411 | Y | L203 | L196 | i4412 | Y | L203 | L217 |
| i4413 | Y | L204 | L179 | i4414 | Y | L204 | L180 | i4415 | Y | L204 | L196 | i4416 | Y | L204 | L217 |
| i4417 | Y | L205 | L179 | i4418 | Y | L205 | L180 | i4419 | Y | L205 | L196 | i4420 | Y | L205 | L217 |
| i4421 | Y | L206 | L179 | i4422 | Y | L206 | L180 | i4423 | Y | L206 | L196 | i4424 | Y | L206 | L217 |
| i4425 | Y | L207 | L179 | i4426 | Y | L207 | L180 | i4427 | Y | L207 | L196 | i4428 | Y | L207 | L217 |
| i4429 | Y | L208 | L179 | i4430 | Y | L208 | L180 | i4431 | Y | L208 | L196 | i4432 | Y | L208 | L217 |
| i4433 | Y | L209 | L179 | i4434 | Y | L209 | L180 | i4435 | Y | L209 | L196 | i4436 | Y | L209 | L217 |
| i4437 | Y | L210 | L179 | i4438 | Y | L210 | L180 | i4439 | Y | L210 | L196 | i4440 | Y | L210 | L217 |
| i4441 | Y | L211 | L179 | i4442 | Y | L211 | L180 | i4443 | Y | L211 | L196 | i4444 | Y | L211 | L217 |
| i4445 | Y | L212 | L179 | i4446 | Y | L212 | L180 | i4447 | Y | L212 | L196 | i4448 | Y | L212 | L217 |
| i4449 | Y | L213 | L179 | i4450 | Y | L213 | L180 | i4451 | Y | L213 | L196 | i4452 | Y | L213 | L217 |
| i4453 | Y | L214 | L179 | i4454 | Y | L214 | L180 | i4455 | Y | L214 | L196 | i4456 | Y | L214 | L217 |
| i4457 | Y | L215 | L179 | i4458 | Y | L215 | L180 | i4459 | Y | L215 | L196 | i4460 | Y | L215 | L217 |
| i4461 | Y | L216 | L179 | i4462 | Y | L216 | L180 | i4463 | Y | L216 | L196 | i4464 | Y | L216 | L217 |
| i4465 | Y | L217 | L179 | i4466 | Y | L217 | L180 | i4467 | Y | L217 | L196 | i4468 | Y | L217 | L217 |
| i4469 | Y | L218 | L179 | i4470 | Y | L218 | L180 | i4471 | Y | L218 | L196 | i4472 | Y | L218 | L217 |
| i4473 | Y | L219 | L179 | i4474 | Y | L219 | L180 | i4475 | Y | L219 | L196 | i4476 | Y | L219 | L217 |
| i4477 | Y | L220 | L179 | i4478 | Y | L220 | L180 | i4479 | Y | L220 | L196 | i4480 | Y | L220 | L217 |
| i4481 | Y | L221 | L179 | i4482 | Y | L221 | L180 | i4483 | Y | L221 | L196 | i4484 | Y | L221 | L217 |
| i4485 | Y | L222 | L179 | i4486 | Y | L222 | L180 | i4487 | Y | L222 | L196 | i4488 | Y | L222 | L217 |
| i4489 | Y | L401 | L179 | i4490 | Y | L401 | L180 | i4491 | Y | L401 | L196 | i4492 | Y | L401 | L217 |
| i4493 | Y | L402 | L179 | i4494 | Y | L402 | L180 | i4495 | Y | L402 | L196 | i4496 | Y | L402 | L217 |
| i4497 | Y | L403 | L179 | i4498 | Y | L403 | L180 | i4499 | Y | L403 | L196 | i4500 | Y | L403 | L217 |
| i4501 | Y | L404 | L179 | i4502 | Y | L404 | L180 | i4503 | Y | L404 | L196 | i4504 | Y | L404 | L217 |
| i4505 | Y | L405 | L179 | i4506 | Y | L405 | L180 | i4507 | Y | L405 | L196 | i4508 | Y | L405 | L217 |
| i4509 | Y | L406 | L179 | i4510 | Y | L406 | L180 | i4511 | Y | L406 | L196 | i4512 | Y | L406 | L217 |
| i4513 | Y | L407 | L179 | i4514 | Y | L407 | L180 | i4515 | Y | L407 | L196 | i4516 | Y | L407 | L217 |
| i4517 | Y | L408 | L179 | i4518 | Y | L408 | L180 | i4519 | Y | L408 | L196 | i4520 | Y | L408 | L217 |
| i4521 | Y | L409 | L179 | i4522 | Y | L409 | L180 | i4523 | Y | L409 | L196 | i4524 | Y | L409 | L217 |
| i4525 | Y | L410 | L179 | i4526 | Y | L410 | L180 | i4527 | Y | L410 | L196 | i4528 | Y | L410 | L217 |
| i4529 | Y | L411 | L179 | i4530 | Y | L411 | L180 | i4531 | Y | L411 | L196 | i4532 | Y | L411 | L217 |
| i4533 | Y | L412 | L179 | i4534 | Y | L412 | L180 | i4535 | Y | L412 | L196 | i4536 | Y | L412 | L217 |
| i4537 | Y | L413 | L179 | i4538 | Y | L413 | L180 | i4539 | Y | L413 | L196 | i4540 | Y | L413 | L217 |
| i4541 | Y | L414 | L179 | i4542 | Y | L414 | L180 | i4543 | Y | L414 | L196 | i4544 | Y | L414 | L217 |
| i4545 | Y | L415 | L179 | i4546 | Y | L415 | L180 | i4547 | Y | L415 | L196 | i4548 | Y | L415 | L217 |
| i4549 | Y | L416 | L179 | i4550 | Y | L416 | L180 | i4551 | Y | L416 | L196 | i4552 | Y | L416 | L217 |
| i4553 | Y | L417 | L179 | i4554 | Y | L417 | L180 | i4555 | Y | L417 | L196 | i4556 | Y | L417 | L217 |
| i4557 | Y | L418 | L179 | i4558 | Y | L418 | L180 | i4559 | Y | L418 | L196 | i4560 | Y | L418 | L217 |
| i4561 | Y | L419 | L179 | i4562 | Y | L419 | L180 | i4563 | Y | L419 | L196 | i4564 | Y | L419 | L217 |
| i4565 | Y | L420 | L179 | i4566 | Y | L420 | L180 | i4567 | Y | L420 | L196 | i4568 | Y | L420 | L217 |
| i4569 | Y | L421 | L179 | i4570 | Y | L421 | L180 | i4571 | Y | L421 | L196 | i4572 | Y | L421 | L217 |
| i4573 | Y | L422 | L179 | i4574 | Y | L422 | L180 | i4575 | Y | L422 | L196 | i4576 | Y | L422 | L217 |
| i4577 | Y | L423 | L179 | i4578 | Y | L423 | L180 | i4579 | Y | L423 | L196 | i4580 | Y | L423 | L217 |
| i4581 | Y | L424 | L179 | i4582 | Y | L424 | L180 | i4583 | Y | L424 | L196 | i4584 | Y | L424 | L217 |
| i4585 | Y | L425 | L179 | i4586 | Y | L425 | L180 | i4587 | Y | L425 | L196 | i4588 | Y | L425 | L217 |
| i4589 | Y | L501 | L179 | i4590 | Y | L501 | L180 | i4591 | Y | L501 | L196 | i4592 | Y | L501 | L217 |
| i4593 | Y | L502 | L179 | i4594 | Y | L502 | L180 | i4595 | Y | L502 | L196 | i4596 | Y | L502 | L217 |
| i4597 | Y | L503 | L179 | i4598 | Y | L503 | L180 | i4599 | Y | L503 | L196 | i4600 | Y | L503 | L217 |
| i4601 | Y | L504 | L179 | i4602 | Y | L504 | L180 | i4603 | Y | L504 | L196 | i4604 | Y | L504 | L217 |
| i4605 | Y | L505 | L179 | i4606 | Y | L505 | L180 | i4607 | Y | L505 | L196 | i4608 | Y | L505 | L217 |
| i4609 | Y | L506 | L179 | i4610 | Y | L506 | L180 | i4611 | Y | L506 | L196 | i4612 | Y | L506 | L217 |
| i4613 | Y | L507 | L179 | i4614 | Y | L507 | L180 | i4615 | Y | L507 | L196 | i4616 | Y | L507 | L217 |
| i4617 | Y | L508 | L179 | i4618 | Y | L508 | L180 | i4619 | Y | L508 | L196 | i4620 | Y | L508 | L217 |
| i4621 | Y | L509 | L179 | i4622 | Y | L509 | L180 | i4623 | Y | L509 | L196 | i4624 | Y | L509 | L217 |
| i4625 | Y | L510 | L179 | i4626 | Y | L510 | L180 | i4627 | Y | L510 | L196 | i4628 | Y | L510 | L217 |
| i4629 | Y | L511 | L179 | i4630 | Y | L511 | L180 | i4631 | Y | L511 | L196 | i4632 | Y | L511 | L217 |
| i4633 | Y | L512 | L179 | i4634 | Y | L512 | L180 | i4635 | Y | L512 | L196 | i4636 | Y | L512 | L217 |
| i4637 | Y | L513 | L179 | i4638 | Y | L513 | L180 | i4639 | Y | L513 | L196 | i4640 | Y | L513 | L217 |
| i4641 | Y | L514 | L179 | i4642 | Y | L514 | L180 | i4643 | Y | L514 | L196 | i4644 | Y | L514 | L217 |
| i4645 | Y | L515 | L179 | i4646 | Y | L515 | L180 | i4647 | Y | L515 | L196 | i4648 | Y | L515 | L217 |
| i4649 | Y | L516 | L179 | i4650 | Y | L516 | L180 | i4651 | Y | L516 | L196 | i4652 | Y | L516 | L217 |

TABLE 1-continued

Compositions "i1" to "i9919"

| | | | | | | | | | | | | | | |
|---|---|---|---|---|---|---|---|---|---|---|---|---|---|---|
| i4653 | Y | L517 | L179 | i4654 | Y | L517 | L180 | i4655 | Y | L517 | L196 | i4656 | Y | L517 | L217 |
| i4657 | Y | L518 | L179 | i4658 | Y | L518 | L180 | i4659 | Y | L518 | L196 | i4660 | Y | L518 | L217 |
| i4661 | Y | L519 | L179 | i4662 | Y | L519 | L180 | i4663 | Y | L519 | L196 | i4664 | Y | L519 | L217 |
| i4665 | Y | L520 | L179 | i4666 | Y | L520 | L180 | i4667 | Y | L520 | L196 | i4668 | Y | L520 | L217 |
| i4669 | Y | L521 | L179 | i4670 | Y | L521 | L180 | i4671 | Y | L521 | L196 | i4672 | Y | L521 | L217 |
| i4673 | Y | L522 | L179 | i4674 | Y | L522 | L180 | i4675 | Y | L522 | L196 | i4676 | Y | L522 | L217 |
| i4677 | Y | L523 | L179 | i4678 | Y | L523 | L180 | i4679 | Y | L523 | L196 | i4680 | Y | L523 | L217 |
| i4681 | Y | L524 | L179 | i4682 | Y | L524 | L180 | i4683 | Y | L524 | L196 | i4684 | Y | L524 | L217 |
| i4685 | Y | L525 | L179 | i4686 | Y | L525 | L180 | i4687 | Y | L525 | L196 | i4688 | Y | L525 | L217 |
| i4689 | Y | L526 | L179 | i4690 | Y | L526 | L180 | i4691 | Y | L526 | L196 | i4692 | Y | L526 | L217 |
| i4693 | Y | L527 | L179 | i4694 | Y | L527 | L180 | i4695 | Y | L527 | L196 | i4696 | Y | L527 | L217 |
| i4697 | Y | L528 | L179 | i4698 | Y | L528 | L180 | i4699 | Y | L528 | L196 | i4700 | Y | L528 | L217 |
| i4701 | Y | L529 | L179 | i4702 | Y | L529 | L180 | i4703 | Y | L529 | L196 | i4704 | Y | L529 | L217 |
| i4705 | Y | L530 | L179 | i4706 | Y | L530 | L180 | i4707 | Y | L530 | L196 | i4708 | Y | L530 | L217 |
| i4709 | Y | L531 | L179 | i4710 | Y | L531 | L180 | i4711 | Y | L531 | L196 | i4712 | Y | L531 | L217 |
| i4713 | Y | L532 | L179 | i4714 | Y | L532 | L180 | i4715 | Y | L532 | L196 | i4716 | Y | L532 | L217 |
| i4717 | Y | L533 | L179 | i4718 | Y | L533 | L180 | i4719 | Y | L533 | L196 | i4720 | Y | L533 | L217 |
| i4721 | Y | L534 | L179 | i4722 | Y | L534 | L180 | i4723 | Y | L534 | L196 | i4724 | Y | L534 | L217 |
| i4725 | Y | L535 | L179 | i4726 | Y | L535 | L180 | i4727 | Y | L535 | L196 | i4728 | Y | L535 | L217 |
| i4729 | Y | L536 | L179 | i4730 | Y | L536 | L180 | i4731 | Y | L536 | L196 | i4732 | Y | L536 | L217 |
| i4733 | Y | L537 | L179 | i4734 | Y | L537 | L180 | i4735 | Y | L537 | L196 | i4736 | Y | L537 | L217 |
| i4737 | Y | L538 | L179 | i4738 | Y | L538 | L180 | i4739 | Y | L538 | L196 | i4740 | Y | L538 | L217 |
| i4741 | Y | L539 | L179 | i4742 | Y | L539 | L180 | i4743 | Y | L539 | L196 | i4744 | Y | L539 | L217 |
| i4745 | Y | L540 | L179 | i4746 | Y | L540 | L180 | i4747 | Y | L540 | L196 | i4748 | Y | L540 | L217 |
| i4749 | Y | L541 | L179 | i4750 | Y | L541 | L180 | i4751 | Y | L541 | L196 | i4752 | Y | L541 | L217 |
| i4753 | Y | L542 | L179 | i4754 | Y | L542 | L180 | i4755 | Y | L542 | L196 | i4756 | Y | L542 | L217 |
| i4757 | Y | L543 | L179 | i4758 | Y | L543 | L180 | i4759 | Y | L543 | L196 | i4760 | Y | L543 | L217 |
| i4761 | Y | L544 | L179 | i4762 | Y | L544 | L180 | i4763 | Y | L544 | L196 | i4764 | Y | L544 | L217 |
| i4765 | Y | L545 | L179 | i4766 | Y | L545 | L180 | i4767 | Y | L545 | L196 | i4768 | Y | L545 | L217 |
| i4769 | Y | L546 | L179 | i4770 | Y | L546 | L180 | i4771 | Y | L546 | L196 | i4772 | Y | L546 | L217 |
| i4773 | Y | L547 | L179 | i4774 | Y | L547 | L180 | i4775 | Y | L547 | L196 | i4776 | Y | L547 | L217 |
| i4777 | Y | L548 | L179 | i4778 | Y | L548 | L180 | i4779 | Y | L548 | L196 | i4780 | Y | L548 | L217 |
| i4781 | Y | L549 | L179 | i4782 | Y | L549 | L180 | i4783 | Y | L549 | L196 | i4784 | Y | L549 | L217 |
| i4785 | Y | L550 | L179 | i4786 | Y | L550 | L180 | i4787 | Y | L550 | L196 | i4788 | Y | L550 | L217 |
| i4789 | Y | L551 | L179 | i4790 | Y | L551 | L180 | i4791 | Y | L551 | L196 | i4792 | Y | L551 | L217 |
| i4793 | Y | L552 | L179 | i4794 | Y | L552 | L180 | i4795 | Y | L552 | L196 | i4796 | Y | L552 | L217 |
| i4797 | Y | L553 | L179 | i4798 | Y | L553 | L180 | i4799 | Y | L553 | L196 | i4800 | Y | L553 | L217 |
| i4801 | Y | L554 | L179 | i4802 | Y | L554 | L180 | i4803 | Y | L554 | L196 | i4804 | Y | L554 | L217 |
| i4805 | Y | L555 | L179 | i4806 | Y | L555 | L180 | i4807 | Y | L555 | L196 | i4808 | Y | L555 | L217 |
| i4809 | Y | L556 | L179 | i4810 | Y | L556 | L180 | i4811 | Y | L556 | L196 | i4812 | Y | L556 | L217 |
| i4813 | Y | L557 | L179 | i4814 | Y | L557 | L180 | i4815 | Y | L557 | L196 | i4816 | Y | L557 | L217 |
| i4817 | Y | L558 | L179 | i4818 | Y | L558 | L180 | i4819 | Y | L558 | L196 | i4820 | Y | L558 | L217 |
| i4821 | Y | L559 | L179 | i4822 | Y | L559 | L180 | i4823 | Y | L559 | L196 | i4824 | Y | L559 | L217 |
| i4825 | Y | L560 | L179 | i4826 | Y | L560 | L180 | i4827 | Y | L560 | L196 | i4828 | Y | L560 | L217 |
| i4829 | Y | L561 | L179 | i4830 | Y | L561 | L180 | i4831 | Y | L561 | L196 | i4832 | Y | L561 | L217 |
| i4833 | Y | L562 | L179 | i4834 | Y | L562 | L180 | i4835 | Y | L562 | L196 | i4836 | Y | L562 | L217 |
| i4837 | Y | L563 | L179 | i4838 | Y | L563 | L180 | i4839 | Y | L563 | L196 | i4840 | Y | L563 | L217 |
| i4841 | Y | L564 | L179 | i4842 | Y | L564 | L180 | i4843 | Y | L564 | L196 | i4844 | Y | L564 | L217 |
| i4845 | Y | L565 | L179 | i4846 | Y | L565 | L180 | i4847 | Y | L565 | L196 | i4848 | Y | L565 | L217 |
| i4849 | Y | L566 | L179 | i4850 | Y | L566 | L180 | i4851 | Y | L566 | L196 | i4852 | Y | L566 | L217 |
| i4853 | Y | L567 | L179 | i4854 | Y | L567 | L180 | i4855 | Y | L567 | L196 | i4856 | Y | L567 | L217 |
| i4857 | Y | L568 | L179 | i4858 | Y | L568 | L180 | i4859 | Y | L568 | L196 | i4860 | Y | L568 | L217 |
| i4861 | Y | L569 | L179 | i4862 | Y | L569 | L180 | i4863 | Y | L569 | L196 | i4864 | Y | L569 | L217 |
| i4865 | Y | L570 | L179 | i4866 | Y | L570 | L180 | i4867 | Y | L570 | L196 | i4868 | Y | L570 | L217 |
| i4869 | Y | L571 | L179 | i4870 | Y | L571 | L180 | i4871 | Y | L571 | L196 | i4872 | Y | L571 | L217 |
| i4873 | Y | L572 | L179 | i4874 | Y | L572 | L180 | i4875 | Y | L572 | L196 | i4876 | Y | L572 | L217 |
| i4877 | Y | L843 | L179 | i4878 | Y | L843 | L180 | i4879 | Y | L843 | L196 | i4880 | Y | L843 | L217 |
| i4881 | Y | L844 | L179 | i4882 | Y | L844 | L180 | i4883 | Y | L844 | L196 | i4884 | Y | L844 | L217 |
| i4885 | Y | L845 | L179 | i4886 | Y | L845 | L180 | i4887 | Y | L845 | L196 | i4888 | Y | L845 | L217 |
| i4889 | Y | L846 | L179 | i4890 | Y | L846 | L180 | i4891 | Y | L846 | L196 | i4892 | Y | L846 | L217 |
| i4893 | Y | L847 | L179 | i4894 | Y | L847 | L180 | i4895 | Y | L847 | L196 | i4896 | Y | L847 | L217 |
| i4897 | Y | L848 | L179 | i4898 | Y | L848 | L180 | i4899 | Y | L848 | L196 | i4900 | Y | L848 | L217 |
| i4901 | Y | L10 | L201 | i4902 | Y | L10 | L206 | i4903 | Y | L10 | L220 | i4904 | Y | L10 | L215 |
| i4905 | Y | L11 | L201 | i4906 | Y | L11 | L206 | i4907 | Y | L11 | L220 | i4908 | Y | L11 | L215 |
| i4909 | Y | L20 | L201 | i4910 | Y | L20 | L206 | i4911 | Y | L20 | L220 | i4912 | Y | L20 | L215 |
| i4913 | Y | L21 | L201 | i4914 | Y | L21 | L206 | i4915 | Y | L21 | L220 | i4916 | Y | L21 | L215 |
| i4917 | Y | L22 | L201 | i4918 | Y | L22 | L206 | i4919 | Y | L22 | L220 | i4920 | Y | L22 | L215 |
| i4921 | Y | L23 | L201 | i4922 | Y | L23 | L206 | i4923 | Y | L23 | L220 | i4924 | Y | L23 | L215 |
| i4925 | Y | L24 | L201 | i4926 | Y | L24 | L206 | i4927 | Y | L24 | L220 | i4928 | Y | L24 | L215 |
| i4929 | Y | L25 | L201 | i4930 | Y | L25 | L206 | i4931 | Y | L25 | L220 | i4932 | Y | L25 | L215 |
| i4933 | Y | L26 | L201 | i4934 | Y | L26 | L206 | i4935 | Y | L26 | L220 | i4936 | Y | L26 | L215 |
| i4937 | Y | L27 | L201 | i4938 | Y | L27 | L206 | i4939 | Y | L27 | L220 | i4940 | Y | L27 | L215 |
| i4941 | Y | L28 | L201 | i4942 | Y | L28 | L206 | i4943 | Y | L28 | L220 | i4944 | Y | L28 | L215 |
| i4945 | Y | L12 | L201 | i4946 | Y | L12 | L206 | i4947 | Y | L12 | L220 | i4948 | Y | L12 | L215 |
| i4949 | Y | L13 | L201 | i4950 | Y | L13 | L206 | i4951 | Y | L13 | L220 | i4952 | Y | L13 | L215 |
| i4953 | Y | L14 | L201 | i4954 | Y | L14 | L206 | i4955 | Y | L14 | L220 | i4956 | Y | L14 | L215 |
| i4957 | Y | L15 | L201 | i4958 | Y | L15 | L206 | i4959 | Y | L15 | L220 | i4960 | Y | L15 | L215 |
| i4961 | Y | L16 | L201 | i4962 | Y | L16 | L206 | i4963 | Y | L16 | L220 | i4964 | Y | L16 | L215 |

TABLE 1-continued

Compositions "i1" to "i9919"

| | | | | | | | | | | | | | | | |
|---|---|---|---|---|---|---|---|---|---|---|---|---|---|---|---|
| i4965 | Y | L17 | L201 | i4966 | Y | L17 | L206 | i4967 | Y | L17 | L220 | i4968 | Y | L17 | L215 |
| i4969 | Y | L18 | L201 | i4970 | Y | L18 | L206 | i4971 | Y | L18 | L220 | i4972 | Y | L18 | L215 |
| i4973 | Y | L19 | L201 | i4974 | Y | L19 | L206 | i4975 | Y | L19 | L220 | i4976 | Y | L19 | L215 |
| i4977 | Y | L2 | L201 | i4978 | Y | L2 | L206 | i4979 | Y | L2 | L220 | i4980 | Y | L2 | L215 |
| i4981 | Y | L101 | L201 | i4982 | Y | L101 | L206 | i4983 | Y | L101 | L220 | i4984 | Y | L101 | L215 |
| i4985 | Y | L102 | L201 | i4986 | Y | L102 | L206 | i4987 | Y | L102 | L220 | i4988 | Y | L102 | L215 |
| i4989 | Y | L103 | L201 | i4990 | Y | L103 | L206 | i4991 | Y | L103 | L220 | i4992 | Y | L103 | L215 |
| i4993 | Y | L104 | L201 | i4994 | Y | L104 | L206 | i4995 | Y | L104 | L220 | i4996 | Y | L104 | L215 |
| i4997 | Y | L105 | L201 | i4998 | Y | L105 | L206 | i4999 | Y | L105 | L220 | i5000 | Y | L105 | L215 |
| i5001 | Y | L106 | L201 | i5002 | Y | L106 | L206 | i5003 | Y | L106 | L220 | i5004 | Y | L106 | L215 |
| i5005 | Y | L107 | L201 | i5006 | Y | L107 | L206 | i5007 | Y | L107 | L220 | i5008 | Y | L107 | L215 |
| i5009 | Y | L108 | L201 | i5010 | Y | L108 | L206 | i5011 | Y | L108 | L220 | i5012 | Y | L108 | L215 |
| i5013 | Y | L109 | L201 | i5014 | Y | L109 | L206 | i5015 | Y | L109 | L220 | i5016 | Y | L109 | L215 |
| i5017 | Y | L110 | L201 | i5018 | Y | L110 | L206 | i5019 | Y | L110 | L220 | i5020 | Y | L110 | L215 |
| i5021 | Y | L111 | L201 | i5022 | Y | L111 | L206 | i5023 | Y | L111 | L220 | i5024 | Y | L111 | L215 |
| i5025 | Y | L112 | L201 | i5026 | Y | L112 | L206 | i5027 | Y | L112 | L220 | i5028 | Y | L112 | L215 |
| i5029 | Y | L113 | L201 | i5030 | Y | L113 | L206 | i5031 | Y | L113 | L220 | i5032 | Y | L113 | L215 |
| i5033 | Y | L114 | L201 | i5034 | Y | L114 | L206 | i5035 | Y | L114 | L220 | i5036 | Y | L114 | L215 |
| i5037 | Y | L115 | L201 | i5038 | Y | L115 | L206 | i5039 | Y | L115 | L220 | i5040 | Y | L115 | L215 |
| i5041 | Y | L116 | L201 | i5042 | Y | L116 | L206 | i5043 | Y | L116 | L220 | i5044 | Y | L116 | L215 |
| i5045 | Y | L117 | L201 | i5046 | Y | L117 | L206 | i5047 | Y | L117 | L220 | i5048 | Y | L117 | L215 |
| i5049 | Y | L118 | L201 | i5050 | Y | L118 | L206 | i5051 | Y | L118 | L220 | i5052 | Y | L118 | L215 |
| i5053 | Y | L119 | L201 | i5054 | Y | L119 | L206 | i5055 | Y | L119 | L220 | i5056 | Y | L119 | L215 |
| i5057 | Y | L120 | L201 | i5058 | Y | L120 | L206 | i5059 | Y | L120 | L220 | i5060 | Y | L120 | L215 |
| i5061 | Y | L121 | L201 | i5062 | Y | L121 | L206 | i5063 | Y | L121 | L220 | i5064 | Y | L121 | L215 |
| i5065 | Y | L122 | L201 | i5066 | Y | L122 | L206 | i5067 | Y | L122 | L220 | i5068 | Y | L122 | L215 |
| i5069 | Y | L123 | L201 | i5070 | Y | L123 | L206 | i5071 | Y | L123 | L220 | i5072 | Y | L123 | L215 |
| i5073 | Y | L124 | L201 | i5074 | Y | L124 | L206 | i5075 | Y | L124 | L220 | i5076 | Y | L124 | L215 |
| i5077 | Y | L125 | L201 | i5078 | Y | L125 | L206 | i5079 | Y | L125 | L220 | i5080 | Y | L125 | L215 |
| i5081 | Y | L126 | L201 | i5082 | Y | L126 | L206 | i5083 | Y | L126 | L220 | i5084 | Y | L126 | L215 |
| i5085 | Y | L127 | L201 | i5086 | Y | L127 | L206 | i5087 | Y | L127 | L220 | i5088 | Y | L127 | L215 |
| i5089 | Y | L128 | L201 | i5090 | Y | L128 | L206 | i5091 | Y | L128 | L220 | i5092 | Y | L128 | L215 |
| i5093 | Y | L129 | L201 | i5094 | Y | L129 | L206 | i5095 | Y | L129 | L220 | i5096 | Y | L129 | L215 |
| i5097 | Y | L130 | L201 | i5098 | Y | L130 | L206 | i5099 | Y | L130 | L220 | i5100 | Y | L130 | L215 |
| i5101 | Y | L131 | L201 | i5102 | Y | L131 | L206 | i5103 | Y | L131 | L220 | i5104 | Y | L131 | L215 |
| i5105 | Y | L132 | L201 | i5106 | Y | L132 | L206 | i5107 | Y | L132 | L220 | i5108 | Y | L132 | L215 |
| i5109 | Y | L133 | L201 | i5110 | Y | L133 | L206 | i5111 | Y | L133 | L220 | i5112 | Y | L133 | L215 |
| i5113 | Y | L134 | L201 | i5114 | Y | L134 | L206 | i5115 | Y | L134 | L220 | i5116 | Y | L134 | L215 |
| i5117 | Y | L135 | L201 | i5118 | Y | L135 | L206 | i5119 | Y | L135 | L220 | i5120 | Y | L135 | L215 |
| i5121 | Y | L136 | L201 | i5122 | Y | L136 | L206 | i5123 | Y | L136 | L220 | i5124 | Y | L136 | L215 |
| i5125 | Y | L137 | L201 | i5126 | Y | L137 | L206 | i5127 | Y | L137 | L220 | i5128 | Y | L137 | L215 |
| i5129 | Y | L138 | L201 | i5130 | Y | L138 | L206 | i5131 | Y | L138 | L220 | i5132 | Y | L138 | L215 |
| i5133 | Y | L139 | L201 | i5134 | Y | L139 | L206 | i5135 | Y | L139 | L220 | i5136 | Y | L139 | L215 |
| i5137 | Y | L140 | L201 | i5138 | Y | L140 | L206 | i5139 | Y | L140 | L220 | i5140 | Y | L140 | L215 |
| i5141 | Y | L141 | L201 | i5142 | Y | L141 | L206 | i5143 | Y | L141 | L220 | i5144 | Y | L141 | L215 |
| i5145 | Y | L142 | L201 | i5146 | Y | L142 | L206 | i5147 | Y | L142 | L220 | i5148 | Y | L142 | L215 |
| i5149 | Y | L143 | L201 | i5150 | Y | L143 | L206 | i5151 | Y | L143 | L220 | i5152 | Y | L143 | L215 |
| i5153 | Y | L144 | L201 | i5154 | Y | L144 | L206 | i5155 | Y | L144 | L220 | i5156 | Y | L144 | L215 |
| i5157 | Y | L145 | L201 | i5158 | Y | L145 | L206 | i5159 | Y | L145 | L220 | i5160 | Y | L145 | L215 |
| i5161 | Y | L146 | L201 | i5162 | Y | L146 | L206 | i5163 | Y | L146 | L220 | i5164 | Y | L146 | L215 |
| i5165 | Y | L147 | L201 | i5166 | Y | L147 | L206 | i5167 | Y | L147 | L220 | i5168 | Y | L147 | L215 |
| i5169 | Y | L148 | L201 | i5170 | Y | L148 | L206 | i5171 | Y | L148 | L220 | i5172 | Y | L148 | L215 |
| i5173 | Y | L149 | L201 | i5174 | Y | L149 | L206 | i5175 | Y | L149 | L220 | i5176 | Y | L149 | L215 |
| i5177 | Y | L150 | L201 | i5178 | Y | L150 | L206 | i5179 | Y | L150 | L220 | i5180 | Y | L150 | L215 |
| i5181 | Y | L151 | L201 | i5182 | Y | L151 | L206 | i5183 | Y | L151 | L220 | i5184 | Y | L151 | L215 |
| i5185 | Y | L152 | L201 | i5186 | Y | L152 | L206 | i5187 | Y | L152 | L220 | i5188 | Y | L152 | L215 |
| i5189 | Y | L153 | L201 | i5190 | Y | L153 | L206 | i5191 | Y | L153 | L220 | i5192 | Y | L153 | L215 |
| i5193 | Y | L154 | L201 | i5194 | Y | L154 | L206 | i5195 | Y | L154 | L220 | i5196 | Y | L154 | L215 |
| i5197 | Y | L155 | L201 | i5198 | Y | L155 | L206 | i5199 | Y | L155 | L220 | i5200 | Y | L155 | L215 |
| i5201 | Y | L156 | L201 | i5202 | Y | L156 | L206 | i5203 | Y | L156 | L220 | i5204 | Y | L156 | L215 |
| i5205 | Y | L157 | L201 | i5206 | Y | L157 | L206 | i5207 | Y | L157 | L220 | i5208 | Y | L157 | L215 |
| i5209 | Y | L158 | L201 | i5210 | Y | L158 | L206 | i5211 | Y | L158 | L220 | i5212 | Y | L158 | L215 |
| i5213 | Y | L159 | L201 | i5214 | Y | L159 | L206 | i5215 | Y | L159 | L220 | i5216 | Y | L159 | L215 |
| i5217 | Y | L160 | L201 | i5218 | Y | L160 | L206 | i5219 | Y | L160 | L220 | i5220 | Y | L160 | L215 |
| i5221 | Y | L161 | L201 | i5222 | Y | L161 | L206 | i5223 | Y | L161 | L220 | i5224 | Y | L161 | L215 |
| i5225 | Y | L162 | L201 | i5226 | Y | L162 | L206 | i5227 | Y | L162 | L220 | i5228 | Y | L162 | L215 |
| i5229 | Y | L163 | L201 | i5230 | Y | L163 | L206 | i5231 | Y | L163 | L220 | i5232 | Y | L163 | L215 |
| i5233 | Y | L164 | L201 | i5234 | Y | L164 | L206 | i5235 | Y | L164 | L220 | i5236 | Y | L164 | L215 |
| i5237 | Y | L165 | L201 | i5238 | Y | L165 | L206 | i5239 | Y | L165 | L220 | i5240 | Y | L165 | L215 |
| i5241 | Y | L166 | L201 | i5242 | Y | L166 | L206 | i5243 | Y | L166 | L220 | i5244 | Y | L166 | L215 |
| i5245 | Y | L167 | L201 | i5246 | Y | L167 | L206 | i5247 | Y | L167 | L220 | i5248 | Y | L167 | L215 |
| i5249 | Y | L168 | L201 | i5250 | Y | L168 | L206 | i5251 | Y | L168 | L220 | i5252 | Y | L168 | L215 |
| i5253 | Y | L169 | L201 | i5254 | Y | L169 | L206 | i5255 | Y | L169 | L220 | i5256 | Y | L169 | L215 |
| i5257 | Y | L170 | L201 | i5258 | Y | L170 | L206 | i5259 | Y | L170 | L220 | i5260 | Y | L170 | L215 |
| i5261 | Y | L171 | L201 | i5262 | Y | L171 | L206 | i5263 | Y | L171 | L220 | i5264 | Y | L171 | L215 |
| i5265 | Y | L172 | L201 | i5266 | Y | L172 | L206 | i5267 | Y | L172 | L220 | i5268 | Y | L172 | L215 |
| i5269 | Y | L173 | L201 | i5270 | Y | L173 | L206 | i5271 | Y | L173 | L220 | i5272 | Y | L173 | L215 |
| i5273 | Y | L174 | L201 | i5274 | Y | L174 | L206 | i5275 | Y | L174 | L220 | i5276 | Y | L174 | L215 |

TABLE 1-continued

Compositions "i1" to "i9919"

| | | | | | | | | | | | | | | |
|---|---|---|---|---|---|---|---|---|---|---|---|---|---|---|
| i5277 | Y | L175 | L201 | i5278 | Y | L175 | L206 | i5279 | Y | L175 | L220 | i5280 | Y | L175 | L215 |
| i5281 | Y | L176 | L201 | i5282 | Y | L176 | L206 | i5283 | Y | L176 | L220 | i5284 | Y | L176 | L215 |
| i5285 | Y | L177 | L201 | i5286 | Y | L177 | L206 | i5287 | Y | L177 | L220 | i5288 | Y | L177 | L215 |
| i5289 | Y | L178 | L201 | i5290 | Y | L178 | L206 | i5291 | Y | L178 | L220 | i5292 | Y | L178 | L215 |
| i5293 | Y | L179 | L201 | i5294 | Y | L179 | L206 | i5295 | Y | L179 | L220 | i5296 | Y | L179 | L215 |
| i5297 | Y | L180 | L201 | i5298 | Y | L180 | L206 | i5299 | Y | L180 | L220 | i5300 | Y | L180 | L215 |
| i5301 | Y | L181 | L201 | i5302 | Y | L181 | L206 | i5303 | Y | L181 | L220 | i5304 | Y | L181 | L215 |
| i5305 | Y | L182 | L201 | i5306 | Y | L182 | L206 | i5307 | Y | L182 | L220 | i5308 | Y | L182 | L215 |
| i5309 | Y | L183 | L201 | i5310 | Y | L183 | L206 | i5311 | Y | L183 | L220 | i5312 | Y | L183 | L215 |
| i5313 | Y | L184 | L201 | i5314 | Y | L184 | L206 | i5315 | Y | L184 | L220 | i5316 | Y | L184 | L215 |
| i5317 | Y | L185 | L201 | i5318 | Y | L185 | L206 | i5319 | Y | L185 | L220 | i5320 | Y | L185 | L215 |
| i5321 | Y | L186 | L201 | i5322 | Y | L186 | L206 | i5323 | Y | L186 | L220 | i5324 | Y | L186 | L215 |
| i5325 | Y | L187 | L201 | i5326 | Y | L187 | L206 | i5327 | Y | L187 | L220 | i5328 | Y | L187 | L215 |
| i5329 | Y | L188 | L201 | i5330 | Y | L188 | L206 | i5331 | Y | L188 | L220 | i5332 | Y | L188 | L215 |
| i5333 | Y | L189 | L201 | i5334 | Y | L189 | L206 | i5335 | Y | L189 | L220 | i5336 | Y | L189 | L215 |
| i5337 | Y | L190 | L201 | i5338 | Y | L190 | L206 | i5339 | Y | L190 | L220 | i5340 | Y | L190 | L215 |
| i5341 | Y | L191 | L201 | i5342 | Y | L191 | L206 | i5343 | Y | L191 | L220 | i5344 | Y | L191 | L215 |
| i5345 | Y | L192 | L201 | i5346 | Y | L192 | L206 | i5347 | Y | L192 | L220 | i5348 | Y | L192 | L215 |
| i5349 | Y | L193 | L201 | i5350 | Y | L193 | L206 | i5351 | Y | L193 | L220 | i5352 | Y | L193 | L215 |
| i5353 | Y | L194 | L201 | i5354 | Y | L194 | L206 | i5355 | Y | L194 | L220 | i5356 | Y | L194 | L215 |
| i5357 | Y | L195 | L201 | i5358 | Y | L195 | L206 | i5359 | Y | L195 | L220 | i5360 | Y | L195 | L215 |
| i5361 | Y | L196 | L201 | i5362 | Y | L196 | L206 | i5363 | Y | L196 | L220 | i5364 | Y | L196 | L215 |
| i5365 | Y | L197 | L201 | i5366 | Y | L197 | L206 | i5367 | Y | L197 | L220 | i5368 | Y | L197 | L215 |
| i5369 | Y | L198 | L201 | i5370 | Y | L198 | L206 | i5371 | Y | L198 | L220 | i5372 | Y | L198 | L215 |
| i5373 | Y | L199 | L201 | i5374 | Y | L199 | L206 | i5375 | Y | L199 | L220 | i5376 | Y | L199 | L215 |
| i5377 | Y | L200 | L201 | i5378 | Y | L200 | L206 | i5379 | Y | L200 | L220 | i5380 | Y | L200 | L215 |
| i5381 | Y | L201 | L201 | i5382 | Y | L201 | L206 | i5383 | Y | L201 | L220 | i5384 | Y | L201 | L215 |
| i5385 | Y | L202 | L201 | i5386 | Y | L202 | L206 | i5387 | Y | L202 | L220 | i5388 | Y | L202 | L215 |
| i5389 | Y | L203 | L201 | i5390 | Y | L203 | L206 | i5391 | Y | L203 | L220 | i5392 | Y | L203 | L215 |
| i5393 | Y | L204 | L201 | i5394 | Y | L204 | L206 | i5395 | Y | L204 | L220 | i5396 | Y | L204 | L215 |
| i5397 | Y | L205 | L201 | i5398 | Y | L205 | L206 | i5399 | Y | L205 | L220 | i5400 | Y | L205 | L215 |
| i5401 | Y | L206 | L201 | i5402 | Y | L206 | L206 | i5403 | Y | L206 | L220 | i5404 | Y | L206 | L215 |
| i5405 | Y | L207 | L201 | i5406 | Y | L207 | L206 | i5407 | Y | L207 | L220 | i5408 | Y | L207 | L215 |
| i5409 | Y | L208 | L201 | i5410 | Y | L208 | L206 | i5411 | Y | L208 | L220 | i5412 | Y | L208 | L215 |
| i5413 | Y | L209 | L201 | i5414 | Y | L209 | L206 | i5415 | Y | L209 | L220 | i5416 | Y | L209 | L215 |
| i5417 | Y | L210 | L201 | i5418 | Y | L210 | L206 | i5419 | Y | L210 | L220 | i5420 | Y | L210 | L215 |
| i5421 | Y | L211 | L201 | i5422 | Y | L211 | L206 | i5423 | Y | L211 | L220 | i5424 | Y | L211 | L215 |
| i5425 | Y | L212 | L201 | i5426 | Y | L212 | L206 | i5427 | Y | L212 | L220 | i5428 | Y | L212 | L215 |
| i5429 | Y | L213 | L201 | i5430 | Y | L213 | L206 | i5431 | Y | L213 | L220 | i5432 | Y | L213 | L215 |
| i5433 | Y | L214 | L201 | i5434 | Y | L214 | L206 | i5435 | Y | L214 | L220 | i5436 | Y | L214 | L215 |
| i5437 | Y | L215 | L201 | i5438 | Y | L215 | L206 | i5439 | Y | L215 | L220 | i5440 | Y | L215 | L215 |
| i5441 | Y | L216 | L201 | i5442 | Y | L216 | L206 | i5443 | Y | L216 | L220 | i5444 | Y | L216 | L215 |
| i5445 | Y | L217 | L201 | i5446 | Y | L217 | L206 | i5447 | Y | L217 | L220 | i5448 | Y | L217 | L215 |
| i5449 | Y | L218 | L201 | i5450 | Y | L218 | L206 | i5451 | Y | L218 | L220 | i5452 | Y | L218 | L215 |
| i5453 | Y | L219 | L201 | i5454 | Y | L219 | L206 | i5455 | Y | L219 | L220 | i5456 | Y | L219 | L215 |
| i5457 | Y | L220 | L201 | i5458 | Y | L220 | L206 | i5459 | Y | L220 | L220 | i5460 | Y | L220 | L215 |
| i5461 | Y | L221 | L201 | i5462 | Y | L221 | L206 | i5463 | Y | L221 | L220 | i5464 | Y | L221 | L215 |
| i5465 | Y | L222 | L201 | i5466 | Y | L222 | L206 | i5467 | Y | L222 | L220 | i5468 | Y | L222 | L215 |
| i5469 | Y | L401 | L201 | i5470 | Y | L401 | L206 | i5471 | Y | L401 | L220 | i5472 | Y | L401 | L215 |
| i5473 | Y | L402 | L201 | i5474 | Y | L402 | L206 | i5475 | Y | L402 | L220 | i5476 | Y | L402 | L215 |
| i5477 | Y | L403 | L201 | i5478 | Y | L403 | L206 | i5479 | Y | L403 | L220 | i5480 | Y | L403 | L215 |
| i5481 | Y | L404 | L201 | i5482 | Y | L404 | L206 | i5483 | Y | L404 | L220 | i5484 | Y | L404 | L215 |
| i5485 | Y | L405 | L201 | i5486 | Y | L405 | L206 | i5487 | Y | L405 | L220 | i5488 | Y | L405 | L215 |
| i5489 | Y | L406 | L201 | i5490 | Y | L406 | L206 | i5491 | Y | L406 | L220 | i5492 | Y | L406 | L215 |
| i5493 | Y | L407 | L201 | i5494 | Y | L407 | L206 | i5495 | Y | L407 | L220 | i5496 | Y | L407 | L215 |
| i5497 | Y | L408 | L201 | i5498 | Y | L408 | L206 | i5499 | Y | L408 | L220 | i5500 | Y | L408 | L215 |
| i5501 | Y | L409 | L201 | i5502 | Y | L409 | L206 | i5503 | Y | L409 | L220 | i5504 | Y | L409 | L215 |
| i5505 | Y | L410 | L201 | i5506 | Y | L410 | L206 | i5507 | Y | L410 | L220 | i5508 | Y | L410 | L215 |
| i5509 | Y | L411 | L201 | i5510 | Y | L411 | L206 | i5511 | Y | L411 | L220 | i5512 | Y | L411 | L215 |
| i5513 | Y | L412 | L201 | i5514 | Y | L412 | L206 | i5515 | Y | L412 | L220 | i5516 | Y | L412 | L215 |
| i5517 | Y | L413 | L201 | i5518 | Y | L413 | L206 | i5519 | Y | L413 | L220 | i5520 | Y | L413 | L215 |
| i5521 | Y | L414 | L201 | i5522 | Y | L414 | L206 | i5523 | Y | L414 | L220 | i5524 | Y | L414 | L215 |
| i5525 | Y | L415 | L201 | i5526 | Y | L415 | L206 | i5527 | Y | L415 | L220 | i5528 | Y | L415 | L215 |
| i5529 | Y | L416 | L201 | i5530 | Y | L416 | L206 | i5531 | Y | L416 | L220 | i5532 | Y | L416 | L215 |
| i5533 | Y | L417 | L201 | i5534 | Y | L417 | L206 | i5535 | Y | L417 | L220 | i5536 | Y | L417 | L215 |
| i5537 | Y | L418 | L201 | i5538 | Y | L418 | L206 | i5539 | Y | L418 | L220 | i5540 | Y | L418 | L215 |
| i5541 | Y | L419 | L201 | i5542 | Y | L419 | L206 | i5543 | Y | L419 | L220 | i5544 | Y | L419 | L215 |
| i5545 | Y | L420 | L201 | i5546 | Y | L420 | L206 | i5547 | Y | L420 | L220 | i5548 | Y | L420 | L215 |
| i5549 | Y | L421 | L201 | i5550 | Y | L421 | L206 | i5551 | Y | L421 | L220 | i5552 | Y | L421 | L215 |
| i5553 | Y | L422 | L201 | i5554 | Y | L422 | L206 | i5555 | Y | L422 | L220 | i5556 | Y | L422 | L215 |
| i5557 | Y | L423 | L201 | i5558 | Y | L423 | L206 | i5559 | Y | L423 | L220 | i5560 | Y | L423 | L215 |
| i5561 | Y | L424 | L201 | i5562 | Y | L424 | L206 | i5563 | Y | L424 | L220 | i5564 | Y | L424 | L215 |
| i5565 | Y | L425 | L201 | i5566 | Y | L425 | L206 | i5567 | Y | L425 | L220 | i5568 | Y | L425 | L215 |
| i5569 | Y | L501 | L201 | i5570 | Y | L501 | L206 | i5571 | Y | L501 | L220 | i5572 | Y | L501 | L215 |
| i5573 | Y | L502 | L201 | i5574 | Y | L502 | L206 | i5575 | Y | L502 | L220 | i5576 | Y | L502 | L215 |
| i5577 | Y | L503 | L201 | i5578 | Y | L503 | L206 | i5579 | Y | L503 | L220 | i5580 | Y | L503 | L215 |
| i5581 | Y | L504 | L201 | i5582 | Y | L504 | L206 | i5583 | Y | L504 | L220 | i5584 | Y | L504 | L215 |
| i5585 | Y | L505 | L201 | i5586 | Y | L505 | L206 | i5587 | Y | L505 | L220 | i5588 | Y | L505 | L215 |

TABLE 1-continued

Compositions "i1" to "i9919"

| | | | | | | | | | | | | |
|---|---|---|---|---|---|---|---|---|---|---|---|---|
| i5589 | Y | L506 | L201 | i5590 | Y | L506 | L206 | i5591 | Y | L506 | L220 | i5592 | Y | L506 | L215 |
| i5593 | Y | L507 | L201 | i5594 | Y | L507 | L206 | i5595 | Y | L507 | L220 | i5596 | Y | L507 | L215 |
| i5597 | Y | L508 | L201 | i5598 | Y | L508 | L206 | i5599 | Y | L508 | L220 | i5600 | Y | L508 | L215 |
| i5601 | Y | L509 | L201 | i5602 | Y | L509 | L206 | i5603 | Y | L509 | L220 | i5604 | Y | L509 | L215 |
| i5605 | Y | L510 | L201 | i5606 | Y | L510 | L206 | i5607 | Y | L510 | L220 | i5608 | Y | L510 | L215 |
| i5609 | Y | L511 | L201 | i5610 | Y | L511 | L206 | i5611 | Y | L511 | L220 | i5612 | Y | L511 | L215 |
| i5613 | Y | L512 | L201 | i5614 | Y | L512 | L206 | i5615 | Y | L512 | L220 | i5616 | Y | L512 | L215 |
| i5617 | Y | L513 | L201 | i5618 | Y | L513 | L206 | i5619 | Y | L513 | L220 | i5620 | Y | L513 | L215 |
| i5621 | Y | L514 | L201 | i5622 | Y | L514 | L206 | i5623 | Y | L514 | L220 | i5624 | Y | L514 | L215 |
| i5625 | Y | L515 | L201 | i5626 | Y | L515 | L206 | i5627 | Y | L515 | L220 | i5628 | Y | L515 | L215 |
| i5629 | Y | L516 | L201 | i5630 | Y | L516 | L206 | i5631 | Y | L516 | L220 | i5632 | Y | L516 | L215 |
| i5633 | Y | L517 | L201 | i5634 | Y | L517 | L206 | i5635 | Y | L517 | L220 | i5636 | Y | L517 | L215 |
| i5637 | Y | L518 | L201 | i5638 | Y | L518 | L206 | i5639 | Y | L518 | L220 | i5640 | Y | L518 | L215 |
| i5641 | Y | L519 | L201 | i5642 | Y | L519 | L206 | i5643 | Y | L519 | L220 | i5644 | Y | L519 | L215 |
| i5645 | Y | L520 | L201 | i5646 | Y | L520 | L206 | i5647 | Y | L520 | L220 | i5648 | Y | L520 | L215 |
| i5649 | Y | L521 | L201 | i5650 | Y | L521 | L206 | i5651 | Y | L521 | L220 | i5652 | Y | L521 | L215 |
| i5653 | Y | L522 | L201 | i5654 | Y | L522 | L206 | i5655 | Y | L522 | L220 | i5656 | Y | L522 | L215 |
| i5657 | Y | L523 | L201 | i5658 | Y | L523 | L206 | i5659 | Y | L523 | L220 | i5660 | Y | L523 | L215 |
| i5661 | Y | L524 | L201 | i5662 | Y | L524 | L206 | i5663 | Y | L524 | L220 | i5664 | Y | L524 | L215 |
| i5665 | Y | L525 | L201 | i5666 | Y | L525 | L206 | i5667 | Y | L525 | L220 | i5668 | Y | L525 | L215 |
| i5669 | Y | L526 | L201 | i5670 | Y | L526 | L206 | i5671 | Y | L526 | L220 | i5672 | Y | L526 | L215 |
| i5673 | Y | L527 | L201 | i5674 | Y | L527 | L206 | i5675 | Y | L527 | L220 | i5676 | Y | L527 | L215 |
| i5677 | Y | L528 | L201 | i5678 | Y | L528 | L206 | i5679 | Y | L528 | L220 | i5680 | Y | L528 | L215 |
| i5681 | Y | L529 | L201 | i5682 | Y | L529 | L206 | i5683 | Y | L529 | L220 | i5684 | Y | L529 | L215 |
| i5685 | Y | L530 | L201 | i5686 | Y | L530 | L206 | i5687 | Y | L530 | L220 | i5688 | Y | L530 | L215 |
| i5689 | Y | L531 | L201 | i5690 | Y | L531 | L206 | i5691 | Y | L531 | L220 | i5692 | Y | L531 | L215 |
| i5693 | Y | L532 | L201 | i5694 | Y | L532 | L206 | i5695 | Y | L532 | L220 | i5696 | Y | L532 | L215 |
| i5697 | Y | L533 | L201 | i5698 | Y | L533 | L206 | i5699 | Y | L533 | L220 | i5700 | Y | L533 | L215 |
| i5701 | Y | L534 | L201 | i5702 | Y | L534 | L206 | i5703 | Y | L534 | L220 | i5704 | Y | L534 | L215 |
| i5705 | Y | L535 | L201 | i5706 | Y | L535 | L206 | i5707 | Y | L535 | L220 | i5708 | Y | L535 | L215 |
| i5709 | Y | L536 | L201 | i5710 | Y | L536 | L206 | i5711 | Y | L536 | L220 | i5712 | Y | L536 | L215 |
| i5713 | Y | L537 | L201 | i5714 | Y | L537 | L206 | i5715 | Y | L537 | L220 | i5716 | Y | L537 | L215 |
| i5717 | Y | L538 | L201 | i5718 | Y | L538 | L206 | i5719 | Y | L538 | L220 | i5720 | Y | L538 | L215 |
| i5721 | Y | L539 | L201 | i5722 | Y | L539 | L206 | i5723 | Y | L539 | L220 | i5724 | Y | L539 | L215 |
| i5725 | Y | L540 | L201 | i5726 | Y | L540 | L206 | i5727 | Y | L540 | L220 | i5728 | Y | L540 | L215 |
| i5729 | Y | L541 | L201 | i5730 | Y | L541 | L206 | i5731 | Y | L541 | L220 | i5732 | Y | L541 | L215 |
| i5733 | Y | L542 | L201 | i5734 | Y | L542 | L206 | i5735 | Y | L542 | L220 | i5736 | Y | L542 | L215 |
| i5737 | Y | L543 | L201 | i5738 | Y | L543 | L206 | i5739 | Y | L543 | L220 | i5740 | Y | L543 | L215 |
| i5741 | Y | L544 | L201 | i5742 | Y | L544 | L206 | i5743 | Y | L544 | L220 | i5744 | Y | L544 | L215 |
| i5745 | Y | L545 | L201 | i5746 | Y | L545 | L206 | i5747 | Y | L545 | L220 | i5748 | Y | L545 | L215 |
| i5749 | Y | L546 | L201 | i5750 | Y | L546 | L206 | i5751 | Y | L546 | L220 | i5752 | Y | L546 | L215 |
| i5753 | Y | L547 | L201 | i5754 | Y | L547 | L206 | i5755 | Y | L547 | L220 | i5756 | Y | L547 | L215 |
| i5757 | Y | L548 | L201 | i5758 | Y | L548 | L206 | i5759 | Y | L548 | L220 | i5760 | Y | L548 | L215 |
| i5761 | Y | L549 | L201 | i5762 | Y | L549 | L206 | i5763 | Y | L549 | L220 | i5764 | Y | L549 | L215 |
| i5765 | Y | L550 | L201 | i5766 | Y | L550 | L206 | i5767 | Y | L550 | L220 | i5768 | Y | L550 | L215 |
| i5769 | Y | L551 | L201 | i5770 | Y | L551 | L206 | i5771 | Y | L551 | L220 | i5772 | Y | L551 | L215 |
| i5773 | Y | L552 | L201 | i5774 | Y | L552 | L206 | i5775 | Y | L552 | L220 | i5776 | Y | L552 | L215 |
| i5777 | Y | L553 | L201 | i5778 | Y | L553 | L206 | i5779 | Y | L553 | L220 | i5780 | Y | L553 | L215 |
| i5781 | Y | L554 | L201 | i5782 | Y | L554 | L206 | i5783 | Y | L554 | L220 | i5784 | Y | L554 | L215 |
| i5785 | Y | L555 | L201 | i5786 | Y | L555 | L206 | i5787 | Y | L555 | L220 | i5788 | Y | L555 | L215 |
| i5789 | Y | L556 | L201 | i5790 | Y | L556 | L206 | i5791 | Y | L556 | L220 | i5792 | Y | L556 | L215 |
| i5793 | Y | L557 | L201 | i5794 | Y | L557 | L206 | i5795 | Y | L557 | L220 | i5796 | Y | L557 | L215 |
| i5797 | Y | L558 | L201 | i5798 | Y | L558 | L206 | i5799 | Y | L558 | L220 | i5800 | Y | L558 | L215 |
| i5801 | Y | L559 | L201 | i5802 | Y | L559 | L206 | i5803 | Y | L559 | L220 | i5804 | Y | L559 | L215 |
| i5805 | Y | L560 | L201 | i5806 | Y | L560 | L206 | i5807 | Y | L560 | L220 | i5808 | Y | L560 | L215 |
| i5809 | Y | L561 | L201 | i5810 | Y | L561 | L206 | i5811 | Y | L561 | L220 | i5812 | Y | L561 | L215 |
| i5813 | Y | L562 | L201 | i5814 | Y | L562 | L206 | i5815 | Y | L562 | L220 | i5816 | Y | L562 | L215 |
| i5817 | Y | L563 | L201 | i5818 | Y | L563 | L206 | i5819 | Y | L563 | L220 | i5820 | Y | L563 | L215 |
| i5821 | Y | L564 | L201 | i5822 | Y | L564 | L206 | i5823 | Y | L564 | L220 | i5824 | Y | L564 | L215 |
| i5825 | Y | L565 | L201 | i5826 | Y | L565 | L206 | i5827 | Y | L565 | L220 | i5828 | Y | L565 | L215 |
| i5829 | Y | L566 | L201 | i5830 | Y | L566 | L206 | i5831 | Y | L566 | L220 | i5832 | Y | L566 | L215 |
| i5833 | Y | L567 | L201 | i5834 | Y | L567 | L206 | i5835 | Y | L567 | L220 | i5836 | Y | L567 | L215 |
| i5837 | Y | L568 | L201 | i5838 | Y | L568 | L206 | i5839 | Y | L568 | L220 | i5840 | Y | L568 | L215 |
| i5841 | Y | L569 | L201 | i5842 | Y | L569 | L206 | i5843 | Y | L569 | L220 | i5844 | Y | L569 | L215 |
| i5845 | Y | L570 | L201 | i5846 | Y | L570 | L206 | i5847 | Y | L570 | L220 | i5848 | Y | L570 | L215 |
| i5849 | Y | L571 | L201 | i5850 | Y | L571 | L206 | i5851 | Y | L571 | L220 | i5852 | Y | L571 | L215 |
| i5853 | Y | L572 | L201 | i5854 | Y | L572 | L206 | i5855 | Y | L572 | L220 | i5856 | Y | L572 | L215 |
| i5857 | Y | L843 | L201 | i5858 | Y | L843 | L206 | i5859 | Y | L843 | L220 | i5860 | Y | L843 | L215 |
| i5861 | Y | L844 | L201 | i5862 | Y | L844 | L206 | i5863 | Y | L844 | L220 | i5864 | Y | L844 | L215 |
| i5865 | Y | L845 | L201 | i5866 | Y | L845 | L206 | i5867 | Y | L845 | L220 | i5868 | Y | L845 | L215 |
| i5869 | Y | L846 | L201 | i5870 | Y | L846 | L206 | i5871 | Y | L846 | L220 | i5872 | Y | L846 | L215 |
| i5873 | Y | L847 | L201 | i5874 | Y | L847 | L206 | i5875 | Y | L847 | L220 | i5876 | Y | L847 | L215 |
| i5877 | Y | L848 | L201 | i5878 | Y | L848 | L206 | i5879 | Y | L848 | L220 | i5880 | Y | L848 | L215 |
| i5881 | Y | L10 | L211 | i5882 | Y | L10 | L212 | i5883 | Y | L10 | L426 | i5884 | Y | L10 | L427 |
| i5885 | Y | L11 | L211 | i5886 | Y | L11 | L212 | i5887 | Y | L11 | L426 | i5888 | Y | L11 | L427 |
| i5889 | Y | L20 | L211 | i5890 | Y | L20 | L212 | i5891 | Y | L20 | L426 | i5892 | Y | L20 | L427 |
| i5893 | Y | L21 | L211 | i5894 | Y | L21 | L212 | i5895 | Y | L21 | L426 | i5896 | Y | L21 | L427 |
| i5897 | Y | L22 | L211 | i5898 | Y | L22 | L212 | i5899 | Y | L22 | L426 | i5900 | Y | L22 | L427 |

TABLE 1-continued

Compositions "i1" to "i9919"

| | | | | | | | | | | | | | | | |
|---|---|---|---|---|---|---|---|---|---|---|---|---|---|---|---|
| i5901 | Y | L23 | L211 | i5902 | Y | L23 | L212 | i5903 | Y | L23 | L426 | i5904 | Y | L23 | L427 |
| i5905 | Y | L24 | L211 | i5906 | Y | L24 | L212 | i5907 | Y | L24 | L426 | i5908 | Y | L24 | L427 |
| i5909 | Y | L25 | L211 | i5910 | Y | L25 | L212 | i5911 | Y | L25 | L426 | i5912 | Y | L25 | L427 |
| i5913 | Y | L26 | L211 | i5914 | Y | L26 | L212 | i5915 | Y | L26 | L426 | i5916 | Y | L26 | L427 |
| i5917 | Y | L27 | L211 | i5918 | Y | L27 | L212 | i5919 | Y | L27 | L426 | i5920 | Y | L27 | L427 |
| i5921 | Y | L28 | L211 | i5922 | Y | L28 | L212 | i5923 | Y | L28 | L426 | i5924 | Y | L28 | L427 |
| i5925 | Y | L12 | L211 | i5926 | Y | L12 | L212 | i5927 | Y | L12 | L426 | i5928 | Y | L12 | L427 |
| i5929 | Y | L13 | L211 | i5930 | Y | L13 | L212 | i5931 | Y | L13 | L426 | i5932 | Y | L13 | L427 |
| i5933 | Y | L14 | L211 | i5934 | Y | L14 | L212 | i5935 | Y | L14 | L426 | i5936 | Y | L14 | L427 |
| i5937 | Y | L15 | L211 | i5938 | Y | L15 | L212 | i5939 | Y | L15 | L426 | i5940 | Y | L15 | L427 |
| i5941 | Y | L16 | L211 | i5942 | Y | L16 | L212 | i5943 | Y | L16 | L426 | i5944 | Y | L16 | L427 |
| i5945 | Y | L17 | L211 | i5946 | Y | L17 | L212 | i5947 | Y | L17 | L426 | i5948 | Y | L17 | L427 |
| i5949 | Y | L18 | L211 | i5950 | Y | L18 | L212 | i5951 | Y | L18 | L426 | i5952 | Y | L18 | L427 |
| i5953 | Y | L19 | L211 | i5954 | Y | L19 | L212 | i5955 | Y | L19 | L426 | i5956 | Y | L19 | L427 |
| i5957 | Y | L2 | L211 | i5958 | Y | L2 | L212 | i5959 | Y | L2 | L426 | i5960 | Y | L2 | L427 |
| i5961 | Y | L101 | L211 | i5962 | Y | L101 | L212 | i5963 | Y | L101 | L426 | i5964 | Y | L101 | L427 |
| i5965 | Y | L102 | L211 | i5966 | Y | L102 | L212 | i5967 | Y | L102 | L426 | i5968 | Y | L102 | L427 |
| i5969 | Y | L103 | L211 | i5970 | Y | L103 | L212 | i5971 | Y | L103 | L426 | i5972 | Y | L103 | L427 |
| i5973 | Y | L104 | L211 | i5974 | Y | L104 | L212 | i5975 | Y | L104 | L426 | i5976 | Y | L104 | L427 |
| i5977 | Y | L105 | L211 | i5978 | Y | L105 | L212 | i5979 | Y | L105 | L426 | i5980 | Y | L105 | L427 |
| i5981 | Y | L106 | L211 | i5982 | Y | L106 | L212 | i5983 | Y | L106 | L426 | i5984 | Y | L106 | L427 |
| i5985 | Y | L107 | L211 | i5986 | Y | L107 | L212 | i5987 | Y | L107 | L426 | i5988 | Y | L107 | L427 |
| i5989 | Y | L108 | L211 | i5990 | Y | L108 | L212 | i5991 | Y | L108 | L426 | i5992 | Y | L108 | L427 |
| i5993 | Y | L109 | L211 | i5994 | Y | L109 | L212 | i5995 | Y | L109 | L426 | i5996 | Y | L109 | L427 |
| i5997 | Y | L110 | L211 | i5998 | Y | L110 | L212 | i5999 | Y | L110 | L426 | i6000 | Y | L110 | L427 |
| i6001 | Y | L111 | L211 | i6002 | Y | L111 | L212 | i6003 | Y | L111 | L426 | i6004 | Y | L111 | L427 |
| i6005 | Y | L112 | L211 | i6006 | Y | L112 | L212 | i6007 | Y | L112 | L426 | i6008 | Y | L112 | L427 |
| i6009 | Y | L113 | L211 | i6010 | Y | L113 | L212 | i6011 | Y | L113 | L426 | i6012 | Y | L113 | L427 |
| i6013 | Y | L114 | L211 | i6014 | Y | L114 | L212 | i6015 | Y | L114 | L426 | i6016 | Y | L114 | L427 |
| i6017 | Y | L115 | L211 | i6018 | Y | L115 | L212 | i6019 | Y | L115 | L426 | i6020 | Y | L115 | L427 |
| i6021 | Y | L116 | L211 | i6022 | Y | L116 | L212 | i6023 | Y | L116 | L426 | i6024 | Y | L116 | L427 |
| i6025 | Y | L117 | L211 | i6026 | Y | L117 | L212 | i6027 | Y | L117 | L426 | i6028 | Y | L117 | L427 |
| i6029 | Y | L118 | L211 | i6030 | Y | L118 | L212 | i6031 | Y | L118 | L426 | i6032 | Y | L118 | L427 |
| i6033 | Y | L119 | L211 | i6034 | Y | L119 | L212 | i6035 | Y | L119 | L426 | i6036 | Y | L119 | L427 |
| i6037 | Y | L120 | L211 | i6038 | Y | L120 | L212 | i6039 | Y | L120 | L426 | i6040 | Y | L120 | L427 |
| i6041 | Y | L121 | L211 | i6042 | Y | L121 | L212 | i6043 | Y | L121 | L426 | i6044 | Y | L121 | L427 |
| i6045 | Y | L122 | L211 | i6046 | Y | L122 | L212 | i6047 | Y | L122 | L426 | i6048 | Y | L122 | L427 |
| i6049 | Y | L123 | L211 | i6050 | Y | L123 | L212 | i6051 | Y | L123 | L426 | i6052 | Y | L123 | L427 |
| i6053 | Y | L124 | L211 | i6054 | Y | L124 | L212 | i6055 | Y | L124 | L426 | i6056 | Y | L124 | L427 |
| i6057 | Y | L125 | L211 | i6058 | Y | L125 | L212 | i6059 | Y | L125 | L426 | i6060 | Y | L125 | L427 |
| i6061 | Y | L126 | L211 | i6062 | Y | L126 | L212 | i6063 | Y | L126 | L426 | i6064 | Y | L126 | L427 |
| i6065 | Y | L127 | L211 | i6066 | Y | L127 | L212 | i6067 | Y | L127 | L426 | i6068 | Y | L127 | L427 |
| i6069 | Y | L128 | L211 | i6070 | Y | L128 | L212 | i6071 | Y | L128 | L426 | i6072 | Y | L128 | L427 |
| i6073 | Y | L129 | L211 | i6074 | Y | L129 | L212 | i6075 | Y | L129 | L426 | i6076 | Y | L129 | L427 |
| i6077 | Y | L130 | L211 | i6078 | Y | L130 | L212 | i6079 | Y | L130 | L426 | i6080 | Y | L130 | L427 |
| i6081 | Y | L131 | L211 | i6082 | Y | L131 | L212 | i6083 | Y | L131 | L426 | i6084 | Y | L131 | L427 |
| i6085 | Y | L132 | L211 | i6086 | Y | L132 | L212 | i6087 | Y | L132 | L426 | i6088 | Y | L132 | L427 |
| i6089 | Y | L133 | L211 | i6090 | Y | L133 | L212 | i6091 | Y | L133 | L426 | i6092 | Y | L133 | L427 |
| i6093 | Y | L134 | L211 | i6094 | Y | L134 | L212 | i6095 | Y | L134 | L426 | i6096 | Y | L134 | L427 |
| i6097 | Y | L135 | L211 | i6098 | Y | L135 | L212 | i6099 | Y | L135 | L426 | i6100 | Y | L135 | L427 |
| i6101 | Y | L136 | L211 | i6102 | Y | L136 | L212 | i6103 | Y | L136 | L426 | i6104 | Y | L136 | L427 |
| i6105 | Y | L137 | L211 | i6106 | Y | L137 | L212 | i6107 | Y | L137 | L426 | i6108 | Y | L137 | L427 |
| i6109 | Y | L138 | L211 | i6110 | Y | L138 | L212 | i6111 | Y | L138 | L426 | i6112 | Y | L138 | L427 |
| i6113 | Y | L139 | L211 | i6114 | Y | L139 | L212 | i6115 | Y | L139 | L426 | i6116 | Y | L139 | L427 |
| i6117 | Y | L140 | L211 | i6118 | Y | L140 | L212 | i6119 | Y | L140 | L426 | i6120 | Y | L140 | L427 |
| i6121 | Y | L141 | L211 | i6122 | Y | L141 | L212 | i6123 | Y | L141 | L426 | i6124 | Y | L141 | L427 |
| i6125 | Y | L142 | L211 | i6126 | Y | L142 | L212 | i6127 | Y | L142 | L426 | i6128 | Y | L142 | L427 |
| i6129 | Y | L143 | L211 | i6130 | Y | L143 | L212 | i6131 | Y | L143 | L426 | i6132 | Y | L143 | L427 |
| i6133 | Y | L144 | L211 | i6134 | Y | L144 | L212 | i6135 | Y | L144 | L426 | i6136 | Y | L144 | L427 |
| i6137 | Y | L145 | L211 | i6138 | Y | L145 | L212 | i6139 | Y | L145 | L426 | i6140 | Y | L145 | L427 |
| i6141 | Y | L146 | L211 | i6142 | Y | L146 | L212 | i6143 | Y | L146 | L426 | i6144 | Y | L146 | L427 |
| i6145 | Y | L147 | L211 | i6146 | Y | L147 | L212 | i6147 | Y | L147 | L426 | i6148 | Y | L147 | L427 |
| i6149 | Y | L148 | L211 | i6150 | Y | L148 | L212 | i6151 | Y | L148 | L426 | i6152 | Y | L148 | L427 |
| i6153 | Y | L149 | L211 | i6154 | Y | L149 | L212 | i6155 | Y | L149 | L426 | i6156 | Y | L149 | L427 |
| i6157 | Y | L150 | L211 | i6158 | Y | L150 | L212 | i6159 | Y | L150 | L426 | i6160 | Y | L150 | L427 |
| i6161 | Y | L151 | L211 | i6162 | Y | L151 | L212 | i6163 | Y | L151 | L426 | i6164 | Y | L151 | L427 |
| i6165 | Y | L152 | L211 | i6166 | Y | L152 | L212 | i6167 | Y | L152 | L426 | i6168 | Y | L152 | L427 |
| i6169 | Y | L153 | L211 | i6170 | Y | L153 | L212 | i6171 | Y | L153 | L426 | i6172 | Y | L153 | L427 |
| i6173 | Y | L154 | L211 | i6174 | Y | L154 | L212 | i6175 | Y | L154 | L426 | i6176 | Y | L154 | L427 |
| i6177 | Y | L155 | L211 | i6178 | Y | L155 | L212 | i6179 | Y | L155 | L426 | i6180 | Y | L155 | L427 |
| i6181 | Y | L156 | L211 | i6182 | Y | L156 | L212 | i6183 | Y | L156 | L426 | i6184 | Y | L156 | L427 |
| i6185 | Y | L157 | L211 | i6186 | Y | L157 | L212 | i6187 | Y | L157 | L426 | i6188 | Y | L157 | L427 |
| i6189 | Y | L158 | L211 | i6190 | Y | L158 | L212 | i6191 | Y | L158 | L426 | i6192 | Y | L158 | L427 |
| i6193 | Y | L159 | L211 | i6194 | Y | L159 | L212 | i6195 | Y | L159 | L426 | i6196 | Y | L159 | L427 |
| i6197 | Y | L160 | L211 | i6198 | Y | L160 | L212 | i6199 | Y | L160 | L426 | i6200 | Y | L160 | L427 |
| i6201 | Y | L161 | L211 | i6202 | Y | L161 | L212 | i6203 | Y | L161 | L426 | i6204 | Y | L161 | L427 |
| i6205 | Y | L162 | L211 | i6206 | Y | L162 | L212 | i6207 | Y | L162 | L426 | i6208 | Y | L162 | L427 |
| i6209 | Y | L163 | L211 | i6210 | Y | L163 | L212 | i6211 | Y | L163 | L426 | i6212 | Y | L163 | L427 |

TABLE 1-continued

Compositions "i1" to "i9919"

| | | | | | | | | | | | |
|---|---|---|---|---|---|---|---|---|---|---|---|
| i6213 Y | L164 | L211 | i6214 Y | L164 | L212 | i6215 Y | L164 | L426 | i6216 Y | L164 | L427 |
| i6217 Y | L165 | L211 | i6218 Y | L165 | L212 | i6219 Y | L165 | L426 | i6220 Y | L165 | L427 |
| i6221 Y | L166 | L211 | i6222 Y | L166 | L212 | i6223 Y | L166 | L426 | i6224 Y | L166 | L427 |
| i6225 Y | L167 | L211 | i6226 Y | L167 | L212 | i6227 Y | L167 | L426 | i6228 Y | L167 | L427 |
| i6229 Y | L168 | L211 | i6230 Y | L168 | L212 | i6231 Y | L168 | L426 | i6232 Y | L168 | L427 |
| i6233 Y | L169 | L211 | i6234 Y | L169 | L212 | i6235 Y | L169 | L426 | i6236 Y | L169 | L427 |
| i6237 Y | L170 | L211 | i6238 Y | L170 | L212 | i6239 Y | L170 | L426 | i6240 Y | L170 | L427 |
| i6241 Y | L171 | L211 | i6242 Y | L171 | L212 | i6243 Y | L171 | L426 | i6244 Y | L171 | L427 |
| i6245 Y | L172 | L211 | i6246 Y | L172 | L212 | i6247 Y | L172 | L426 | i6248 Y | L172 | L427 |
| i6249 Y | L173 | L211 | i6250 Y | L173 | L212 | i6251 Y | L173 | L426 | i6252 Y | L173 | L427 |
| i6253 Y | L174 | L211 | i6254 Y | L174 | L212 | i6255 Y | L174 | L426 | i6256 Y | L174 | L427 |
| i6257 Y | L175 | L211 | i6258 Y | L175 | L212 | i6259 Y | L175 | L426 | i6260 Y | L175 | L427 |
| i6261 Y | L176 | L211 | i6262 Y | L176 | L212 | i6263 Y | L176 | L426 | i6264 Y | L176 | L427 |
| i6265 Y | L177 | L211 | i6266 Y | L177 | L212 | i6267 Y | L177 | L426 | i6268 Y | L177 | L427 |
| i6269 Y | L178 | L211 | i6270 Y | L178 | L212 | i6271 Y | L178 | L426 | i6272 Y | L178 | L427 |
| i6273 Y | L179 | L211 | i6274 Y | L179 | L212 | i6275 Y | L179 | L426 | i6276 Y | L179 | L427 |
| i6277 Y | L180 | L211 | i6278 Y | L180 | L212 | i6279 Y | L180 | L426 | i6280 Y | L180 | L427 |
| i6281 Y | L181 | L211 | i6282 Y | L181 | L212 | i6283 Y | L181 | L426 | i6284 Y | L181 | L427 |
| i6285 Y | L182 | L211 | i6286 Y | L182 | L212 | i6287 Y | L182 | L426 | i6288 Y | L182 | L427 |
| i6289 Y | L183 | L211 | i6290 Y | L183 | L212 | i6291 Y | L183 | L426 | i6292 Y | L183 | L427 |
| i6293 Y | L184 | L211 | i6294 Y | L184 | L212 | i6295 Y | L184 | L426 | i6296 Y | L184 | L427 |
| i6297 Y | L185 | L211 | i6298 Y | L185 | L212 | i6299 Y | L185 | L426 | i6300 Y | L185 | L427 |
| i6301 Y | L186 | L211 | i6302 Y | L186 | L212 | i6303 Y | L186 | L426 | i6304 Y | L186 | L427 |
| i6305 Y | L187 | L211 | i6306 Y | L187 | L212 | i6307 Y | L187 | L426 | i6308 Y | L187 | L427 |
| i6309 Y | L188 | L211 | i6310 Y | L188 | L212 | i6311 Y | L188 | L426 | i6312 Y | L188 | L427 |
| i6313 Y | L189 | L211 | i6314 Y | L189 | L212 | i6315 Y | L189 | L426 | i6316 Y | L189 | L427 |
| i6317 Y | L190 | L211 | i6318 Y | L190 | L212 | i6319 Y | L190 | L426 | i6320 Y | L190 | L427 |
| i6321 Y | L191 | L211 | i6322 Y | L191 | L212 | i6323 Y | L191 | L426 | i6324 Y | L191 | L427 |
| i6325 Y | L192 | L211 | i6326 Y | L192 | L212 | i6327 Y | L192 | L426 | i6328 Y | L192 | L427 |
| i6329 Y | L193 | L211 | i6330 Y | L193 | L212 | i6331 Y | L193 | L426 | i6332 Y | L193 | L427 |
| i6333 Y | L194 | L211 | i6334 Y | L194 | L212 | i6335 Y | L194 | L426 | i6336 Y | L194 | L427 |
| i6337 Y | L195 | L211 | i6338 Y | L195 | L212 | i6339 Y | L195 | L426 | i6340 Y | L195 | L427 |
| i6341 Y | L196 | L211 | i6342 Y | L196 | L212 | i6343 Y | L196 | L426 | i6344 Y | L196 | L427 |
| i6345 Y | L197 | L211 | i6346 Y | L197 | L212 | i6347 Y | L197 | L426 | i6348 Y | L197 | L427 |
| i6349 Y | L198 | L211 | i6350 Y | L198 | L212 | i6351 Y | L198 | L426 | i6352 Y | L198 | L427 |
| i6353 Y | L199 | L211 | i6354 Y | L199 | L212 | i6355 Y | L199 | L426 | i6356 Y | L199 | L427 |
| i6357 Y | L200 | L211 | i6358 Y | L200 | L212 | i6359 Y | L200 | L426 | i6360 Y | L200 | L427 |
| i6361 Y | L201 | L211 | i6362 Y | L201 | L212 | i6363 Y | L201 | L426 | i6364 Y | L201 | L427 |
| i6365 Y | L202 | L211 | i6366 Y | L202 | L212 | i6367 Y | L202 | L426 | i6368 Y | L202 | L427 |
| i6369 Y | L203 | L211 | i6370 Y | L203 | L212 | i6371 Y | L203 | L426 | i6372 Y | L203 | L427 |
| i6373 Y | L204 | L211 | i6374 Y | L204 | L212 | i6375 Y | L204 | L426 | i6376 Y | L204 | L427 |
| i6377 Y | L205 | L211 | i6378 Y | L205 | L212 | i6379 Y | L205 | L426 | i6380 Y | L205 | L427 |
| i6381 Y | L206 | L211 | i6382 Y | L206 | L212 | i6383 Y | L206 | L426 | i6384 Y | L206 | L427 |
| i6385 Y | L207 | L211 | i6386 Y | L207 | L212 | i6387 Y | L207 | L426 | i6388 Y | L207 | L427 |
| i6389 Y | L208 | L211 | i6390 Y | L208 | L212 | i6391 Y | L208 | L426 | i6392 Y | L208 | L427 |
| i6393 Y | L209 | L211 | i6394 Y | L209 | L212 | i6395 Y | L209 | L426 | i6396 Y | L209 | L427 |
| i6397 Y | L210 | L211 | i6398 Y | L210 | L212 | i6399 Y | L210 | L426 | i6400 Y | L210 | L427 |
| i6401 Y | L211 | L211 | i6402 Y | L211 | L212 | i6403 Y | L211 | L426 | i6404 Y | L211 | L427 |
| i6405 Y | L212 | L211 | i6406 Y | L212 | L212 | i6407 Y | L212 | L426 | i6408 Y | L212 | L427 |
| i6409 Y | L213 | L211 | i6410 Y | L213 | L212 | i6411 Y | L213 | L426 | i6412 Y | L213 | L427 |
| i6413 Y | L214 | L211 | i6414 Y | L214 | L212 | i6415 Y | L214 | L426 | i6416 Y | L214 | L427 |
| i6417 Y | L215 | L211 | i6418 Y | L215 | L212 | i6419 Y | L215 | L426 | i6420 Y | L215 | L427 |
| i6421 Y | L216 | L211 | i6422 Y | L216 | L212 | i6423 Y | L216 | L426 | i6424 Y | L216 | L427 |
| i6425 Y | L217 | L211 | i6426 Y | L217 | L212 | i6427 Y | L217 | L426 | i6428 Y | L217 | L427 |
| i6429 Y | L218 | L211 | i6430 Y | L218 | L212 | i6431 Y | L218 | L426 | i6432 Y | L218 | L427 |
| i6433 Y | L219 | L211 | i6434 Y | L219 | L212 | i6435 Y | L219 | L426 | i6436 Y | L219 | L427 |
| i6437 Y | L220 | L211 | i6438 Y | L220 | L212 | i6439 Y | L220 | L426 | i6440 Y | L220 | L427 |
| i6441 Y | L221 | L211 | i6442 Y | L221 | L212 | i6443 Y | L221 | L426 | i6444 Y | L221 | L427 |
| i6445 Y | L222 | L211 | i6446 Y | L222 | L212 | i6447 Y | L222 | L426 | i6448 Y | L222 | L427 |
| i6449 Y | L401 | L211 | i6450 Y | L401 | L212 | i6451 Y | L401 | L426 | i6452 Y | L401 | L427 |
| i6453 Y | L402 | L211 | i6454 Y | L402 | L212 | i6455 Y | L402 | L426 | i6456 Y | L402 | L427 |
| i6457 Y | L403 | L211 | i6458 Y | L403 | L212 | i6459 Y | L403 | L426 | i6460 Y | L403 | L427 |
| i6461 Y | L404 | L211 | i6462 Y | L404 | L212 | i6463 Y | L404 | L426 | i6464 Y | L404 | L427 |
| i6465 Y | L405 | L211 | i6466 Y | L405 | L212 | i6467 Y | L405 | L426 | i6468 Y | L405 | L427 |
| i6469 Y | L406 | L211 | i6470 Y | L406 | L212 | i6471 Y | L406 | L426 | i6472 Y | L406 | L427 |
| i6473 Y | L407 | L211 | i6474 Y | L407 | L212 | i6475 Y | L407 | L426 | i6476 Y | L407 | L427 |
| i6477 Y | L408 | L211 | i6478 Y | L408 | L212 | i6479 Y | L408 | L426 | i6480 Y | L408 | L427 |
| i6481 Y | L409 | L211 | i6482 Y | L409 | L212 | i6483 Y | L409 | L426 | i6484 Y | L409 | L427 |
| i6485 Y | L410 | L211 | i6486 Y | L410 | L212 | i6487 Y | L410 | L426 | i6488 Y | L410 | L427 |
| i6489 Y | L411 | L211 | i6490 Y | L411 | L212 | i6491 Y | L411 | L426 | i6492 Y | L411 | L427 |
| i6493 Y | L412 | L211 | i6494 Y | L412 | L212 | i6495 Y | L412 | L426 | i6496 Y | L412 | L427 |
| i6497 Y | L413 | L211 | i6498 Y | L413 | L212 | i6499 Y | L413 | L426 | i6500 Y | L413 | L427 |
| i6501 Y | L414 | L211 | i6502 Y | L414 | L212 | i6503 Y | L414 | L426 | i6504 Y | L414 | L427 |
| i6505 Y | L415 | L211 | i6506 Y | L415 | L212 | i6507 Y | L415 | L426 | i6508 Y | L415 | L427 |
| i6509 Y | L416 | L211 | i6510 Y | L416 | L212 | i6511 Y | L416 | L426 | i6512 Y | L416 | L427 |
| i6513 Y | L417 | L211 | i6514 Y | L417 | L212 | i6515 Y | L417 | L426 | i6516 Y | L417 | L427 |
| i6517 Y | L418 | L211 | i6518 Y | L418 | L212 | i6519 Y | L418 | L426 | i6520 Y | L418 | L427 |
| i6521 Y | L419 | L211 | i6522 Y | L419 | L212 | i6523 Y | L419 | L426 | i6524 Y | L419 | L427 |

TABLE 1-continued

Compositions "i1" to "i9919"

| | | | | | | | | | | | | | | |
|---|---|---|---|---|---|---|---|---|---|---|---|---|---|---|
| i6525 | Y | L420 | L211 | i6526 | Y | L420 | L212 | i6527 | Y | L420 | L426 | i6528 | Y | L420 | L427 |
| i6529 | Y | L421 | L211 | i6530 | Y | L421 | L212 | i6531 | Y | L421 | L426 | i6532 | Y | L421 | L427 |
| i6533 | Y | L422 | L211 | i6534 | Y | L422 | L212 | i6535 | Y | L422 | L426 | i6536 | Y | L422 | L427 |
| i6537 | Y | L423 | L211 | i6538 | Y | L423 | L212 | i6539 | Y | L423 | L426 | i6540 | Y | L423 | L427 |
| i6541 | Y | L424 | L211 | i6542 | Y | L424 | L212 | i6543 | Y | L424 | L426 | i6544 | Y | L424 | L427 |
| i6545 | Y | L425 | L211 | i6546 | Y | L425 | L212 | i6547 | Y | L425 | L426 | i6548 | Y | L425 | L427 |
| i6549 | Y | L501 | L211 | i6550 | Y | L501 | L212 | i6551 | Y | L501 | L426 | i6552 | Y | L501 | L427 |
| i6553 | Y | L502 | L211 | i6554 | Y | L502 | L212 | i6555 | Y | L502 | L426 | i6556 | Y | L502 | L427 |
| i6557 | Y | L503 | L211 | i6558 | Y | L503 | L212 | i6559 | Y | L503 | L426 | i6560 | Y | L503 | L427 |
| i6561 | Y | L504 | L211 | i6562 | Y | L504 | L212 | i6563 | Y | L504 | L426 | i6564 | Y | L504 | L427 |
| i6565 | Y | L505 | L211 | i6566 | Y | L505 | L212 | i6567 | Y | L505 | L426 | i6568 | Y | L505 | L427 |
| i6569 | Y | L506 | L211 | i6570 | Y | L506 | L212 | i6571 | Y | L506 | L426 | i6572 | Y | L506 | L427 |
| i6573 | Y | L507 | L211 | i6574 | Y | L507 | L212 | i6575 | Y | L507 | L426 | i6576 | Y | L507 | L427 |
| i6577 | Y | L508 | L211 | i6578 | Y | L508 | L212 | i6579 | Y | L508 | L426 | i6580 | Y | L508 | L427 |
| i6581 | Y | L509 | L211 | i6582 | Y | L509 | L212 | i6583 | Y | L509 | L426 | i6584 | Y | L509 | L427 |
| i6585 | Y | L510 | L211 | i6586 | Y | L510 | L212 | i6587 | Y | L510 | L426 | i6588 | Y | L510 | L427 |
| i6589 | Y | L511 | L211 | i6590 | Y | L511 | L212 | i6591 | Y | L511 | L426 | i6592 | Y | L511 | L427 |
| i6593 | Y | L512 | L211 | i6594 | Y | L512 | L212 | i6595 | Y | L512 | L426 | i6596 | Y | L512 | L427 |
| i6597 | Y | L513 | L211 | i6598 | Y | L513 | L212 | i6599 | Y | L513 | L426 | i6600 | Y | L513 | L427 |
| i6601 | Y | L514 | L211 | i6602 | Y | L514 | L212 | i6603 | Y | L514 | L426 | i6604 | Y | L514 | L427 |
| i6605 | Y | L515 | L211 | i6606 | Y | L515 | L212 | i6607 | Y | L515 | L426 | i6608 | Y | L515 | L427 |
| i6609 | Y | L516 | L211 | i6610 | Y | L516 | L212 | i6611 | Y | L516 | L426 | i6612 | Y | L516 | L427 |
| i6613 | Y | L517 | L211 | i6614 | Y | L517 | L212 | i6615 | Y | L517 | L426 | i6616 | Y | L517 | L427 |
| i6617 | Y | L518 | L211 | i6618 | Y | L518 | L212 | i6619 | Y | L518 | L426 | i6620 | Y | L518 | L427 |
| i6621 | Y | L519 | L211 | i6622 | Y | L519 | L212 | i6623 | Y | L519 | L426 | i6624 | Y | L519 | L427 |
| i6625 | Y | L520 | L211 | i6626 | Y | L520 | L212 | i6627 | Y | L520 | L426 | i6628 | Y | L520 | L427 |
| i6629 | Y | L521 | L211 | i6630 | Y | L521 | L212 | i6631 | Y | L521 | L426 | i6632 | Y | L521 | L427 |
| i6633 | Y | L522 | L211 | i6634 | Y | L522 | L212 | i6635 | Y | L522 | L426 | i6636 | Y | L522 | L427 |
| i6637 | Y | L523 | L211 | i6638 | Y | L523 | L212 | i6639 | Y | L523 | L426 | i6640 | Y | L523 | L427 |
| i6641 | Y | L524 | L211 | i6642 | Y | L524 | L212 | i6643 | Y | L524 | L426 | i6644 | Y | L524 | L427 |
| i6645 | Y | L525 | L211 | i6646 | Y | L525 | L212 | i6647 | Y | L525 | L426 | i6648 | Y | L525 | L427 |
| i6649 | Y | L526 | L211 | i6650 | Y | L526 | L212 | i6651 | Y | L526 | L426 | i6652 | Y | L526 | L427 |
| i6653 | Y | L527 | L211 | i6654 | Y | L527 | L212 | i6655 | Y | L527 | L426 | i6656 | Y | L527 | L427 |
| i6657 | Y | L528 | L211 | i6658 | Y | L528 | L212 | i6659 | Y | L528 | L426 | i6660 | Y | L528 | L427 |
| i6661 | Y | L529 | L211 | i6662 | Y | L529 | L212 | i6663 | Y | L529 | L426 | i6664 | Y | L529 | L427 |
| i6665 | Y | L530 | L211 | i6666 | Y | L530 | L212 | i6667 | Y | L530 | L426 | i6668 | Y | L530 | L427 |
| i6669 | Y | L531 | L211 | i6670 | Y | L531 | L212 | i6671 | Y | L531 | L426 | i6672 | Y | L531 | L427 |
| i6673 | Y | L532 | L211 | i6674 | Y | L532 | L212 | i6675 | Y | L532 | L426 | i6676 | Y | L532 | L427 |
| i6677 | Y | L533 | L211 | i6678 | Y | L533 | L212 | i6679 | Y | L533 | L426 | i6680 | Y | L533 | L427 |
| i6681 | Y | L534 | L211 | i6682 | Y | L534 | L212 | i6683 | Y | L534 | L426 | i6684 | Y | L534 | L427 |
| i6685 | Y | L535 | L211 | i6686 | Y | L535 | L212 | i6687 | Y | L535 | L426 | i6688 | Y | L535 | L427 |
| i6689 | Y | L536 | L211 | i6690 | Y | L536 | L212 | i6691 | Y | L536 | L426 | i6692 | Y | L536 | L427 |
| i6693 | Y | L537 | L211 | i6694 | Y | L537 | L212 | i6695 | Y | L537 | L426 | i6696 | Y | L537 | L427 |
| i6697 | Y | L538 | L211 | i6698 | Y | L538 | L212 | i6699 | Y | L538 | L426 | i6700 | Y | L538 | L427 |
| i6701 | Y | L539 | L211 | i6702 | Y | L539 | L212 | i6703 | Y | L539 | L426 | i6704 | Y | L539 | L427 |
| i6705 | Y | L540 | L211 | i6706 | Y | L540 | L212 | i6707 | Y | L540 | L426 | i6708 | Y | L540 | L427 |
| i6709 | Y | L541 | L211 | i6710 | Y | L541 | L212 | i6711 | Y | L541 | L426 | i6712 | Y | L541 | L427 |
| i6713 | Y | L542 | L211 | i6714 | Y | L542 | L212 | i6715 | Y | L542 | L426 | i6716 | Y | L542 | L427 |
| i6717 | Y | L543 | L211 | i6718 | Y | L543 | L212 | i6719 | Y | L543 | L426 | i6720 | Y | L543 | L427 |
| i6721 | Y | L544 | L211 | i6722 | Y | L544 | L212 | i6723 | Y | L544 | L426 | i6724 | Y | L544 | L427 |
| i6725 | Y | L545 | L211 | i6726 | Y | L545 | L212 | i6727 | Y | L545 | L426 | i6728 | Y | L545 | L427 |
| i6729 | Y | L546 | L211 | i6730 | Y | L546 | L212 | i6731 | Y | L546 | L426 | i6732 | Y | L546 | L427 |
| i6733 | Y | L547 | L211 | i6734 | Y | L547 | L212 | i6735 | Y | L547 | L426 | i6736 | Y | L547 | L427 |
| i6737 | Y | L548 | L211 | i6738 | Y | L548 | L212 | i6739 | Y | L548 | L426 | i6740 | Y | L548 | L427 |
| i6741 | Y | L549 | L211 | i6742 | Y | L549 | L212 | i6743 | Y | L549 | L426 | i6744 | Y | L549 | L427 |
| i6745 | Y | L550 | L211 | i6746 | Y | L550 | L212 | i6747 | Y | L550 | L426 | i6748 | Y | L550 | L427 |
| i6749 | Y | L551 | L211 | i6750 | Y | L551 | L212 | i6751 | Y | L551 | L426 | i6752 | Y | L551 | L427 |
| i6753 | Y | L552 | L211 | i6754 | Y | L552 | L212 | i6755 | Y | L552 | L426 | i6756 | Y | L552 | L427 |
| i6757 | Y | L553 | L211 | i6758 | Y | L553 | L212 | i6759 | Y | L553 | L426 | i6760 | Y | L553 | L427 |
| i6761 | Y | L554 | L211 | i6762 | Y | L554 | L212 | i6763 | Y | L554 | L426 | i6764 | Y | L554 | L427 |
| i6765 | Y | L555 | L211 | i6766 | Y | L555 | L212 | i6767 | Y | L555 | L426 | i6768 | Y | L555 | L427 |
| i6769 | Y | L556 | L211 | i6770 | Y | L556 | L212 | i6771 | Y | L556 | L426 | i6772 | Y | L556 | L427 |
| i6773 | Y | L557 | L211 | i6774 | Y | L557 | L212 | i6775 | Y | L557 | L426 | i6776 | Y | L557 | L427 |
| i6777 | Y | L558 | L211 | i6778 | Y | L558 | L212 | i6779 | Y | L558 | L426 | i6780 | Y | L558 | L427 |
| i6781 | Y | L559 | L211 | i6782 | Y | L559 | L212 | i6783 | Y | L559 | L426 | i6784 | Y | L559 | L427 |
| i6785 | Y | L560 | L211 | i6786 | Y | L560 | L212 | i6787 | Y | L560 | L426 | i6788 | Y | L560 | L427 |
| i6789 | Y | L561 | L211 | i6790 | Y | L561 | L212 | i6791 | Y | L561 | L426 | i6792 | Y | L561 | L427 |
| i6793 | Y | L562 | L211 | i6794 | Y | L562 | L212 | i6795 | Y | L562 | L426 | i6796 | Y | L562 | L427 |
| i6797 | Y | L563 | L211 | i6798 | Y | L563 | L212 | i6799 | Y | L563 | L426 | i6800 | Y | L563 | L427 |
| i6801 | Y | L564 | L211 | i6802 | Y | L564 | L212 | i6803 | Y | L564 | L426 | i6804 | Y | L564 | L427 |
| i6805 | Y | L565 | L211 | i6806 | Y | L565 | L212 | i6807 | Y | L565 | L426 | i6808 | Y | L565 | L427 |
| i6809 | Y | L566 | L211 | i6810 | Y | L566 | L212 | i6811 | Y | L566 | L426 | i6812 | Y | L566 | L427 |
| i6813 | Y | L567 | L211 | i6814 | Y | L567 | L212 | i6815 | Y | L567 | L426 | i6816 | Y | L567 | L427 |
| i6817 | Y | L568 | L211 | i6818 | Y | L568 | L212 | i6819 | Y | L568 | L426 | i6820 | Y | L568 | L427 |
| i6821 | Y | L569 | L211 | i6822 | Y | L569 | L212 | i6823 | Y | L569 | L426 | i6824 | Y | L569 | L427 |
| i6825 | Y | L570 | L211 | i6826 | Y | L570 | L212 | i6827 | Y | L570 | L426 | i6828 | Y | L570 | L427 |
| i6829 | Y | L571 | L211 | i6830 | Y | L571 | L212 | i6831 | Y | L571 | L426 | i6832 | Y | L571 | L427 |
| i6833 | Y | L572 | L211 | i6834 | Y | L572 | L212 | i6835 | Y | L572 | L426 | i6836 | Y | L572 | L427 |

TABLE 1-continued

Compositions "i1" to "i9919"

| | | | | | | | | | | | | |
|---|---|---|---|---|---|---|---|---|---|---|---|---|
| i6837 | Y | L843 | L211 | i6838 | Y | L843 | L212 | i6839 | Y | L843 | L426 | i6840 | Y | L843 | L427 |
| i6841 | Y | L844 | L211 | i6842 | Y | L844 | L212 | i6843 | Y | L844 | L426 | i6844 | Y | L844 | L427 |
| i6845 | Y | L845 | L211 | i6846 | Y | L845 | L212 | i6847 | Y | L845 | L426 | i6848 | Y | L845 | L427 |
| i6849 | Y | L846 | L211 | i6850 | Y | L846 | L212 | i6851 | Y | L846 | L426 | i6852 | Y | L846 | L427 |
| i6853 | Y | L847 | L211 | i6854 | Y | L847 | L212 | i6855 | Y | L847 | L426 | i6856 | Y | L847 | L427 |
| i6857 | Y | L848 | L211 | i6858 | Y | L848 | L212 | i6859 | Y | L848 | L426 | i6860 | Y | L848 | L427 |
| i6861 | Y | L10 | L428 | i6862 | Y | L10 | L429 | i6863 | Y | L10 | L430 | i6864 | Y | L10 | L431 |
| i6865 | Y | L11 | L428 | i6866 | Y | L11 | L429 | i6867 | Y | L11 | L430 | i6868 | Y | L11 | L431 |
| i6869 | Y | L20 | L428 | i6870 | Y | L20 | L429 | i6871 | Y | L20 | L430 | i6872 | Y | L20 | L431 |
| i6873 | Y | L21 | L428 | i6874 | Y | L21 | L429 | i6875 | Y | L21 | L430 | i6876 | Y | L21 | L431 |
| i6877 | Y | L22 | L428 | i6878 | Y | L22 | L429 | i6879 | Y | L22 | L430 | i6880 | Y | L22 | L431 |
| i6881 | Y | L23 | L428 | i6882 | Y | L23 | L429 | i6883 | Y | L23 | L430 | i6884 | Y | L23 | L431 |
| i6885 | Y | L24 | L428 | i6886 | Y | L24 | L429 | i6887 | Y | L24 | L430 | i6888 | Y | L24 | L431 |
| i6889 | Y | L25 | L428 | i6890 | Y | L25 | L429 | i6891 | Y | L25 | L430 | i6892 | Y | L25 | L431 |
| i6893 | Y | L26 | L428 | i6894 | Y | L26 | L429 | i6895 | Y | L26 | L430 | i6896 | Y | L26 | L431 |
| i6897 | Y | L27 | L428 | i6898 | Y | L27 | L429 | i6899 | Y | L27 | L430 | i6900 | Y | L27 | L431 |
| i6901 | Y | L28 | L428 | i6902 | Y | L28 | L429 | i6903 | Y | L28 | L430 | i6904 | Y | L28 | L431 |
| i6905 | Y | L12 | L428 | i6906 | Y | L12 | L429 | i6907 | Y | L12 | L430 | i6908 | Y | L12 | L431 |
| i6909 | Y | L13 | L428 | i6910 | Y | L13 | L429 | i6911 | Y | L13 | L430 | i6912 | Y | L13 | L431 |
| i6913 | Y | L14 | L428 | i6914 | Y | L14 | L429 | i6915 | Y | L14 | L430 | i6916 | Y | L14 | L431 |
| i6917 | Y | L15 | L428 | i6918 | Y | L15 | L429 | i6919 | Y | L15 | L430 | i6920 | Y | L15 | L431 |
| i6921 | Y | L16 | L428 | i6922 | Y | L16 | L429 | i6923 | Y | L16 | L430 | i6924 | Y | L16 | L431 |
| i6925 | Y | L17 | L428 | i6926 | Y | L17 | L429 | i6927 | Y | L17 | L430 | i6928 | Y | L17 | L431 |
| i6929 | Y | L18 | L428 | i6930 | Y | L18 | L429 | i6931 | Y | L18 | L430 | i6932 | Y | L18 | L431 |
| i6933 | Y | L19 | L428 | i6934 | Y | L19 | L429 | i6935 | Y | L19 | L430 | i6936 | Y | L19 | L431 |
| i6937 | Y | L2 | L428 | i6938 | Y | L2 | L429 | i6939 | Y | L2 | L430 | i6940 | Y | L2 | L431 |
| i6941 | Y | L101 | L428 | i6942 | Y | L101 | L429 | i6943 | Y | L101 | L430 | i6944 | Y | L101 | L431 |
| i6945 | Y | L102 | L428 | i6946 | Y | L102 | L429 | i6947 | Y | L102 | L430 | i6948 | Y | L102 | L431 |
| i6949 | Y | L103 | L428 | i6950 | Y | L103 | L429 | i6951 | Y | L103 | L430 | i6952 | Y | L103 | L431 |
| i6953 | Y | L104 | L428 | i6954 | Y | L104 | L429 | i6955 | Y | L104 | L430 | i6956 | Y | L104 | L431 |
| i6957 | Y | L105 | L428 | i6958 | Y | L105 | L429 | i6959 | Y | L105 | L430 | i6960 | Y | L105 | L431 |
| i6961 | Y | L106 | L428 | i6962 | Y | L106 | L429 | i6963 | Y | L106 | L430 | i6964 | Y | L106 | L431 |
| i6965 | Y | L107 | L428 | i6966 | Y | L107 | L429 | i6967 | Y | L107 | L430 | i6968 | Y | L107 | L431 |
| i6969 | Y | L108 | L428 | i6970 | Y | L108 | L429 | i6971 | Y | L108 | L430 | i6972 | Y | L108 | L431 |
| i6973 | Y | L109 | L428 | i6974 | Y | L109 | L429 | i6975 | Y | L109 | L430 | i6976 | Y | L109 | L431 |
| i6977 | Y | L110 | L428 | i6978 | Y | L110 | L429 | i6979 | Y | L110 | L430 | i6980 | Y | L110 | L431 |
| i6981 | Y | L111 | L428 | i6982 | Y | L111 | L429 | i6983 | Y | L111 | L430 | i6984 | Y | L111 | L431 |
| i6985 | Y | L112 | L428 | i6986 | Y | L112 | L429 | i6987 | Y | L112 | L430 | i6988 | Y | L112 | L431 |
| i6989 | Y | L113 | L428 | i6990 | Y | L113 | L429 | i6991 | Y | L113 | L430 | i6992 | Y | L113 | L431 |
| i6993 | Y | L114 | L428 | i6994 | Y | L114 | L429 | i6995 | Y | L114 | L430 | i6996 | Y | L114 | L431 |
| i6997 | Y | L115 | L428 | i6998 | Y | L115 | L429 | i6999 | Y | L115 | L430 | i7000 | Y | L115 | L431 |
| i7001 | Y | L116 | L428 | i7002 | Y | L116 | L429 | i7003 | Y | L116 | L430 | i7004 | Y | L116 | L431 |
| i7005 | Y | L117 | L428 | i7006 | Y | L117 | L429 | i7007 | Y | L117 | L430 | i7008 | Y | L117 | L431 |
| i7009 | Y | L118 | L428 | i7010 | Y | L118 | L429 | i7011 | Y | L118 | L430 | i7012 | Y | L118 | L431 |
| i7013 | Y | L119 | L428 | i7014 | Y | L119 | L429 | i7015 | Y | L119 | L430 | i7016 | Y | L119 | L431 |
| i7017 | Y | L120 | L428 | i7018 | Y | L120 | L429 | i7019 | Y | L120 | L430 | i7020 | Y | L120 | L431 |
| i7021 | Y | L121 | L428 | i7022 | Y | L121 | L429 | i7023 | Y | L121 | L430 | i7024 | Y | L121 | L431 |
| i7025 | Y | L122 | L428 | i7026 | Y | L122 | L429 | i7027 | Y | L122 | L430 | i7028 | Y | L122 | L431 |
| i7029 | Y | L123 | L428 | i7030 | Y | L123 | L429 | i7031 | Y | L123 | L430 | i7032 | Y | L123 | L431 |
| i7033 | Y | L124 | L428 | i7034 | Y | L124 | L429 | i7035 | Y | L124 | L430 | i7036 | Y | L124 | L431 |
| i7037 | Y | L125 | L428 | i7038 | Y | L125 | L429 | i7039 | Y | L125 | L430 | i7040 | Y | L125 | L431 |
| i7041 | Y | L126 | L428 | i7042 | Y | L126 | L429 | i7043 | Y | L126 | L430 | i7044 | Y | L126 | L431 |
| i7045 | Y | L127 | L428 | i7046 | Y | L127 | L429 | i7047 | Y | L127 | L430 | i7048 | Y | L127 | L431 |
| i7049 | Y | L128 | L428 | i7050 | Y | L128 | L429 | i7051 | Y | L128 | L430 | i7052 | Y | L128 | L431 |
| i7053 | Y | L129 | L428 | i7054 | Y | L129 | L429 | i7055 | Y | L129 | L430 | i7056 | Y | L129 | L431 |
| i7057 | Y | L130 | L428 | i7058 | Y | L130 | L429 | i7059 | Y | L130 | L430 | i7060 | Y | L130 | L431 |
| i7061 | Y | L131 | L428 | i7062 | Y | L131 | L429 | i7063 | Y | L131 | L430 | i7064 | Y | L131 | L431 |
| i7065 | Y | L132 | L428 | i7066 | Y | L132 | L429 | i7067 | Y | L132 | L430 | i7068 | Y | L132 | L431 |
| i7069 | Y | L133 | L428 | i7070 | Y | L133 | L429 | i7071 | Y | L133 | L430 | i7072 | Y | L133 | L431 |
| i7073 | Y | L134 | L428 | i7074 | Y | L134 | L429 | i7075 | Y | L134 | L430 | i7076 | Y | L134 | L431 |
| i7077 | Y | L135 | L428 | i7078 | Y | L135 | L429 | i7079 | Y | L135 | L430 | i7080 | Y | L135 | L431 |
| i7081 | Y | L136 | L428 | i7082 | Y | L136 | L429 | i7083 | Y | L136 | L430 | i7084 | Y | L136 | L431 |
| i7085 | Y | L137 | L428 | i7086 | Y | L137 | L429 | i7087 | Y | L137 | L430 | i7088 | Y | L137 | L431 |
| i7089 | Y | L138 | L428 | i7090 | Y | L138 | L429 | i7091 | Y | L138 | L430 | i7092 | Y | L138 | L431 |
| i7093 | Y | L139 | L428 | i7094 | Y | L139 | L429 | i7095 | Y | L139 | L430 | i7096 | Y | L139 | L431 |
| i7097 | Y | L140 | L428 | i7098 | Y | L140 | L429 | i7099 | Y | L140 | L430 | i7100 | Y | L140 | L431 |
| i7101 | Y | L141 | L428 | i7102 | Y | L141 | L429 | i7103 | Y | L141 | L430 | i7104 | Y | L141 | L431 |
| i7105 | Y | L142 | L428 | i7106 | Y | L142 | L429 | i7107 | Y | L142 | L430 | i7108 | Y | L142 | L431 |
| i7109 | Y | L143 | L428 | i7110 | Y | L143 | L429 | i7111 | Y | L143 | L430 | i7112 | Y | L143 | L431 |
| i7113 | Y | L144 | L428 | i7114 | Y | L144 | L429 | i7115 | Y | L144 | L430 | i7116 | Y | L144 | L431 |
| i7117 | Y | L145 | L428 | i7118 | Y | L145 | L429 | i7119 | Y | L145 | L430 | i7120 | Y | L145 | L431 |
| i7121 | Y | L146 | L428 | i7122 | Y | L146 | L429 | i7123 | Y | L146 | L430 | i7124 | Y | L146 | L431 |
| i7125 | Y | L147 | L428 | i7126 | Y | L147 | L429 | i7127 | Y | L147 | L430 | i7128 | Y | L147 | L431 |
| i7129 | Y | L148 | L428 | i7130 | Y | L148 | L429 | i7131 | Y | L148 | L430 | i7132 | Y | L148 | L431 |
| i7133 | Y | L149 | L428 | i7134 | Y | L149 | L429 | i7135 | Y | L149 | L430 | i7136 | Y | L149 | L431 |
| i7137 | Y | L150 | L428 | i7138 | Y | L150 | L429 | i7139 | Y | L150 | L430 | i7140 | Y | L150 | L431 |
| i7141 | Y | L151 | L428 | i7142 | Y | L151 | L429 | i7143 | Y | L151 | L430 | i7144 | Y | L151 | L431 |
| i7145 | Y | L152 | L428 | i7146 | Y | L152 | L429 | i7147 | Y | L152 | L430 | i7148 | Y | L152 | L431 |

TABLE 1-continued

Compositions "i1" to "i9919"

| | | | | | | | | | | | | | | |
|---|---|---|---|---|---|---|---|---|---|---|---|---|---|---|
| i7149 | Y | L153 | L428 | i7150 | Y | L153 | L429 | i7151 | Y | L153 | L430 | i7152 | Y | L153 L431 |
| i7153 | Y | L154 | L428 | i7154 | Y | L154 | L429 | i7155 | Y | L154 | L430 | i7156 | Y | L154 L431 |
| i7157 | Y | L155 | L428 | i7158 | Y | L155 | L429 | i7159 | Y | L155 | L430 | i7160 | Y | L155 L431 |
| i7161 | Y | L156 | L428 | i7162 | Y | L156 | L429 | i7163 | Y | L156 | L430 | i7164 | Y | L156 L431 |
| i7165 | Y | L157 | L428 | i7166 | Y | L157 | L429 | i7167 | Y | L157 | L430 | i7168 | Y | L157 L431 |
| i7169 | Y | L158 | L428 | i7170 | Y | L158 | L429 | i7171 | Y | L158 | L430 | i7172 | Y | L158 L431 |
| i7173 | Y | L159 | L428 | i7174 | Y | L159 | L429 | i7175 | Y | L159 | L430 | i7176 | Y | L159 L431 |
| i7177 | Y | L160 | L428 | i7178 | Y | L160 | L429 | i7179 | Y | L160 | L430 | i7180 | Y | L160 L431 |
| i7181 | Y | L161 | L428 | i7182 | Y | L161 | L429 | i7183 | Y | L161 | L430 | i7184 | Y | L161 L431 |
| i7185 | Y | L162 | L428 | i7186 | Y | L162 | L429 | i7187 | Y | L162 | L430 | i7188 | Y | L162 L431 |
| i7189 | Y | L163 | L428 | i7190 | Y | L163 | L429 | i7191 | Y | L163 | L430 | i7192 | Y | L163 L431 |
| i7193 | Y | L164 | L428 | i7194 | Y | L164 | L429 | i7195 | Y | L164 | L430 | i7196 | Y | L164 L431 |
| i7197 | Y | L165 | L428 | i7198 | Y | L165 | L429 | i7199 | Y | L165 | L430 | i7200 | Y | L165 L431 |
| i7201 | Y | L166 | L428 | i7202 | Y | L166 | L429 | i7203 | Y | L166 | L430 | i7204 | Y | L166 L431 |
| i7205 | Y | L167 | L428 | i7206 | Y | L167 | L429 | i7207 | Y | L167 | L430 | i7208 | Y | L167 L431 |
| i7209 | Y | L168 | L428 | i7210 | Y | L168 | L429 | i7211 | Y | L168 | L430 | i7212 | Y | L168 L431 |
| i7213 | Y | L169 | L428 | i7214 | Y | L169 | L429 | i7215 | Y | L169 | L430 | i7216 | Y | L169 L431 |
| i7217 | Y | L170 | L428 | i7218 | Y | L170 | L429 | i7219 | Y | L170 | L430 | i7220 | Y | L170 L431 |
| i7221 | Y | L171 | L428 | i7222 | Y | L171 | L429 | i7223 | Y | L171 | L430 | i7224 | Y | L171 L431 |
| i7225 | Y | L172 | L428 | i7226 | Y | L172 | L429 | i7227 | Y | L172 | L430 | i7228 | Y | L172 L431 |
| i7229 | Y | L173 | L428 | i7230 | Y | L173 | L429 | i7231 | Y | L173 | L430 | i7232 | Y | L173 L431 |
| i7233 | Y | L174 | L428 | i7234 | Y | L174 | L429 | i7235 | Y | L174 | L430 | i7236 | Y | L174 L431 |
| i7237 | Y | L175 | L428 | i7238 | Y | L175 | L429 | i7239 | Y | L175 | L430 | i7240 | Y | L175 L431 |
| i7241 | Y | L176 | L428 | i7242 | Y | L176 | L429 | i7243 | Y | L176 | L430 | i7244 | Y | L176 L431 |
| i7245 | Y | L177 | L428 | i7246 | Y | L177 | L429 | i7247 | Y | L177 | L430 | i7248 | Y | L177 L431 |
| i7249 | Y | L178 | L428 | i7250 | Y | L178 | L429 | i7251 | Y | L178 | L430 | i7252 | Y | L178 L431 |
| i7253 | Y | L179 | L428 | i7254 | Y | L179 | L429 | i7255 | Y | L179 | L430 | i7256 | Y | L179 L431 |
| i7257 | Y | L180 | L428 | i7258 | Y | L180 | L429 | i7259 | Y | L180 | L430 | i7260 | Y | L180 L431 |
| i7261 | Y | L181 | L428 | i7262 | Y | L181 | L429 | i7263 | Y | L181 | L430 | i7264 | Y | L181 L431 |
| i7265 | Y | L182 | L428 | i7266 | Y | L182 | L429 | i7267 | Y | L182 | L430 | i7268 | Y | L182 L431 |
| i7269 | Y | L183 | L428 | i7270 | Y | L183 | L429 | i7271 | Y | L183 | L430 | i7272 | Y | L183 L431 |
| i7273 | Y | L184 | L428 | i7274 | Y | L184 | L429 | i7275 | Y | L184 | L430 | i7276 | Y | L184 L431 |
| i7277 | Y | L185 | L428 | i7278 | Y | L185 | L429 | i7279 | Y | L185 | L430 | i7280 | Y | L185 L431 |
| i7281 | Y | L186 | L428 | i7282 | Y | L186 | L429 | i7283 | Y | L186 | L430 | i7284 | Y | L186 L431 |
| i7285 | Y | L187 | L428 | i7286 | Y | L187 | L429 | i7287 | Y | L187 | L430 | i7288 | Y | L187 L431 |
| i7289 | Y | L188 | L428 | i7290 | Y | L188 | L429 | i7291 | Y | L188 | L430 | i7292 | Y | L188 L431 |
| i7293 | Y | L189 | L428 | i7294 | Y | L189 | L429 | i7295 | Y | L189 | L430 | i7296 | Y | L189 L431 |
| i7297 | Y | L190 | L428 | i7298 | Y | L190 | L429 | i7299 | Y | L190 | L430 | i7300 | Y | L190 L431 |
| i7301 | Y | L191 | L428 | i7302 | Y | L191 | L429 | i7303 | Y | L191 | L430 | i7304 | Y | L191 L431 |
| i7305 | Y | L192 | L428 | i7306 | Y | L192 | L429 | i7307 | Y | L192 | L430 | i7308 | Y | L192 L431 |
| i7309 | Y | L193 | L428 | i7310 | Y | L193 | L429 | i7311 | Y | L193 | L430 | i7312 | Y | L193 L431 |
| i7313 | Y | L194 | L428 | i7314 | Y | L194 | L429 | i7315 | Y | L194 | L430 | i7316 | Y | L194 L431 |
| i7317 | Y | L195 | L428 | i7318 | Y | L195 | L429 | i7319 | Y | L195 | L430 | i7320 | Y | L195 L431 |
| i7321 | Y | L196 | L428 | i7322 | Y | L196 | L429 | i7323 | Y | L196 | L430 | i7324 | Y | L196 L431 |
| i7325 | Y | L197 | L428 | i7326 | Y | L197 | L429 | i7327 | Y | L197 | L430 | i7328 | Y | L197 L431 |
| i7329 | Y | L198 | L428 | i7330 | Y | L198 | L429 | i7331 | Y | L198 | L430 | i7332 | Y | L198 L431 |
| i7333 | Y | L199 | L428 | i7334 | Y | L199 | L429 | i7335 | Y | L199 | L430 | i7336 | Y | L199 L431 |
| i7337 | Y | L200 | L428 | i7338 | Y | L200 | L429 | i7339 | Y | L200 | L430 | i7340 | Y | L200 L431 |
| i7341 | Y | L201 | L428 | i7342 | Y | L201 | L429 | i7343 | Y | L201 | L430 | i7344 | Y | L201 L431 |
| i7345 | Y | L202 | L428 | i7346 | Y | L202 | L429 | i7347 | Y | L202 | L430 | i7348 | Y | L202 L431 |
| i7349 | Y | L203 | L428 | i7350 | Y | L203 | L429 | i7351 | Y | L203 | L430 | i7352 | Y | L203 L431 |
| i7353 | Y | L204 | L428 | i7354 | Y | L204 | L429 | i7355 | Y | L204 | L430 | i7356 | Y | L204 L431 |
| i7357 | Y | L205 | L428 | i7358 | Y | L205 | L429 | i7359 | Y | L205 | L430 | i7360 | Y | L205 L431 |
| i7361 | Y | L206 | L428 | i7362 | Y | L206 | L429 | i7363 | Y | L206 | L430 | i7364 | Y | L206 L431 |
| i7365 | Y | L207 | L428 | i7366 | Y | L207 | L429 | i7367 | Y | L207 | L430 | i7368 | Y | L207 L431 |
| i7369 | Y | L208 | L428 | i7370 | Y | L208 | L429 | i7371 | Y | L208 | L430 | i7372 | Y | L208 L431 |
| i7373 | Y | L209 | L428 | i7374 | Y | L209 | L429 | i7375 | Y | L209 | L430 | i7376 | Y | L209 L431 |
| i7377 | Y | L210 | L428 | i7378 | Y | L210 | L429 | i7379 | Y | L210 | L430 | i7380 | Y | L210 L431 |
| i7381 | Y | L211 | L428 | i7382 | Y | L211 | L429 | i7383 | Y | L211 | L430 | i7384 | Y | L211 L431 |
| i7385 | Y | L212 | L428 | i7386 | Y | L212 | L429 | i7387 | Y | L212 | L430 | i7388 | Y | L212 L431 |
| i7389 | Y | L213 | L428 | i7390 | Y | L213 | L429 | i7391 | Y | L213 | L430 | i7392 | Y | L213 L431 |
| i7393 | Y | L214 | L428 | i7394 | Y | L214 | L429 | i7395 | Y | L214 | L430 | i7396 | Y | L214 L431 |
| i7397 | Y | L215 | L428 | i7398 | Y | L215 | L429 | i7399 | Y | L215 | L430 | i7400 | Y | L215 L431 |
| i7401 | Y | L216 | L428 | i7402 | Y | L216 | L429 | i7403 | Y | L216 | L430 | i7404 | Y | L216 L431 |
| i7405 | Y | L217 | L428 | i7406 | Y | L217 | L429 | i7407 | Y | L217 | L430 | i7408 | Y | L217 L431 |
| i7409 | Y | L218 | L428 | i7410 | Y | L218 | L429 | i7411 | Y | L218 | L430 | i7412 | Y | L218 L431 |
| i7413 | Y | L219 | L428 | i7414 | Y | L219 | L429 | i7415 | Y | L219 | L430 | i7416 | Y | L219 L431 |
| i7417 | Y | L220 | L428 | i7418 | Y | L220 | L429 | i7419 | Y | L220 | L430 | i7420 | Y | L220 L431 |
| i7421 | Y | L221 | L428 | i7422 | Y | L221 | L429 | i7423 | Y | L221 | L430 | i7424 | Y | L221 L431 |
| i7425 | Y | L222 | L428 | i7426 | Y | L222 | L429 | i7427 | Y | L222 | L430 | i7428 | Y | L222 L431 |
| i7429 | Y | L401 | L428 | i7430 | Y | L401 | L429 | i7431 | Y | L401 | L430 | i7432 | Y | L401 L431 |
| i7433 | Y | L402 | L428 | i7434 | Y | L402 | L429 | i7435 | Y | L402 | L430 | i7436 | Y | L402 L431 |
| i7437 | Y | L403 | L428 | i7438 | Y | L403 | L429 | i7439 | Y | L403 | L430 | i7440 | Y | L403 L431 |
| i7441 | Y | L404 | L428 | i7442 | Y | L404 | L429 | i7443 | Y | L404 | L430 | i7444 | Y | L404 L431 |
| i7445 | Y | L405 | L428 | i7446 | Y | L405 | L429 | i7447 | Y | L405 | L430 | i7448 | Y | L405 L431 |
| i7449 | Y | L406 | L428 | i7450 | Y | L406 | L429 | i7451 | Y | L406 | L430 | i7452 | Y | L406 L431 |
| i7453 | Y | L407 | L428 | i7454 | Y | L407 | L429 | i7455 | Y | L407 | L430 | i7456 | Y | L407 L431 |
| i7457 | Y | L408 | L428 | i7458 | Y | L408 | L429 | i7459 | Y | L408 | L430 | i7460 | Y | L408 L431 |

TABLE 1-continued

Compositions "i1" to "i9919"

| | | | | | | | | | | | | | | |
|---|---|---|---|---|---|---|---|---|---|---|---|---|---|---|
| i7461 | Y | L409 | L428 | i7462 | Y | L409 | L429 | i7463 | Y | L409 | L430 | i7464 | Y | L409 | L431 |
| i7465 | Y | L410 | L428 | i7466 | Y | L410 | L429 | i7467 | Y | L410 | L430 | i7468 | Y | L410 | L431 |
| i7469 | Y | L411 | L428 | i7470 | Y | L411 | L429 | i7471 | Y | L411 | L430 | i7472 | Y | L411 | L431 |
| i7473 | Y | L412 | L428 | i7474 | Y | L412 | L429 | i7475 | Y | L412 | L430 | i7476 | Y | L412 | L431 |
| i7477 | Y | L413 | L428 | i7478 | Y | L413 | L429 | i7479 | Y | L413 | L430 | i7480 | Y | L413 | L431 |
| i7481 | Y | L414 | L428 | i7482 | Y | L414 | L429 | i7483 | Y | L414 | L430 | i7484 | Y | L414 | L431 |
| i7485 | Y | L415 | L428 | i7486 | Y | L415 | L429 | i7487 | Y | L415 | L430 | i7488 | Y | L415 | L431 |
| i7489 | Y | L416 | L428 | i7490 | Y | L416 | L429 | i7491 | Y | L416 | L430 | i7492 | Y | L416 | L431 |
| i7493 | Y | L417 | L428 | i7494 | Y | L417 | L429 | i7495 | Y | L417 | L430 | i7496 | Y | L417 | L431 |
| i7497 | Y | L418 | L428 | i7498 | Y | L418 | L429 | i7499 | Y | L418 | L430 | i7500 | Y | L418 | L431 |
| i7501 | Y | L419 | L428 | i7502 | Y | L419 | L429 | i7503 | Y | L419 | L430 | i7504 | Y | L419 | L431 |
| i7505 | Y | L420 | L428 | i7506 | Y | L420 | L429 | i7507 | Y | L420 | L430 | i7508 | Y | L420 | L431 |
| i7509 | Y | L421 | L428 | i7510 | Y | L421 | L429 | i7511 | Y | L421 | L430 | i7512 | Y | L421 | L431 |
| i7513 | Y | L422 | L428 | i7514 | Y | L422 | L429 | i7515 | Y | L422 | L430 | i7516 | Y | L422 | L431 |
| i7517 | Y | L423 | L428 | i7518 | Y | L423 | L429 | i7519 | Y | L423 | L430 | i7520 | Y | L423 | L431 |
| i7521 | Y | L424 | L428 | i7522 | Y | L424 | L429 | i7523 | Y | L424 | L430 | i7524 | Y | L424 | L431 |
| i7525 | Y | L425 | L428 | i7526 | Y | L425 | L429 | i7527 | Y | L425 | L430 | i7528 | Y | L425 | L431 |
| i7529 | Y | L501 | L428 | i7530 | Y | L501 | L429 | i7531 | Y | L501 | L430 | i7532 | Y | L501 | L431 |
| i7533 | Y | L502 | L428 | i7534 | Y | L502 | L429 | i7535 | Y | L502 | L430 | i7536 | Y | L502 | L431 |
| i7537 | Y | L503 | L428 | i7538 | Y | L503 | L429 | i7539 | Y | L503 | L430 | i7540 | Y | L503 | L431 |
| i7541 | Y | L504 | L428 | i7542 | Y | L504 | L429 | i7543 | Y | L504 | L430 | i7544 | Y | L504 | L431 |
| i7545 | Y | L505 | L428 | i7546 | Y | L505 | L429 | i7547 | Y | L505 | L430 | i7548 | Y | L505 | L431 |
| i7549 | Y | L506 | L428 | i7550 | Y | L506 | L429 | i7551 | Y | L506 | L430 | i7552 | Y | L506 | L431 |
| i7553 | Y | L507 | L428 | i7554 | Y | L507 | L429 | i7555 | Y | L507 | L430 | i7556 | Y | L507 | L431 |
| i7557 | Y | L508 | L428 | i7558 | Y | L508 | L429 | i7559 | Y | L508 | L430 | i7560 | Y | L508 | L431 |
| i7561 | Y | L509 | L428 | i7562 | Y | L509 | L429 | i7563 | Y | L509 | L430 | i7564 | Y | L509 | L431 |
| i7565 | Y | L510 | L428 | i7566 | Y | L510 | L429 | i7567 | Y | L510 | L430 | i7568 | Y | L510 | L431 |
| i7569 | Y | L511 | L428 | i7570 | Y | L511 | L429 | i7571 | Y | L511 | L430 | i7572 | Y | L511 | L431 |
| i7573 | Y | L512 | L428 | i7574 | Y | L512 | L429 | i7575 | Y | L512 | L430 | i7576 | Y | L512 | L431 |
| i7577 | Y | L513 | L428 | i7578 | Y | L513 | L429 | i7579 | Y | L513 | L430 | i7580 | Y | L513 | L431 |
| i7581 | Y | L514 | L428 | i7582 | Y | L514 | L429 | i7583 | Y | L514 | L430 | i7584 | Y | L514 | L431 |
| i7585 | Y | L515 | L428 | i7586 | Y | L515 | L429 | i7587 | Y | L515 | L430 | i7588 | Y | L515 | L431 |
| i7589 | Y | L516 | L428 | i7590 | Y | L516 | L429 | i7591 | Y | L516 | L430 | i7592 | Y | L516 | L431 |
| i7593 | Y | L517 | L428 | i7594 | Y | L517 | L429 | i7595 | Y | L517 | L430 | i7596 | Y | L517 | L431 |
| i7597 | Y | L518 | L428 | i7598 | Y | L518 | L429 | i7599 | Y | L518 | L430 | i7600 | Y | L518 | L431 |
| i7601 | Y | L519 | L428 | i7602 | Y | L519 | L429 | i7603 | Y | L519 | L430 | i7604 | Y | L519 | L431 |
| i7605 | Y | L520 | L428 | i7606 | Y | L520 | L429 | i7607 | Y | L520 | L430 | i7608 | Y | L520 | L431 |
| i7609 | Y | L521 | L428 | i7610 | Y | L521 | L429 | i7611 | Y | L521 | L430 | i7612 | Y | L521 | L431 |
| i7613 | Y | L522 | L428 | i7614 | Y | L522 | L429 | i7615 | Y | L522 | L430 | i7616 | Y | L522 | L431 |
| i7617 | Y | L523 | L428 | i7618 | Y | L523 | L429 | i7619 | Y | L523 | L430 | i7620 | Y | L523 | L431 |
| i7621 | Y | L524 | L428 | i7622 | Y | L524 | L429 | i7623 | Y | L524 | L430 | i7624 | Y | L524 | L431 |
| i7625 | Y | L525 | L428 | i7626 | Y | L525 | L429 | i7627 | Y | L525 | L430 | i7628 | Y | L525 | L431 |
| i7629 | Y | L526 | L428 | i7630 | Y | L526 | L429 | i7631 | Y | L526 | L430 | i7632 | Y | L526 | L431 |
| i7633 | Y | L527 | L428 | i7634 | Y | L527 | L429 | i7635 | Y | L527 | L430 | i7636 | Y | L527 | L431 |
| i7637 | Y | L528 | L428 | i7638 | Y | L528 | L429 | i7639 | Y | L528 | L430 | i7640 | Y | L528 | L431 |
| i7641 | Y | L529 | L428 | i7642 | Y | L529 | L429 | i7643 | Y | L529 | L430 | i7644 | Y | L529 | L431 |
| i7645 | Y | L530 | L428 | i7646 | Y | L530 | L429 | i7647 | Y | L530 | L430 | i7648 | Y | L530 | L431 |
| i7649 | Y | L531 | L428 | i7650 | Y | L531 | L429 | i7651 | Y | L531 | L430 | i7652 | Y | L531 | L431 |
| i7653 | Y | L532 | L428 | i7654 | Y | L532 | L429 | i7655 | Y | L532 | L430 | i7656 | Y | L532 | L431 |
| i7657 | Y | L533 | L428 | i7658 | Y | L533 | L429 | i7659 | Y | L533 | L430 | i7660 | Y | L533 | L431 |
| i7661 | Y | L534 | L428 | i7662 | Y | L534 | L429 | i7663 | Y | L534 | L430 | i7664 | Y | L534 | L431 |
| i7665 | Y | L535 | L428 | i7666 | Y | L535 | L429 | i7667 | Y | L535 | L430 | i7668 | Y | L535 | L431 |
| i7669 | Y | L536 | L428 | i7670 | Y | L536 | L429 | i7671 | Y | L536 | L430 | i7672 | Y | L536 | L431 |
| i7673 | Y | L537 | L428 | i7674 | Y | L537 | L429 | i7675 | Y | L537 | L430 | i7676 | Y | L537 | L431 |
| i7677 | Y | L538 | L428 | i7678 | Y | L538 | L429 | i7679 | Y | L538 | L430 | i7680 | Y | L538 | L431 |
| i7681 | Y | L539 | L428 | i7682 | Y | L539 | L429 | i7683 | Y | L539 | L430 | i7684 | Y | L539 | L431 |
| i7685 | Y | L540 | L428 | i7686 | Y | L540 | L429 | i7687 | Y | L540 | L430 | i7688 | Y | L540 | L431 |
| i7689 | Y | L541 | L428 | i7690 | Y | L541 | L429 | i7691 | Y | L541 | L430 | i7692 | Y | L541 | L431 |
| i7693 | Y | L542 | L428 | i7694 | Y | L542 | L429 | i7695 | Y | L542 | L430 | i7696 | Y | L542 | L431 |
| i7697 | Y | L543 | L428 | i7698 | Y | L543 | L429 | i7699 | Y | L543 | L430 | i7700 | Y | L543 | L431 |
| i7701 | Y | L544 | L428 | i7702 | Y | L544 | L429 | i7703 | Y | L544 | L430 | i7704 | Y | L544 | L431 |
| i7705 | Y | L545 | L428 | i7706 | Y | L545 | L429 | i7707 | Y | L545 | L430 | i7708 | Y | L545 | L431 |
| i7709 | Y | L546 | L428 | i7710 | Y | L546 | L429 | i7711 | Y | L546 | L430 | i7712 | Y | L546 | L431 |
| i7713 | Y | L547 | L428 | i7714 | Y | L547 | L429 | i7715 | Y | L547 | L430 | i7716 | Y | L547 | L431 |
| i7717 | Y | L548 | L428 | i7718 | Y | L548 | L429 | i7719 | Y | L548 | L430 | i7720 | Y | L548 | L431 |
| i7721 | Y | L549 | L428 | i7722 | Y | L549 | L429 | i7723 | Y | L549 | L430 | i7724 | Y | L549 | L431 |
| i7725 | Y | L550 | L428 | i7726 | Y | L550 | L429 | i7727 | Y | L550 | L430 | i7728 | Y | L550 | L431 |
| i7729 | Y | L551 | L428 | i7730 | Y | L551 | L429 | i7731 | Y | L551 | L430 | i7732 | Y | L551 | L431 |
| i7733 | Y | L552 | L428 | i7734 | Y | L552 | L429 | i7735 | Y | L552 | L430 | i7736 | Y | L552 | L431 |
| i7737 | Y | L553 | L428 | i7738 | Y | L553 | L429 | i7739 | Y | L553 | L430 | i7740 | Y | L553 | L431 |
| i7741 | Y | L554 | L428 | i7742 | Y | L554 | L429 | i7743 | Y | L554 | L430 | i7744 | Y | L554 | L431 |
| i7745 | Y | L555 | L428 | i7746 | Y | L555 | L429 | i7747 | Y | L555 | L430 | i7748 | Y | L555 | L431 |
| i7749 | Y | L556 | L428 | i7750 | Y | L556 | L429 | i7751 | Y | L556 | L430 | i7752 | Y | L556 | L431 |
| i7753 | Y | L557 | L428 | i7754 | Y | L557 | L429 | i7755 | Y | L557 | L430 | i7756 | Y | L557 | L431 |
| i7757 | Y | L558 | L428 | i7758 | Y | L558 | L429 | i7759 | Y | L558 | L430 | i7760 | Y | L558 | L431 |
| i7761 | Y | L559 | L428 | i7762 | Y | L559 | L429 | i7763 | Y | L559 | L430 | i7764 | Y | L559 | L431 |
| i7765 | Y | L560 | L428 | i7766 | Y | L560 | L429 | i7767 | Y | L560 | L430 | i7768 | Y | L560 | L431 |
| i7769 | Y | L561 | L428 | i7770 | Y | L561 | L429 | i7771 | Y | L561 | L430 | i7772 | Y | L561 | L431 |

TABLE 1-continued

Compositions "i1" to "i9919"

| i# | A | (L)i | (L)ii | i# | A | (L)i | (L)ii | i# | A | (L)i | (L)ii | i# | A | (L)i | (L)ii |
|---|---|---|---|---|---|---|---|---|---|---|---|---|---|---|---|
| i7773 | Y | L562 | L428 | i7774 | Y | L562 | L429 | i7775 | Y | L562 | L430 | i7776 | Y | L562 | L431 |
| i7777 | Y | L563 | L428 | i7778 | Y | L563 | L429 | i7779 | Y | L563 | L430 | i7780 | Y | L563 | L431 |
| i7781 | Y | L564 | L428 | i7782 | Y | L564 | L429 | i7783 | Y | L564 | L430 | i7784 | Y | L564 | L431 |
| i7785 | Y | L565 | L428 | i7786 | Y | L565 | L429 | i7787 | Y | L565 | L430 | i7788 | Y | L565 | L431 |
| i7789 | Y | L566 | L428 | i7790 | Y | L566 | L429 | i7791 | Y | L566 | L430 | i7792 | Y | L566 | L431 |
| i7793 | Y | L567 | L428 | i7794 | Y | L567 | L429 | i7795 | Y | L567 | L430 | i7796 | Y | L567 | L431 |
| i7797 | Y | L568 | L428 | i7798 | Y | L568 | L429 | i7799 | Y | L568 | L430 | i7800 | Y | L568 | L431 |
| i7801 | Y | L569 | L428 | i7802 | Y | L569 | L429 | i7803 | Y | L569 | L430 | i7804 | Y | L569 | L431 |
| i7805 | Y | L570 | L428 | i7806 | Y | L570 | L429 | i7807 | Y | L570 | L430 | i7808 | Y | L570 | L431 |
| i7809 | Y | L571 | L428 | i7810 | Y | L571 | L429 | i7811 | Y | L571 | L430 | i7812 | Y | L571 | L431 |
| i7813 | Y | L572 | L428 | i7814 | Y | L572 | L429 | i7815 | Y | L572 | L430 | i7816 | Y | L572 | L431 |
| i7817 | Y | L843 | L428 | i7818 | Y | L843 | L429 | i7819 | Y | L843 | L430 | i7820 | Y | L843 | L431 |
| i7821 | Y | L844 | L428 | i7822 | Y | L844 | L429 | i7823 | Y | L844 | L430 | i7824 | Y | L844 | L431 |
| i7825 | Y | L845 | L428 | i7826 | Y | L845 | L429 | i7827 | Y | L845 | L430 | i7828 | Y | L845 | L431 |
| i7829 | Y | L846 | L428 | i7830 | Y | L846 | L429 | i7831 | Y | L846 | L430 | i7832 | Y | L846 | L431 |
| i7833 | Y | L847 | L428 | i7834 | Y | L847 | L429 | i7835 | Y | L847 | L430 | i7836 | Y | L847 | L431 |
| i7837 | Y | L848 | L428 | i7838 | Y | L848 | L429 | i7839 | Y | L848 | L430 | i7840 | Y | L848 | L431 |

| i# | A | (L)i | (L)ii | (L)iii | i# | A | (L)i | (L)ii | (L)iii | i# | A | (L)i | (L)ii | (L)iii |
|---|---|---|---|---|---|---|---|---|---|---|---|---|---|---|
| i7841 | Y | L10 | L12 | — | i7842 | Y | L10 | L13 | — | i7843 | Y | L10 | L14 | — |
| i7844 | Y | L11 | L12 | — | i7845 | Y | L11 | L13 | — | i7846 | Y | L11 | L14 | — |
| i7847 | Y | L20 | L12 | — | i7848 | Y | L20 | L13 | — | i7849 | Y | L20 | L14 | — |
| i7850 | Y | L21 | L12 | — | i7851 | Y | L21 | L13 | — | i7852 | Y | L21 | L14 | — |
| i7853 | Y | L22 | L12 | — | i7854 | Y | L22 | L13 | — | i7855 | Y | L22 | L14 | — |
| i7856 | Y | L23 | L12 | — | i7857 | Y | L23 | L13 | — | i7858 | Y | L23 | L14 | — |
| i7859 | Y | L24 | L12 | — | i7860 | Y | L24 | L13 | — | i7861 | Y | L24 | L14 | — |
| i7862 | Y | L25 | L12 | — | i7863 | Y | L25 | L13 | — | i7864 | Y | L25 | L14 | — |
| i7865 | Y | L26 | L12 | — | i7866 | Y | L26 | L13 | — | i7867 | Y | L26 | L14 | — |
| i7868 | Y | L27 | L12 | — | i7869 | Y | L27 | L13 | — | i7870 | Y | L27 | L14 | — |
| i7871 | Y | L28 | L12 | — | i7872 | Y | L28 | L13 | — | i7873 | Y | L28 | L14 | — |
| i7874 | Y | L179 | L12 | — | i7875 | Y | L179 | L13 | — | i7876 | Y | L179 | L14 | — |
| i7877 | Y | L180 | L12 | — | i7878 | Y | L180 | L13 | — | i7879 | Y | L180 | L14 | — |
| i7880 | Y | L196 | L12 | — | i7881 | Y | L196 | L13 | — | i7882 | Y | L196 | L14 | — |
| i7883 | Y | L201 | L12 | — | i7884 | Y | L201 | L13 | — | i7885 | Y | L201 | L14 | — |
| i7886 | Y | L206 | L12 | — | i7887 | Y | L206 | L13 | — | i7888 | Y | L206 | L14 | — |
| i7889 | Y | L211 | L12 | — | i7890 | Y | L211 | L13 | — | i7891 | Y | L211 | L14 | — |
| i7892 | Y | L212 | L12 | — | i7893 | Y | L212 | L13 | — | i7894 | Y | L212 | L14 | — |
| i7895 | Y | L215 | L12 | — | i7896 | Y | L215 | L13 | — | i7897 | Y | L215 | L14 | — |
| i7898 | Y | L217 | L12 | — | i7899 | Y | L217 | L13 | — | i7900 | Y | L217 | L14 | — |
| i7901 | Y | L220 | L12 | — | i7902 | Y | L220 | L13 | — | i7903 | Y | L220 | L14 | — |
| i7904 | Y | L10 | L15 | — | i7905 | Y | L10 | L16 | — | i7906 | Y | L10 | L17 | — |
| i7907 | Y | L11 | L15 | — | i7908 | Y | L11 | L16 | — | i7909 | Y | L11 | L17 | — |
| i7910 | Y | L20 | L15 | — | i7911 | Y | L20 | L16 | — | i7912 | Y | L20 | L17 | — |
| i7913 | Y | L21 | L15 | — | i7914 | Y | L21 | L16 | — | i7915 | Y | L21 | L17 | — |
| i7916 | Y | L22 | L15 | — | i7917 | Y | L22 | L16 | — | i7918 | Y | L22 | L17 | — |
| i7919 | Y | L23 | L15 | — | i7920 | Y | L23 | L16 | — | i7921 | Y | L23 | L17 | — |
| i7922 | Y | L24 | L15 | — | i7923 | Y | L24 | L16 | — | i7924 | Y | L24 | L17 | — |
| i7925 | Y | L25 | L15 | — | i7926 | Y | L25 | L16 | — | i7927 | Y | L25 | L17 | — |
| i7928 | Y | L26 | L15 | — | i7929 | Y | L26 | L16 | — | i7930 | Y | L26 | L17 | — |
| i7931 | Y | L27 | L15 | — | i7932 | Y | L27 | L16 | — | i7933 | Y | L27 | L17 | — |
| i7934 | Y | L28 | L15 | — | i7935 | Y | L28 | L16 | — | i7936 | Y | L28 | L17 | — |
| i7937 | Y | L179 | L15 | — | i7938 | Y | L179 | L16 | — | i7939 | Y | L179 | L17 | — |
| i7940 | Y | L180 | L15 | — | i7941 | Y | L180 | L16 | — | i7942 | Y | L180 | L17 | — |
| i7943 | Y | L196 | L15 | — | i7944 | Y | L196 | L16 | — | i7945 | Y | L196 | L17 | — |
| i7946 | Y | L201 | L15 | — | i7947 | Y | L201 | L16 | — | i7948 | Y | L201 | L17 | — |
| i7949 | Y | L206 | L15 | — | i7950 | Y | L206 | L16 | — | i7951 | Y | L206 | L17 | — |
| i7952 | Y | L211 | L15 | — | i7953 | Y | L211 | L16 | — | i7954 | Y | L211 | L17 | — |
| i7955 | Y | L212 | L15 | — | i7956 | Y | L212 | L16 | — | i7957 | Y | L212 | L17 | — |
| i7958 | Y | L215 | L15 | — | i7959 | Y | L215 | L16 | — | i7960 | Y | L215 | L17 | — |
| i7961 | Y | L217 | L15 | — | i7962 | Y | L217 | L16 | — | i7963 | Y | L217 | L17 | — |
| i7964 | Y | L220 | L15 | — | i7965 | Y | L220 | L16 | — | i7966 | Y | L220 | L17 | — |
| i7967 | Y | L10 | L18 | — | i7968 | Y | L10 | L19 | — | i7969 | Y | L10 | L569 | — |
| i7970 | Y | L11 | L18 | — | i7971 | Y | L11 | L19 | — | i7972 | Y | L11 | L569 | — |
| i7973 | Y | L20 | L18 | — | i7974 | Y | L20 | L19 | — | i7975 | Y | L20 | L569 | — |
| i7976 | Y | L21 | L18 | — | i7977 | Y | L21 | L19 | — | i7978 | Y | L21 | L569 | — |
| i7979 | Y | L22 | L18 | — | i7980 | Y | L22 | L19 | — | i7981 | Y | L22 | L569 | — |
| i7982 | Y | L23 | L18 | — | i7983 | Y | L23 | L19 | — | i7984 | Y | L23 | L569 | — |
| i7985 | Y | L24 | L18 | — | i7986 | Y | L24 | L19 | — | i7987 | Y | L24 | L569 | — |
| i7988 | Y | L25 | L18 | — | i7989 | Y | L25 | L19 | — | i7990 | Y | L25 | L569 | — |
| i7991 | Y | L26 | L18 | — | i7992 | Y | L26 | L19 | — | i7993 | Y | L26 | L569 | — |
| i7994 | Y | L27 | L18 | — | i7995 | Y | L27 | L19 | — | i7996 | Y | L27 | L569 | — |
| i7997 | Y | L28 | L18 | — | i7998 | Y | L28 | L19 | — | i7999 | Y | L28 | L569 | — |
| i8000 | Y | L179 | L18 | — | i8001 | Y | L179 | L19 | — | i8002 | Y | L179 | L569 | — |
| i8003 | Y | L180 | L18 | — | i8004 | Y | L180 | L19 | — | i8005 | Y | L180 | L569 | — |
| i8006 | Y | L196 | L18 | — | i8007 | Y | L196 | L19 | — | i8008 | Y | L196 | L569 | — |
| i8009 | Y | L201 | L18 | — | i8010 | Y | L201 | L19 | — | i8011 | Y | L201 | L569 | — |
| i8012 | Y | L206 | L18 | — | i8013 | Y | L206 | L19 | — | i8014 | Y | L206 | L569 | — |

TABLE 1-continued

Compositions "i1" to "i9919"

| | | | | | | | | | | | | |
|---|---|---|---|---|---|---|---|---|---|---|---|---|
| i8015 | Y | L211 | L18 | — | i8016 | Y | L211 | L19 | — | i8017 | Y | L211 | L569 | — |
| i8018 | Y | L212 | L18 | — | i8019 | Y | L212 | L19 | — | i8020 | Y | L212 | L569 | — |
| i8021 | Y | L215 | L18 | — | i8022 | Y | L215 | L19 | — | i8023 | Y | L215 | L569 | — |
| i8024 | Y | L217 | L18 | — | i8025 | Y | L217 | L19 | — | i8026 | Y | L217 | L569 | — |
| i8027 | Y | L220 | L18 | — | i8028 | Y | L220 | L19 | — | i8029 | Y | L220 | L569 | — |
| i8030 | Y | L10 | L12 | L422 | i8031 | Y | L10 | L13 | L422 | i8032 | Y | L10 | L14 | L422 |
| i8033 | Y | L11 | L12 | L422 | i8034 | Y | L11 | L13 | L422 | i8035 | Y | L11 | L14 | L422 |
| i8036 | Y | L20 | L12 | L422 | i8037 | Y | L20 | L13 | L422 | i8038 | Y | L20 | L14 | L422 |
| i8039 | Y | L21 | L12 | L422 | i8040 | Y | L21 | L13 | L422 | i8041 | Y | L21 | L14 | L422 |
| i8042 | Y | L22 | L12 | L422 | i8043 | Y | L22 | L13 | L422 | i8044 | Y | L22 | L14 | L422 |
| i8045 | Y | L23 | L12 | L422 | i8046 | Y | L23 | L13 | L422 | i8047 | Y | L23 | L14 | L422 |
| i8048 | Y | L24 | L12 | L422 | i8049 | Y | L24 | L13 | L422 | i8050 | Y | L24 | L14 | L422 |
| i8051 | Y | L25 | L12 | L422 | i8052 | Y | L25 | L13 | L422 | i8053 | Y | L25 | L14 | L422 |
| i8054 | Y | L26 | L12 | L422 | i8055 | Y | L26 | L13 | L422 | i8056 | Y | L26 | L14 | L422 |
| i8057 | Y | L27 | L12 | L422 | i8058 | Y | L27 | L13 | L422 | i8059 | Y | L27 | L14 | L422 |
| i8060 | Y | L28 | L12 | L422 | i8061 | Y | L28 | L13 | L422 | i8062 | Y | L28 | L14 | L422 |
| i8063 | Y | L179 | L12 | L422 | i8064 | Y | L179 | L13 | L422 | i8065 | Y | L179 | L14 | L422 |
| i8066 | Y | L180 | L12 | L422 | i8067 | Y | L180 | L13 | L422 | i8068 | Y | L180 | L14 | L422 |
| i8069 | Y | L196 | L12 | L422 | i8070 | Y | L196 | L13 | L422 | i8071 | Y | L196 | L14 | L422 |
| i8072 | Y | L201 | L12 | L422 | i8073 | Y | L201 | L13 | L422 | i8074 | Y | L201 | L14 | L422 |
| i8075 | Y | L206 | L12 | L422 | i8076 | Y | L206 | L13 | L422 | i8077 | Y | L206 | L14 | L422 |
| i8078 | Y | L211 | L12 | L422 | i8079 | Y | L211 | L13 | L422 | i8080 | Y | L211 | L14 | L422 |
| i8081 | Y | L212 | L12 | L422 | i8082 | Y | L212 | L13 | L422 | i8083 | Y | L212 | L14 | L422 |
| i8084 | Y | L215 | L12 | L422 | i8085 | Y | L215 | L13 | L422 | i8086 | Y | L215 | L14 | L422 |
| i8087 | Y | L217 | L12 | L422 | i8088 | Y | L217 | L13 | L422 | i8089 | Y | L217 | L14 | L422 |
| i8090 | Y | L220 | L12 | L422 | i8091 | Y | L220 | L13 | L422 | i8092 | Y | L220 | L14 | L422 |
| i8093 | Y | L10 | L15 | L422 | i8094 | Y | L10 | L16 | L422 | i8095 | Y | L10 | L17 | L422 |
| i8096 | Y | L11 | L15 | L422 | i8097 | Y | L11 | L16 | L422 | i8098 | Y | L11 | L17 | L422 |
| i8099 | Y | L20 | L15 | L422 | i8100 | Y | L20 | L16 | L422 | i8101 | Y | L20 | L17 | L422 |
| i8102 | Y | L21 | L15 | L422 | i8103 | Y | L21 | L16 | L422 | i8104 | Y | L21 | L17 | L422 |
| i8105 | Y | L22 | L15 | L422 | i8106 | Y | L22 | L16 | L422 | i8107 | Y | L22 | L17 | L422 |
| i8108 | Y | L23 | L15 | L422 | i8109 | Y | L23 | L16 | L422 | i8110 | Y | L23 | L17 | L422 |
| i8111 | Y | L24 | L15 | L422 | i8112 | Y | L24 | L16 | L422 | i8113 | Y | L24 | L17 | L422 |
| i8114 | Y | L25 | L15 | L422 | i8115 | Y | L25 | L16 | L422 | i8116 | Y | L25 | L17 | L422 |
| i8117 | Y | L26 | L15 | L422 | i8118 | Y | L26 | L16 | L422 | i8119 | Y | L26 | L17 | L422 |
| i8120 | Y | L27 | L15 | L422 | i8121 | Y | L27 | L16 | L422 | i8122 | Y | L27 | L17 | L422 |
| i8123 | Y | L28 | L15 | L422 | i8124 | Y | L28 | L16 | L422 | i8125 | Y | L28 | L17 | L422 |
| i8126 | Y | L179 | L15 | L422 | i8127 | Y | L179 | L16 | L422 | i8128 | Y | L179 | L17 | L422 |
| i8129 | Y | L180 | L15 | L422 | i8130 | Y | L180 | L16 | L422 | i8131 | Y | L180 | L17 | L422 |
| i8132 | Y | L196 | L15 | L422 | i8133 | Y | L196 | L16 | L422 | i8134 | Y | L196 | L17 | L422 |
| i8135 | Y | L201 | L15 | L422 | i8136 | Y | L201 | L16 | L422 | i8137 | Y | L201 | L17 | L422 |
| i8138 | Y | L206 | L15 | L422 | i8139 | Y | L206 | L16 | L422 | i8140 | Y | L206 | L17 | L422 |
| i8141 | Y | L211 | L15 | L422 | i8142 | Y | L211 | L16 | L422 | i8143 | Y | L211 | L17 | L422 |
| i8144 | Y | L212 | L15 | L422 | i8145 | Y | L212 | L16 | L422 | i8146 | Y | L212 | L17 | L422 |
| i8147 | Y | L215 | L15 | L422 | i8148 | Y | L215 | L16 | L422 | i8149 | Y | L215 | L17 | L422 |
| i8150 | Y | L217 | L15 | L422 | i8151 | Y | L217 | L16 | L422 | i8152 | Y | L217 | L17 | L422 |
| i8153 | Y | L220 | L15 | L422 | i8154 | Y | L220 | L16 | L422 | i8155 | Y | L220 | L17 | L422 |
| i8156 | Y | L10 | L18 | L422 | i8157 | Y | L10 | L19 | L422 | i8158 | Y | L10 | L569 | L422 |
| i8159 | Y | L11 | L18 | L422 | i8160 | Y | L11 | L19 | L422 | i8161 | Y | L11 | L569 | L422 |
| i8162 | Y | L20 | L18 | L422 | i8163 | Y | L20 | L19 | L422 | i8164 | Y | L20 | L569 | L422 |
| i8165 | Y | L21 | L18 | L422 | i8166 | Y | L21 | L19 | L422 | i8167 | Y | L21 | L569 | L422 |
| i8168 | Y | L22 | L18 | L422 | i8169 | Y | L22 | L19 | L422 | i8170 | Y | L22 | L569 | L422 |
| i8171 | Y | L23 | L18 | L422 | i8172 | Y | L23 | L19 | L422 | i8173 | Y | L23 | L569 | L422 |
| i8174 | Y | L24 | L18 | L422 | i8175 | Y | L24 | L19 | L422 | i8176 | Y | L24 | L569 | L422 |
| i8177 | Y | L25 | L18 | L422 | i8178 | Y | L25 | L19 | L422 | i8179 | Y | L25 | L569 | L422 |
| i8180 | Y | L26 | L18 | L422 | i8181 | Y | L26 | L19 | L422 | i8182 | Y | L26 | L569 | L422 |
| i8183 | Y | L27 | L18 | L422 | i8184 | Y | L27 | L19 | L422 | i8185 | Y | L27 | L569 | L422 |
| i8186 | Y | L28 | L18 | L422 | i8187 | Y | L28 | L19 | L422 | i8188 | Y | L28 | L569 | L422 |
| i8189 | Y | L179 | L18 | L422 | i8190 | Y | L179 | L19 | L422 | i8191 | Y | L179 | L569 | L422 |
| i8192 | Y | L180 | L18 | L422 | i8193 | Y | L180 | L19 | L422 | i8194 | Y | L180 | L569 | L422 |
| i8195 | Y | L196 | L18 | L422 | i8196 | Y | L196 | L19 | L422 | i8197 | Y | L196 | L569 | L422 |
| i8198 | Y | L201 | L18 | L422 | i8199 | Y | L201 | L19 | L422 | i8200 | Y | L201 | L569 | L422 |
| i8201 | Y | L206 | L18 | L422 | i8202 | Y | L206 | L19 | L422 | i8203 | Y | L206 | L569 | L422 |
| i8204 | Y | L211 | L18 | L422 | i8205 | Y | L211 | L19 | L422 | i8206 | Y | L211 | L569 | L422 |
| i8207 | Y | L212 | L18 | L422 | i8208 | Y | L212 | L19 | L422 | i8209 | Y | L212 | L569 | L422 |
| i8210 | Y | L215 | L18 | L422 | i8211 | Y | L215 | L19 | L422 | i8212 | Y | L215 | L569 | L422 |
| i8213 | Y | L217 | L18 | L422 | i8214 | Y | L217 | L19 | L422 | i8215 | Y | L217 | L569 | L422 |
| i8216 | Y | L220 | L18 | L422 | i8217 | Y | L220 | L19 | L422 | i8218 | Y | L220 | L569 | L422 |
| i8219 | Y | L10 | L12 | L425 | i8220 | Y | L10 | L13 | L425 | i8221 | Y | L10 | L14 | L425 |
| i8222 | Y | L11 | L12 | L425 | i8223 | Y | L11 | L13 | L425 | i8224 | Y | L11 | L14 | L425 |
| i8225 | Y | L20 | L12 | L425 | i8226 | Y | L20 | L13 | L425 | i8227 | Y | L20 | L14 | L425 |
| i8228 | Y | L21 | L12 | L425 | i8229 | Y | L21 | L13 | L425 | i8230 | Y | L21 | L14 | L425 |
| i8231 | Y | L22 | L12 | L425 | i8232 | Y | L22 | L13 | L425 | i8233 | Y | L22 | L14 | L425 |
| i8234 | Y | L23 | L12 | L425 | i8235 | Y | L23 | L13 | L425 | i8236 | Y | L23 | L14 | L425 |
| i8237 | Y | L24 | L12 | L425 | i8238 | Y | L24 | L13 | L425 | i8239 | Y | L24 | L14 | L425 |
| i8240 | Y | L25 | L12 | L425 | i8241 | Y | L25 | L13 | L425 | i8242 | Y | L25 | L14 | L425 |
| i8243 | Y | L26 | L12 | L425 | i8244 | Y | L26 | L13 | L425 | i8245 | Y | L26 | L14 | L425 |
| i8246 | Y | L27 | L12 | L425 | i8247 | Y | L27 | L13 | L425 | i8248 | Y | L27 | L14 | L425 |

TABLE 1-continued

Compositions "i1" to "i9919"

| | | | | | | | | | | | |
|---|---|---|---|---|---|---|---|---|---|---|---|
| i8249 | Y | L28 | L12 | L425 | i8250 | Y | L28 | L13 | L425 | i8251 | Y | L28 | L14 | L425 |
| i8252 | Y | L179 | L12 | L425 | i8253 | Y | L179 | L13 | L425 | i8254 | Y | L179 | L14 | L425 |
| i8255 | Y | L180 | L12 | L425 | i8256 | Y | L180 | L13 | L425 | i8257 | Y | L180 | L14 | L425 |
| i8258 | Y | L196 | L12 | L425 | i8259 | Y | L196 | L13 | L425 | i8260 | Y | L196 | L14 | L425 |
| i8261 | Y | L201 | L12 | L425 | i8262 | Y | L201 | L13 | L425 | i8263 | Y | L201 | L14 | L425 |
| i8264 | Y | L206 | L12 | L425 | i8265 | Y | L206 | L13 | L425 | i8266 | Y | L206 | L14 | L425 |
| i8267 | Y | L211 | L12 | L425 | i8268 | Y | L211 | L13 | L425 | i8269 | Y | L211 | L14 | L425 |
| i8270 | Y | L212 | L12 | L425 | i8271 | Y | L212 | L13 | L425 | i8272 | Y | L212 | L14 | L425 |
| i8273 | Y | L215 | L12 | L425 | i8274 | Y | L215 | L13 | L425 | i8275 | Y | L215 | L14 | L425 |
| i8276 | Y | L217 | L12 | L425 | i8277 | Y | L217 | L13 | L425 | i8278 | Y | L217 | L14 | L425 |
| i8279 | Y | L220 | L12 | L425 | i8280 | Y | L220 | L13 | L425 | i8281 | Y | L220 | L14 | L425 |
| i8282 | Y | L10 | L15 | L425 | i8283 | Y | L10 | L16 | L425 | i8284 | Y | L10 | L17 | L425 |
| i8285 | Y | L11 | L15 | L425 | i8286 | Y | L11 | L16 | L425 | i8287 | Y | L11 | L17 | L425 |
| i8288 | Y | L20 | L15 | L425 | i8289 | Y | L20 | L16 | L425 | i8290 | Y | L20 | L17 | L425 |
| i8291 | Y | L21 | L15 | L425 | i8292 | Y | L21 | L16 | L425 | i8293 | Y | L21 | L17 | L425 |
| i8294 | Y | L22 | L15 | L425 | i8295 | Y | L22 | L16 | L425 | i8296 | Y | L22 | L17 | L425 |
| i8297 | Y | L23 | L15 | L425 | i8298 | Y | L23 | L16 | L425 | i8299 | Y | L23 | L17 | L425 |
| i8300 | Y | L24 | L15 | L425 | i8301 | Y | L24 | L16 | L425 | i8302 | Y | L24 | L17 | L425 |
| i8303 | Y | L25 | L15 | L425 | i8304 | Y | L25 | L16 | L425 | i8305 | Y | L25 | L17 | L425 |
| i8306 | Y | L26 | L15 | L425 | i8307 | Y | L26 | L16 | L425 | i8308 | Y | L26 | L17 | L425 |
| i8309 | Y | L27 | L15 | L425 | i8310 | Y | L27 | L16 | L425 | i8311 | Y | L27 | L17 | L425 |
| i8312 | Y | L28 | L15 | L425 | i8313 | Y | L28 | L16 | L425 | i8314 | Y | L28 | L17 | L425 |
| i8315 | Y | L179 | L15 | L425 | i8316 | Y | L179 | L16 | L425 | i8317 | Y | L179 | L17 | L425 |
| i8318 | Y | L180 | L15 | L425 | i8319 | Y | L180 | L16 | L425 | i8320 | Y | L180 | L17 | L425 |
| i8321 | Y | L196 | L15 | L425 | i8322 | Y | L196 | L16 | L425 | i8323 | Y | L196 | L17 | L425 |
| i8324 | Y | L201 | L15 | L425 | i8325 | Y | L201 | L16 | L425 | i8326 | Y | L201 | L17 | L425 |
| i8327 | Y | L206 | L15 | L425 | i8328 | Y | L206 | L16 | L425 | i8329 | Y | L206 | L17 | L425 |
| i8330 | Y | L211 | L15 | L425 | i8331 | Y | L211 | L16 | L425 | i8332 | Y | L211 | L17 | L425 |
| i8333 | Y | L212 | L15 | L425 | i8334 | Y | L212 | L16 | L425 | i8335 | Y | L212 | L17 | L425 |
| i8336 | Y | L215 | L15 | L425 | i8337 | Y | L215 | L16 | L425 | i8338 | Y | L215 | L17 | L425 |
| i8339 | Y | L217 | L15 | L425 | i8340 | Y | L217 | L16 | L425 | i8341 | Y | L217 | L17 | L425 |
| i8342 | Y | L220 | L15 | L425 | i8343 | Y | L220 | L16 | L425 | i8344 | Y | L220 | L17 | L425 |
| i8345 | Y | L10 | L18 | L425 | i8346 | Y | L10 | L19 | L425 | i8347 | Y | L10 | L569 | L425 |
| i8348 | Y | L11 | L18 | L425 | i8349 | Y | L11 | L19 | L425 | i8350 | Y | L11 | L569 | L425 |
| i8351 | Y | L20 | L18 | L425 | i8352 | Y | L20 | L19 | L425 | i8353 | Y | L20 | L569 | L425 |
| i8354 | Y | L21 | L18 | L425 | i8355 | Y | L21 | L19 | L425 | i8356 | Y | L21 | L569 | L425 |
| i8357 | Y | L22 | L18 | L425 | i8358 | Y | L22 | L19 | L425 | i8359 | Y | L22 | L569 | L425 |
| i8360 | Y | L23 | L18 | L425 | i8361 | Y | L23 | L19 | L425 | i8362 | Y | L23 | L569 | L425 |
| i8363 | Y | L24 | L18 | L425 | i8364 | Y | L24 | L19 | L425 | i8365 | Y | L24 | L569 | L425 |
| i8366 | Y | L25 | L18 | L425 | i8367 | Y | L25 | L19 | L425 | i8368 | Y | L25 | L569 | L425 |
| i8369 | Y | L26 | L18 | L425 | i8370 | Y | L26 | L19 | L425 | i8371 | Y | L26 | L569 | L425 |
| i8372 | Y | L27 | L18 | L425 | i8373 | Y | L27 | L19 | L425 | i8374 | Y | L27 | L569 | L425 |
| i8375 | Y | L28 | L18 | L425 | i8376 | Y | L28 | L19 | L425 | i8377 | Y | L28 | L569 | L425 |
| i8378 | Y | L179 | L18 | L425 | i8379 | Y | L179 | L19 | L425 | i8380 | Y | L179 | L569 | L425 |
| i8381 | Y | L180 | L18 | L425 | i8382 | Y | L180 | L19 | L425 | i8383 | Y | L180 | L569 | L425 |
| i8384 | Y | L196 | L18 | L425 | i8385 | Y | L196 | L19 | L425 | i8386 | Y | L196 | L569 | L425 |
| i8387 | Y | L201 | L18 | L425 | i8388 | Y | L201 | L19 | L425 | i8389 | Y | L201 | L569 | L425 |
| i8390 | Y | L206 | L18 | L425 | i8391 | Y | L206 | L19 | L425 | i8392 | Y | L206 | L569 | L425 |
| i8393 | Y | L211 | L18 | L425 | i8394 | Y | L211 | L19 | L425 | i8395 | Y | L211 | L569 | L425 |
| i8396 | Y | L212 | L18 | L425 | i8397 | Y | L212 | L19 | L425 | i8398 | Y | L212 | L569 | L425 |
| i8399 | Y | L215 | L18 | L425 | i8400 | Y | L215 | L19 | L425 | i8401 | Y | L215 | L569 | L425 |
| i8402 | Y | L217 | L18 | L425 | i8403 | Y | L217 | L19 | L425 | i8404 | Y | L217 | L569 | L425 |
| i8405 | Y | L220 | L18 | L425 | i8406 | Y | L220 | L19 | L425 | i8407 | Y | L220 | L569 | L425 |
| i8408 | Y | L10 | L12 | L418 | i8409 | Y | L10 | L13 | L418 | i8410 | Y | L10 | L14 | L418 |
| i8411 | Y | L11 | L12 | L418 | i8412 | Y | L11 | L13 | L418 | i8413 | Y | L11 | L14 | L418 |
| i8414 | Y | L20 | L12 | L418 | i8415 | Y | L20 | L13 | L418 | i8416 | Y | L20 | L14 | L418 |
| i8417 | Y | L21 | L12 | L418 | i8418 | Y | L21 | L13 | L418 | i8419 | Y | L21 | L14 | L418 |
| i8420 | Y | L22 | L12 | L418 | i8421 | Y | L22 | L13 | L418 | i8422 | Y | L22 | L14 | L418 |
| i8423 | Y | L23 | L12 | L418 | i8424 | Y | L23 | L13 | L418 | i8425 | Y | L23 | L14 | L418 |
| i8426 | Y | L24 | L12 | L418 | i8427 | Y | L24 | L13 | L418 | i8428 | Y | L24 | L14 | L418 |
| i8429 | Y | L25 | L12 | L418 | i8430 | Y | L25 | L13 | L418 | i8431 | Y | L25 | L14 | L418 |
| i8432 | Y | L26 | L12 | L418 | i8433 | Y | L26 | L13 | L418 | i8434 | Y | L26 | L14 | L418 |
| i8435 | Y | L27 | L12 | L418 | i8436 | Y | L27 | L13 | L418 | i8437 | Y | L27 | L14 | L418 |
| i8438 | Y | L28 | L12 | L418 | i8439 | Y | L28 | L13 | L418 | i8440 | Y | L28 | L14 | L418 |
| i8441 | Y | L179 | L12 | L418 | i8442 | Y | L179 | L13 | L418 | i8443 | Y | L179 | L14 | L418 |
| i8444 | Y | L180 | L12 | L418 | i8445 | Y | L180 | L13 | L418 | i8446 | Y | L180 | L14 | L418 |
| i8447 | Y | L196 | L12 | L418 | i8448 | Y | L196 | L13 | L418 | i8449 | Y | L196 | L14 | L418 |
| i8450 | Y | L201 | L12 | L418 | i8451 | Y | L201 | L13 | L418 | i8452 | Y | L201 | L14 | L418 |
| i8453 | Y | L206 | L12 | L418 | i8454 | Y | L206 | L13 | L418 | i8455 | Y | L206 | L14 | L418 |
| i8456 | Y | L211 | L12 | L418 | i8457 | Y | L211 | L13 | L418 | i8458 | Y | L211 | L14 | L418 |
| i8459 | Y | L212 | L12 | L418 | i8460 | Y | L212 | L13 | L418 | i8461 | Y | L212 | L14 | L418 |
| i8462 | Y | L215 | L12 | L418 | i8463 | Y | L215 | L13 | L418 | i8464 | Y | L215 | L14 | L418 |
| i8465 | Y | L217 | L12 | L418 | i8466 | Y | L217 | L13 | L418 | i8467 | Y | L217 | L14 | L418 |
| i8468 | Y | L220 | L12 | L418 | i8469 | Y | L220 | L13 | L418 | i8470 | Y | L220 | L14 | L418 |
| i8471 | Y | L10 | L15 | L418 | i8472 | Y | L10 | L16 | L418 | i8473 | Y | L10 | L17 | L418 |
| i8474 | Y | L11 | L15 | L418 | i8475 | Y | L11 | L16 | L418 | i8476 | Y | L11 | L17 | L418 |
| i8477 | Y | L20 | L15 | L418 | i8478 | Y | L20 | L16 | L418 | i8479 | Y | L20 | L17 | L418 |
| i8480 | Y | L21 | L15 | L418 | i8481 | Y | L21 | L16 | L418 | i8482 | Y | L21 | L17 | L418 |

TABLE 1-continued

Compositions "i1" to "i9919"

| | | | | | | | | | | | |
|---|---|---|---|---|---|---|---|---|---|---|---|
| i8483 | Y | L22 | L15 | L418 | i8484 | Y | L22 | L16 | L418 | i8485 | Y | L22 | L17 | L418 |
| i8486 | Y | L23 | L15 | L418 | i8487 | Y | L23 | L16 | L418 | i8488 | Y | L23 | L17 | L418 |
| i8489 | Y | L24 | L15 | L418 | i8490 | Y | L24 | L16 | L418 | i8491 | Y | L24 | L17 | L418 |
| i8492 | Y | L25 | L15 | L418 | i8493 | Y | L25 | L16 | L418 | i8494 | Y | L25 | L17 | L418 |
| i8495 | Y | L26 | L15 | L418 | i8496 | Y | L26 | L16 | L418 | i8497 | Y | L26 | L17 | L418 |
| i8498 | Y | L27 | L15 | L418 | i8499 | Y | L27 | L16 | L418 | i8500 | Y | L27 | L17 | L418 |
| i8501 | Y | L28 | L15 | L418 | i8502 | Y | L28 | L16 | L418 | i8503 | Y | L28 | L17 | L418 |
| i8504 | Y | L179 | L15 | L418 | i8505 | Y | L179 | L16 | L418 | i8506 | Y | L179 | L17 | L418 |
| i8507 | Y | L180 | L15 | L418 | i8508 | Y | L180 | L16 | L418 | i8509 | Y | L180 | L17 | L418 |
| i8510 | Y | L196 | L15 | L418 | i8511 | Y | L196 | L16 | L418 | i8512 | Y | L196 | L17 | L418 |
| i8513 | Y | L201 | L15 | L418 | i8514 | Y | L201 | L16 | L418 | i8515 | Y | L201 | L17 | L418 |
| i8516 | Y | L206 | L15 | L418 | i8517 | Y | L206 | L16 | L418 | i8518 | Y | L206 | L17 | L418 |
| i8519 | Y | L211 | L15 | L418 | i8520 | Y | L211 | L16 | L418 | i8521 | Y | L211 | L17 | L418 |
| i8522 | Y | L212 | L15 | L418 | i8523 | Y | L212 | L16 | L418 | i8524 | Y | L212 | L17 | L418 |
| i8525 | Y | L215 | L15 | L418 | i8526 | Y | L215 | L16 | L418 | i8527 | Y | L215 | L17 | L418 |
| i8528 | Y | L217 | L15 | L418 | i8529 | Y | L217 | L16 | L418 | i8530 | Y | L217 | L17 | L418 |
| i8531 | Y | L220 | L15 | L418 | i8532 | Y | L220 | L16 | L418 | i8533 | Y | L220 | L17 | L418 |
| i8534 | Y | L10 | L18 | L418 | i8535 | Y | L10 | L19 | L418 | i8536 | Y | L10 | L569 | L418 |
| i8537 | Y | L11 | L18 | L418 | i8538 | Y | L11 | L19 | L418 | i8539 | Y | L11 | L569 | L418 |
| i8540 | Y | L20 | L18 | L418 | i8541 | Y | L20 | L19 | L418 | i8542 | Y | L20 | L569 | L418 |
| i8543 | Y | L21 | L18 | L418 | i8544 | Y | L21 | L19 | L418 | i8545 | Y | L21 | L569 | L418 |
| i8546 | Y | L22 | L18 | L418 | i8547 | Y | L22 | L19 | L418 | i8548 | Y | L22 | L569 | L418 |
| i8549 | Y | L23 | L18 | L418 | i8550 | Y | L23 | L19 | L418 | i8551 | Y | L23 | L569 | L418 |
| i8552 | Y | L24 | L18 | L418 | i8553 | Y | L24 | L19 | L418 | i8554 | Y | L24 | L569 | L418 |
| i8555 | Y | L25 | L18 | L418 | i8556 | Y | L25 | L19 | L418 | i8557 | Y | L25 | L569 | L418 |
| i8558 | Y | L26 | L18 | L418 | i8559 | Y | L26 | L19 | L418 | i8560 | Y | L26 | L569 | L418 |
| i8561 | Y | L27 | L18 | L418 | i8562 | Y | L27 | L19 | L418 | i8563 | Y | L27 | L569 | L418 |
| i8564 | Y | L28 | L18 | L418 | i8565 | Y | L28 | L19 | L418 | i8566 | Y | L28 | L569 | L418 |
| i8567 | Y | L179 | L18 | L418 | i8568 | Y | L179 | L19 | L418 | i8569 | Y | L179 | L569 | L418 |
| i8570 | Y | L180 | L18 | L418 | i8571 | Y | L180 | L19 | L418 | i8572 | Y | L180 | L569 | L418 |
| i8573 | Y | L196 | L18 | L418 | i8574 | Y | L196 | L19 | L418 | i8575 | Y | L196 | L569 | L418 |
| i8576 | Y | L201 | L18 | L418 | i8577 | Y | L201 | L19 | L418 | i8578 | Y | L201 | L569 | L418 |
| i8579 | Y | L206 | L18 | L418 | i8580 | Y | L206 | L19 | L418 | i8581 | Y | L206 | L569 | L418 |
| i8582 | Y | L211 | L18 | L418 | i8583 | Y | L211 | L19 | L418 | i8584 | Y | L211 | L569 | L418 |
| i8585 | Y | L212 | L18 | L418 | i8586 | Y | L212 | L19 | L418 | i8587 | Y | L212 | L569 | L418 |
| i8588 | Y | L215 | L18 | L418 | i8589 | Y | L215 | L19 | L418 | i8590 | Y | L215 | L569 | L418 |
| i8591 | Y | L217 | L18 | L418 | i8592 | Y | L217 | L19 | L418 | i8593 | Y | L217 | L569 | L418 |
| i8594 | Y | L220 | L18 | L418 | i8595 | Y | L220 | L19 | L418 | i8596 | Y | L220 | L569 | L418 |
| i8597 | Y | L10 | L12 | L424 | i8598 | Y | L10 | L13 | L424 | i8599 | Y | L10 | L14 | L424 |
| i8600 | Y | L11 | L12 | L424 | i8601 | Y | L11 | L13 | L424 | i8602 | Y | L11 | L14 | L424 |
| i8603 | Y | L20 | L12 | L424 | i8604 | Y | L20 | L13 | L424 | i8605 | Y | L20 | L14 | L424 |
| i8606 | Y | L21 | L12 | L424 | i8607 | Y | L21 | L13 | L424 | i8608 | Y | L21 | L14 | L424 |
| i8609 | Y | L22 | L12 | L424 | i8610 | Y | L22 | L13 | L424 | i8611 | Y | L22 | L14 | L424 |
| i8612 | Y | L23 | L12 | L424 | i8613 | Y | L23 | L13 | L424 | i8614 | Y | L23 | L14 | L424 |
| i8615 | Y | L24 | L12 | L424 | i8616 | Y | L24 | L13 | L424 | i8617 | Y | L24 | L14 | L424 |
| i8618 | Y | L25 | L12 | L424 | i8619 | Y | L25 | L13 | L424 | i8620 | Y | L25 | L14 | L424 |
| i8621 | Y | L26 | L12 | L424 | i8622 | Y | L26 | L13 | L424 | i8623 | Y | L26 | L14 | L424 |
| i8624 | Y | L27 | L12 | L424 | i8625 | Y | L27 | L13 | L424 | i8626 | Y | L27 | L14 | L424 |
| i8627 | Y | L28 | L12 | L424 | i8628 | Y | L28 | L13 | L424 | i8629 | Y | L28 | L14 | L424 |
| i8630 | Y | L179 | L12 | L424 | i8631 | Y | L179 | L13 | L424 | i8632 | Y | L179 | L14 | L424 |
| i8633 | Y | L180 | L12 | L424 | i8634 | Y | L180 | L13 | L424 | i8635 | Y | L180 | L14 | L424 |
| i8636 | Y | L196 | L12 | L424 | i8637 | Y | L196 | L13 | L424 | i8638 | Y | L196 | L14 | L424 |
| i8639 | Y | L201 | L12 | L424 | i8640 | Y | L201 | L13 | L424 | i8641 | Y | L201 | L14 | L424 |
| i8642 | Y | L206 | L12 | L424 | i8643 | Y | L206 | L13 | L424 | i8644 | Y | L206 | L14 | L424 |
| i8645 | Y | L211 | L12 | L424 | i8646 | Y | L211 | L13 | L424 | i8647 | Y | L211 | L14 | L424 |
| i8648 | Y | L212 | L12 | L424 | i8649 | Y | L212 | L13 | L424 | i8650 | Y | L212 | L14 | L424 |
| i8651 | Y | L215 | L12 | L424 | i8652 | Y | L215 | L13 | L424 | i8653 | Y | L215 | L14 | L424 |
| i8654 | Y | L217 | L12 | L424 | i8655 | Y | L217 | L13 | L424 | i8656 | Y | L217 | L14 | L424 |
| i8657 | Y | L220 | L12 | L424 | i8658 | Y | L220 | L13 | L424 | i8659 | Y | L220 | L14 | L424 |
| i8660 | Y | L10 | L15 | L424 | i8661 | Y | L10 | L16 | L424 | i8662 | Y | L10 | L17 | L424 |
| i8663 | Y | L11 | L15 | L424 | i8664 | Y | L11 | L16 | L424 | i8665 | Y | L11 | L17 | L424 |
| i8666 | Y | L20 | L15 | L424 | i8667 | Y | L20 | L16 | L424 | i8668 | Y | L20 | L17 | L424 |
| i8669 | Y | L21 | L15 | L424 | i8670 | Y | L21 | L16 | L424 | i8671 | Y | L21 | L17 | L424 |
| i8672 | Y | L22 | L15 | L424 | i8673 | Y | L22 | L16 | L424 | i8674 | Y | L22 | L17 | L424 |
| i8675 | Y | L23 | L15 | L424 | i8676 | Y | L23 | L16 | L424 | i8677 | Y | L23 | L17 | L424 |
| i8678 | Y | L24 | L15 | L424 | i8679 | Y | L24 | L16 | L424 | i8680 | Y | L24 | L17 | L424 |
| i8681 | Y | L25 | L15 | L424 | i8682 | Y | L25 | L16 | L424 | i8683 | Y | L25 | L17 | L424 |
| i8684 | Y | L26 | L15 | L424 | i8685 | Y | L26 | L16 | L424 | i8686 | Y | L26 | L17 | L424 |
| i8687 | Y | L27 | L15 | L424 | i8688 | Y | L27 | L16 | L424 | i8689 | Y | L27 | L17 | L424 |
| i8690 | Y | L28 | L15 | L424 | i8691 | Y | L28 | L16 | L424 | i8692 | Y | L28 | L17 | L424 |
| i8693 | Y | L179 | L15 | L424 | i8694 | Y | L179 | L16 | L424 | i8695 | Y | L179 | L17 | L424 |
| i8696 | Y | L180 | L15 | L424 | i8697 | Y | L180 | L16 | L424 | i8698 | Y | L180 | L17 | L424 |
| i8699 | Y | L196 | L15 | L424 | i8700 | Y | L196 | L16 | L424 | i8701 | Y | L196 | L17 | L424 |
| i8702 | Y | L201 | L15 | L424 | i8703 | Y | L201 | L16 | L424 | i8704 | Y | L201 | L17 | L424 |
| i8705 | Y | L206 | L15 | L424 | i8706 | Y | L206 | L16 | L424 | i8707 | Y | L206 | L17 | L424 |
| i8708 | Y | L211 | L15 | L424 | i8709 | Y | L211 | L16 | L424 | i8710 | Y | L211 | L17 | L424 |
| i8711 | Y | L212 | L15 | L424 | i8712 | Y | L212 | L16 | L424 | i8713 | Y | L212 | L17 | L424 |
| i8714 | Y | L215 | L15 | L424 | i8715 | Y | L215 | L16 | L424 | i8716 | Y | L215 | L17 | L424 |

TABLE 1-continued

Compositions "i1" to "i9919"

| | | | | | | | | | | | |
|---|---|---|---|---|---|---|---|---|---|---|---|
| i8717 | Y | L217 | L15 | L424 | i8718 | Y | L217 | L16 | L424 | i8719 | Y | L217 | L17 | L424 |
| i8720 | Y | L220 | L15 | L424 | i8721 | Y | L220 | L16 | L424 | i8722 | Y | L220 | L17 | L424 |
| i8723 | Y | L10 | L18 | L424 | i8724 | Y | L10 | L19 | L424 | i8725 | Y | L10 | L569 | L424 |
| i8726 | Y | L11 | L18 | L424 | i8727 | Y | L11 | L19 | L424 | i8728 | Y | L11 | L569 | L424 |
| i8729 | Y | L20 | L18 | L424 | i8730 | Y | L20 | L19 | L424 | i8731 | Y | L20 | L569 | L424 |
| i8732 | Y | L21 | L18 | L424 | i8733 | Y | L21 | L19 | L424 | i8734 | Y | L21 | L569 | L424 |
| i8735 | Y | L22 | L18 | L424 | i8736 | Y | L22 | L19 | L424 | i8737 | Y | L22 | L569 | L424 |
| i8738 | Y | L23 | L18 | L424 | i8739 | Y | L23 | L19 | L424 | i8740 | Y | L23 | L569 | L424 |
| i8741 | Y | L24 | L18 | L424 | i8742 | Y | L24 | L19 | L424 | i8743 | Y | L24 | L569 | L424 |
| i8744 | Y | L25 | L18 | L424 | i8745 | Y | L25 | L19 | L424 | i8746 | Y | L25 | L569 | L424 |
| i8747 | Y | L26 | L18 | L424 | i8748 | Y | L26 | L19 | L424 | i8749 | Y | L26 | L569 | L424 |
| i8750 | Y | L27 | L18 | L424 | i8751 | Y | L27 | L19 | L424 | i8752 | Y | L27 | L569 | L424 |
| i8753 | Y | L28 | L18 | L424 | i8754 | Y | L28 | L19 | L424 | i8755 | Y | L28 | L569 | L424 |
| i8756 | Y | L179 | L18 | L424 | i8757 | Y | L179 | L19 | L424 | i8758 | Y | L179 | L569 | L424 |
| i8759 | Y | L180 | L18 | L424 | i8760 | Y | L180 | L19 | L424 | i8761 | Y | L180 | L569 | L424 |
| i8762 | Y | L196 | L18 | L424 | i8763 | Y | L196 | L19 | L424 | i8764 | Y | L196 | L569 | L424 |
| i8765 | Y | L201 | L18 | L424 | i8766 | Y | L201 | L19 | L424 | i8767 | Y | L201 | L569 | L424 |
| i8768 | Y | L206 | L18 | L424 | i8769 | Y | L206 | L19 | L424 | i8770 | Y | L206 | L569 | L424 |
| i8771 | Y | L211 | L18 | L424 | i8772 | Y | L211 | L19 | L424 | i8773 | Y | L211 | L569 | L424 |
| i8774 | Y | L212 | L18 | L424 | i8775 | Y | L212 | L19 | L424 | i8776 | Y | L212 | L569 | L424 |
| i8777 | Y | L215 | L18 | L424 | i8778 | Y | L215 | L19 | L424 | i8779 | Y | L215 | L569 | L424 |
| i8780 | Y | L217 | L18 | L424 | i8781 | Y | L217 | L19 | L424 | i8782 | Y | L217 | L569 | L424 |
| i8783 | Y | L220 | L18 | L424 | i8784 | Y | L220 | L19 | L424 | i8785 | Y | L220 | L569 | L424 |
| i8786 | Y | L10 | L12 | L410 | i8787 | Y | L10 | L13 | L410 | i8788 | Y | L10 | L14 | L410 |
| i8789 | Y | L11 | L12 | L410 | i8790 | Y | L11 | L13 | L410 | i8791 | Y | L11 | L14 | L410 |
| i8792 | Y | L20 | L12 | L410 | i8793 | Y | L20 | L13 | L410 | i8794 | Y | L20 | L14 | L410 |
| i8795 | Y | L21 | L12 | L410 | i8796 | Y | L21 | L13 | L410 | i8797 | Y | L21 | L14 | L410 |
| i8798 | Y | L22 | L12 | L410 | i8799 | Y | L22 | L13 | L410 | i8800 | Y | L22 | L14 | L410 |
| i8801 | Y | L23 | L12 | L410 | i8802 | Y | L23 | L13 | L410 | i8803 | Y | L23 | L14 | L410 |
| i8804 | Y | L24 | L12 | L410 | i8805 | Y | L24 | L13 | L410 | i8806 | Y | L24 | L14 | L410 |
| i8807 | Y | L25 | L12 | L410 | i8808 | Y | L25 | L13 | L410 | i8809 | Y | L25 | L14 | L410 |
| i8810 | Y | L26 | L12 | L410 | i8811 | Y | L26 | L13 | L410 | i8812 | Y | L26 | L14 | L410 |
| i8813 | Y | L27 | L12 | L410 | i8814 | Y | L27 | L13 | L410 | i8815 | Y | L27 | L14 | L410 |
| i8816 | Y | L28 | L12 | L410 | i8817 | Y | L28 | L13 | L410 | i8818 | Y | L28 | L14 | L410 |
| i8819 | Y | L179 | L12 | L410 | i8820 | Y | L179 | L13 | L410 | i8821 | Y | L179 | L14 | L410 |
| i8822 | Y | L180 | L12 | L410 | i8823 | Y | L180 | L13 | L410 | i8824 | Y | L180 | L14 | L410 |
| i8825 | Y | L196 | L12 | L410 | i8826 | Y | L196 | L13 | L410 | i8827 | Y | L196 | L14 | L410 |
| i8828 | Y | L201 | L12 | L410 | i8829 | Y | L201 | L13 | L410 | i8830 | Y | L201 | L14 | L410 |
| i8831 | Y | L206 | L12 | L410 | i8832 | Y | L206 | L13 | L410 | i8833 | Y | L206 | L14 | L410 |
| i8834 | Y | L211 | L12 | L410 | i8835 | Y | L211 | L13 | L410 | i8836 | Y | L211 | L14 | L410 |
| i8837 | Y | L212 | L12 | L410 | i8838 | Y | L212 | L13 | L410 | i8839 | Y | L212 | L14 | L410 |
| i8840 | Y | L215 | L12 | L410 | i8841 | Y | L215 | L13 | L410 | i8842 | Y | L215 | L14 | L410 |
| i8843 | Y | L217 | L12 | L410 | i8844 | Y | L217 | L13 | L410 | i8845 | Y | L217 | L14 | L410 |
| i8846 | Y | L220 | L12 | L410 | i8847 | Y | L220 | L13 | L410 | i8848 | Y | L220 | L14 | L410 |
| i8849 | Y | L10 | L15 | L410 | i8850 | Y | L10 | L16 | L410 | i8851 | Y | L10 | L17 | L410 |
| i8852 | Y | L11 | L15 | L410 | i8853 | Y | L11 | L16 | L410 | i8854 | Y | L11 | L17 | L410 |
| i8855 | Y | L20 | L15 | L410 | i8856 | Y | L20 | L16 | L410 | i8857 | Y | L20 | L17 | L410 |
| i8858 | Y | L21 | L15 | L410 | i8859 | Y | L21 | L16 | L410 | i8860 | Y | L21 | L17 | L410 |
| i8861 | Y | L22 | L15 | L410 | i8862 | Y | L22 | L16 | L410 | i8863 | Y | L22 | L17 | L410 |
| i8864 | Y | L23 | L15 | L410 | i8865 | Y | L23 | L16 | L410 | i8866 | Y | L23 | L17 | L410 |
| i8867 | Y | L24 | L15 | L410 | i8868 | Y | L24 | L16 | L410 | i8869 | Y | L24 | L17 | L410 |
| i8870 | Y | L25 | L15 | L410 | i8871 | Y | L25 | L16 | L410 | i8872 | Y | L25 | L17 | L410 |
| i8873 | Y | L26 | L15 | L410 | i8874 | Y | L26 | L16 | L410 | i8875 | Y | L26 | L17 | L410 |
| i8876 | Y | L27 | L15 | L410 | i8877 | Y | L27 | L16 | L410 | i8878 | Y | L27 | L17 | L410 |
| i8879 | Y | L28 | L15 | L410 | i8880 | Y | L28 | L16 | L410 | i8881 | Y | L28 | L17 | L410 |
| i8882 | Y | L179 | L15 | L410 | i8883 | Y | L179 | L16 | L410 | i8884 | Y | L179 | L17 | L410 |
| i8885 | Y | L180 | L15 | L410 | i8886 | Y | L180 | L16 | L410 | i8887 | Y | L180 | L17 | L410 |
| i8888 | Y | L196 | L15 | L410 | i8889 | Y | L196 | L16 | L410 | i8890 | Y | L196 | L17 | L410 |
| i8891 | Y | L201 | L15 | L410 | i8892 | Y | L201 | L16 | L410 | i8893 | Y | L201 | L17 | L410 |
| i8894 | Y | L206 | L15 | L410 | i8895 | Y | L206 | L16 | L410 | i8896 | Y | L206 | L17 | L410 |
| i8897 | Y | L211 | L15 | L410 | i8898 | Y | L211 | L16 | L410 | i8899 | Y | L211 | L17 | L410 |
| i8900 | Y | L212 | L15 | L410 | i8901 | Y | L212 | L16 | L410 | i8902 | Y | L212 | L17 | L410 |
| i8903 | Y | L215 | L15 | L410 | i8904 | Y | L215 | L16 | L410 | i8905 | Y | L215 | L17 | L410 |
| i8906 | Y | L217 | L15 | L410 | i8907 | Y | L217 | L16 | L410 | i8908 | Y | L217 | L17 | L410 |
| i8909 | Y | L220 | L15 | L410 | i8910 | Y | L220 | L16 | L410 | i8911 | Y | L220 | L17 | L410 |
| i8912 | Y | L10 | L18 | L410 | i8913 | Y | L10 | L19 | L410 | i8914 | Y | L10 | L569 | L410 |
| i8915 | Y | L11 | L18 | L410 | i8916 | Y | L11 | L19 | L410 | i8917 | Y | L11 | L569 | L410 |
| i8918 | Y | L20 | L18 | L410 | i8919 | Y | L20 | L19 | L410 | i8920 | Y | L20 | L569 | L410 |
| i8921 | Y | L21 | L18 | L410 | i8922 | Y | L21 | L19 | L410 | i8923 | Y | L21 | L569 | L410 |
| i8924 | Y | L22 | L18 | L410 | i8925 | Y | L22 | L19 | L410 | i8926 | Y | L22 | L569 | L410 |
| i8927 | Y | L23 | L18 | L410 | i8928 | Y | L23 | L19 | L410 | i8929 | Y | L23 | L569 | L410 |
| i8930 | Y | L24 | L18 | L410 | i8931 | Y | L24 | L19 | L410 | i8932 | Y | L24 | L569 | L410 |
| i8933 | Y | L25 | L18 | L410 | i8934 | Y | L25 | L19 | L410 | i8935 | Y | L25 | L569 | L410 |
| i8936 | Y | L26 | L18 | L410 | i8937 | Y | L26 | L19 | L410 | i8938 | Y | L26 | L569 | L410 |
| i8939 | Y | L27 | L18 | L410 | i8940 | Y | L27 | L19 | L410 | i8941 | Y | L27 | L569 | L410 |
| i8942 | Y | L28 | L18 | L410 | i8943 | Y | L28 | L19 | L410 | i8944 | Y | L28 | L569 | L410 |
| i8945 | Y | L179 | L18 | L410 | i8946 | Y | L179 | L19 | L410 | i8947 | Y | L179 | L569 | L410 |
| i8948 | Y | L180 | L18 | L410 | i8949 | Y | L180 | L19 | L410 | i8950 | Y | L180 | L569 | L410 |

TABLE 1-continued

Compositions "i1" to "i9919"

| | | | | | | | | | | | |
|---|---|---|---|---|---|---|---|---|---|---|---|
| i8951 | Y | L196 | L18 | L410 | i8952 | Y | L196 | L19 | L410 | i8953 | Y | L196 | L569 | L410 |
| i8954 | Y | L201 | L18 | L410 | i8955 | Y | L201 | L19 | L410 | i8956 | Y | L201 | L569 | L410 |
| i8957 | Y | L206 | L18 | L410 | i8958 | Y | L206 | L19 | L410 | i8959 | Y | L206 | L569 | L410 |
| i8960 | Y | L211 | L18 | L410 | i8961 | Y | L211 | L19 | L410 | i8962 | Y | L211 | L569 | L410 |
| i8963 | Y | L212 | L18 | L410 | i8964 | Y | L212 | L19 | L410 | i8965 | Y | L212 | L569 | L410 |
| i8966 | Y | L215 | L18 | L410 | i8967 | Y | L215 | L19 | L410 | i8968 | Y | L215 | L569 | L410 |
| i8969 | Y | L217 | L18 | L410 | i8970 | Y | L217 | L19 | L410 | i8971 | Y | L217 | L569 | L410 |
| i8972 | Y | L220 | L18 | L410 | i8973 | Y | L220 | L19 | L410 | i8974 | Y | L220 | L569 | L410 |
| i8975 | Y | L10 | L12 | L404 | i8976 | Y | L10 | L13 | L404 | i8977 | Y | L10 | L14 | L404 |
| i8978 | Y | L11 | L12 | L404 | i8979 | Y | L11 | L13 | L404 | i8980 | Y | L11 | L14 | L404 |
| i8981 | Y | L20 | L12 | L404 | i8982 | Y | L20 | L13 | L404 | i8983 | Y | L20 | L14 | L404 |
| i8984 | Y | L21 | L12 | L404 | i8985 | Y | L21 | L13 | L404 | i8986 | Y | L21 | L14 | L404 |
| i8987 | Y | L22 | L12 | L404 | i8988 | Y | L22 | L13 | L404 | i8989 | Y | L22 | L14 | L404 |
| i8990 | Y | L23 | L12 | L404 | i8991 | Y | L23 | L13 | L404 | i8992 | Y | L23 | L14 | L404 |
| i8993 | Y | L24 | L12 | L404 | i8994 | Y | L24 | L13 | L404 | i8995 | Y | L24 | L14 | L404 |
| i8996 | Y | L25 | L12 | L404 | i8997 | Y | L25 | L13 | L404 | i8998 | Y | L25 | L14 | L404 |
| i8999 | Y | L26 | L12 | L404 | i9000 | Y | L26 | L13 | L404 | i9001 | Y | L26 | L14 | L404 |
| i9002 | Y | L27 | L12 | L404 | i9003 | Y | L27 | L13 | L404 | i9004 | Y | L27 | L14 | L404 |
| i9005 | Y | L28 | L12 | L404 | i9006 | Y | L28 | L13 | L404 | i9007 | Y | L28 | L14 | L404 |
| i9008 | Y | L179 | L12 | L404 | i9009 | Y | L179 | L13 | L404 | i9010 | Y | L179 | L14 | L404 |
| i9011 | Y | L180 | L12 | L404 | i9012 | Y | L180 | L13 | L404 | i9013 | Y | L180 | L14 | L404 |
| i9014 | Y | L196 | L12 | L404 | i9015 | Y | L196 | L13 | L404 | i9016 | Y | L196 | L14 | L404 |
| i9017 | Y | L201 | L12 | L404 | i9018 | Y | L201 | L13 | L404 | i9019 | Y | L201 | L14 | L404 |
| i9020 | Y | L206 | L12 | L404 | i9021 | Y | L206 | L13 | L404 | i9022 | Y | L206 | L14 | L404 |
| i9023 | Y | L211 | L12 | L404 | i9024 | Y | L211 | L13 | L404 | i9025 | Y | L211 | L14 | L404 |
| i9026 | Y | L212 | L12 | L404 | i9027 | Y | L212 | L13 | L404 | i9028 | Y | L212 | L14 | L404 |
| i9029 | Y | L215 | L12 | L404 | i9030 | Y | L215 | L13 | L404 | i9031 | Y | L215 | L14 | L404 |
| i9032 | Y | L217 | L12 | L404 | i9033 | Y | L217 | L13 | L404 | i9034 | Y | L217 | L14 | L404 |
| i9035 | Y | L220 | L12 | L404 | i9036 | Y | L220 | L13 | L404 | i9037 | Y | L220 | L14 | L404 |
| i9038 | Y | L10 | L15 | L404 | i9039 | Y | L10 | L16 | L404 | i9040 | Y | L10 | L17 | L404 |
| i9041 | Y | L11 | L15 | L404 | i9042 | Y | L11 | L16 | L404 | i9043 | Y | L11 | L17 | L404 |
| i9044 | Y | L20 | L15 | L404 | i9045 | Y | L20 | L16 | L404 | i9046 | Y | L20 | L17 | L404 |
| i9047 | Y | L21 | L15 | L404 | i9048 | Y | L21 | L16 | L404 | i9049 | Y | L21 | L17 | L404 |
| i9050 | Y | L22 | L15 | L404 | i9051 | Y | L22 | L16 | L404 | i9052 | Y | L22 | L17 | L404 |
| i9053 | Y | L23 | L15 | L404 | i9054 | Y | L23 | L16 | L404 | i9055 | Y | L23 | L17 | L404 |
| i9056 | Y | L24 | L15 | L404 | i9057 | Y | L24 | L16 | L404 | i9058 | Y | L24 | L17 | L404 |
| i9059 | Y | L25 | L15 | L404 | i9060 | Y | L25 | L16 | L404 | i9061 | Y | L25 | L17 | L404 |
| i9062 | Y | L26 | L15 | L404 | i9063 | Y | L26 | L16 | L404 | i9064 | Y | L26 | L17 | L404 |
| i9065 | Y | L27 | L15 | L404 | i9066 | Y | L27 | L16 | L404 | i9067 | Y | L27 | L17 | L404 |
| i9068 | Y | L28 | L15 | L404 | i9069 | Y | L28 | L16 | L404 | i9070 | Y | L28 | L17 | L404 |
| i9071 | Y | L179 | L15 | L404 | i9072 | Y | L179 | L16 | L404 | i9073 | Y | L179 | L17 | L404 |
| i9074 | Y | L180 | L15 | L404 | i9075 | Y | L180 | L16 | L404 | i9076 | Y | L180 | L17 | L404 |
| i9077 | Y | L196 | L15 | L404 | i9078 | Y | L196 | L16 | L404 | i9079 | Y | L196 | L17 | L404 |
| i9080 | Y | L201 | L15 | L404 | i9081 | Y | L201 | L16 | L404 | i9082 | Y | L201 | L17 | L404 |
| i9083 | Y | L206 | L15 | L404 | i9084 | Y | L206 | L16 | L404 | i9085 | Y | L206 | L17 | L404 |
| i9086 | Y | L211 | L15 | L404 | i9087 | Y | L211 | L16 | L404 | i9088 | Y | L211 | L17 | L404 |
| i9089 | Y | L212 | L15 | L404 | i9090 | Y | L212 | L16 | L404 | i9091 | Y | L212 | L17 | L404 |
| i9092 | Y | L215 | L15 | L404 | i9093 | Y | L215 | L16 | L404 | i9094 | Y | L215 | L17 | L404 |
| i9095 | Y | L217 | L15 | L404 | i9096 | Y | L217 | L16 | L404 | i9097 | Y | L217 | L17 | L404 |
| i9098 | Y | L220 | L15 | L404 | i9099 | Y | L220 | L16 | L404 | i9100 | Y | L220 | L17 | L404 |
| i9101 | Y | L10 | L18 | L404 | i9102 | Y | L10 | L19 | L404 | i9103 | Y | L10 | L569 | L404 |
| i9104 | Y | L11 | L18 | L404 | i9105 | Y | L11 | L19 | L404 | i9106 | Y | L11 | L569 | L404 |
| i9107 | Y | L20 | L18 | L404 | i9108 | Y | L20 | L19 | L404 | i9109 | Y | L20 | L569 | L404 |
| i9110 | Y | L21 | L18 | L404 | i9111 | Y | L21 | L19 | L404 | i9112 | Y | L21 | L569 | L404 |
| i9113 | Y | L22 | L18 | L404 | i9114 | Y | L22 | L19 | L404 | i9115 | Y | L22 | L569 | L404 |
| i9116 | Y | L23 | L18 | L404 | i9117 | Y | L23 | L19 | L404 | i9118 | Y | L23 | L569 | L404 |
| i9119 | Y | L24 | L18 | L404 | i9120 | Y | L24 | L19 | L404 | i9121 | Y | L24 | L569 | L404 |
| i9122 | Y | L25 | L18 | L404 | i9123 | Y | L25 | L19 | L404 | i9124 | Y | L25 | L569 | L404 |
| i9125 | Y | L26 | L18 | L404 | i9126 | Y | L26 | L19 | L404 | i9127 | Y | L26 | L569 | L404 |
| i9128 | Y | L27 | L18 | L404 | i9129 | Y | L27 | L19 | L404 | i9130 | Y | L27 | L569 | L404 |
| i9131 | Y | L28 | L18 | L404 | i9132 | Y | L28 | L19 | L404 | i9133 | Y | L28 | L569 | L404 |
| i9134 | Y | L179 | L18 | L404 | i9135 | Y | L179 | L19 | L404 | i9136 | Y | L179 | L569 | L404 |
| i9137 | Y | L180 | L18 | L404 | i9138 | Y | L180 | L19 | L404 | i9139 | Y | L180 | L569 | L404 |
| i9140 | Y | L196 | L18 | L404 | i9141 | Y | L196 | L19 | L404 | i9142 | Y | L196 | L569 | L404 |
| i9143 | Y | L201 | L18 | L404 | i9144 | Y | L201 | L19 | L404 | i9145 | Y | L201 | L569 | L404 |
| i9146 | Y | L206 | L18 | L404 | i9147 | Y | L206 | L19 | L404 | i9148 | Y | L206 | L569 | L404 |
| i9149 | Y | L211 | L18 | L404 | i9150 | Y | L211 | L19 | L404 | i9151 | Y | L211 | L569 | L404 |
| i9152 | Y | L212 | L18 | L404 | i9153 | Y | L212 | L19 | L404 | i9154 | Y | L212 | L569 | L404 |
| i9155 | Y | L215 | L18 | L404 | i9156 | Y | L215 | L19 | L404 | i9157 | Y | L215 | L569 | L404 |
| i9158 | Y | L217 | L18 | L404 | i9159 | Y | L217 | L19 | L404 | i9160 | Y | L217 | L569 | L404 |
| i9161 | Y | L220 | L18 | L404 | i9162 | Y | L220 | L19 | L404 | i9163 | Y | L220 | L569 | L404 |
| i9164 | Y | L10 | L12 | L426 | i9165 | Y | L10 | L13 | L426 | i9166 | Y | L10 | L14 | L426 |
| i9167 | Y | L11 | L12 | L426 | i9168 | Y | L11 | L13 | L426 | i9169 | Y | L11 | L14 | L426 |
| i9170 | Y | L20 | L12 | L426 | i9171 | Y | L20 | L13 | L426 | i9172 | Y | L20 | L14 | L426 |
| i9173 | Y | L21 | L12 | L426 | i9174 | Y | L21 | L13 | L426 | i9175 | Y | L21 | L14 | L426 |
| i9176 | Y | L22 | L12 | L426 | i9177 | Y | L22 | L13 | L426 | i9178 | Y | L22 | L14 | L426 |
| i9179 | Y | L23 | L12 | L426 | i9180 | Y | L23 | L13 | L426 | i9181 | Y | L23 | L14 | L426 |
| i9182 | Y | L24 | L12 | L426 | i9183 | Y | L24 | L13 | L426 | i9184 | Y | L24 | L14 | L426 |

TABLE 1-continued

Compositions "i1" to "i9919"

| | | | | | | | | | | | |
|---|---|---|---|---|---|---|---|---|---|---|---|
| i9185 | Y | L25 | L12 | L426 | i9186 | Y | L25 | L13 | L426 | i9187 | Y | L25 | L14 | L426 |
| i9188 | Y | L26 | L12 | L426 | i9189 | Y | L26 | L13 | L426 | i9190 | Y | L26 | L14 | L426 |
| i9191 | Y | L27 | L12 | L426 | i9192 | Y | L27 | L13 | L426 | i9193 | Y | L27 | L14 | L426 |
| i9194 | Y | L28 | L12 | L426 | i9195 | Y | L28 | L13 | L426 | i9196 | Y | L28 | L14 | L426 |
| i9197 | Y | L179 | L12 | L426 | i9198 | Y | L179 | L13 | L426 | i9199 | Y | L179 | L14 | L426 |
| i9200 | Y | L180 | L12 | L426 | i9201 | Y | L180 | L13 | L426 | i9202 | Y | L180 | L14 | L426 |
| i9203 | Y | L196 | L12 | L426 | i9204 | Y | L196 | L13 | L426 | i9205 | Y | L196 | L14 | L426 |
| i9206 | Y | L201 | L12 | L426 | i9207 | Y | L201 | L13 | L426 | i9208 | Y | L201 | L14 | L426 |
| i9209 | Y | L206 | L12 | L426 | i9210 | Y | L206 | L13 | L426 | i9211 | Y | L206 | L14 | L426 |
| i9212 | Y | L211 | L12 | L426 | i9213 | Y | L211 | L13 | L426 | i9214 | Y | L211 | L14 | L426 |
| i9215 | Y | L212 | L12 | L426 | i9216 | Y | L212 | L13 | L426 | i9217 | Y | L212 | L14 | L426 |
| i9218 | Y | L215 | L12 | L426 | i9219 | Y | L215 | L13 | L426 | i9220 | Y | L215 | L14 | L426 |
| i9221 | Y | L217 | L12 | L426 | i9222 | Y | L217 | L13 | L426 | i9223 | Y | L217 | L14 | L426 |
| i9224 | Y | L220 | L12 | L426 | i9225 | Y | L220 | L13 | L426 | i9226 | Y | L220 | L14 | L426 |
| i9227 | Y | L10 | L15 | L426 | i9228 | Y | L10 | L16 | L426 | i9229 | Y | L10 | L17 | L426 |
| i9230 | Y | L11 | L15 | L426 | i9231 | Y | L11 | L16 | L426 | i9232 | Y | L11 | L17 | L426 |
| i9233 | Y | L20 | L15 | L426 | i9234 | Y | L20 | L16 | L426 | i9235 | Y | L20 | L17 | L426 |
| i9236 | Y | L21 | L15 | L426 | i9237 | Y | L21 | L16 | L426 | i9238 | Y | L21 | L17 | L426 |
| i9239 | Y | L22 | L15 | L426 | i9240 | Y | L22 | L16 | L426 | i9241 | Y | L22 | L17 | L426 |
| i9242 | Y | L23 | L15 | L426 | i9243 | Y | L23 | L16 | L426 | i9244 | Y | L23 | L17 | L426 |
| i9245 | Y | L24 | L15 | L426 | i9246 | Y | L24 | L16 | L426 | i9247 | Y | L24 | L17 | L426 |
| i9248 | Y | L25 | L15 | L426 | i9249 | Y | L25 | L16 | L426 | i9250 | Y | L25 | L17 | L426 |
| i9251 | Y | L26 | L15 | L426 | i9252 | Y | L26 | L16 | L426 | i9253 | Y | L26 | L17 | L426 |
| i9254 | Y | L27 | L15 | L426 | i9255 | Y | L27 | L16 | L426 | i9256 | Y | L27 | L17 | L426 |
| i9257 | Y | L28 | L15 | L426 | i9258 | Y | L28 | L16 | L426 | i9259 | Y | L28 | L17 | L426 |
| i9260 | Y | L179 | L15 | L426 | i9261 | Y | L179 | L16 | L426 | i9262 | Y | L179 | L17 | L426 |
| i9263 | Y | L180 | L15 | L426 | i9264 | Y | L180 | L16 | L426 | i9265 | Y | L180 | L17 | L426 |
| i9266 | Y | L196 | L15 | L426 | i9267 | Y | L196 | L16 | L426 | i9268 | Y | L196 | L17 | L426 |
| i9269 | Y | L201 | L15 | L426 | i9270 | Y | L201 | L16 | L426 | i9271 | Y | L201 | L17 | L426 |
| i9272 | Y | L206 | L15 | L426 | i9273 | Y | L206 | L16 | L426 | i9274 | Y | L206 | L17 | L426 |
| i9275 | Y | L211 | L15 | L426 | i9276 | Y | L211 | L16 | L426 | i9277 | Y | L211 | L17 | L426 |
| i9278 | Y | L212 | L15 | L426 | i9279 | Y | L212 | L16 | L426 | i9280 | Y | L212 | L17 | L426 |
| i9281 | Y | L215 | L15 | L426 | i9282 | Y | L215 | L16 | L426 | i9283 | Y | L215 | L17 | L426 |
| i9284 | Y | L217 | L15 | L426 | i9285 | Y | L217 | L16 | L426 | i9286 | Y | L217 | L17 | L426 |
| i9287 | Y | L220 | L15 | L426 | i9288 | Y | L220 | L16 | L426 | i9289 | Y | L220 | L17 | L426 |
| i9290 | Y | L10 | L18 | L426 | i9291 | Y | L10 | L19 | L426 | i9292 | Y | L10 | L569 | L426 |
| i9293 | Y | L11 | L18 | L426 | i9294 | Y | L11 | L19 | L426 | i9295 | Y | L11 | L569 | L426 |
| i9296 | Y | L20 | L18 | L426 | i9297 | Y | L20 | L19 | L426 | i9298 | Y | L20 | L569 | L426 |
| i9299 | Y | L21 | L18 | L426 | i9300 | Y | L21 | L19 | L426 | i9301 | Y | L21 | L569 | L426 |
| i9302 | Y | L22 | L18 | L426 | i9303 | Y | L22 | L19 | L426 | i9304 | Y | L22 | L569 | L426 |
| i9305 | Y | L23 | L18 | L426 | i9306 | Y | L23 | L19 | L426 | i9307 | Y | L23 | L569 | L426 |
| i9308 | Y | L24 | L18 | L426 | i9309 | Y | L24 | L19 | L426 | i9310 | Y | L24 | L569 | L426 |
| i9311 | Y | L25 | L18 | L426 | i9312 | Y | L25 | L19 | L426 | i9313 | Y | L25 | L569 | L426 |
| i9314 | Y | L26 | L18 | L426 | i9315 | Y | L26 | L19 | L426 | i9316 | Y | L26 | L569 | L426 |
| i9317 | Y | L27 | L18 | L426 | i9318 | Y | L27 | L19 | L426 | i9319 | Y | L27 | L569 | L426 |
| i9320 | Y | L28 | L18 | L426 | i9321 | Y | L28 | L19 | L426 | i9322 | Y | L28 | L569 | L426 |
| i9323 | Y | L179 | L18 | L426 | i9324 | Y | L179 | L19 | L426 | i9325 | Y | L179 | L569 | L426 |
| i9326 | Y | L180 | L18 | L426 | i9327 | Y | L180 | L19 | L426 | i9328 | Y | L180 | L569 | L426 |
| i9329 | Y | L196 | L18 | L426 | i9330 | Y | L196 | L19 | L426 | i9331 | Y | L196 | L569 | L426 |
| i9332 | Y | L201 | L18 | L426 | i9333 | Y | L201 | L19 | L426 | i9334 | Y | L201 | L569 | L426 |
| i9335 | Y | L206 | L18 | L426 | i9336 | Y | L206 | L19 | L426 | i9337 | Y | L206 | L569 | L426 |
| i9338 | Y | L211 | L18 | L426 | i9339 | Y | L211 | L19 | L426 | i9340 | Y | L211 | L569 | L426 |
| i9341 | Y | L212 | L18 | L426 | i9342 | Y | L212 | L19 | L426 | i9343 | Y | L212 | L569 | L426 |
| i9344 | Y | L215 | L18 | L426 | i9345 | Y | L215 | L19 | L426 | i9346 | Y | L215 | L569 | L426 |
| i9347 | Y | L217 | L18 | L426 | i9348 | Y | L217 | L19 | L426 | i9349 | Y | L217 | L569 | L426 |
| i9350 | Y | L220 | L18 | L426 | i9351 | Y | L220 | L19 | L426 | i9352 | Y | L220 | L569 | L426 |
| i9353 | Y | L10 | L12 | L427 | i9354 | Y | L10 | L13 | L427 | i9355 | Y | L10 | L14 | L427 |
| i9356 | Y | L11 | L12 | L427 | i9357 | Y | L11 | L13 | L427 | i9358 | Y | L11 | L14 | L427 |
| i9359 | Y | L20 | L12 | L427 | i9360 | Y | L20 | L13 | L427 | i9361 | Y | L20 | L14 | L427 |
| i9362 | Y | L21 | L12 | L427 | i9363 | Y | L21 | L13 | L427 | i9364 | Y | L21 | L14 | L427 |
| i9365 | Y | L22 | L12 | L427 | i9366 | Y | L22 | L13 | L427 | i9367 | Y | L22 | L14 | L427 |
| i9368 | Y | L23 | L12 | L427 | i9369 | Y | L23 | L13 | L427 | i9370 | Y | L23 | L14 | L427 |
| i9371 | Y | L24 | L12 | L427 | i9372 | Y | L24 | L13 | L427 | i9373 | Y | L24 | L14 | L427 |
| i9374 | Y | L25 | L12 | L427 | i9375 | Y | L25 | L13 | L427 | i9376 | Y | L25 | L14 | L427 |
| i9377 | Y | L26 | L12 | L427 | i9378 | Y | L26 | L13 | L427 | i9379 | Y | L26 | L14 | L427 |
| i9380 | Y | L27 | L12 | L427 | i9381 | Y | L27 | L13 | L427 | i9382 | Y | L27 | L14 | L427 |
| i9383 | Y | L28 | L12 | L427 | i9384 | Y | L28 | L13 | L427 | i9385 | Y | L28 | L14 | L427 |
| i9386 | Y | L179 | L12 | L427 | i9387 | Y | L179 | L13 | L427 | i9388 | Y | L179 | L14 | L427 |
| i9389 | Y | L180 | L12 | L427 | i9390 | Y | L180 | L13 | L427 | i9391 | Y | L180 | L14 | L427 |
| i9392 | Y | L196 | L12 | L427 | i9393 | Y | L196 | L13 | L427 | i9394 | Y | L196 | L14 | L427 |
| i9395 | Y | L201 | L12 | L427 | i9396 | Y | L201 | L13 | L427 | i9397 | Y | L201 | L14 | L427 |
| i9398 | Y | L206 | L12 | L427 | i9399 | Y | L206 | L13 | L427 | i9400 | Y | L206 | L14 | L427 |
| i9401 | Y | L211 | L12 | L427 | i9402 | Y | L211 | L13 | L427 | i9403 | Y | L211 | L14 | L427 |
| i9404 | Y | L212 | L12 | L427 | i9405 | Y | L212 | L13 | L427 | i9406 | Y | L212 | L14 | L427 |
| i9407 | Y | L215 | L12 | L427 | i9408 | Y | L215 | L13 | L427 | i9409 | Y | L215 | L14 | L427 |
| i9410 | Y | L217 | L12 | L427 | i9411 | Y | L217 | L13 | L427 | i9412 | Y | L217 | L14 | L427 |
| i9413 | Y | L220 | L12 | L427 | i9414 | Y | L220 | L13 | L427 | i9415 | Y | L220 | L14 | L427 |
| i9416 | Y | L10 | L15 | L427 | i9417 | Y | L10 | L16 | L427 | i9418 | Y | L10 | L17 | L427 |

TABLE 1-continued

Compositions "i1" to "i9919"

| | | | | | | | | | | | |
|---|---|---|---|---|---|---|---|---|---|---|---|
| i9419 | Y | L11 | L15 | L427 | i9420 | Y | L11 | L16 | L427 | i9421 | Y | L11 | L17 | L427 |
| i9422 | Y | L20 | L15 | L427 | i9423 | Y | L20 | L16 | L427 | i9424 | Y | L20 | L17 | L427 |
| i9425 | Y | L21 | L15 | L427 | i9426 | Y | L21 | L16 | L427 | i9427 | Y | L21 | L17 | L427 |
| i9428 | Y | L22 | L15 | L427 | i9429 | Y | L22 | L16 | L427 | i9430 | Y | L22 | L17 | L427 |
| i9431 | Y | L23 | L15 | L427 | i9432 | Y | L23 | L16 | L427 | i9433 | Y | L23 | L17 | L427 |
| i9434 | Y | L24 | L15 | L427 | i9435 | Y | L24 | L16 | L427 | i9436 | Y | L24 | L17 | L427 |
| i9437 | Y | L25 | L15 | L427 | i9438 | Y | L25 | L16 | L427 | i9439 | Y | L25 | L17 | L427 |
| i9440 | Y | L26 | L15 | L427 | i9441 | Y | L26 | L16 | L427 | i9442 | Y | L26 | L17 | L427 |
| i9443 | Y | L27 | L15 | L427 | i9444 | Y | L27 | L16 | L427 | i9445 | Y | L27 | L17 | L427 |
| i9446 | Y | L28 | L15 | L427 | i9447 | Y | L28 | L16 | L427 | i9448 | Y | L28 | L17 | L427 |
| i9449 | Y | L179 | L15 | L427 | i9450 | Y | L179 | L16 | L427 | i9451 | Y | L179 | L17 | L427 |
| i9452 | Y | L180 | L15 | L427 | i9453 | Y | L180 | L16 | L427 | i9454 | Y | L180 | L17 | L427 |
| i9455 | Y | L196 | L15 | L427 | i9456 | Y | L196 | L16 | L427 | i9457 | Y | L196 | L17 | L427 |
| i9458 | Y | L201 | L15 | L427 | i9459 | Y | L201 | L16 | L427 | i9460 | Y | L201 | L17 | L427 |
| i9461 | Y | L206 | L15 | L427 | i9462 | Y | L206 | L16 | L427 | i9463 | Y | L206 | L17 | L427 |
| i9464 | Y | L211 | L15 | L427 | i9465 | Y | L211 | L16 | L427 | i9466 | Y | L211 | L17 | L427 |
| i9467 | Y | L212 | L15 | L427 | i9468 | Y | L212 | L16 | L427 | i9469 | Y | L212 | L17 | L427 |
| i9470 | Y | L215 | L15 | L427 | i9471 | Y | L215 | L16 | L427 | i9472 | Y | L215 | L17 | L427 |
| i9473 | Y | L217 | L15 | L427 | i9474 | Y | L217 | L16 | L427 | i9475 | Y | L217 | L17 | L427 |
| i9476 | Y | L220 | L15 | L427 | i9477 | Y | L220 | L16 | L427 | i9478 | Y | L220 | L17 | L427 |
| i9479 | Y | L10 | L18 | L427 | i9480 | Y | L10 | L19 | L427 | i9481 | Y | L10 | L569 | L427 |
| i9482 | Y | L11 | L18 | L427 | i9483 | Y | L11 | L19 | L427 | i9484 | Y | L11 | L569 | L427 |
| i9485 | Y | L20 | L18 | L427 | i9486 | Y | L20 | L19 | L427 | i9487 | Y | L20 | L569 | L427 |
| i9488 | Y | L21 | L18 | L427 | i9489 | Y | L21 | L19 | L427 | i9490 | Y | L21 | L569 | L427 |
| i9491 | Y | L22 | L18 | L427 | i9492 | Y | L22 | L19 | L427 | i9493 | Y | L22 | L569 | L427 |
| i9494 | Y | L23 | L18 | L427 | i9495 | Y | L23 | L19 | L427 | i9496 | Y | L23 | L569 | L427 |
| i9497 | Y | L24 | L18 | L427 | i9498 | Y | L24 | L19 | L427 | i9499 | Y | L24 | L569 | L427 |
| i9500 | Y | L25 | L18 | L427 | i9501 | Y | L25 | L19 | L427 | i9502 | Y | L25 | L569 | L427 |
| i9503 | Y | L26 | L18 | L427 | i9504 | Y | L26 | L19 | L427 | i9505 | Y | L26 | L569 | L427 |
| i9506 | Y | L27 | L18 | L427 | i9507 | Y | L27 | L19 | L427 | i9508 | Y | L27 | L569 | L427 |
| i9509 | Y | L28 | L18 | L427 | i9510 | Y | L28 | L19 | L427 | i9511 | Y | L28 | L569 | L427 |
| i9512 | Y | L179 | L18 | L427 | i9513 | Y | L179 | L19 | L427 | i9514 | Y | L179 | L569 | L427 |
| i9515 | Y | L180 | L18 | L427 | i9516 | Y | L180 | L19 | L427 | i9517 | Y | L180 | L569 | L427 |
| i9518 | Y | L196 | L18 | L427 | i9519 | Y | L196 | L19 | L427 | i9520 | Y | L196 | L569 | L427 |
| i9521 | Y | L201 | L18 | L427 | i9522 | Y | L201 | L19 | L427 | i9523 | Y | L201 | L569 | L427 |
| i9524 | Y | L206 | L18 | L427 | i9525 | Y | L206 | L19 | L427 | i9526 | Y | L206 | L569 | L427 |
| i9527 | Y | L211 | L18 | L427 | i9528 | Y | L211 | L19 | L427 | i9529 | Y | L211 | L569 | L427 |
| i9530 | Y | L212 | L18 | L427 | i9531 | Y | L212 | L19 | L427 | i9532 | Y | L212 | L569 | L427 |
| i9533 | Y | L215 | L18 | L427 | i9534 | Y | L215 | L19 | L427 | i9535 | Y | L215 | L569 | L427 |
| i9536 | Y | L217 | L18 | L427 | i9537 | Y | L217 | L19 | L427 | i9538 | Y | L217 | L569 | L427 |
| i9539 | Y | L220 | L18 | L427 | i9540 | Y | L220 | L19 | L427 | i9541 | Y | L220 | L569 | L427 |
| i9542 | Y | L10 | L12 | L428 | i9543 | Y | L10 | L13 | L428 | i9544 | Y | L10 | L14 | L428 |
| i9545 | Y | L11 | L12 | L428 | i9546 | Y | L11 | L13 | L428 | i9547 | Y | L11 | L14 | L428 |
| i9548 | Y | L20 | L12 | L428 | i9549 | Y | L20 | L13 | L428 | i9550 | Y | L20 | L14 | L428 |
| i9551 | Y | L21 | L12 | L428 | i9552 | Y | L21 | L13 | L428 | i9553 | Y | L21 | L14 | L428 |
| i9554 | Y | L22 | L12 | L428 | i9555 | Y | L22 | L13 | L428 | i9556 | Y | L22 | L14 | L428 |
| i9557 | Y | L23 | L12 | L428 | i9558 | Y | L23 | L13 | L428 | i9559 | Y | L23 | L14 | L428 |
| i9560 | Y | L24 | L12 | L428 | i9561 | Y | L24 | L13 | L428 | i9562 | Y | L24 | L14 | L428 |
| i9563 | Y | L25 | L12 | L428 | i9564 | Y | L25 | L13 | L428 | i9565 | Y | L25 | L14 | L428 |
| i9566 | Y | L26 | L12 | L428 | i9567 | Y | L26 | L13 | L428 | i9568 | Y | L26 | L14 | L428 |
| i9569 | Y | L27 | L12 | L428 | i9570 | Y | L27 | L13 | L428 | i9571 | Y | L27 | L14 | L428 |
| i9572 | Y | L28 | L12 | L428 | i9573 | Y | L28 | L13 | L428 | i9574 | Y | L28 | L14 | L428 |
| i9575 | Y | L179 | L12 | L428 | i9576 | Y | L179 | L13 | L428 | i9577 | Y | L179 | L14 | L428 |
| i9578 | Y | L180 | L12 | L428 | i9579 | Y | L180 | L13 | L428 | i9580 | Y | L180 | L14 | L428 |
| i9581 | Y | L196 | L12 | L428 | i9582 | Y | L196 | L13 | L428 | i9583 | Y | L196 | L14 | L428 |
| i9584 | Y | L201 | L12 | L428 | i9585 | Y | L201 | L13 | L428 | i9586 | Y | L201 | L14 | L428 |
| i9587 | Y | L206 | L12 | L428 | i9588 | Y | L206 | L13 | L428 | i9589 | Y | L206 | L14 | L428 |
| i9590 | Y | L211 | L12 | L428 | i9591 | Y | L211 | L13 | L428 | i9592 | Y | L211 | L14 | L428 |
| i9593 | Y | L212 | L12 | L428 | i9594 | Y | L212 | L13 | L428 | i9595 | Y | L212 | L14 | L428 |
| i9596 | Y | L215 | L12 | L428 | i9597 | Y | L215 | L13 | L428 | i9598 | Y | L215 | L14 | L428 |
| i9599 | Y | L217 | L12 | L428 | i9600 | Y | L217 | L13 | L428 | i9601 | Y | L217 | L14 | L428 |
| i9602 | Y | L220 | L12 | L428 | i9603 | Y | L220 | L13 | L428 | i9604 | Y | L220 | L14 | L428 |
| i9605 | Y | L10 | L15 | L428 | i9606 | Y | L10 | L16 | L428 | i9607 | Y | L10 | L17 | L428 |
| i9608 | Y | L11 | L15 | L428 | i9609 | Y | L11 | L16 | L428 | i9610 | Y | L11 | L17 | L428 |
| i9611 | Y | L20 | L15 | L428 | i9612 | Y | L20 | L16 | L428 | i9613 | Y | L20 | L17 | L428 |
| i9614 | Y | L21 | L15 | L428 | i9615 | Y | L21 | L16 | L428 | i9616 | Y | L21 | L17 | L428 |
| i9617 | Y | L22 | L15 | L428 | i9618 | Y | L22 | L16 | L428 | i9619 | Y | L22 | L17 | L428 |
| i9620 | Y | L23 | L15 | L428 | i9621 | Y | L23 | L16 | L428 | i9622 | Y | L23 | L17 | L428 |
| i9623 | Y | L24 | L15 | L428 | i9624 | Y | L24 | L16 | L428 | i9625 | Y | L24 | L17 | L428 |
| i9626 | Y | L25 | L15 | L428 | i9627 | Y | L25 | L16 | L428 | i9628 | Y | L25 | L17 | L428 |
| i9629 | Y | L26 | L15 | L428 | i9630 | Y | L26 | L16 | L428 | i9631 | Y | L26 | L17 | L428 |
| i9632 | Y | L27 | L15 | L428 | i9633 | Y | L27 | L16 | L428 | i9634 | Y | L27 | L17 | L428 |
| i9635 | Y | L28 | L15 | L428 | i9636 | Y | L28 | L16 | L428 | i9637 | Y | L28 | L17 | L428 |
| i9638 | Y | L179 | L15 | L428 | i9639 | Y | L179 | L16 | L428 | i9640 | Y | L179 | L17 | L428 |
| i9641 | Y | L180 | L15 | L428 | i9642 | Y | L180 | L16 | L428 | i9643 | Y | L180 | L17 | L428 |
| i9644 | Y | L196 | L15 | L428 | i9645 | Y | L196 | L16 | L428 | i9646 | Y | L196 | L17 | L428 |
| i9647 | Y | L201 | L15 | L428 | i9648 | Y | L201 | L16 | L428 | i9649 | Y | L201 | L17 | L428 |
| i9650 | Y | L206 | L15 | L428 | i9651 | Y | L206 | L16 | L428 | i9652 | Y | L206 | L17 | L428 |

TABLE 1-continued

Compositions "i1" to "i9919"

| | | | | | | | | | | | |
|---|---|---|---|---|---|---|---|---|---|---|---|
| i9653 | Y | L211 | L15 | L428 | i9654 | Y | L211 | L16 | L428 | i9655 | Y | L211 | L17 | L428 |
| i9656 | Y | L212 | L15 | L428 | i9657 | Y | L212 | L16 | L428 | i9658 | Y | L212 | L17 | L428 |
| i9659 | Y | L215 | L15 | L428 | i9660 | Y | L215 | L16 | L428 | i9661 | Y | L215 | L17 | L428 |
| i9662 | Y | L217 | L15 | L428 | i9663 | Y | L217 | L16 | L428 | i9664 | Y | L217 | L17 | L428 |
| i9665 | Y | L220 | L15 | L428 | i9666 | Y | L220 | L16 | L428 | i9667 | Y | L220 | L17 | L428 |
| i9668 | Y | L10 | L18 | L428 | i9669 | Y | L10 | L19 | L428 | i9670 | Y | L10 | L569 | L428 |
| i9671 | Y | L11 | L18 | L428 | i9672 | Y | L11 | L19 | L428 | i9673 | Y | L11 | L569 | L428 |
| i9674 | Y | L20 | L18 | L428 | i9675 | Y | L20 | L19 | L428 | i9676 | Y | L20 | L569 | L428 |
| i9677 | Y | L21 | L18 | L428 | i9678 | Y | L21 | L19 | L428 | i9679 | Y | L21 | L569 | L428 |
| i9680 | Y | L22 | L18 | L428 | i9681 | Y | L22 | L19 | L428 | i9682 | Y | L22 | L569 | L428 |
| i9683 | Y | L23 | L18 | L428 | i9684 | Y | L23 | L19 | L428 | i9685 | Y | L23 | L569 | L428 |
| i9686 | Y | L24 | L18 | L428 | i9687 | Y | L24 | L19 | L428 | i9688 | Y | L24 | L569 | L428 |
| i9689 | Y | L25 | L18 | L428 | i9690 | Y | L25 | L19 | L428 | i9691 | Y | L25 | L569 | L428 |
| i9692 | Y | L26 | L18 | L428 | i9693 | Y | L26 | L19 | L428 | i9694 | Y | L26 | L569 | L428 |
| i9695 | Y | L27 | L18 | L428 | i9696 | Y | L27 | L19 | L428 | i9697 | Y | L27 | L569 | L428 |
| i9698 | Y | L28 | L18 | L428 | i9699 | Y | L28 | L19 | L428 | i9700 | Y | L28 | L569 | L428 |
| i9701 | Y | L179 | L18 | L428 | i9702 | Y | L179 | L19 | L428 | i9703 | Y | L179 | L569 | L428 |
| i9704 | Y | L180 | L18 | L428 | i9705 | Y | L180 | L19 | L428 | i9706 | Y | L180 | L569 | L428 |
| i9707 | Y | L196 | L18 | L428 | i9708 | Y | L196 | L19 | L428 | i9709 | Y | L196 | L569 | L428 |
| i9710 | Y | L201 | L18 | L428 | i9711 | Y | L201 | L19 | L428 | i9712 | Y | L201 | L569 | L428 |
| i9713 | Y | L206 | L18 | L428 | i9714 | Y | L206 | L19 | L428 | i9715 | Y | L206 | L569 | L428 |
| i9716 | Y | L211 | L18 | L428 | i9717 | Y | L211 | L19 | L428 | i9718 | Y | L211 | L569 | L428 |
| i9719 | Y | L212 | L18 | L428 | i9720 | Y | L212 | L19 | L428 | i9721 | Y | L212 | L569 | L428 |
| i9722 | Y | L215 | L18 | L428 | i9723 | Y | L215 | L19 | L428 | i9724 | Y | L215 | L569 | L428 |
| i9725 | Y | L217 | L18 | L428 | i9726 | Y | L217 | L19 | L428 | i9727 | Y | L217 | L569 | L428 |
| i9728 | Y | L220 | L18 | L428 | i9729 | Y | L220 | L19 | L428 | i9730 | Y | L220 | L569 | L428 |
| i9731 | Y | L10 | L12 | L430 | i9732 | Y | L10 | L13 | L430 | i9733 | Y | L10 | L14 | L430 |
| i9734 | Y | L11 | L12 | L430 | i9735 | Y | L11 | L13 | L430 | i9736 | Y | L11 | L14 | L430 |
| i9737 | Y | L20 | L12 | L430 | i9738 | Y | L20 | L13 | L430 | i9739 | Y | L20 | L14 | L430 |
| i9740 | Y | L21 | L12 | L430 | i9741 | Y | L21 | L13 | L430 | i9742 | Y | L21 | L14 | L430 |
| i9743 | Y | L22 | L12 | L430 | i9744 | Y | L22 | L13 | L430 | i9745 | Y | L22 | L14 | L430 |
| i9746 | Y | L23 | L12 | L430 | i9747 | Y | L23 | L13 | L430 | i9748 | Y | L23 | L14 | L430 |
| i9749 | Y | L24 | L12 | L430 | i9750 | Y | L24 | L13 | L430 | i9751 | Y | L24 | L14 | L430 |
| i9752 | Y | L25 | L12 | L430 | i9753 | Y | L25 | L13 | L430 | i9754 | Y | L25 | L14 | L430 |
| i9755 | Y | L26 | L12 | L430 | i9756 | Y | L26 | L13 | L430 | i9757 | Y | L26 | L14 | L430 |
| i9758 | Y | L27 | L12 | L430 | i9759 | Y | L27 | L13 | L430 | i9760 | Y | L27 | L14 | L430 |
| i9761 | Y | L28 | L12 | L430 | i9762 | Y | L28 | L13 | L430 | i9763 | Y | L28 | L14 | L430 |
| i9764 | Y | L179 | L12 | L430 | i9765 | Y | L179 | L13 | L430 | i9766 | Y | L179 | L14 | L430 |
| i9767 | Y | L180 | L12 | L430 | i9768 | Y | L180 | L13 | L430 | i9769 | Y | L180 | L14 | L430 |
| i9770 | Y | L196 | L12 | L430 | i9771 | Y | L196 | L13 | L430 | i9772 | Y | L196 | L14 | L430 |
| i9773 | Y | L201 | L12 | L430 | i9774 | Y | L201 | L13 | L430 | i9775 | Y | L201 | L14 | L430 |
| i9776 | Y | L206 | L12 | L430 | i9777 | Y | L206 | L13 | L430 | i9778 | Y | L206 | L14 | L430 |
| i9779 | Y | L211 | L12 | L430 | i9780 | Y | L211 | L13 | L430 | i9781 | Y | L211 | L14 | L430 |
| i9782 | Y | L212 | L12 | L430 | i9783 | Y | L212 | L13 | L430 | i9784 | Y | L212 | L14 | L430 |
| i9785 | Y | L215 | L12 | L430 | i9786 | Y | L215 | L13 | L430 | i9787 | Y | L215 | L14 | L430 |
| i9788 | Y | L217 | L12 | L430 | i9789 | Y | L217 | L13 | L430 | i9790 | Y | L217 | L14 | L430 |
| i9791 | Y | L220 | L12 | L430 | i9792 | Y | L220 | L13 | L430 | i9793 | Y | L220 | L14 | L430 |
| i9794 | Y | L10 | L15 | L430 | i9795 | Y | L10 | L16 | L430 | i9796 | Y | L10 | L17 | L430 |
| i9797 | Y | L11 | L15 | L430 | i9798 | Y | L11 | L16 | L430 | i9799 | Y | L11 | L17 | L430 |
| i9800 | Y | L20 | L15 | L430 | i9801 | Y | L20 | L16 | L430 | i9802 | Y | L20 | L17 | L430 |
| i9803 | Y | L21 | L15 | L430 | i9804 | Y | L21 | L16 | L430 | i9805 | Y | L21 | L17 | L430 |
| i9806 | Y | L22 | L15 | L430 | i9807 | Y | L22 | L16 | L430 | i9808 | Y | L22 | L17 | L430 |
| i9809 | Y | L23 | L15 | L430 | i9810 | Y | L23 | L16 | L430 | i9811 | Y | L23 | L17 | L430 |
| i9812 | Y | L24 | L15 | L430 | i9813 | Y | L24 | L16 | L430 | i9814 | Y | L24 | L17 | L430 |
| i9815 | Y | L25 | L15 | L430 | i9816 | Y | L25 | L16 | L430 | i9817 | Y | L25 | L17 | L430 |
| i9818 | Y | L26 | L15 | L430 | i9819 | Y | L26 | L16 | L430 | i9820 | Y | L26 | L17 | L430 |
| i9821 | Y | L27 | L15 | L430 | i9822 | Y | L27 | L16 | L430 | i9823 | Y | L27 | L17 | L430 |
| i9824 | Y | L28 | L15 | L430 | i9825 | Y | L28 | L16 | L430 | i9826 | Y | L28 | L17 | L430 |
| i9827 | Y | L179 | L15 | L430 | i9828 | Y | L179 | L16 | L430 | i9829 | Y | L179 | L17 | L430 |
| i9830 | Y | L180 | L15 | L430 | i9831 | Y | L180 | L16 | L430 | i9832 | Y | L180 | L17 | L430 |
| i9833 | Y | L196 | L15 | L430 | i9834 | Y | L196 | L16 | L430 | i9835 | Y | L196 | L17 | L430 |
| i9836 | Y | L201 | L15 | L430 | i9837 | Y | L201 | L16 | L430 | i9838 | Y | L201 | L17 | L430 |
| i9839 | Y | L206 | L15 | L430 | i9840 | Y | L206 | L16 | L430 | i9841 | Y | L206 | L17 | L430 |
| i9842 | Y | L211 | L15 | L430 | i9843 | Y | L211 | L16 | L430 | i9844 | Y | L211 | L17 | L430 |
| i9845 | Y | L212 | L15 | L430 | i9846 | Y | L212 | L16 | L430 | i9847 | Y | L212 | L17 | L430 |
| i9848 | Y | L215 | L15 | L430 | i9849 | Y | L215 | L16 | L430 | i9850 | Y | L215 | L17 | L430 |
| i9851 | Y | L217 | L15 | L430 | i9852 | Y | L217 | L16 | L430 | i9853 | Y | L217 | L17 | L430 |
| i9854 | Y | L220 | L15 | L430 | i9855 | Y | L220 | L16 | L430 | i9856 | Y | L220 | L17 | L430 |
| i9857 | Y | L10 | L18 | L430 | i9858 | Y | L10 | L19 | L430 | i9859 | Y | L10 | L569 | L430 |
| i9860 | Y | L11 | L18 | L430 | i9861 | Y | L11 | L19 | L430 | i9862 | Y | L11 | L569 | L430 |
| i9863 | Y | L20 | L18 | L430 | i9864 | Y | L20 | L19 | L430 | i9865 | Y | L20 | L569 | L430 |
| i9866 | Y | L21 | L18 | L430 | i9867 | Y | L21 | L19 | L430 | i9868 | Y | L21 | L569 | L430 |
| i9869 | Y | L22 | L18 | L430 | i9870 | Y | L22 | L19 | L430 | i9871 | Y | L22 | L569 | L430 |
| i9872 | Y | L23 | L18 | L430 | i9873 | Y | L23 | L19 | L430 | i9874 | Y | L23 | L569 | L430 |
| i9875 | Y | L24 | L18 | L430 | i9876 | Y | L24 | L19 | L430 | i9877 | Y | L24 | L569 | L430 |
| i9878 | Y | L25 | L18 | L430 | i9879 | Y | L25 | L19 | L430 | i9880 | Y | L25 | L569 | L430 |
| i9881 | Y | L26 | L18 | L430 | i9882 | Y | L26 | L19 | L430 | i9883 | Y | L26 | L569 | L430 |
| i9884 | Y | L27 | L18 | L430 | i9885 | Y | L27 | L19 | L430 | i9886 | Y | L27 | L569 | L430 |

TABLE 1-continued

Compositions "i1" to "i9919"

| | | | | | | | | | | | |
|---|---|---|---|---|---|---|---|---|---|---|---|
| i9887 | Y | L28 | L18 | L430 | i9888 | Y | L28 | L19 | L430 | i9889 Y L28 L569 L430 |
| i9890 | Y | L179 | L18 | L430 | i9891 | Y | L179 | L19 | L430 | i9892 Y L179 L569 L430 |
| i9893 | Y | L180 | L18 | L430 | i9894 | Y | L180 | L19 | L430 | i9895 Y L180 L569 L430 |
| i9896 | Y | L196 | L18 | L430 | i9897 | Y | L196 | L19 | L430 | i9898 Y L196 L569 L430 |
| i9899 | Y | L201 | L18 | L430 | i9900 | Y | L201 | L19 | L430 | i9901 Y L201 L569 L430 |
| i9902 | Y | L206 | L18 | L430 | i9903 | Y | L206 | L19 | L430 | i9904 Y L206 L569 L430 |
| i9905 | Y | L211 | L18 | L430 | i9906 | Y | L211 | L19 | L430 | i9907 Y L211 L569 L430 |
| i9908 | Y | L212 | L18 | L430 | i9909 | Y | L212 | L19 | L430 | i9910 Y L212 L569 L430 |
| i9911 | Y | L215 | L18 | L430 | i9912 | Y | L215 | L19 | L430 | i9913 Y L215 L569 L430 |
| i9914 | Y | L217 | L18 | L430 | i9915 | Y | L217 | L19 | L430 | i9916 Y L217 L569 L430 |
| i9917 | Y | L220 | L18 | L430 | i9918 | Y | L220 | L19 | L430 | i9919 Y L220 L569 L430 |

The following abbreviations are used for the examples and especially for Table 2:

CpEx=comparative example
DEIPA=N,N-Bis(2-hydroxyethyl)-isopropanolamine
DGBE=Diethylene glycol monobutyl ether
DML=N,N-dimethyllactamide
ExNo.=Example no.
InvEx=example of the invention
LTM=technical mixture (with a 100% concentration of NxPT) containing 25% NPPT and 75% NBPT
LEO=polytriethanolamine with a weight average molecular weight of 8,000 g/mol as measured by GPC (viscosity 4000 mPa·s, pH value 10.5, charge density (cationic) 5 meq/g (Dry Substance), total amine content 420 mg KOH/g, density 1.13 g/cm$^2$), prepared through reaction of polyethyleneimine with epoxyethane (=ethylene oxide)
LFG=polyethyleneimine with a weight average molecular weight of 800 g/mol as measured by GPC (dry substance, at pH 4.5)
LGA=polyethyleneimine (free of water) with a weight average molecular weight of 1300 g/mol as measured by GPC (dry substance, at pH 4.5)
LPEI=linear polyethyleneimine (L612)
NxPT=Mixture (A) comprising NBPT and NPPT (the content of NxPT is the sum of the content of NBPT and NPPT)
PEIEO=PEI600 (=polyethyleneimine with a weight average molecular weight of 600 g/mol as measured by GPC) plus 0.9 EO (ethylene oxide) per NH unit, free of water, synthesis procedure see WO2009/060059.
PEIPO=PEI600 plus 0.9 PO (propylene oxide) per NH unit, free of water, synthesis procedure see WO2009/060059.
PG=propylene glycol
TEOA=triethanolamine
TGBE=Triethylene glycol monobutyl ether The examples which follow illustrate the invention without restricting it.

Preparation of the Formulations

According to the ratios and components as specified in Table 2, all components were mixed, and the resulting mixture was stirred until complete dissolution of the solid and analyzed for the content of NBPT, NPPT, NxPT (by HPLC), viscosity, dissolution (2%) in water and pH.

For example, in case of Example no. 8, the technical mixture LTM (25% pure NxPT) was mixed with 15% DMSO, 5% LFG, and ad100% propylene glycol. The mixture was stirred until complete dissolution of the solid and analyzed for NxPT content (by HPLC), viscosity at 20° C. with a shear rate of 100 sec-1, dissolution (2%) in water and pH.

According to the ratios and components specified in Table 2, in a first step NBPT+NPPT resp. NxPT are completely dissolved in propylene glycol. Optional heating (e.g. to 50° C.) can accelerate the dissolution of the actives. Following the other specified components are added under stirring. The final formulation is analyzed for the content of NBPT, NPPT, NxPT (by HPLC), viscosity at 20° C. with a shear rate of 100 sec-1, dissolution (2%) in water and pH.

Formulation Stability

The mixture of each example (e.g. Example no. 8) was stored in closed bottles for 14 days at 54° C. (referred to as heat stability test in the following) and then analyzed for the content of NxPT. The storage stability in % was calculated as difference between the content before and after storage.

The mixture of each example (e.g. Example no. 8) was also stored in closed bottles for 14 days at different temperatures (−10° C. to 20° C.) (referred to as cold stability test in the following). After 7 days each sample was seeded with few crystals of NBPT and NPPT and stored for another 7 days at the same temperature. Then the solution was visually evaluated if further crystallization occurred. "(+)" means that no crystals were seen, and "(−)" means that crystals have been seen in the visual evaluation.

Coating of Urea

Example 1.1

500 g granulated urea was charged to a rotating drum (Type Hege 11) and 2 g of the formulation of each example (e.g. Example no. 8) was sprayed on the urea using a rotating disc. The homogeneous coated urea was discharged after 1 min and analyzed for the content of NBPT, NPPT, NxPT (by HPLC).

Stability on Urea

The coated urea sample of 300 g was stored in a petri dish for 4 weeks at 50% humidity at 40° C. in a climate chamber. For analysis the sample was homogenized and analyzed for the content of NBPT, NPPT, NxPT (by HPLC). The stability on urea in % was calculated as difference between the content before and after storage.

The content of NxPT measured by HPLC measurement is always the sum of the both components NBPT and NBPT.

Viscosity was measured at the undiluted formulation with a cone-plate rheometer AR 2000ex (TA Instruments) at shear rate of 100 s$^{-1}$ and 20° C.

The pH value was measured at 2% concentration in CIPAC water D.

All examples of the inventions are liquid, clear compositions which are either colourless or yellow.

TABLE 2

Examples of the compositions of the invention and of comparative compositions, and data on their viscosity, pH value, cold stability, formulation stability and stability on urea

| Formulation | ExNo. | InvEx 1 | InvEx 2 | InvEx 3 | InvEx 4 | InvEx 5 | CpEx 6 | CpEx 7 |
|---|---|---|---|---|---|---|---|---|
| Active ingredient | [%] | 25% LTM | 25% LTM | 25% LTM | 25% LTM | 25% LTM | 30% NBPT | 20% NBPT |
| Formulation | Solvent (ad 100%) | PG | PG | PG | PG | PG | 30%-60% PG | PG |
| Formulation | Cosolvent | 20% DMSO | 20% DMSO | 20% DMSO | 25% DML | 25% DML | 15%-40% TGBE and 1%-5% DGBE | 30% DMSO |
| Formulation | Polymers | 6.25% LFG | 6.25% LFG | 6.25% LFG | 6.25% LFG | 6.25% LFG | | |
| Formulation | Amine | | 10% TEOA | 10% DEIPA | | 10% DEIPA | | |
| Formulation | Colorant | 1% | 1% | 1% | 1% | 1% | | |
| Viscosity | [mPa*s] | 53 | 70 | 69 | 77 | 103 | 15 | 21 |
| pH | 1% | 10.7 | 10.7 | 10.7 | 10.7 | 10.7 | 7.5 | 9 |
| Cold stability 1 w/1 w seeded | 20° C. | (+) | (+) | (+) | (+) | (+) | (+) | (+) |
| | 15° C. | (+) | (+) | (+) | (+) | (+) | (+) | (+) |
| | 10° C. | (+) | (+) | (+) | (+) | (+) | (+) | (+) |
| | 5° C. | (+) | (+) | (+) | (+) | (+) | (+) | (+) |
| | 0° C. | (+) | (+) | (+) | (+) | (+) | (+) | (+) |
| | −5° C. | (+) | (+) | (+) | (+) | (+) | (+) | (+) |
| | −10° C. | (+) | (+) | (+) | (+) | (+) | (+) | (+) |
| Formulation stability [%] | 14 d/54° C. | 99.4 | 97.70 | 99.7 | 99.0 | 99.9 | 98.5 | 98.10 |
| Stability on urea [%] | 4 w/40° C./50% rH | 78 | 86 | 76 | 80 | 74 | 46 | 54 |

| Formulation | ExNo. | InvEx 8 | InvEx 9 | InvEx 10 | InvEx 11 | InvEx 12 | InvEx 13 | InvEx 14 |
|---|---|---|---|---|---|---|---|---|
| Active ingredient | [%] | 25% LTM | 25% LTM | 25% LTM | 25% LTM | 25% LTM | 25% LTM | 25% LTM |
| Formulation | Solvent (ad 100%) | PG | PG | PG | PG | PG | PG | PG |
| Formulation | Cosolvent | 15% DMSO | 15% DMSO | 25% DML | 15% DMSO | 15% DMSO | 15% DMSO | 15% DMSO |
| Formulation | Polymers | 5% LFG | 10% LFG | 5% LFG | 5% LEO | 15% LEO | 20% LEO | 10% LEO |
| Viscosity | [mPa*s] | 52 | 81 | 62 | 42 | 61 | 78 | 49 |
| pH | 1% | 10.5 | 10.7 | 10.4 | 9.2 | 9.5 | 9.6 | 9.4 |
| Cold stability 1 w/1 w seeded | 20° C. | (+) | (+) | (+) | (+) | (+) | (+) | (+) |
| | 15° C. | (+) | (+) | (+) | (+) | (+) | (+) | (+) |
| | 10° C. | (+) | (+) | (+) | (+) | (+) | (+) | (+) |
| | 5° C. | (+) | (+) | (+) | (+) | (+) | (+) | (+) |
| | 0° C. | (+) | (+) | (+) | (+) | (+) | (+) | (+) |
| | −5° C. | (+) | (+) | (+) | (+) | (+) | (+) | (+) |
| | −10° C. | (−) | (−) | (−) | (−) | (−) | (+) | (−) |
| Formulation stability [%] | 14 d/54° C. | 99.71 | 99.19 | 99.55 | 99.02 | 97.13 | 99.74 | 98.95 |
| Stability on urea [%] | 4 w/40° C./50% rH | 72.29 | 77.9 | 74.36 | 60 | 70 | 78.05 | 76.74 |

| Formulation | ExNo. | InvEx 15 | InvEx 16 | InvEx 17 | InvEx 18 | InvEx 19 | InvEx 20 | InvEx 21 | CpEx 30 |
|---|---|---|---|---|---|---|---|---|---|
| Active ingredient | [%] | 25% LTM | 25% LTM | 25% LTM | 25% LTM | 25% LTM | 25% LTM | 25% LTM | 25% LTM |
| Formulation | Solvent (ad 100%) | PG | PG | PG | PG | PG | PG | PG | PG |
| Formulation | Cosolvent | 25% DML | 15% DMSO | 15% DMSO | 25% DML | 15% DMSO | 25% DML | 15% DMSO | 15% DMSO |
| Formulation | Polymers | 10% LEO | 5% LGA | 10% LGA | 5% LGA | 10% PEIEO | 10% PEIEO | 10% PEIPO | |
| Viscosity | [mPa*s] | 62 | 53 | 85 | 62 | 66 | 77 | 61 | 34 |
| pH | 1% | 9.3 | 10.4 | 10.6 | 10.3 | 10 | 10 | 9.9 | 7.6 |
| Cold stability 1 w/1 w seeded | 20° C. | (+) | (+) | (+) | (+) | (+) | (+) | (+) | (+) |
| | 15° C. | (+) | (+) | (+) | (+) | (+) | (+) | (+) | (+) |
| | 10° C. | (+) | (+) | (+) | (+) | (+) | (+) | (+) | (+) |
| | 5° C. | (+) | (+) | (+) | (+) | (+) | (+) | (+) | (+) |
| | 0° C. | (+) | (+) | (+) | (+) | (+) | (+) | (+) | (+) |
| | −5° C. | (+) | (+) | (+) | (+) | (+) | (+) | (+) | (+) |
| | −10° C. | (−) | (−) | (−) | (−) | (−) | (−) | (−) | (−) |
| Formulation stability [%] | 14 d/54° C. | 98.7 | 99.95 | 100 | 99.79 | 99.33 | 97.96 | 99.41 | 99.05 |
| Stability on urea | 4 w/40° C./ | 66.67 | 59.52 | 78.05 | 60 | 77.38 | 82.05 | 72.5 | 42.86 |

TABLE 2-continued

Examples of the compositions of the invention and of comparative compositions, and data on their viscosity, pH value, cold stability, formulation stability and stability on urea

| urea [%] | 50% rH | | | | | | | | |
|---|---|---|---|---|---|---|---|---|---|
| Formulation | ExNo. | InvEx 22 | InvEx 23 | InvEx 24 | InvEx 25 | InvEx 26 | InvEx 27 | InvEx 28 | CpEx 29 |
| Active ingredient | [%] | 25% LTM | 25% LTM | 25% LTM | 25% LTM | 25% LTM | 25% LTM | 25% LTM | 25% LTM |
| Formulation | Solvent (ad 100%) | PG | PG | PG | PG | PG | PG | PG | PG |
| Formulation | Cosolvent | 25% DML | 15% DMSO | 25% DML | 15% DMSO | 25% DML | 15% DMSO | 25% DML | 25% DML |
| Formulation | Polymers | 10% PEIPO | 10% Poly-lysine (L604) | 10% Poly-lysine (L604) | 10% Poly-lysine (L605) | 10% Poly-lysine (L605) | 10% LPEI | 10% LPEI | |
| Viscosity | [mPa*s] | 72 | 103 | 127 | 94 | 117 | 116 | 145 | 40 |
| PH | 1% | 9.9 | 10.2 | 10.2 | 10.2 | 10.1 | 9.8 | 9.8 | 7.2 |
| Cold stability 1 w/1 w seeded | 20° C. | (+) | (+) | (+) | (+) | (+) | (+) | (+) | (+) |
| | 15° C. | (+) | (+) | (+) | (+) | (+) | (+) | (+) | (+) |
| | 10° C. | (+) | (+) | (+) | (+) | (+) | (+) | (+) | (+) |
| | 5° C. | (+) | (+) | (+) | (+) | (+) | (+) | (+) | (+) |
| | 0° C. | (+) | (+) | (+) | (+) | (+) | (+) | (+) | (+) |
| | -5° C. | (+) | (+) | (+) | (+) | (+) | (+) | (+) | (+) |
| | -10° C. | (-) | (-) | (-) | (-) | (-) | (-) | (-) | (-) |
| Formulation stability [%] | 14 d/54° C. | 99.28 | 99.55 | 98.78 | 97.5 | 98.91 | 100 | 100 | 99.3 |
| Stability on urea [%] | 4 w/40° C./ 50% rH | 72.09 | 61.9 | 62.65 | 69.88 | 69.51 | 79.52 | 74.39 | 45 |

Study on Ammonia Volatilization Losses

Material and Methods—Laboratory Studies

The method used to measure NH3 volatilization losses from urea in the laboratory is described by Fenn & Kissel (1973) and Terman (1979). In brief, air passes for up to 21 days over 200 g soil Limburgerhof (loamy sand, pH(CaCl2) 6.8), with a moisture content of about 55% water holding capacity, in a gas exchange vessel after surface application of 0.25 g nitrogen in form of differently formulated urea. To scrub NH3 from the air leaving the vessel at a rate of about 4 L/min, it is bubbled through a solution of 200 mL 0.15 NH2SO4. NH3-N is quantified at regular intervals in the solution as NH4-N by means of an autoanalyzer.

Fenn, L. B. and D. E. Kissel (1973) Ammonia volatilization from surface applications of ammonium compounds on calcareous soils: I. General theory. Soil Sci. Am. Proc. 37, 855-859.

Terman, G. L. (1979) Volatilization losses of nitrogen as ammonia from surface-applied fertilizers, organic amendments and crop residues.

Advances in Agronomy 31, 189-223.

The results of the study on ammonia volatilization losses is shown in FIG. 1. In FIG. 1, the axis "X" stands for "days after urea application", the axis "Y" stands for "NH3-N losses, cumulated (% of applied urea nitrogen)", the unfilled circles "(i)" stand for "urea", the filled squares "(ii)" stand for "0.04% (A1) in propylene glycol formulation", the filled circles "(iii)" stand for "0.04% (A1) in AD25 formulation".

The invention claimed is:

1. A composition comprising:
(A) a mixture comprising at least one (thio)phosphoric acid triamide according to the general formula (I)

$R^1R^2NP(X)(NH_2)_2$, wherein
X is oxygen or sulfur;
$R^1$ is a $C_1$ to $C_{20}$ alkyl, $C_3$ to $C_{20}$ cycloalkyl, $C_6$ to $C_{20}$ aryl, or dialkylaminocarbonyl group;

$R^2$ is H, or $R^1$ and $R^2$ together with the nitrogen atom linking them define a 5- or 6-membered saturated or unsaturated heterocyclic radical, which optionally comprises 1 or 2 further heteroatoms selected from the group consisting of nitrogen, oxygen, and sulfur;

and (L14) polyethyleneimine according to the general formula (V)

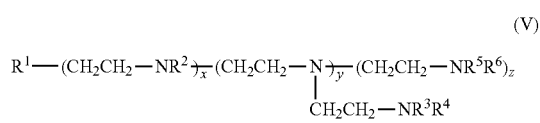

which has an average molar mass (MW) of from 200 to 1,000,000 g/mol and in which $R^1$ to $R^6$ are independently from each other—hydrogen, linear or branched $C_1$- to $C_{20}$-alkyl, -alkoxy, -polyoxyalkylene, -polyoxyethylene, -hydroxyalkyl, -(alkyl)carboxy, -phosphonoalkyl, -alkylamino radicals, $C_2$- to $C_{20}$-alkenyl radicals or $C_6$- to $C_{20}$-aryl, -aryloxy, -hydroxyaryl, -arylcarboxy or -arylamino radicals which are optionally further substituted, and $R^2$, $R^3$ and $R^5$ may—independently from each other—optionally be each additionally further polyethyleneimine polymer chains, and $R^1$ may optionally be an $NR^3R^4$ or an $NH_2$ radical, and x, y and z are—independently from each other—0 or an integer, wherein the sum of x, y and z must be chosen in such a way that the average molar mass is within the specified range;

further comprising a mixture of propane-1,2-diol (alpha-propylene glycol) and DMSO.

2. The composition according to claim 1, wherein the mixture (A) comprises at least one N-n-butylthiophosphoric acid triamide (NBPT) and N-n-propylthiophosphoric acid triamide (NPPT).

3. The composition according to claim 1, further comprising
(D) at least one amide according to the general formula (III)

$$R^{31}CO-NR^{32}R^{33}$$

wherein
$R^{31}CO$ is an acyl radical having 1 to 22 carbon atoms;
$R^{32}$ is H or alkyl; and
$R^{33}$ is H or alkyl; or
$R^{32}$ and $R^{33}$ together with the nitrogen atom linking them define a 5- or 6-membered saturated or unsaturated heterocyclic radical, which optionally comprises 1 or 2 further heteroatoms selected from the group consisting of nitrogen, oxygen, and sulfur.

4. The composition according to claim 3, wherein (D) is a N,N-dialkyl amide based on lactic acid, citric acid, tartaric acid, ricinoleic acid, 12-hydroxy stearic acid, or their mixtures.

5. The composition according to claim 1, further comprising:
(C) at least one amine selected from the group consisting of:
(C1) a polymeric polyamine; and
(C2) an amine containing not more than one amino group and at least three alkoxy- or hydroxy-substituted $C_2$ to $C_{12}$ alkyl groups $R^{21}$, wherein at least one of the groups $R^{21}$ is different to the other groups $R^{21}$;
(C3) an amine containing not more than one amino group and at least two alkoxy- or hydroxy-substituted $C_2$ to $C_{12}$ alkyl groups $R^{22}$, wherein at least one of the groups $R^{22}$ bears the alkoxy or hydroxy substituent at a secondary or tertiary carbon atom and wherein at least one of the groups $R^{22}$ is different to the other group(s) $R^{22}$;
(C4) an amine containing at least one saturated or unsaturated $C_8$ to $C_{40}$ alkyl group $R^{23}$; and
(C5) a saturated or unsaturated heterocyclic amine which contains at least one oxygen atom as ring atom and which does not contain a further alkoxy group.

6. The composition according to claim 1, further comprising:
(K1) an amine selected from the group consisting of:
(L211) methyldiethanolamine;
(L212) tetrahydroxypropylethylenediamine;
(L213) trimethylaminoethylethanolamine;
(L214) N,N,N',N'-tetramethyl-1,6-hexanediamine;
(L215) N,N',N''-tris(dimethylaminopropyl)hexahydrotriazine; and
(L216) 2,2'-dimorpholinyldiethyl ether.

7. The composition according to claim 1, further comprising an amine selected from the group consisting of:
(L217) triethanolamine;
(L218) tripropanolamine;
(L219) diisopropanolamine;
(L220) triisopropanolamine;
(L221) diethanolamine; and
(L222) methyldipropanolamine.

8. The composition according to claim 1, wherein the polyethyleneimine (L14) is selected from the group consisting of:
(L525) polyethyleneimine according to the general formula (V) having an average molar mass (MW) of from 250 to 100,000 g/mol;
(L526) polyethyleneimine according to the general formula (V) having an average molar mass (MW) of from 300 to 25,000 g/mol;
(L527) polyethyleneimine according to the general formula (V) in which $R^1$ to $R^6$ are each hydrogen, methyl, ethyl, carboxymethyl, carboxyethyl, phosphonomethyl, 2-hydroxyethyl, 2-(2'-hydroxyethoxy)ethyl or 2-[2'-(2''-hydroxyethoxy)-ethoxy]ethyl;
(L528) branched polyethyleneimine having a molecular weight of approx. 800 (GPC) and a charge density of approximately 16 meq/g of dry substance, determined at pH 4.5, and having a ratio primary/secondary/tertiary amino (as determined by 13C-NMR) of 1/0.9/0.5;
(L529) Branched polyethyleneimine having a molecular weight of approx. 25000 (GPC), a charge density of approximately 17 meq/g of dry substance, determined at pH 4.5, and having a ratio primary/secondary/tertiary amino (as determined by 13C-NMR) of 1/1.1/0.7; and
(L610) a linear polyethyleneimine.

* * * * *